United States Patent
Bryant et al.

(10) Patent No.: US 7,504,410 B2
(45) Date of Patent: Mar. 17, 2009

(54) CHK-, PDK- AND AKT-INHIBITORY PYRIMIDINES, THEIR PRODUCTION AND USE AS PHARMACEUTICAL AGENTS

(75) Inventors: Judi Bryant, Mill Valley, CA (US); Monica J. Kochanny, Benicia, CA (US); Shendong Yuan, Hercules, CA (US); Seock-Kyu Khim, Hercules, CA (US); Brad O. Buckman, Oakland, CA (US); Damian O. Arnaiz, Hercules, CA (US); Ulf Bomer, Glienicke/Nordbahn (DE); Hans Briem, Bremen (DE); Peter Esperling, Berlin (DE); Christoph Huwe, Berlin (DE); Joachim Kuhnke, Postdam (DE); Martina Schafer, Berlin (DE); Lars Wortmann, Berlin (DE); Dirk Kosemund, Erfurt (DE); Emil Eckle, Kuchen (DE); Richard I. Feldman, El Cerrito, CA (US); Gary B. Phillips, Pleasant Hill, CA (US)

(73) Assignee: Schering Aktiengesellschaft, Berlin (DE)

( * ) Notice: Subject to any disclaimer, the term of this patent is extended or adjusted under 35 U.S.C. 154(b) by 141 days.

(21) Appl. No.: 10/722,591

(22) Filed: Nov. 28, 2003

(65) Prior Publication Data
US 2004/0186118 A1 Sep. 23, 2004

Related U.S. Application Data

(60) Provisional application No. 60/430,084, filed on Dec. 2, 2002.

(30) Foreign Application Priority Data
Nov. 28, 2002 (EP) .................................. 02026607

(51) Int. Cl.
*C07D 239/47* (2006.01)
*C07D 239/48* (2006.01)
*C07D 403/12* (2006.01)
*C07D 417/12* (2006.01)
*A61K 31/505* (2006.01)
*A61K 31/506* (2006.01)
*A61K 31/397* (2006.01)
*A61P 35/02* (2006.01)
*A61P 35/00* (2006.01)

(52) U.S. Cl. .................. 514/272; 514/275; 514/210.02; 544/321; 544/323; 544/324; 540/200

(58) Field of Classification Search ................ 544/321, 544/323, 324; 514/272, 275; 540/200
See application file for complete search history.

(56) References Cited

U.S. PATENT DOCUMENTS

| 4,666,915 A | * | 5/1987 | Ozeki et al. ................. 514/272 |
| 4,814,338 A | * | 3/1989 | Ito et al. ..................... 514/275 |
| 5,733,914 A | * | 3/1998 | Blankley et al. ......... 514/264.1 |
| 6,197,779 B1 | * | 3/2001 | Andries et al. ............. 514/272 |
| 6,906,065 B2 | | 6/2005 | Thomas |
| 6,908,920 B2 | | 6/2005 | Thomas et al. |
| 7,166,599 B2 | * | 1/2007 | Bornemann et al. ...... 514/235.8 |
| 7,169,778 B2 | * | 1/2007 | Denny et al. ............. 514/234.5 |
| 2003/0134838 A1 | * | 7/2003 | Bomemann et al. ...... 514/210.2 |
| 2003/0162802 A1 | * | 8/2003 | Guo et al. .................. 514/269 |
| 2003/0171359 A1 | * | 9/2003 | Dahmann et al. ...... 514/217.06 |
| 2004/0102630 A1 | * | 5/2004 | Brumby et al. ............. 544/326 |

FOREIGN PATENT DOCUMENTS

| DE | 4029650 | * | 3/1992 |
| WO | WO 00/29404 | * | 5/2000 |
| WO | WO 01/72717 | | 10/2001 |
| WO | WO 02/04429 | | 1/2002 |

OTHER PUBLICATIONS

Cecil Textbook of Medicine, edited by Bennet, J.C., and Plum F., 20th edition, vol. 1, 1004-1010, 1996.*
Wolft Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
West, Anthony R., Solid State Chemistry and its Applications, Wiley, New York, 1988, pp. 358 & 365.*
Vippagunta et al., Advanced Drug Delivery Reviews 48: 3-26, 2001.*
Mass, R. D., Int. J. Radiation Oncology Bio. Phys.vol. 58(3): 932-940, 2004.*
Fabbro et al. Pharmacology & therapeutics 93, 79-98, 2002.*
Pimlott SL., Nucl. Med. Commun. 26(3): 183-188, 2005.*
Johnson et al. American Chemical Journal 38, 237-49, 1907; CA 1:11862, 1907.*
Naito et al., Chemical & Pharmaceutical Bulletin, 6, 338-343, 1958; CA 53:7084, 1959.*
Minn et al. CA 117:48596, 1992.*

* cited by examiner

*Primary Examiner*—Venkataraman Balasubramanian
(74) *Attorney, Agent, or Firm*—Millen, White, Zelano & Branigan, P.C.

(57) ABSTRACT

This invention relates to pyrimidine derivatives of general formula (I) as inhibitors of kinases, their production as well as their use as medications for treating various diseases.

22 Claims, No Drawings

CHK-, PDK- AND AKT-INHIBITORY PYRIMIDINES, THEIR PRODUCTION AND USE AS PHARMACEUTICAL AGENTS

This application claims the benefit of U.S. Provisional Application Ser. No. 60/430,084, filed Dec. 2, 2002.

This invention relates to pyrimidine derivatives, their production as well as their use as medications for treating various diseases.

The Chks (checkpoint kinases)-, Akts (protein kinases B) and Pdks (phosphoinositide-dependent kinases) are enzyme families that play an important role in the regulation of the cell cycle and thus is an especially advantageous target for the development of small inhibitory molecules. Akts and Pdks may be involved in common signal transduction pathways. Preferential inhibitors of the Chks and Akts and/or Pdks, particularly of Pdk1 can be used for treating cancer of other diseases that cause disruptions of cell proliferation.

Pyrimidines and analogs are already described as active ingredients, such as, for Example, the 2-anilino pyrimidines as fungicides (DE A-4029650) or substituted pyrimidine derivatives for treating neurological or neurodegenerative diseases (WO 99/19305). As CDK-Inhibitors, the most varied pyrimidine derivatives are described, for example bis(anilino)-pyrimidine derivatives (WO 00/12486), 2-amino-4-substituted pyrimidines (WO 01/14375), purines (WO 99/02162), 5-cyano pyrimidines (WO 02/04429), anilinopyrimidines (WO 00/12488) and 2-hydroxy-3-N,N-dimethylaminopropoxy-pyrimidines (WO 00/39101).

Protein ligands and receptor tyrosine kinases that specifically regulate endothelial cell function are substantially involved in physiological as well as in disease-related angiogenesis. These ligand/receptor systems include the Vascular Endothelial Growth Factor (VEGF) and the Angiopoietin (Ang) families, and their receptors, the VEGF receptor family and the tyrosine kinase with immunoglobulin like and epidermal growth factor homology domains (Tie) family. The members of the two families of receptor tyrosine kinases are expressed primarily on endothelial cells. The VEGF receptor family includes Flt1 (VEGF-R1), Flk1/KDR (VEGF-R2), and Flt4 (VEGF-R3). These receptors are recognized by members of the VEGF-related growth factors in that the ligands of Flt1 are VEGF and placenta growth factor (PlGF), whereas Flk1/KDR binds VEGF, VEGF-C and VEGF-D, and the ligands of Flt4 are VEGF-C and VEGF-D (Nicosia, Am. J. Pathol. 153, 11-16, 1998). The second family of endothelial cell specific receptor tyrosine kinases is represented by Tie1 and Tie2 (also kown as Tek) Whereas Tie1 remains an orphan receptor, three secreted glycoprotein ligands of Tie2, Ang1, Ang2, and Ang3/Ang4 have been discovered (Davis et al., Cell 87, 1161-1169, 1996; Maisonpierre et al., Science 277, 55-60, 1997; Valenzuela et al, Proc. Natl Acad. Sci. USA 96, 1904-1909, 1999; patents. U.S. Pat. Nos. 5,521,073; 5,650, 490, 5,814,464). Preferential inhibitors of the angiogenesis related kinases can be used for treating cancer or other diseases that are related to angiogenesis.

The object of this invention is to provide compounds that are inhibitors of cell cycle dependent kinases, in particular Chk, Akt, Pdk, CDK (cyclin dependent kinases) and/or angiogenesis related kinases, in particular VEGF-R (vascular endothelial growth factor receptor) kinases which have better properties than the inhibitors that are already known. The substances that are described here are more effective, since they already inhibit in the nanomolar range and can be distinguished from other already known Cdk-inhibitors such as, e.g., olomoucine and roscovitine.

It has now been found that the novel compounds of general formula I

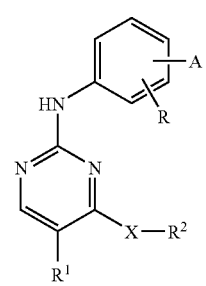

(I)

in which

A or B in each case independently of one another represent cyano, halogen, hydrogen, hydroxy, aryl or the group —$NO_2$, —$NH_2$, —$NR^3R^4$, —$C_{1-6}$alkyl-$NR^3R^4$, —$N(C_{1-6}$-hydroxyalkyl$)_2$, —NH—C(NH)—$CH_3$, —NH(CO)—$R^5$, —$NHCOOR^6$, —$NR^7$—(CO) $NR^8R^9$, —$NR^7$—(CS)—$NR^8R^9$, —$COOR^5$, —CO $NR^8R^9$, —CONH—$C_{1-6}$-alkyl-COOH, —$SO_2$—$CH_3$, 4-bromo-1-methyl-1H-pyrazolo-3yl or represent $C_{1-6}$ alkyl optionally substituted in one or more places, the same way or differently with halogen, hydroxy, cyano or with the group —$COOR^5$, —$CONR^5R^9$, —$NH_2$, —NH—$SO_2$—$CH_3$, —$NR^8R^9$, —NH—(CO)—$R^5$, —$NR^7$—(CO)—$N^8R^9$, —SO2-$NHR^3$, —O—(CO)—$R^5$ or —O—(CO)—$C_{1-8}$-alkyl $R^5$, X represents an oxygen atom or the group —NH— or —$NR^3R^4$, $R^1$ represents hydrogen, halogen, hydroxymethyl, $C_{1-6}$-alkyl, cyano or the group —COOH, —COO-iso propyl, —$NO_2$, —NH—(CO)—$(CH_2)_2$—COOH or —NH—(CO)—$(CH_2)_2$—COO—$C_{1-6}$-alkyl, whereby the $C_{1-6}$-alkyl can optionally be substituted in one or more places, in the same way or differently with halogen, $R^2$ represents hydrogen or the group —NH—(CO)-aryl or $C_{1-6}$-alkyl optionally substituted in one or more places, the same way or differently with cyano, hydroxy, aryl, heteroaryl, $C_{3-6}$-heterocycloalkylring, which can optionally be interrupted with one or more nitrogen atoms, or substituted with the group —$NR^8R^9$, —NH—(CO)—$NR^8R^9$, —NH—(CO)—S—$C_{1-6}$-alkyl, —NH—(CS)—$NR^8R^9$, NH—(CO)O—$CH_2$-phenyl, —NH(CO)H, —NH(CO)—$R^5$, —NH(CO)—$OR^5$, —(CO)—NH—$NH_2$, —(CO)—NH—$CH_2$—(CO)—$NH_2$, —(CO)—NH $C_{1-6}$-alkyl, —COOH,

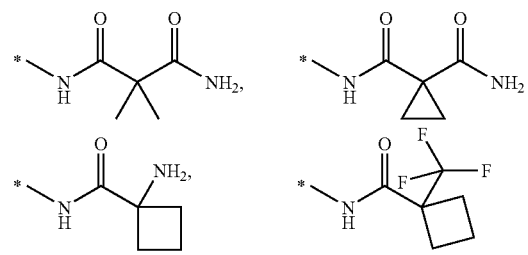

-continued

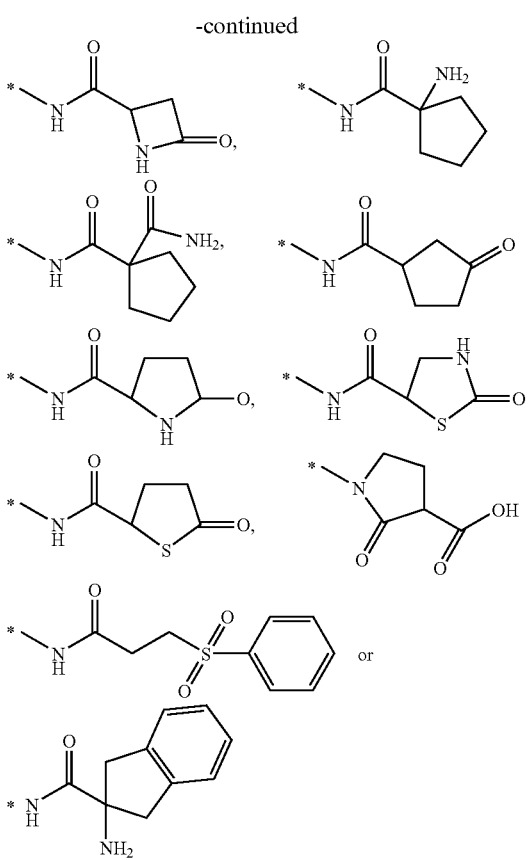

whereby the aryl or the heteroaryl can optionally be substituted in one or more places, the same or differently with halogen, hydroxy, $C_{1-6}$-alkyl, —$NH_2$, NH—(CO)—$CH_2$—$NH_2$, —$NO_2$, —(CO)—C($CH_2$)—$C_2H_5$, —$COOR^5$, —$COOC(CH_3)_3$, or represents $C_3$-alkinyl, $R^3$ and $R^4$ in each case independently of one another represent hydrogen or $C_{1-6}$-alkyl optionally substituted in one or more places, the same way or differently with hydroxy, phenyl or hydroxyphenyl, or $R^3$ or $R^4$ together form a $C_{3-6}$-heterocycloalkylring containing at least one nitrogen atom and optionally can be interrupted by one or more oxygen and/or sulfur atoms and/or can be interrupted by one or more —(CO)— groups in the ring and/or optionally can contain one or more possible double bonds in the ring, whereby the $C_{3-6}$-heterocycloalkylring can optionally be substituted with $C_{1-6}$-alkyl, $C_{1-6}$-alkyl COOH or $C_{1-6}$-alkyl-$NH_2$, $R^5$ represents hydrogen $C_{1-6}$-alkyl, $C_{1-6}$-alkoxy, $C_{2-8}$-alkenyl, $C_{3-6}$-cycloalkylring, aryl, heteroaryl, the group —(CO)—$NH_2$ or $C_{3-6}$-heterocycloalkylring that can optionally be interrupted with one or more nitrogen and/or oxygen and/or sulfur atoms and/or can be interrupted by one or more —(CO)— groups in the ring and/or optionally can contain one or more possible double bonds in the ring and $C_{1-6}$-alkyl, $C_{2-6}$-alkenyl, $C_{3-6}$-cycloalkylring, $C_{3-6}$-heterocycloalkylring defined above, aryl or heteroaryl can optionally be substituted in one or more places, the same way or differently with halogen, hydroxy, $C_{1-6}$-alkyl, $C_{1-6}$-alkoxy, $C_{3-6}$-cycloalkyl, $C_{3-6}$-heterocycloalkylring defined above, aryl, heteroaryl or with the group $NR^8R^9$, —$NO_2$, —$NR^7$—(CO)—$R^5$, —NH(CO)$C_{1-6}$-alkyl-NH—(CO)—$C_{1-6}$-alkyl, $NR^7$—(CO)—$NR^8R^9$, —CO—$CH_3$, —COOH, —CO—$NR^8R^9$, —$SO_2$-aryl, —SH, —S—$C_{1-6}$-alkyl, —$SO_2$—$NR^8R^9$, whereby aryl itself can optionally be substituted in one or more places, the same way or differently with halogen, hydroxy, $C_{1-6}$-alkyl or $C_{1-6}$-alkoxy, $R^6$ represents $C_{1-6}$-alkyl, $C_{2-6}$-alkenyl or phenyl, whereby $C_{1-6}$-alkyl may optionally be substituted with $C_{3-6}$-heterocycloalkylring that can optionally be interrupted with one or more nitrogen and/or oxygen and/or sulfur atoms and/or can be interrupted by one or more —(CO)— groups in the ring and/or optionally can contain one or more possible double bonds in the ring, $R^7$ represents hydrogen or $C_{1-6}$-alkyl, $R^8$ or $R^9$ in each case independently of one another represent hydrogen, $C_{1-6}$-alkyl, $C_{2-5}$-alkenyl, $C_{3-8}$-cycloalkyl, aryl or heteroaryl or the group $R^{10}$, whereby $C_{1-6}$-alkyl, $C_{2-6}$-alkenyl, $C_{3-6}$-cycloalkyl, aryl or heteroaryl can optionally be substituted in one or more places, the same way or differently with halogen, heteroaryl, hydroxy, $C_{1-6}$-alkoxy, hydroxy-$C_{1-6}$-alkoxy or the group —COOH, —$NO_2$, —$NR^8R^9$, —N($C_{1-6}$-alkyl)$_2$ or with a $C_{3-6}$-heterocycloalkylring can optionally be interrupted with one or more nitrogen and/or oxygen and/or sulfur atoms and/or can be interrupted by one or more —(CO)— groups in the ring and/or optionally can contain one or more possible double bonds in the ring, or $R^8$ and $R^9$ together form a $C_{3-6}$-heterocycloalkylring containing at least one nitrogen atom and optionally can be interrupted by one or more oxygen and/or sulfur atoms and/or can be interrupted by one or more —(CO)— groups in the ring and/or optionally can contain one or more possible double bonds in the ring, whereby the $C_{3-6}$-heterocycloalkylring can optionally be substituted in one or more places, the same way or differently with hydroxy or the group —$NR^8R^9$, —NH(CO)—$R^5$, hydroxy-$C_{1-6}$alkyl or COOH and $R^{10}$ represents —$SO_2$-aryl, —$SO_2$-heteroaryl or —$SO_2$—$NH_2$ or —$SO_2$—$C_{1-6}$-alkyl, whereby the aryl can be substituted with —$C_{1-6}$-alkyl, with the following provisos:

whereby if X represents —$NR^3R^4$ then $R^2$ does not represent a substituent, whereby if A and B represent hydrogen, X represents —NH— and $R^2$ represents $C_{1-6}$-alkyl, then $R^1$ represents —NH—(CO)—CH($NH_2$)—(CH2)$_2$—COOH or —NH—(CO)—CH(NH2)—(CH2)$_2$—COOC$_2$H$_5$, whereby it A represents (CO)—OC$_2$H$_5$ or hydroxy, B represents hydrogen, X represents oxygen, $R^1$ represents halogen, then $R^2$ represents $C_3$-alkinyl, whereby if A represents —(CO)—OC$_2$H$_5$ or hydroxy, B represents hydrogen, X represents —NH—, $R^1$ represents —$NO_2$, then $R^2$ represents $C_3$-alkinyl, whereby if A represents —(CO)—OCH$_3$, then X represents oxygen, $R^1$ represents halogen, $R^2$ represents $C_3$-alkinyl and B represents —$NH_2$, —NHC$_2$H$_4$OH, —N(C$_2$H$_4$OH)$_2$, —NH—(CO)—CH$_2$—O(CO)CH$_3$, whereby if A represents —(CO)—OCH$_3$, then X represents —NH—, $R^1$ represents halogen, $R^2$ represents —$C_2H_4$-imidazolyl and B represents hydrogen —$NH_2$, whereby if A represents —$NHSO_2$—$CH_3$, then B represents hydrogen, X represents —NH—, $R^1$ represents halogen and $R^2$ represents —$C_2H_4$-imidazolyl, whereby if $R^1$ represents —(COO)-iso-propyl, then X represents —NH— and $R^2$ represents C3-alkinyl and A or B independently of one another represent the group —$NO_2$ or —NH—(CO)—$CF_3$, whereby if $R^1$ represents halogen, X represents —NH—, B represents hydrogen and $R^2$ represents $C_{1-6}$-alkyl substituted with —$NH_2$, then A represents —NH—(CO)—$C_6$-cycloalkyl-$NH_2$, whereby if $R^1$ represents halogen, X represents —NH—, B represents —S—$CH_3$ and $R^2$ represents imidazolyl, then A represents the group

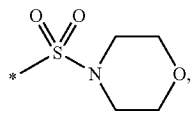

as well as all related isotopes, diastereomers, enantiomers, solvates, polymorphs or pharmaceutically acceptable salts thereof are capable of inhibiting kinases which are involved in the regulation of the cell cycle, particulary Chks, Akt, Pdks and/or Cdks as well as angiogenesis related kinases, particulary VEGF-R kinases.

A more detailed explanation of the terms used in the claims and the description is given in the following:

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

Preferred aspects of the present invention are described in the claims. A more detailed explanation of the terms used in the claims is given in the following;

"Alkyl" is defined in each case as a straight-chain or branched alkyl radical, such as, for example, methyl, ethyl, propyl, isopropyl, butyl, isobutyl, sec butyl, tert-butyl, pentyl, isopentyl, hexyl, heptyl, octyl, nonyl and decyl.

"Alkoxy" is defined in each case as a straight-chain or branched alkoxy radical, such as, for example, methyloxy, ethyloxy, propyloxy, isopropyloxy, butyloxy, isobutyloxy, sec-butyloxy, tert-butyloxy, pentyloxy, isopentyloxy, or hexyloxy.

"Hydroxy Alkoxy" is defined in each case as a straight-chain or branched alkoxy radical, such as, for example, methyloxy, ethyloxy, propyloxy, isopropyloxy, butyloxy, isobutyloxy, sec-butyloxy, tert-butyloxy, pentyloxy, isopentyloxy, or hexyloxy is substituted one or more times with hydroxy.

"Alkylthio" is defined in each case as a straight-chain or branched alkylthio radical, such as, for example, methylthio, ethylthio, propylthio, isopropylthio, butylthio, isobutylthio, sec-butylthio, tert-bulythio, penylthio, isopentylthio or hexylthio.

"Cycloalkyl" is defined in general as monocyclic, alkyl rings, such as cyclopropyl, cyclobutyl, cyclopentyl, cyclohoxy, cycloheptyl, cyclooctyl, cyclononyl or cyclodecyl, but also bicyclic rings or tricyclic rings such as, for example, norbornyl, adamantanyl, etc.

The ring systems, in which optionally one or more possible double bonds can be contained in the ring, are defined as, for example, cycloalkenyls, such as cyclopropenyl, cyclobutenyl, cyclopentenyl, cyclohexenyl, or cyclohephenyl, whereby the linkage can be carried out both to the double bond and to the single bonds.

If $R^3$ and $R^4$ or $R^8$ and $R^9$ as defined in the claims, in each case independently of one another, together form a $C_3$-$C_{10}$-cycloalkyl ring, which optionally can be interrupted by one or more heteroatoms, such as nitrogen atoms, oxygen atoms and/or sulfur atoms, and/or can be interrupted by one or more —(CO)— groups in the ring and/or optionally one or more possible double bonds can be contained in the ring, however, the above-mentioned definitions are also intended to include heteroaryl radical or heterocycloalkyl and heterocycloalkenyl. In terms of this invention interrupted can mean either that the heteroatoms in addition to the carbon atoms form the ring or that the heteroatoms are substitutes for one or more carbon atoms.

"Halogen" is defined in each case as fluorine, chlorine, bromine or iodine.

The "alkenyl" substituents in each case are straight-chain or branched, whereby, for examples the following radicals are meant: vinyl, propen-1-yl, propen-2-yl, but-1-en-1-yl, but-1-en-2-yl, but-2-en-1-yl, but-2-en-2-yl, 2-methyl-prop-2-en-1-yl, 2-methyl prop 1-en-1-yl, but-1-en-3-yl, ethinyl, prop-1-in-1-yl, but-1-in-1-yl, but-2-in-1-yl, but-3-en-1-yl, and allyl.

"Alkinyl" is defined in each case as a straight chain or branched alkinyl radical that contains 2-6, preferably 2-4 C atoms. For example, the following radicals can be mentioned, acetylene, propin-1-yl, propin 3-yl, but-1-in-1-yl, but-1-in-4-yl, but-2-in-1-yl, but-1-in-3-yl, etc.

The "aryl" radical in each case comprises 3-16 carbon atoms and in each case can be benzocondensed.

For example, there can be mentioned: cyclopropenyl, cyclopentadlenyl, phenyl, tropyl, cyclooctadienyl, indenyl, naphthyl, azulenyl, biphenyl, fluorenyl, anthracenyl, etc.

The "heteroaryl" radical in each case comprises 3-16 ring atoms, and instead of the carbon can contain one or more heteroatoms that are the same or different, such as oxygen, nitrogen or sulfur, in the ring, and can be monocyclic, bicyclic, or tricyclic and in addition in each case can be benzocondensed.

For example, there can be mentioned:

Thienyl, furanyl, pyrrolyl, oxazolyl, thiazolyl, imidazolyl, pyrazolyl, isoxazolyl, isothiazolyl, oxadiazolyl, triazolyl, thiadiazolyl, etc., and benzo derivatives thereof, such as, e.g., benzofuranyl, benzothienyl, benzoxazolyl, benzimidazolyl, indazolyl, indolyl, isoindolyl, etc.; or pyridyl, pyridazinyl, pyrimidinyl, pyrazinyl, triazinyl, etc., and benzo derivatives thereof, such as. e.g., quinolyl, isoquinolyl, etc., or azocinyl, indolizinyl, purinyl, etc., and benzo derivatives thereof; or quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, oxepinyl, etc.

"Heterocycloalkyl" stands for an alkyl ring that comprises 3-6 carbon atoms, which can optionally be interrupted with one or more nitrogen and/or oxygen and/or sulfur atoms and/or can be interrupted by one or more —(CO)— groups in the ring and/or optionally can contain one or more possible double bonds in the ring. In terms of this invention interrupted can mean either that the heteroatoms in addition to the carbon atoms form the ring or that the heteroatoms are substitutes for one or more carbon atoms.

For purposes of this invention, the heterocycloalkyl radical may be a monocyclic, or bicyclic ring system, which may include fused or bridged ring systems; and additionally the nitrogen or sulfur atoms in the heterocyclyl radical may be optionally oxidized; the nitrogen atom nay be optionally quaternized; and the heterocyclyl radical may be aromatic or partially or fully saturated.

As heterocycloalkyls, there can be mentioned, e.g.: oxiranyl, oxethanyl, aziridinyl, azetidinyl, tetrahydrofuranyl, pyrrolidinyl, pyrrolidinonyl, dioxolanyl, imidazolidinyl, imidazolidinonyl, thiazolidinonyl, pyrazolidinyl, pyrazolidinonyl, dioxanyl, piperidinyl, piperidinonyl, morpholinyl, dithianyl, thiomorpholinyl, piperazinyl, trithianyl, quinuclidinyl, oxazolidinyl, oxazolidinonyl, hydantoin, pyran, thiin, dihydroacet, etc.

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention. As used herein, "methods known to one of ordinary skill in the art" may be identified though various reference books and databases. Suitable reference books and treatise that detail the synthesis of reactants useful in the preparation of compounds of the present invention, or provide references to article that describe the preparation, include for example, "Synthetic Organic Chemistry", John Wiley & Sons, Inc., New York; S. R. Sandier et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C. may be contacted for more details). Chemicals that are known but not commercially available in catalogs may be prepared by custom chemical synthesis houses, where many of the standard chemical supply houses (e.g., those listed above) provide custom synthesis services, "Stable compound"and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts. "Pharmaceutically acceptable acid addition salt" refers to those salts which retain the biological effectiveness and properties of the tree bases, which are not biologically or otherwise undesirable, and which are formed with inorganic acids such as hydrochloric acid, hydrobromic acid, sulfuric acid, nitric acid, phosphoric acid and the like and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline, caffeine, N-methyl-glucamine, dimethyl-glucamine, ethyl-glucamine, lysine, 1,6-hexadiamine, ethanel-amine, glucosamine, sarcosine, serinol, tris-hydroxy-methyl amino methane, aminopropane diol, Sovak base, and 1-amino-2,3,4-butanetriol.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK). Avocado Research (Lancashire U.K.), BDH Inc. (Toronto, Canada), Bionet (Cornwall, U K), Chemservice Inc. (West Chester Pa.) (Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), IGN Biomedicals, Inc, (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.). Pierce Chemical Co. (Rockford Ill.), Riedel de Haen A G (Hannover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandier et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. I. Gilchrist, "Heterocyclic Chemistry", 2nd Ed. John Wiley & Sons, New York, 1992, J. March, "Advanced Organic Chemistry: Reactions, Mechanisms and Structure", 4th Ed., Wiley Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C. may be contacted for more details). Chemicals that are known but not commercially available in catalogs may be prepared by custom chemical synthesis houses, where many of the standard chemical supply houses (e.g. those listed above) provide custom synthesis services.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blond. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," A.C.S. Symposium Series. Vol. 14, and in Bioreversible Carriers in Drug Design, ed. Edward B. Roche, American Pharmaceutical Association and Pergamon Press 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or tree mercapto group, respectively. Examples of prodrugs include, but are not limited to acetate, formate and benzoate derivatives of alcohol and amine functional groups in the compounds of the invention and the like.

"Therapeutically effective amount" refers to that amount of a compound of formula (I) which, when administered to a mammal, preferably a human, is sufficient to effect treatment, as defined below, for a disease-state alleviated by the inhibition of AKT-, PDK-, CHK, CDK- or VEGF-R-activity, such as cancer. The amount of a compound of formula (I) which constitutes a "therapeutically effective amount" will vary depending on the compound, die condition and its severity, and the age of the mammal to be treated, but can be determined routinely by one of ordinary skill in the art having regard to his own knowledge avid to this disclosure.

"Treating" or "treatment" as used herein covers the treatment of disease-states alleviated by the inhibition of AKT-, PDK-, CHK-, CDK- or VEGF-R-activity, such as cancer, as disclosed herein, in a mammal, preferably a human, and includes;

(i) preventing the disease-state from occurring in a mammal, in particular, when such mammal is predisposed to the disease-state but has not yet been diagnosed as having it;

(ii) inhibiting the disease-state, i.e. . . . , arresting its development; or (iii) relieving the disease-state, i.e. . . . , causing regression of the condition.

The compounds of formula (I), or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the formulae described herein contain olefinic double bonds or other centers of geometric asymmetry, unless specified otherwise, it is intended that the formulae include both E and Z geometric isomers, as well as all tautomeric forms. In addition, all compound names herein, unless specified otherwise, are intended to include all single enantiomers, diastereomers, and mixtures thereof, as well as racemic and non racemic mixtures.

Compounds which preferentially inhibit AKT and/or PDK kinases are the compounds of formula I in which A or B in each case independently of one another represent cyano, halogen, hydrogen, hydroxy, tetrazolyl or the group —$NH_2$, $NR^3R^4$, —$C_{1-6}$-alkyl-$NR^3R^4$, —NH—C(NH)—$CH_3$, —NH(CO)—$R^5$, —NHCOOR$^6$, —$NR^7$—(CO)—$NR^8R^9$, —$C_{1-6}$-alkyl COOH, —COOH —$CONH_2$, —CONH—$C_{1-6}$-alkyl-COOH, or represent $C_{1-6}$-alkyl optionally substituted in one or more places, the same way or differently with halogen, hydroxy or with the group —COOH, —$CONR^8R^9$, NH $SO_2$ $CH_3$ or —$NR^8R^9$, X represents the group —NH— or —$NR^3R^4$, $R^1$ represents cyano, hydrogen, halogen or $C_{1-6}$-alkyl, whereby the $C_{1-6}$-alkyl can optionally be substituted in one or more places, in the same way or differently with halogen, $R^2$ represents hydrogen or the group —NH—(CO)-aryl or —$C_{1-6}$-alkyl optionally substituted in one or more places, the same way or differently with cyano, hydroxy, aryl, heteroaryl, $C_{3-6}$-heterocycloalkyl ring which can be optionally be interrupted in one or more places with one or more nitrogen atoms, or substituted with the group —NR$^8$R$^9$, —NH—(CO)—NR$^8$R$^9$, —NH—(CO)—S—C$_{1-6}$-alkyl, —NH—(CS)—NR$^8$R$^9$, —NH(CO)—R$^5$, —NH(CO)—OR$^5$, —(CO)NH—NH$_2$, —(CO)—NH—CH(CO)—NH$_2$, —(CO)—NH—C$_{1-6}$-alkyl, —COOH whereby the aryl or the heteroaryl can optionally be substituted in one or more places, the same way or differently with hydroxy, C$_{1-6}$ alkyl, NH$_2$, NH—(CO)—CH$_2$—NH$_2$, —NO$_2$—COOR$^6$,

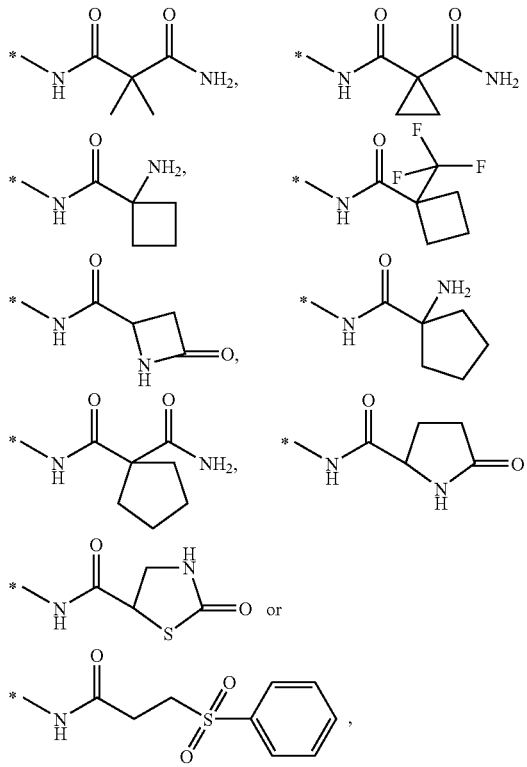

R$^3$ or R$^4$ in each case independently of one another represent hydrogen, C$_{1-6}$-alkyl optionally substituted in one or more places, the same way or differently with hydroxy, phenyl or hydroxyphenyl, or R$^3$ and R$^4$ together form a C$_{3-6}$-heterocycloalkylring containing at least one nitrogen atom and optionally can be interrupted by one or more oxygen and/or sulfur atoms and/or can be interrupted by one or more —(CO)— groups in the ring and/or optionally can contain one or more possible double bonds in the ring, whereby the C$_{3-6}$ heterocycloalkylring can optionally be substituted with C$_{1-6}$-alkyl, C$_{1-6}$-alkyl-COOH or C$_{1-6}$-alkyl-NH2, R$^6$ represents hydrogen, C$_{1-6}$-alkyl, C$_{1-6}$-alkoxy, C$_{2-6}$-alkenyl, C$_{3-6}$-cycloalkylring, heteroaryl, the group —(CO)—NH$_2$ or C$_{3-6}$-heterocycloalkylring that can optionally be interrupted with one or more nitrogen and/or oxygen and/or sulfur atoms and/or can be interrupted by one or more —(CO)— groups in the ring and/or optionally can contain one or more possible double bonds in the ring and C$_{1-6}$-alkyl, C$_{2-6}$-alkenyl, C$_{3-6}$-heterocycloalkylring define above, aryl or heteroaryl can optionally be substituted in one or more places, the same way or differently with halogen, hydroxy, C$_{1-6}$-alkyl, C$_{1-6}$-alkoxy, C$_{3-6}$-cycloalkyl, C$_{3-6}$ heterocycloalkylring define above, aryl, heteroaryl, or with the —NR$^8$R$^9$, —NO$_2$, —NR$^7$—(CO)—R$^5$, —NH(CO)—C$_{1-6}$-alkyl-NH—(CO)—C$_{1-6}$-alkyl, —NR$_7$—(CO)—NR$^5$R$^9$, —CO—CH$_3$, —COOH, —CO—NR$^8$R$^9$, —SO$_2$-aryl, —SH, —S—C$_{1-6}$-alkyl, —SO$_2$—NR$^8$R$^9$, whereby aryl itself can optionally be substituted in one or more places, the same way or differently with halogen or hydroxy, C$_{1-6}$-alkyl or C$_{1-6}$-alkoxy, R$^7$ represents hydrogen or C$_{1-6}$-alkyl, R$^8$ or R$^9$ in case independently of one another represent hydrogen, C$_{1-6}$alkyl, aryl or heteroaryl or the group R$^{10}$, whereby C$_{1-6}$-alkyl, aryl or heteroaryl can optionally be substituted in one or more places, the same way or differently with halogen, heteroaryl, hydroxy, C$_{1-6}$-alkoxy, hydroxy-C$_{1-6}$-alkoxy or with the group —COOH, —NO$_2$, or a C$_{3-6}$-heterocycloalkylring can optionally be interrupted with one or more nitrogen and/or oxygen and/or sulfur atoms and/or can be interrupted by one or more —(CO)— groups in the ring and/or optionally can contain one or more possible double bonds in the ring or R$^8$ and R$^9$ together form a C$_{3-6}$-heterocycloalkylring containing at least one nitrogen atom and optionally can be interrupted by one or more oxygen and/or sulfur atoms and/or can be interrupted by one or more —(CO)— groups in the ring and/or optionally can contain one or more possible double bonds in the ring, whereby the (C$_{3-6}$-heterocycloalkylring can optionally be substituted in one or more places, the same way or differently with hydroxy, hydroxy-C$_{1-6}$-alkyl or the group —NR$^8$R$^9$, —NH(CO)R$^5$ or —COOH and R$^{10}$ represents —SO$_3$—NH$_2$, —SO$_2$—C$_{1-6}$-alkyl, —SO$_2$-aryl, or —SO$_2$-heteroaryl, whereby the aryl can be substituted with —C$_{1-6}$-alkyl, as well as all related isotopes, diastereomers, enantiomers, solvates, polymorphs or pharmaceutically acceptable salts thereof.

Even more preferred are the compounds of formula I, which inhibit preferentially AKT and/or PDK kinases in which A or R in each case independently of one another represent hydrogen, tetrazolyl or the group —N(CH$_3$)$_2$, —NH—(CO)-pyrrolidinyl, —NH—(CO)-pentyl, —NH—(CO)-hexyl, —NH—(CO)-hexyl-NH$_2$, —NH—(CO)—C$_3$H$_7$, —NH—(CO)—CH$_2$-phenyl, —NH—(CO)—CH$_2$—NH$_2$, —NH—(CO)—C$_2$H$_4$—NH$_2$, —NH—(CO)—CH(NH$_2$)—CH$_3$, —NH—(CO)—CH(NH$_2$)-hydroxyphenyl, —NH—(CO)—CH(NH$_2$)—CH$_2$-phenyl, —NH—(CO)—CH(NH$_2$)—CH$_2$-hydroxyphenyl, NH—(CO)—CH(NH—(CO)—CH$_3$)—CH$_2$-phenyl, —NH—(CO)CH$_2$—NH—(CO)—CH$_3$, —NH—(CO)—N(C$_2$H$_5$)(C$_2$H$_4$-piperidinyl), —NH—(CO)—N(CH$_3$)(C$_2$H$_4$-piperidinyl), —NH—(CO)—CH$_2$—NH(CH$_3$)—CH$_2$—N(CH$_3$)$_2$, —NH—(CO)NH—CH$_2$—COOH, hydantoinyl, —CH$_2$—COOH whereby the pyrrolidinyl can optionally be substituted with hydroxy or the group NH$_2$, N(CH$_3$)$_2$ or —NH—(CO)—CH$_3$, and whereby hydantoinyl can be substituted with —CH$_3$, —CH$_2$—COOH, or —(CO)-thiazolidinonyl, X represents or the group —NH—, R$^1$ represents halogen and R$^2$ represents hydrogen or the group —NH—(CO) phenyl or C$_2$H$_4$—, —C$_3$H$_6$— both can optionally be substituted in one or more places, the same way or differently with cyano, hydroxy, phenyl, naphthyl, imidazolyl, thiazol, pyridyl, 2-oxazolinyl, piperidinyl, —NH$_2$, NH CH$_2$ thienyl, —NHpyridinyl-NO₂, —NH-thiazolyl, —SO₂-thienyl, —SO₂—NH₂, —SO₂—CH₃, —SO₂—C₃H₂, pyrrolidinonyl substituted with COOH, —NH—(CO)—NH-thienyl, —NH—(CO)—NH-phenyl, —NH—(CO)—NH—C₂H₆, —NH—(CO)—C(CH₃)₃, —NH—(CO)S—C₂H₅, —NH—(CS)—NH—C₂H₅, —NH—(CO)C₂H₅, —NH—(CO)-thienyl, —(CO)—NH—NH₂, —(CO)—NH—CH₂—(CO)—NH₂, —(CO)—NH—C₂H₅, —COOH whereby the phenyl or the imidazolyl, thiazolyl can optionally be substituted in one or more places, the same way or differently with hydroxy, —CH₃, —NH—(CO)—CH₂—NH₂, —COOC₂H₅, —COOC(CH₃)₃,

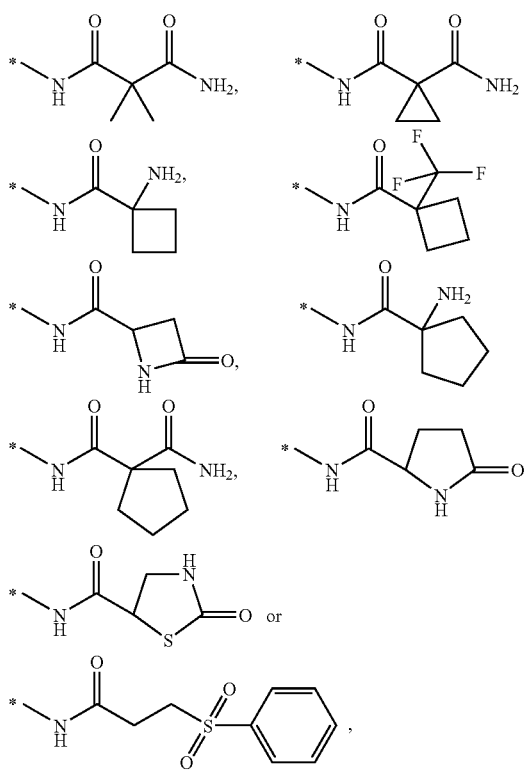

as well as all related isotopes, diastereomers, enantiomers, solvates, polymorphs or pharmaceutically acceptable salts thereof.

Even more preferred are compounds of general formula (I), which inhibit preferentially AKT and/or PDK kinases in which A or B in each case independently of one another represent hydrogen or the group —NH—(CO)-pyrrolidinyl, —NH—(CO)-piperldinyl, —NH—(CO)-morpholinyl, —NH—(CO)-hexyl-NH₂, —NH—(CO)—CH(NH₂)-hydroxyphenyl, —NH—(CO)—CH(NH₂)—CH₂-hydroxyphenyl, hydantoin optionally substituted with —CH3, X represents or the group —NH—.

R¹ represents halogen and

R² represent hydrogen, —C₂H₄-imidazolyl or —C₃H₇ wich can optionally be substituted in one or more places, the same way or differently with the group —NH—CH₂-theinyl, —NH—(CO)—C₂H₅, —NH—(CO)—C(CH₃)₃,

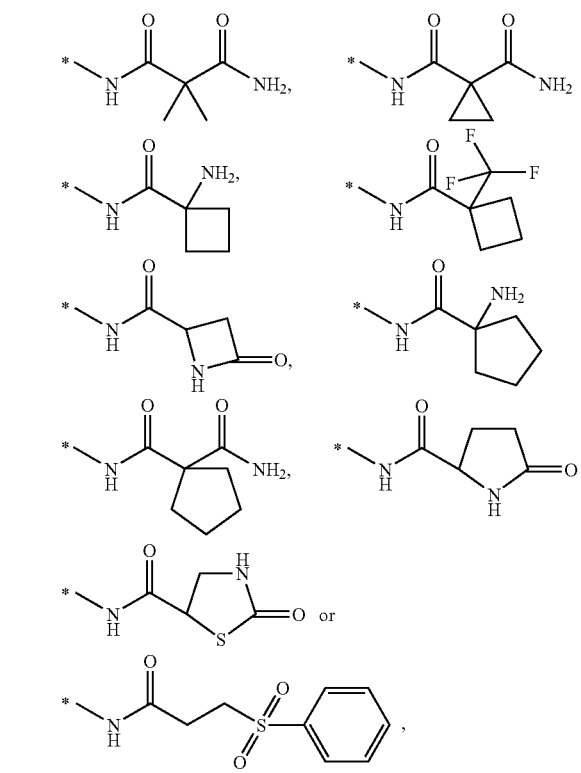

as well as all related isotopes, diastereomers, enantiomers, solvates, polymorphs or pharmaceutically acceptable salts thereof.

In particular the following compounds of general formula (I) are preferred to inhibit preferentially AKT and/or PDK kinases:

N-[3-[[5-bromo-4-[[3-[[[1-(trifluoromethyl)cyclobutyl]carbonyl]amino]propyl]amino]-2-pyrimidinyl]amino]phenyl]-1-pyrrolidinecarboxamide.

N-[3-[[5-bromo-4-[[3-[[1-oxo-3-(phenylsulfonyl)propy]amino]propyl]amino]-2-pyrimidinyl]amino]phenyl]-1-pyrrolidinecarboxamide, N-[3-[[5-bromo-2-[[3-[(1-pyrrolidinylcarbonyl)amino]phenyl]amino]-4-pyrimidinyl]amino]propyl]-2,2-dimethyl-propanediamide, N-[3-[[4-[[3-[[(1-aminocyclopentyl)carbonyl]amino]propyl]amino]-5-bromo-2-pyrimidinyl]amino]phenyl]-1-pyrrolidinecarbonamide.

N-[3-[[4-[[3-[[(1-aminocyclobutyl)carbonyl]amino]propyl]amino]-5-iodo-2-pyrimidinyl]amino]phenyl]-1-pyrrolidinecarboxamide.

N¹-[3-[[5-bromo-2-[[3-[(1-pyrrolidinylcarbonyl)amino]phenyl]amino]-4-pyrimidinyl]amino]propyl]-1,1-cyclopentanedicarboxamide, (4R)-N-[3-[[5-bromo-2-[[3-(2,5-dioxo-1-imidazolidinyl)phenyl]amino]-4-pyrimidinyl]amino]propyl]-2-oxo-4-thiazolidinecarboxamide, (4R)-N-[3-[[5-bromo-2-[[3-(3-methyl-2,5-dioxo-1-imidazolidinyl)phenyl]amino]-4-pyrimidinyl]amino]propyl]-2-oxo-4-thiazolidinecarboxamide, 3-[3 [[5 bromo-1-[[2-(1H-imidazol-4-yl)ethyl]amino]-2-pyrimidinyl]amino]phenyl]-2,4-imidazolidinedione, 3-[3-[[5-bromo-4-[[2-(1H-imidazol-4-yl)ethyl]amino]-2-pyrimidinyl]amino]phenyl]-1-methyl-2,4-imidazolidinedione, N'-[3-[[5-bromo-4-[[2-(1H-imidazol-4-yl)ethyl]amino]-2-pyrimidinyl]amino]phenyl]-N-ethyl-N-[2-(1-piperidinyl)ethyl]-urea, N-[3-[[5-bromo-4-[[3-[(2,2-dimethyl-1-oxopropyl)amino]propyl]amino]-2-pyrimidinyl]amino]phenyl]-1-pyrrolidinecarboxamide, N-[3-[[2-[[3-[[(2S)-2-amino-3-(4-hydroxyphenyl) 1-oxopropyl]amino]phenyl]amino]-5-bromo-4-pyrimidinyl]amino]propyl]-2,2-dimethyl-propanediamide, N-[3-[[2-[[3-[[(1-aminocyclohexyl)carbonyl]amino]phenyl]amino]-5-bromo-4-pyrimidinyl]amino]propyl]-2,2-dimethyl-propanediamide, N-[3-[[2-[[3-[[(2S)-2-amino-2-phenylacetyl]amino]phenyl]amino] 5-bromo-4-pyrimidinyl]amino]propyl]-2,2-dimethyl-propanediamide, N-[3-[[2-[[3-[[(2R)-2 amino-1-oxo-3-phenylpropyl]amino]phenyl]amino]-5-bromo-4-pyrimidinyl]amino]propyl]-5-oxo-2-pyrrolidinecarboxamide, N-[3-[[2-[[3-[[(2R)-2-amino-1-oxo-3-phenylpropyl]amino]phenyl]amino]-5-bromo-4-pyrimidinyl]amino]propyl]-2,2-dimethyl-propanediamide, N¹-[3-[[5-bromo-2-[[3-[[(2S)2-pyrrolidinylcarbonyl]amino]phenyl]amino]-4-pyrimidinyl]amino]propyl]-1,1-cyclopropanedicarboxamide, N-[3-[[5-bromo-2-[[3-(2,5-dioxo-1-imidazolidinyl)phenyl]amino]-4-pyrimidinyl]amino]propyl]-2,2-dimethyl-propanediamide, N-(3-((5-bromo-4-((2-(1H-imidazol-4-yl)ethyl)amino)-2-pyrimidinyl)amino)phenyl)-1-morpholinecarboxamide, N-(3-((5-bromo-4-((2-(1H-imidazol-4-yl)ethyl)amino)-2-pyrimidinyl)amino)phenyl)-1-pyrrolidinecarboxamide, N-(3-((5-bromo-4-((3-((2-thienylcarbonyl)amino)propyl)amino) 2-pyrimidinyl)amino)phenyl)-1-pyrrolidinecarboxamide, N1-(3-((5-bromo-2-((3-((1-pyrrolidinylcarbonyl)amino)phenyl)amino)-4-pyrimidinyl)amino)propyl)-1,1-cyclopropanedicarboxamide, N-(3-((5-bromo-4-((3-((1-oxopropyl)amino)propyl)amino)-2-pyrimidinyl)amino)phenyl)-1-pyrrolidinecarboxamide, N-(3-((5-iodo-4-((3-((2-thienylcarbonyl)amino)propyl)amino)-2-pyrimidinyl)-amino)phenyl)-1-pyrrolidinecarboxamide, N-[3-[[5-bromo-4-[[3-[[[(2S)-4-oxo-2-pyrrolidlnyl]carbonyl]amino]propyl]amino]-2-pyrimidinyl]amino]phenyl]-1-pyrrolidinecarboxamide, N[3-[[5-bromo-1-[[3-[[[(2S)-4-oxo-2-azetidinyl]carbonyl]amino]propyl]amino]-2-pyrimidinyl]amino]phenyl]-1-pyrrolidinecarboxamide, (4R)-N-[3-[[5-bromo-2-[[3-[(1-pyrrolidinylcarbonyl)amino]phenyl]amino]-4-pyrimidinyl]amino]propyl]-2-oxo-4-thiazolidinecarboxamide or N-[3-[[4-[[3-[[(1-aminocyclobutyl)carbonyl]amino]propyl]amino]-5-bromo-2-pyrimidinyl]amino]phenyl]-1-pyrrolidinecarboxamide.

Preffered are also compounds of general formula (I), which inhibit preferentially Chk kinases in which A or B in each case independently of one another represent hydrogen or the group —NO$_2$, —NH$_2$, —NR$^3$R$^4$, —N(C$_{1-6}$-hydroxyalkyl)$_2$, —NH(CO)—R$^5$, —NH—COOR$^6$, —NR$^7$—(CO)—NR$^8$R$^9$, —NR$^7$ (CS) NR$^8$R$^9$, COOR$^5$, CO—NR$^8$R$^9$, —SO$_2$—CH$_3$, 4-bromo-1-methyl-1H-pyrazolo-3yl or C$_{1-6}$-alkyl optionally substituted in one or more places, the same way or differently with cyano, halogen, hydroxy or the group —NH$_2$, —NH—(CO)—R$^5$, —SO$_2$—NHR$^3$, —COOR$^5$, —CONR$^8$R$^9$, —O—(CO)—R$^6$, —O—(CO)—C$_{1-6}$-alkyl-R$^5$, X represents an oxygen atom or the group —NH, R$^1$ represents hydrogen, halogen, hydroxymethyl or the group —COOH, —COO-iso-propyl, —NO$_2$, —NH—(CO)—(CH$_2$)$_2$—COOH or —NH—(CO)(CH$_2$)$_2$—COO—C$_{1-6}$-alkyl, R$^2$ represents C$_{1-6}$-alkyl optionally substituted in one or more places, the same way or differently with hydroxy, imidazolyl or the group —NH$_2$, —NH—(CO)O—CH$_2$-phenyl, —NH(CO)H, —NH—(CO)-phenyl, —NH—(CO)—CH$_2$—O-phenyl, —NH—(CO)—CH$_2$-phenyl, —NH—(CO)—CH(NH$_2$))CH$_2$-phenyl, —NH—(CO)CH$_2$—CH(CH$_3$)-phenyl, —NH—(CO)—CH(NH$_2$)—(CH$_2$)$_2$—COOH,

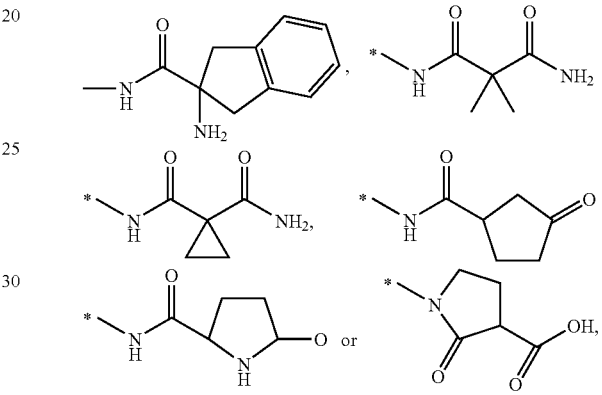

whereby the phenyl can optionally be substituted in one or more places, the same or differently with halogen, C$_{1-6}$-alkyl of —(CO)—C(CH$_2$)—C$_2$H$_5$, or represents C$_3$-alkinyl, R$^3$ or R$^4$ in each case independently of one another represent hydrogen or C$_{1-6}$-alkyl optionally substituted in one or more places, the same way or differently with hydroxy, phenyl or hydroxyphenyl, or R$^3$ and R$^4$ together form a C$_{3-6}$-heterocycloalkylring containing at least one nitrogen atom and optionally can be interrupted by one or more oxygen and/or sulfur atoms and/or can be interrupted by one or more —(CO)— groups in the ring and/or optionally can contain one or more possible double bonds in the ring, whereby the C$_{3-6}$-heterocycloalkylring can optionally be substituted with C$_{1-6}$-alkyl, C$_{1-6}$-alkyl-COOH or C$_{1-6}$-alkyl-NH2, R$^5$ represents C$_{1-6}$-alkyl, C$_{2-6}$-alkenyl, C$_{3-6}$-cycloalkyl or phenyl each can optionally be substituted in one or more places, the same way or differently with halogen, hydroxy, phenyl or with the group —NH$_2$, —NH(CO)—O—C$_{1-6}$-alkyl, whereby phenyl itself can optionally be substituted in one or more places, the same way or differently with halogen, hydroxy or C$_{1-6}$alkyl, R$^6$ represents C$_{1-6}$alkyl, C$_{2-6}$-alkenyl or phenyl, R$^7$ represents hydrogen or C$_{1-6}$-alkyl and R$^8$ or R$^9$ in each case independently of one another represent hydrogen, C$_{1-6}$-alkyl, C$_{2-6}$-alkenyl-C$_{3-6}$-cycloalkyl, aryl or phenyl, whereby aryl or phenyl can optionally be substituted in one or more places, the same way or differently with hydroxy or the group —NO$_2$ or —N(C$_{1-6}$-alkyl)$_2$ or $R^8$ and $R^9$ together form a $C_{3-6}$-heterocycloalkylring containing at least one nitrogen atom and optionally can be interrupted by one or more oxygen and/or sulfur atoms and/or can be interrupted by one or more —(CO)— groups in the ring and/or optionally can contain one or more possible double bonds in the ring, whereby the $C_{3-6}$-heterocycloalkylring can optionally be substituted with the group —$NH_2$, as well as all related isotopes, diastereomers, enantiomers, solvates, polymorphs or pharmaceutically acceptable salts thereof.

Even more preferred are those compounds of general formula (I), which inhibit preferentially Chk kinases in which A or B in each case independently of one another represent hydrogen or the group —NH—$C_2H_4$—OH, —NH—$CH_2$-hydroxyphenyl, —NH—(CO)-pyrrolidinyl, —NH—(CO)—CH($NH_2$)—$CH_2$-phenyl, —NH—(CO)-pentyl-$NH_2$, —NH—(CO)-hexyl-$NH_2$, —NH—(CO)—$CH_2$—$NH_2$, —NH—(CO)—CH($NH_2$)-hydroxyphenyl, —NH—(CO)—$CH_2$-hydroxyphenyl, —NH—(CO)—$CH_2$-methylphenyl, —NH—(CO)—$C_2H_4$-dihydroxyphenyl, —NH—(CO)—CH(OH)-phenyl, —NH—(CO)—CH($NH_2$)—$CH_2$(OH), —NH—(CO)—C($CH_3$)$_2NH_2$, —NH—(CO)—NH($C_2H_5$), —$CH_2$OH, —(CO)—NH-cyclopropyl, —(CO)—NH—CH($CH_3$)$_2$, whereby the pyrrolidinyl can optionally be substituted with hydroxy or the group —$NH_2$, X represents an oxygen atom or the group —NH—, $R^1$ represents halogen or hydroxymethyl and $R^2$ represents —$C_2H_5$ optionally substituted in one or more places, the same way or differently with hydroxy, imidazolyl or represents —$C_3H_7$ or —$C_4H_8$ optionally substituted in one or more places, the same way or differently with the group —$NH_2$, —NH—(CO)—CH($NH_2$)—$C_2H_4$—COOH, —NH—(CO)-phenyl, —NH—(CO)—$CH_2$-phenyl, —NH—(CO)—$CH_2$—CH($CH_3$)-phenyl, —NH—(CO)—$CH_2$—O-phenyl, —NH—(CO)O—$CH_2$-phenyl, —NH—(CO)—CH($NH_2$)$CH_2$-phenyl,

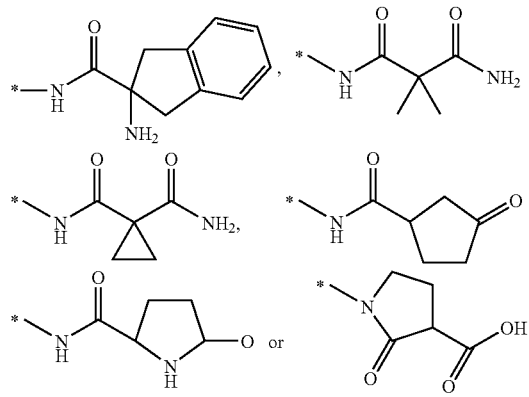

whereby the phenyl can optionally be substituted in one or more places, the same or differently with halogen, —$CH_3$ or —(CO)—C($CH_2$)($C_2H_5$), or represents $C_3$-alkinyl, as well as all related isotopes, diastereomers, enantiomers, solvates, polymorphs or pharmaceutically acceptable salts thereof.

In particular the following compounds for general formula (I) are preferred, which inhibit preferentially AKT and/or PDK kinases:

N-[3-[[2-[[3-[[(2R)-2-amino-1-oxo-3-phenylpropyl]amino]phenyl]amino]-5-bromo-4-pyrimidinyl]amino]propyl]-2,2-dimethyl-propanediamide, 1-[3-[[2-[[3-[[(2R)-2-amino-1-oxo-3-phenylpropyl]amino]phenyl]amino]-5-bromo-4-pyrimidinyl]amino]propyl]-2-oxo-3-pyrrolidinecarboxylic acid, N-[3-[[5-bromo-4-[[3-[[(5-oxo-2-pyrrolidinyl)carbonyl]amino]propyl]amino]-2-pyrimidinyl]amino]phenyl]-1-pyrrolidinecarboxamide, Pyrrolidine-1-carboxylic acid [3-(5-bromo-4-{3-[2-(2,4-dichloro-phenyl)-acetylamino]-propylamino}-pyrimidin-2-ylamino)-phenyl]-amide, Pyrrolidine-1-carboxylic acid [3-(5-bromo-4-{3-[2-(4-bromo-phenyl)-acetylamino]-propylamino}-pyrimidin-2-ylamino)-phenyl]-amide, Pyrrolidine-1-carboxylic acid (3-{5-bromo-4-[3-(2-p-tolyl-acetylamino)-propylamino]-pyrimidin-2-ylamino}-phenyl)-amide, Pyrrolidine-1-carboxylic acid [3-(5-bromo-4-{3-[2-(2,4-difluoro-phenyl)-acetylamino]-propylamino}-pyrimidin-2-ylamino)-phenyl]-amide, Pyrrolidine-1-carboxylic acid {3-[5-bromo-4-(3-{2-[2,3-dichloro-4-(2-methylene-butyryl)-phenoxy]-acetylamino}-propylamino)-pyrimidin-2-ylamino]-phenyl)-amide, Pyrrolidine-1-carboxylic acid [3-(5-bromo-4-{3-[3-(2,3-dichloro-phenyl)-butyrylamino]-propylamino}-pyrimidin-2-ylamino)-phenyl]-amide, Pyrrolidine-1-carboxylic acid (3-{5-bromo-4-[3-(3-bromo-benzoylamino)-propylamino]-pyrimidin-2-ylamino}-phenyl)-amide, N-(3-((4-((4-aminobutyl)amino)-5-bromo-2-pyrimidinyl)amino)phenyl)-1-pyrrolidinecarboxamide, N-[3-[[2-[[3-[[(2R)-2-amino-1-oxo-3-phenylpropyl]amino]phenyl]amino]-5-bromo-4-pyrimidinyl]amino]propyl]-2,2-dimethyl-propanediamide, N-[3-[[(2S)-2-Amino-1-oxo-3-phenylpropyl]amino]-5-[[5-bromo-4-(prop-2-ynyloxy)pyrimidin-2-yl]amino]phenyl]pyrrolidine-1-carboxamide, N-[3-[[(2R)-2-Amino-1-oxo-3-phenylpropyl]amino]-5-[[5-bromo-4-(prop-2-ynyloxy)pyrimidin-2-yl]amino]phenyl]pyrrolidine-1-carboxamide, (αR)-α-Amino-N-[3-[[5-bromo-4-(prop-2-ynyloxy)pyrimidin-2-yl]amino]-5-(hydroxymethyl)phenyl]benzenepropanamide, 2-[3-(5-Bromo-4-prop-2-ynyloxy-pyrimidine-2-ylamino)-5-hydroxymethyl-phenylamino]-ethanol, (2R)-Amino-N-[3-hydroxymethyl-5-(4-prop-2-ynyloxy-pyrimidine-2-ylamino)-phenyl]-3-phenyl-propionamide, 3-((2R)-Amino-3-phenyl-propionylamino)-5-(5-bromo-4-prop-2-ynyloxy-pyrimidine-2-ylamino)-N-cyclopropyl-benzamide, 3-((2R)-Amino-3-phenyl-propionylamino)-5-(5-bromo-4-prop-2-ynyloxy-pyrimidin-2-ylamino)-N-isopropyl-benzamide, Phenylmethyl [3-[[2-[[3-[[(ethylamino)carbonyl]amino]phenyl]amino]-5-(hydroxymethyl)pyrimidine-4-yl]amino]propyl]carbamate, Pyrrolidine-1-carboxylic acid (3-{4-[3-((2R)-amino-3-phenyl-propionylamino)-propylamino]-5-bromo-pyrimidine-2-ylamino}phenyl)-amide, Pyrrolidine-1-carboxylic acid (3-{4-[3-((2S)-amino-3-phenyl-propionylamino)-propylamino]-5-bromo-pyrimidine-2-ylamino}phenyl)-amide,
2-[3-(5-Bromo-4-prop-2-ynyloxy-pyrimidine-2-ylamino)-phenylamino]-ethanol,
1-Amino-cyclopentancarbonylic acid[3-(5-bromo-4-prop-2-ynyloxy-pyrimidine-2-ylamino)-phenyl]-amide,
1-Amino-cyclohexancarbonylic acid-[3-(5-bromo-4-prop-2-ynyloxy-pyrimidine-2-ylamino)-phenyl]-amide,
(2S)-Amino-N-[3-(5-bromo-4-prop-2-ynyloxy-pyrimidine-2-ylamino)-phenyl]-3-phenyl-propionamide,
(2R)-Amino-N-[3-(5-bromo-4-prop-2-ynyloxy-pyrimidine-2-ylamino)-phenyl]-3-phenyl-propionamide,
2-{[3-(5-Bromo-4-prop-2-ynyloxy-pyrimidine-2-ylamino)-phenylamino)-methyl]-methyl}-phenol,
(2R)-Amino-N-[3-(5-bromo-4-prop-2-ynyloxy-pyrimidine-2-ylamino)-phenyl]-3-(4-hydroxy-phenyl)-propionamide,
N-[3-(5-Bromo-4-prop-2-ynyloxy-pyrimidine-2-ylamino)-phenyl]-3-(3,4-dihydroxy-phenyl)-propionamide,
N-[3-(5-Bromo-4-prop-2-ynyloxy-pyrimidine-2-ylamino)-phenyl]-2-hydroxy-(2S)-phenyl-acetamide,
N-[3-(5-Bromo-4 prop-2-ynyloxy-pyrimidine-2-ylamino)-phenyl]2-hydroxy-(2R)-phenyl-acetamide,
(2S)-Amino-N-[3-(5 bromo-4-prop-2-ynyloxy-pyrimidine-2-ylamino)phenyl]-3-hydroxy-propionamide,
(2R)-Amino-N-[3-(5-bromo-4-prop-2-ynyloxy-pyrimidin-2-ylamino) phenyl]-3-hydroxy-propionamide,
2-Amino-N-[3-(5 bromo-4-prop-2-ynyloxy-pyrimidine-2-ylamino)-phenyl]-2-methyl-propionamide,
(2S)-Amino-N-[3-(5-bromo-4-prop-2-ynyloxy-pyrimidine-2-ylamino)-phenyl]-3-(4-hydroxy-phenyl)-propionamide,
(2R)-Amino-N-[3-(5-bromo-4-prop-2-ynyloxy-pyrimidine-2-ylamino)-phenyl]-3-p-tolyl-propionamide or
(2R) Amino-N-[3-(5-bromo-4-prop-2-ynyloxy-pyrimidine-2-ylamino)-phenyl]-3-p-tolyl-propionamide.

Preferred are also the compounds of general formula (I), which inhibit preferentially AKT and VEGF-R kinases in which
A or B in each case independently of one another represent halogen, hydrogen or the group —SO$_2$—CH$_3$, —NO$_2$, —NH$_2$, —CF$_3$, —CH$_2$—NH—(CO)—NH$_2$, —CH2-pyrrolidinyl, NH—(CO)—CH$_3$, —NH—(CO)-hexyl-NH$_2$, —NH—(CO)-phenyl, —NH—(CO)-pyrrolidinyl, —NH—(CO)—CH(NH$_2$)—CH$_2$-phenyl, NH—(CO)—OCH$_3$, —NH—(CO)—OCH(CH$_3$)$_2$, —NH—(CO)—OC$_2$H$_4$-morpholino, —NH—(CO)—NH-cyclopropyl, —NH—(CO)-morpholino, —NH (CO)—NH—C$_2$H$_4$-morpholino, —NH—(CO)—NH-hydroxycycloalkyl, hydantoinyl,
  whereby the pyrrolidinyl can optionally be substituted with hydroxy or the group —NH$_2$ and
  whereby the hydantoinyl can optionally be substituted with the group —CH$_3$ or —(CO)-thiazolidinonyl,
X represents the group —NH—,
R$^1$ represents halogen and
R$^2$ represents —CH$_2$-dihydroxyphenyl, —C$_2$H$_4$-imidazolyl, or —C$_3$H$_7$ optionally substituted in one or more places, the same way or differently with

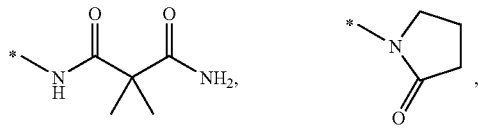

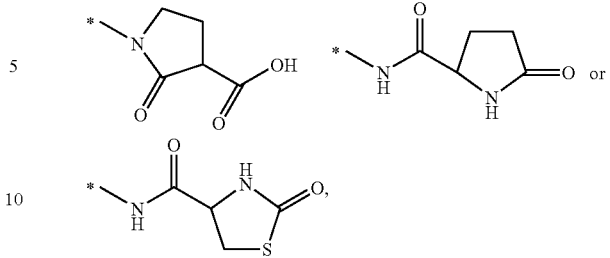

as well as all related isotopes, diastereomers, enantiomers, solvates, polymorphs or pharmaceutically-acceptable salts thereof.

In particular the following compounds of general formula (I) are preferred, which inhibit preferentially AKT and VEGF-R kinases:
4-((4-((2-(1H-imidazol-4-yl)ethyl)amino)-5-iodo-2-pyrimidinyl)amino)-benzenesulfonamide,
N-((3-((5-bromo-4-((2-(1H-imidazol-4-yl)ethyl)amino)-2-pyrimidinyl)amino)phenyl)methyl)-urea,
1-((3-((5-bromo-4-((2-(1H-imidazol-4 yl)ethyl)amino)-2-pyrimidinyl)amino)phenyl)methyl)-3-pyrrolidinol,
(3-((5-bromo-4-((2-(1H-imidazol-4-yl)ethyl)amino)-2-pyrimidinyl)amino)phenyl)-carbamic acid methyl ester,
N2-(3 aminophenyl)-5-bromo-N4-(2-1H-imidazol)ethyl)-2,4-pyrimidinediamine,
N-(3-((5-bromo-4-((2-(1H-imidazol-4-yl)ethyl)amino)-2-pyrimidinyl)amino)phenyl)-N'-cyclopropyl-urea,
N-(3-((5-bromo-4-((2-(1H-imidazol-4-yl)ethyl)amino)-2-pyrimidinyl)amino)phenyl)4-morpholinecarboxamide,
(3-((5-bromo-4-((2-(1H-imidazol-4-yl)ethyl)amino)-2-pyrimidinyl)amino)phenyl)-carbamic acid-1-methylethyl ester,
N-(3-((5-bromo-4-((2-(1H-imidazol 4 yl)ethyl)amino)-2-pyrimidinyl)amino)phenyl)-methanesulfonamide,
N2-(3-amino-5-(trifluoromethyl)phenyl)-5-bromo-N4-(2-(1H-imidazol-4-yl)ethyl)-2,4-pyrimidinediamine,
N-(3-((5-bromo-4-((2-(1H-imidazol-4-yl)ethyl)amino)-2-pyrimidinyl)amino)phenyl)-N'-(2-(4-morpholinyl)ethyl)-urea,
N2-(3-amino-5-chlorophenyl)-5-bromo-N4-(2-(1H-imidazol-4-yl)ethyl)-2,4-pyrimidinediamine,
(3-((5-bromo-4-((2-(1H-imidazol-4-yl)ethyl)amino)-2-pyrimidinyl)amino)phenyl)-carbamic acid-2-(4-morpholinyl)ethyl ester,
N-(3-((5-bromo-4-((2-(1H-imidazol-4-yl)ethyl)amino)-2-pyrimidinyl)amino)phenyl)-N'-(4-hydroxycyclohexyl)-urea,
N-(3-((5-bromo-4-((2-(1H-imidazol-4-yl)ethyl)amino)-2py-rimidinyl)amino)phenyl)-acetamide,
N-(3-((5-bromo-4-((2-(1H-imidazol-4-yl)ethyl)amino)-2-pyrimidinyl)amino)phenyl)-benzamide,
(4R)-N-[3-[[5-bromo-2-[[3-[(1-pyrrolidinylcarbonyl)amino]phenyl]amino]-4-pyrimidinyl]amino]propyl]-2-oxo-4-thiazolidinecarboxamide,
3-[3-[[5-bromo-4-[[2-(1H-imidazol-4-yl)ethyl]amino]-2-pyrimidinyl]amino]phenyl]-2,4-imidazolidinedione,
3-[3-[[5-bromo-4-[[2-(1H-imidazol-4-yl)ethyl]amino]-2-pyrimidinyl]amino]phenyl]-1-methyl-2,1-imidazolidinedione,
1-[3-[[2-[[3-[[(2R)-2-amino-1-oxo-3-phenylpropyl]amino]phenyl]amino]-5-bromo-4-pyrimidinyl]amino]propyl]-2-oxo-3-pyrrolidinecarboxylic acid, 1-[3-[[2-[[3-[[(1-aminocyclohexyl)carbonyl]amino]phenyl]
amino]-5-bromo-4-pyrimidinyl]amino]propyl]-2-oxo-3-
pyrrolidinecarboxylic acid,
N-[3-[[2-[[3-[[(2R)-2-amino-1-oxo-3-phenylpropyl]amino]
phenyl]amino]-5-bromo-4-pyrimidinyl]amino]propyl]-5-
oxo-2-pyrrolidinecarboxamide,
N-[3-[[2-[[3-[[(2R)-2-amino-1-oxo-3-phenylpropyl]amino]
phenyl]amino]-5-chloro-4-pyrimidinyl]amino]propyl]-2,
2-dimethyl-propenediamide,
3-[3-[[5-bromo-4-[[(3,4-dihydroxyphenyl)methyl]amino]-
2-pyrimidinyl]amino]phenyl]-2,4-imidazolidinedione,
3-[3-[[5-bromo-4-[[(3,4-dihydroxyphenyl)methyl]amino]-
2-pyrimidinyl]amino]phenyl]-1-methyl-2,4-imidazo-
lidinedione,
(4R)-N-[3-[[5-bromo-2-[[3-(2,5-dioxo-1-imidazolidinyl)
phenyl]amino]-4-pyrimidinyl]amino]propyl]-2-oxo-4-
thiazolidinecarboxamide,
N-[[3-[[5-bromo-2-[[3-(2,5-dioxo-1-imidazolidinyl]phenyl]
amino]-4-pyrimidinyl]amino]propyl]-5-oxo-2-pyrrolidin-
ecarboxamide,
N-[3-[[5-bromo-2-[[3-(2,5-dioxo-1-imidazolidinyl)phenyl]
amino]-4-pyrimidinyl]amino]propyl]-2,2-dimethyl-pro-
panediamide,
3-[3-[[5-bromo-4-[[3-(2-oxo-1-pyrrolidinyl)propyl]amino]-
2-pyrimidinyl]amino]phenyl]-2,4-imidazolidinedione,
(4R)-N-[3-[[5-bromo-2-[[3-(3-methyl-2,5-dioxo-1-imida-
zolidinyl)phenyl]amino]-4-pyrimidinyl]amino]propyl]-2-
oxo-thiazolidinecarboxamide or
(1R)-N-[3-[[5-bromo-2-[[3-[2,5-dioxo-3-[[(4R)-2-oxo-4-
thiazolidinyl]carbonyl]-1-imidazolidinyl]phenyl]amino]-
4-pyrimidinyl]amino]propyl]-2-oxo-4-thiazolidinecar-
boxamide.

It has also been found that compounds of the following structure are inhibitors of kinases, particularly AKT, PDK, Chk, CDK and/or VEGF-R kinases.

N-(3-((4-((3-(aminomethyl)phenyl)amino)-5-bromo-2-pyri-
midinyl)amino)phenyl)-1-pyrrolidine-carboxamide,
4-[[5-bromo-4-[[2-(1H-imidazol-5-yl)ethyl]amino]-2-pyri-
midinyl]amino]-1-naphthaleneacetic acid,
5-[[5-bromo-4-[[2-(1H-imidazol-5-yl)ethyl]amino]-2-pyri-
midinyl]amino]-1H-indole-2-carboxylic acid, ethyl ester,
5-bromo-N4-[2-(1H-imidazol-5-yl)ethyl]-N2-(2 methyl-6-
quinolinyl)-2,4-pyrimidinediamine,
4-((5 bromo 4 ((2-(1H-imidazol-4-yl)ethyl)amino)-2-pyrim-
idinyl)amino)-benzamide,
4-((4-((2-(1H-imidazol-4-yl)ethyl)amino)-5-iodo-2-pyrim-
idinyl)amino)-benzenesulfonamide,
3-((5-bromo-4-((2-(1H-imidazol-4-yl)ethyl)amino)-2-pyri-
midinyl)amino)-benzamide,
3-((5-bromo-4-((2-(1H-imidazol-4-yl)ethyl)amino)-2-pyri-
midinyl)amino)-benzenesulfonamide,
5-((5-bromo-4-((2-(1H-imidazol-4-yl)ethyl)amino)-2-pyri-
midinyl)amino) 1,3-dihydro-2H-benzimidazol-2-one,
3-((5-bromo-4-((2-(1H-imidazol-4-yl)ethyl)amino)-2-pyri-
midinyl)amino)-benzoic acid methyl aster,
3-amino-5-((5-bromo-4-((2-(1H imidazol-1-yl)ethyl)
amino)-2-pyrimidinyl)amino)-benzoic acid methyl ester,
N-((3-((5-bromo-4-((2-(1H-imidazol-4-yl)ethyl)amino)-2-
pyrimidinyl)amino)phenyl)methyl)-methanesulfonamide,
4-((5-bromo-4-((2-(1H-imidazol-4 yl)ethyl)amino)-2-pyri-
midinyl)amino)-benzoic acid methyl ester,
3-((5-bromo-4-((2-(1H-imidazol4-yl)ethyl)amino)-2-pyrim-
idinyl)amino-phenol,
5-((5-bromo-4-((2-(1H-imidazol-4-yl)ethyl)amino)-2-pyri-
midinyl)amino)-1H-isoindole-1,3(2H)-dione,
5-bromo-N$^4$-(2-(1H-imidazol-4-yl)ethyl)-N$^2$-(3-methylphe-
nyl)-2,4-pyrimidinediamine,
N-(3-((5-bromo-4-((2-(1H-imidazol-4-yl)ethyl)amino)-2-
pyrimidinyl)amino)phenyl)-methanesulfonamide,
4-((4-((2-(1H-imidazolyl)ethyl)amino)-5-methyl-2-pyrim-
idinyl)amino)-benzenesulfonamide,
4-((4-((2-(1H-imidazol-4-yl)ethyl)amino)-5-(trifluorom-
ethyl)-2-pyrimidinyl)amino)-benzenesulfonamide,
4-((4-((3-aminopropyl)amino)-5-bromo-2-pyrimidinyl)
amino)-benzenesulfonamide,
4-((5-bromo-4-((3-(1H-imidazol-1-yl)propyl)amino) 2-pyri-
midinyl)amino)-benzenesulfonamide,
4-((5-bromo-4-((2-(1 pyrrolidinyl)ethyl)amino)-2-pyrimidi-
nyl)amino)-benzenesulfonamide
4-((4-((4-aminobutyl)amino)-5-bromo-2-pyrimidinyl)
amino)-benzenesulfonamide,
4-((2-((4-(aminosulfonyl)phenyl)amino)-5-bromo-4-pyrim-
idinyl)amino) butanoic acid,
4-((4-((3-((aminocarbonyl)amino)propyl)amino)-5-bromo-
2-pyrimidinyl)amino)-benzenesulfonamide,
4-((2-((4-(aminosulfonyl)phenyl)amino)-5-bromo-4-pyrim-
idinyl)amino)-butanoic acid ethyl ester,
4-((5-bromo-4-((4-(methylamino)butyl)amino-2-pyrimidi-
nyl)amino)-benzenesulfonamide,
4-((5-bromo-4-((2-(1H-imidazol-1-yl)ethyl)amino)-2-pyri-
midinyl)amino)-benzenesulfonamide,
4-((5-ethyl-4-((2-(1H-imidazol-4-yl)ethyl)amino)-2-pyrim-
idinyl)amino)-benzenesulfonamide,
4-((4-((2-(1H-imidazol-4-yl)ethyl)amino-2-pyrimidinyl)
amino)-benzenesulfonamide,
4-((5-bromo-4-((2-(2-pyridinyl)ethyl)amino)-2-pyrimidi-
nyl)amino)-benzenesulfonamide,
4-((5-bromo-4-((2-(1H-indol-3-yl)ethyl)amino)-2-pyrimidi-
nyl)amino)-benzenesulfonamide,
2-((2-((4-(aminosulfonyl)phenyl)amino)-5-bromo-4-pyrim-
idinyl)amino)-acetamide,
N-(2-((2-((4-(aminosulfonyl)phenyl)amino)-5-bromo-pyri-
midinyl)amino)ethyl)-acetamide,
3-((2-((4-(aminosulfonyl)phenyl)amino)-5-bromo-4-pyrim-
idinyl)amino)-propanamide,
N-(4-((2-((4-(aminosulfonyl)phenyl)amino)-5-bromo-4-py-
rimidinyl)amino)butyl)-acetamide,
N-(3-((2-((4-(aminosulfonyl)phenyl)amino)-5-bromo-4-py-
rimidinyl)amino)propyl)-acetamide,
N-(3-((2-((4-(aminosulfonyl)phenyl)amino)-5-bromo-4-py-
rimidinyl)amino)propyl)-2-furancarboxamide,
N-(3-((2-((4-(aminosulfonyl)phenyl)amino)-5-bromo-4-py-
rimidinyl)amino)propyl)-1H-pyrrole-2-carboxamide,
4-((2-((4-(aminosulfonyl)phenyl)amino)-5-bromo-4-pyrim-
idinyl)amino-butanamide,
4-((2-((4-aminosulfonyl)phenyl)amino)-5-bromo-4-pyrim-
idinyl)amino)propyl)-2-thiophenecarboxamide,
4-((4-(4-(aminomethyl)-1-piperidinyl)-5-bromo-2-pyrim-
idinyl)amino))-benzenesulfonamide,
4-(5-Brom-4-prop-2-ynylamino-pyrimidin-2-ylamino)-phe-
nyl]-N,N-dimethylaminosulfonylamin,
1-Methyl-1H-imidazol-4-sulfonsäure[4-(5-brom-4-prop-2-
ynylamino-pyrimidin-2-ylamino)-phenyl]amid,
3-(5-Bromo-4-prop-2-ynyloxy-pyrimidine-2-ylamino)-ben-
zoic acid ethyl ester,
4-(5-bromo-4-prop-2-ynyloxy-pyrimidine-2-ylamino)-ben-
zoic acid ethyl ester,
2-(5-Bromo-4-prop-2-ynyloxy-pyrimidine-2-ylamino)-ben-
zoic acid ethyl ester,
2-(5-Bromo-4-prop-2-ynyloxy-pyrimidine-2-ylamino)-phe-
nol,
4-(1-Bromo-4-prop-2-ynyloxy-pyrimidine-2-ylamino)-ben-
zoic acid methyl ester, 3-(5 Nitro-4-prop-2-ynylamino-pyrimidine-2-ylamino)-phenol, 2-(5-Nitro-4-prop-2-ynylamino-pyrimidine-2-ylamino)-benzoic acid ethyl ester, 3-(5-Nitro-4-prop-2-ynylamino-pyrimidine-2-ylamino)-benzoic acid ethyl ester, 4-(5-Nitro-4-prop-2-ynylamino pyrimidine-2-ylamino)-benzoic acid ethyl ester, 4-(5-Nitro-4-prop-2-ynylamino-pyrimidin-2-ylamino)-phenol, Methyl-3-[[5-bromo-4-(prop-2-ynyloxy)pyrimidin-2-yl]amino]-5-[(2-hydroxyethyl)amino]benzoate, Methyl-3-amino-5-[[5-bromo-4-(prop-2-ynyloxy)pyrimidin-2-yl]amino]benzoate or 3-[Bis-(2-hydroxy-ethyl)-amino]-5-5-bromo-4-prop-2-ynyloxy-pyrimidine-2-ylamino)-benzoic acid methyl ester.

Another object of the invention are pharmaceutical composition comprising as an active ingredient at least one compound of general formula (I) or compounds disclosed hereinbefore in an therapeutically effective amount for the prevention or treatment of a disorder caused by, associated with or accompanied by disruptions of cell proliferation and/or angiogenesis together with an pharmaceutically acceptable carrier, diluent or excipient.

A further object of the invention are use of a compound of general formula (I) or compounds disclosed hereinbefore for the manufacture of a medicament for the prevention or treatment of a disorder caused by, associated with or accompanied by any abnormal kinase activity selected from Chk, Akt, Pdk, Cdk and/or VEGF-R activity as well as combinations thereof.

Preferred is the use of compounds of general formula (I), wherein the kinase is selected from PDK1, Akt1, Akt2 and/or Akt3, particularly, wherein the kinase is selected from PDK1, Akt1, Akt2 and/or Akt3 in combination with VFGF-R or wherein the kinase is selected from Chk1 and/or Chk2.

Another objective of this invention is a method of treating a mammal having a disease-state alleviated by the inhibition of Akt, Pdk, chk and/or VEGF-R activity, wherein the method comprises administering to a mammal a the therapeutically effective amount of a compound of general formula (I) or a compound disclosed hereinbefore. In particular the method is objective wherein the mammal is a human.

"Disorders" and/or "disease state" in the meaning of this invention are selected from cancer, angiofribroma, arthritis, eye diseases, auto-immune diseases, chemotherapy agent-induced alopecia and mucositis, Crohn-disease, endometriosis, fibrotic diseases, hemangioma, cardiovaskular diseases, infectious diseases, nephrological diseases, chronic und acute neurodegenerative diseases, like disruptions of nerval tissue, viral infections, to prevent restenosis of vessels, for preventing the formation of scars, preventing or treating keratoma seniles and contact dermatitis, wherein cancer stands for solide tumours, or metastasis growth, Kaposis Sarkom, Hodgkin's disease and/or leukemia, arthritis stands for rheumatoid arthritis, eyes diseases stand for diabetIc retinopathy, neovaskular glaukoma, auto-immune diseases stand for psoriasis, alopecia and/or multiple sklerosis, fibrotic diseases stand for cinhosis or the liver, mesangial cell proliferative diseases, arteriosklerois, infectiouse diseases stand for diseases that are caused by unicellular parasites, cardiovascular diseases stand for stenosis, like stent induced restenosis, arteriosklerosis and restenosis, nephrological diseases stand for glomerulonephritis, diabetic nephropaty, malignant nephrosklerosis, thrombic mikroangiopothis syndrome, transplant rejections and glomerulopathy, chronic neurodegenerative diseases stand for Huntington's disease, amyotrophic lateralsklerosis, Parkinsons disease, AIDS, dementia und Alzheimer's disease.

acute neurodegenerative diseases stand for Ischemias of the brain and neurotraumas, and viral infections stand for cytomegalic infections, herpes, hepatitis B or C and HIV.

The compounds according to the invention essentially inhibit on the one hand cell cycle-associated kinases, particularly serin/threonine kinases, more particularly cyclin-dependent kinases (Cdks), Chks, Akts and/or Pdks or VEGF-R kinases. Preferred is the inhibition of Chks, e.g. Chk1 and/or Chk2, Akts, e.g Akt1, Akt2 and/or Akt3 and/or Pdks, e.g. Pdk1.

On the other hand the compounds according to this invention essentially inhibit angiogenesis related kinases, particularly tyrosine kinases, more particularly VEGF-R kinases.

Of particular interest is a preferential inhibition of specific kinases. For example, the compounds of general formula (I) according to claims 2 to 5 show a preferentiality towards Akts, e.g. Akt1, Akt2 and/or Akt3 and/or Pdks, e.g. Pdk1; the compounds of general formula (I) according to claims 6 to 8 show a preferentiality towards Chks, e.g. Chk1 and/or Chk2 and the compounds of general formula (I) according to claims 9 and 10 show preferentiality towards Akts and VEGF-R kinases upon which is based their action, for example, against cancer, angiofribroma, arthritis, eye diseases, auto immune diseases, chemotherapy agent-induced alopecia and mucositis, Crohn-disease, endometriosis, tibrotic diseases, hemangioma, cardiovaskular diseases, infectious diseases, nephrological diseases, chronic und acute neurodegenerative diseases, like disruptions of nerval tissue, viral infections, to prevent restenosis of vessels, for preventing the formation of scars, preventing or treating keratoma seniles and contact dermatitis. Compounds of general formula (I) according to claims 9 and 10 show the advantage in the treatment of disorders to have an inhibiting effect of two ways, in particular the cell cycle inhibition and the angiogenesis inhibition due to the preferential inhibition of AKT and VEGF compounds.

The eukaryotic cell division ensures the duplication of the genome and its distribution to the daughter cells by passing through a coordinated and regulated sequence of events. The cell cycle is divided into four successive phases: the G1 phase represents the time before the DNA replication, in which the cell grows and is sensitive to external stimuli. In the S phase, the cell replicates its DNA, and in the G2 phase, preparations are made for entry into mitosis. In mitosis (M phase), the replicated DNA separates, and cell division is completed.

The loss of the regulation of the cell cycle and the loss of function of the control points are characteristics of tumor cells.

Changes of the cell cycle control play a role not only in carcinoses. The cell cycle is activated by a number of viruses, both by transforming viruses as well as by non-transforming viruses, to make possible the replication of viruses in the host cell. The false entry into the cell cycle of normally post mitotic cells is associated with various neurodegenerative diseases. The mechanisms of the cell cycle regulation, their changes in diseases and a number of approaches to develop inhibitors of the cell cycle progression and especially the CDKs were already described in a detailed summary in several publications (Slelecki, T. M. et al. (2000). Cyclin-Dependent Kinase Inhibitors: Useful Targets in Cell Cycle Regulation. J. Med. Chem. 43, 1-18; Fry, D. W. & Garrett, M. D. (2000). Inhibitors of Cyclin-Dependent Kinases as Therapeutic Agents for the Treatment of Cancer. Curr. Opin. Oncol. Endo. Metab. Invest. Drugs 2, 40-59 Rosiania, G. R. & Chang, Y. T. (2000). Targeting Hyperproliferative Disorders with Cyclin-Dependent Kinase Inhibitors. Exp. Opin. Ther. Patents 10, 215-230: Meijer L. et al. (1999). Properties and Potential Applications of Chemical Inhibitors of Cyclin Dependent Kinases. Pharmacol. Ther. 82, 279 284; Senderowicz, A. M. & Sausville, F. A. (2000) Preclinical and Clinical Development of Cyclin-Dependent Kinase Modulators. J. Natl. Cancer Inst. 92, 376 387).

The pivotal role of VEGF and of its receptors during vascular development was exemplified in studies on targeted gene inactivation. Even the heterozygous disruption of the VEGF gene resulted in fatal deficiencies in vascularization (Carmeliet et al., Nature 380, 435-439, 1996; Ferrara et al., Nature 380, 439-442, 1996). Mice carrying homozygous disruptions in either Flt1 or Flk1/KDR gene die in mid-gestation of acute vascular defects. However, the phenotypes are distinct in that Flk1/KDR knock-out mice lack both endothelial cells and a developing hematopoietic system (Shalaby et al. Nature 376, 62-66, 1995), whereas Flt1 deficient mice have normal hematopoietic progenitors and endothelial cells, which fail to assemble into functional vessels (Fong at al., 376, 66-70, 1995). Disruption of the Flt4 gene, whose extensive embryonic expression becomes restricted to lymphatic vessels in adults, revealed an essential role of Flt4 for the remodeling and maturation of the primary vascular networks into larger blood vessels during early development of the cardiovascular system (Dumont et al. Science 292, 946-949, 1998). Consistent with the lymphatic expression of Flt4 in adults overexpression of VEGF-C in the skin of transgenic mice resulted in lymphatic, but not vascular, endothelial proliferation and vessel enlargement (Jeltsch et al., Science 276, 1423-1425, 1997). Moreover, VEGF-C was reported to induce neovascularization in mouse cornea and chicken embryo chorioallantoic membrane models of angiogenesis (Cao et al., Proc. Natl. Acad. Sci. USA 96, 14389-14394, 1998).

In pathological settings associated with aberrant neovascularization elevated expression of angiogenic growth factors and of their receptors has been observed. Most solid tumors express high levels of VEGF and the VEGF receptors appear predominantly in endothelial cells of vessels surrounding or penetrating the malignant tissue (Plate et al., Cancer Res. 53, 5822-5827, 1993). Interference with the VEGF/VEGF receptor system by means of VEGF-neutralizing antibodies (Kim et al., Nature 362, 841-844, 1993), retroviral expression of dominant negative VEGF receptor variants (Millauer et al., Nature 367, 576-579, 1994) recombinant VEGF-neutralizing receptor variants (Goldman et al., Proc. Natl. Aid. Sci. USA 95, 8795-8800, 1998), of small molecule inhibitors of VEGF receptor tyrosine kinase (Fong et al., Cancer Res. 59, 99-106, 1999; Wedge et al. Cancer Res. 60, 970-975, 2000: Wood et al. Cancer Res. 60, 2178-2189, 2000), or targeting cytotoxic agents via the VEGF/VEGF receptor system (Arora et al., Cancer Res. 59, 183-188, 1999; EP 0696456A2) resulted in reduced tumor growth and tumor vascularization. However, although many tumors were inhibited by interference with the VEGF/VEGF receptor system, others were unaffected (Millauer et al., Cancer Res. 56, 1615-1620, 1996). Human tumors as well as experimental tumor xenografts contain a large number of immature blood vessels that have not yet recruited periendothellal cells. The fraction of immature vessels is in the range of 40% in slow growing prostate cancer and 90% in fast growing glioblastoma. A selective obliteration of immature tumor vessels was observed upon withdrawal of VEGF by moans of downregulation of VEGF transgene expression in a C6 gliblastoma xenograft model. This result is in accordance with a function of VEGF as endothelial cell survival factor. Similarly, in human prostate cancer shutting off VEGF expression as a consequence of androgen-ablation therapy led to selective apoptotic death of endothelial cells in vessels lacking periendothelial cell coverage. In contrast, the fraction of vessels which resisted VEGF withdrawal showed periendothelial cell coverage (Benjamin et al., J. Clin. Invest. 103, 159-165, 1999).

To use the compounds according to the invention as pharmaceutical agents, the latter are brought into the form of a pharmaceutical preparation, which in addition to the active ingredient for enteral or parenteral administration contains suitable pharmaceutical, organic or inorganic inert carrier materials, such as, for example, water, gelatin, gum arabic, lactose, starch, magnesium stearate, talc, vegetable oils, polyalkylene glycols, etc. The pharmaceutical preparations can be present in solid form, for example as tablets, coated tablets, suppositories, or capsules, or in liquid form, for example as solutions, suspensions, or emulsions. Moreover, they optionally contain adjuvants, such as preservatives, stabilizers, wetting agents or emulsifiers, salts for changing the osmotic pressure or buffers. These pharmaceutical preparations are also subjects of this invention.

For parenteral administration, especially injection solutions or suspensions, especially aqueous solutions of active compounds in polyhydroxy-ethoxylated castor oil, are suitable.

As carrier systems, surface-active adjuvants such as salts of gallic acids or animal or plant phospholipids, as well as mixtures thereof and liposomes or ingredients thereof can also be used.

For oral administration, especially tablets, coated tablets, pills or capsules with talcum and/or hydrocarbon carriers or binders such as, for example, lactose, maize or potato starch, are suitable. The oral application can also be in a liquid form, such as, for example, as a juice, to which optionally a sweetener is added.

Enteral, parenteral and oral administrations are also subjects of this invention. The dosage of the active ingredients ran vary depending on the method of administration, age and weight of the patient, type and severity of the disease to be treated and similar factors. The daily dose is 0.5-1000 mg, preferably 50-200 mg, whereby the dose can be given as a single dose to be administered once or divided into two or more daily doses.

If the production of the starting compounds for the manufacture of the compounds of the invention is not described, these starting compounds are known or can be produced analogously to known compounds or to processes that are described here. It is also possible to perform all reactions that are described here in parallel reactors or by means of combinatory operating procedures.

The isomer mixtures can be separated into the enantiomers or E/Z isomers according to commonly used methods, such as, for example, crystallization, chromatography or salt formation.

The production of the salts is carried out in the usual way by a solution of the compound of formulae I-VII being mixed with the equivalent amount of or excess base or acid, which optionally is in solution, and the precipitate being separated or the solution being worked up in the usual way.

Inhibition of Pdk/Akt Activity

General Remarks

Compounds described herein, potently block an assay in which phosphoinositide-dependent kinase-1 (PDK-1) mediates the activation of AKT, whose activity is measured in the assay. The compounds, therefore, can be blocking the assay by inhibiting PDK-1 enzyme activity, AKT enzyme activity, or the activation of AKT by PDK-1. These compounds are expected to be therapeutically useful in cancer by inhibiting processes critical for tumor progression, including cell proliferation, survival, and tumor angiogenesis (Testa and Bellacosa 2001; Vivanco and Sawyers 2002). As described herein, compounds blocking block colony formation and/or growth of PC-3 prostate and MDA-468 breast cancer cells in soft agar, which is an in vitro measure of potential anti-tumor activity. Furthermore, the compounds described herein are expected to sensitize tumors to the effects of other chemotherapeutic agents and radiation (Page, Lin et al-2000; Brognard, Clark et al. 2001).

PDK-1 is a Ser/Thr kinase that functions to phosphorylate and activate other Ser/Thr kinases in the AGC kinase family (Vanhaesebroeck and Alessi 2000). The best characterized substrate of PDK-1 is the intracellular Serine/Threonine kinase AKT, whose expression and/or activity is elevated in many cancers. Kinase activity of serum and glucocordicoid regulated kinase (SGK), which is structurally related to AKT, can also be phosphorylated and activated by PDK-1. Once activated in tumors, AKT promotes increase tumor cell survival, drug resistance, growth and angiogenesis. Three highly related isoforms of AKT, termed AKT1, AKT2 and AKT3 are known in humans. Activation of AKT is dependent on the activity of phosphatidylinsoitol-3 kinase (PI-3 kinase), whose activity is activated by many signaling molecules elevated in cancer cells, including growth factor receptors (e.g., epidermal growth factor (EGF) receptor, ErbB2 and IGF1 receptor) and oncogenes (e.g, Ras, BCR-abl, and Src). Other potential substrates of PDK-1 include p70 S6, kinase, p90 S6 kinase, protein kinase C. cAMP-dependent protein kinase (PKA), PRK1, Protein kinase G and serum and glucocorticoid regulated kinase (SGK).

PDK-1-mediated phosphorylation of AKT, which is largely in an inactive form in unstimulated cells, converts the enzyme to a catalytically active form. This occurs through the phosphorylation of the activation loop domain of AKT e.g. at Threonine 309 in AKT2 and Theonine-308 in AKT1. Phosphorylation of a homologous domain in many kinases is known to regulate their kinase activity. One stimulus for PDK-1 mediated phosphorylation of AKT is the association PI-3 kinase products $(3,4,5)PIP_3$ or $(3,4)PIP_2$ with the pleckstrin homology (PH) domain of AKT. Although AKT displays low, basal levels of activation in normal, unstimulated cells, AKT often becomes constitutively activated in tumor cells. This occurs through the up-regulation of a variety of different signaling molecules or the presence of oncogenenic mutations commonly found in cancer calls that can promote the activation of AKT, such as PI-3 kinase, growth factor receptors (e.g., EGFR family members), Ras, Src, and BCR-ABL activation. Loss of the tumor suppressor PTEN is another means of greatly increasing AKT activity in cancer cells (Besson, Robbins et al 1999). PTEN mutation or down regulation of PTEN protein is found in a large number of tumors and cancer cell lines. PTEN is a phosphatase that removes the D-3 phosphate from the products of PI-3 kinase such as phosphatidylinositol 3,4,5-trisphosphate and phosphatidylinositol 3,4-bisphosphate (Myers, Pass et al. 1998, Stambolic, Suzuki et al. 1998). Loss of PTEN, therefore, has the effect of increasing products of PI-3 kinase and promoting constitutive activation of AKT. Cancers with highly up-regulated levels of AKT may be especially sensitive to the effects of PDK-1/AKT pathway inhibitors.

Downstream substrates of PDK-1 and/or AKT are associated with a number of cell responses including proliferation, metabolism and cell survival (Testa and Bellacosa 2001; Vivanco and Sawyers 2002). Examples of signaling molecules downstream from PDK-1 or AKT involved in these pathways include BAD, p70 S6 kinase, p21(Waf-1/Cip-1), Forkhead transcription factors, p27(kip-1), GSK-3-alpha/beta, TSC2 (tuberin), and ecNOS. The survival function of AKT is particularly well-characterized cellular activity of AKT (Datta, Brunet et al. 1999). AKT functions to suppress apoptosis induced by a variety of agents, including UV radiation, chemoterateutic drugs, TFG-beta, withdrawal of survival factors, overexpression of oncogenes such as c-myc and detachment of cells from the extracellular matrix.

The ability to escape cell death, also termed apoptosis, is critical characteristic of tumor cells allowing their uncontrolled growth and invasive behavior. One trigger for apoptosis is the perturbation of the normal growth regulation resulting from oncogenic mutations or inappropriate expression signaling molecules coupled to protection from the development and progression of cancer. Cancer cells, however, can escape apoptotic death by selecting for activation of signaling molecules such as AKT that turn off apoptotic signals. Some oncogenes, such as Ras, which is activated in as many as 60% of human tumors, simultaneously promote uncontrolled growth and the activation of AKT. Inhibition of AKT in HIH 313 cells prevents transformation of these cells through transfection with activated Ras. Furthermore, a number of studies have shown that combining expression an oncogene with an activated form of AKT greatly facilitates formation of tumors in vivo (e.g., (Holland, Celestino et al 2000)) Inhibitors of PDK-1, by blocking activation of AKT, are a means of promoting apoptosis in tumors cells especially, but not necessarily limited to those over-expressing AKT activity. By blocking cell survival mechanisms, the compounds described herein could also be useful to promote sensitivity of cancer cells to radiation therapy and to treatment with a variety of chemotherapeutic agents.

Inhibitors of the PDK-1/AKT pathway are also expected to block cancer progression through inhibition of tumor-stimulated angiogenesis (Dimmeler and Zelher 2000; Shiojima and Walsh 2002). AKT has been shown to regulate a number of responses critical for the process of angiogeneisis, including endothelial cell migration, proliferation and survival during new vessel formation, ecNOS regulation, response of endothelial cells to growth factors (including ICF-1, agniopoetin-1 and VECF) and the regulation of hypoxia-inducible factor-1 (HIF-1)-alpla levels.

Inhibition of the cell cycle and growth of tumor cells is yet another expected effect of compounds that block PDK-1 and/or AKT. Inhibition of PDK-1 and/or AKT activity has been shown to regulate growth of cancer cells in a number of studies. These effects may occur through PDK-1 or AKT-mediated regulation of a number of different signaling pathways important in growth regulation. For example AKT has been shown to block nuclear localization and/or expression of the cyclin-dependent kinase inhibitors, p21(Waf-1/Cip-1) and p27(kip1). Compounds blocking these effects would be expected to reduce the activity of cyclin-dependent kinases, blocking progression through the cell cycle and reducing tumor cell growth. AKT was found to inhibit Myt1, thereby acting as an initiator of mitosis in oocytes from the starfish Asterina pectinfera. Furthermore, PDK-1 and/or AKT regulate the expression of proteins important for cell growth through its regulation of mTOR, p70 S6 kinase and eukaryotic initiation factor 4E binding protein 1 (4E-RP1). While the mechanism of this regulation is not firmly established, it has been shown that AKT phosphorylations and reduces expression of TSC2, thereby relieving TSC-2 mediated suppression of mTOR activity This, in turn, promotes the activation p70 S6 kinase activity and the phosphorylation and inhibition of 4E-BP1 (Inoki, Li et al. 2002; Potter. Pedraza et al. 2002). Roth these effects result in increased synthesis or mRNAs encoding proteins important for cell growth. Loss of TSC2 function is associated with the disease tuberous sclerosis, which results in differentiated benign growths (harmatomas) in a wide variety of organs. PDK-1 also has been shown to have a direct role in the phoephorylation and activation p70 S6 kinase (Alessi. Kozlowski et al. 1998).

In summary, the compounds described which block PDK-1 mediated activation of AKT or PDK-1 directly may be useful therapeutic agents in cancer by blocking a number of processes required for tumor progression, including growth, tumor cell survival, and recruitment of new blood vessels. The compounds described may also enhance the anti-tumor effects of radiation or other chemotherepeutic drugs. The compounds may also be useful for the treatment of tuberous sclerosis. Furthermore, the compounds described could be useful modulators of the immune response (Cantrell 2002) and for the treatment of autoimmune diseases such as rheumatoid arthritis and MS.

EXPERIMENTAL PROCEDURES 1

Cell-based Assays

Materials: Prostate cancer cells (PC-3) and breast cancer cells (MDA468) were obtained from the ATCC (Manassas, Va.). Mammalian protein extraction reagent (MPER), Halt protease inhibitor cocktail, BCA protein reagent, and Supersignal Western Chemiluminescent reagent were obtained from Pierce Chemical Co (Rockford, Ill.). 10% Tris-Glycine gels (1.0 mm, 15-well) and nitrocellulose (0.2 micron) were obtained from Invitrogen Life Technologies (Carlsbad, Calif.). Agar agar was purchased from EM Science. Polyclonal antibodies raised against phospho-AKT (Thr308, #9275), phospho-AKT (Ser473, #9271), phospho-S6-kinase (Thr389, #9205), and anti-rabbit IgG-HRP conjugate were obtained from Cell Signaling Technologies (Beverly, Mass.). Nitrobluc tetrazolium reagent and staurosporine were purchased from Sigma Chemical Co. (St. Louis, Mo.). LY294002 was purchased from Cayman Chemicals, (Ann Arbor, Mich.). All other materials were of reagent-grade quality.

Cell growth conditions: PC-3 cells were grown in F12K medium, supplemented with 7% (v/v) fetal calf serum (fcs) and 2 mM glutamine. MDA468 cells were grown in MEM-alpha, supplemented with 10% (v/v) tcs, 2 mM glutamine, 1 mM sodium pyruvate, 0.1 mM non-essential amino acids, 10 mM Hepes, 1 µg/ml insulin. All cell lines were incubated in a 37□C humidified incubator, with a 5% $CO_2$ atmosphere.

Cell-based assays using Western blot analysis: PC-3 cells were seeded into 24-well plates (Corning Costar) at 100-120, 000 cells per well and allowed to grow overnight to 90% confluence. On the next day, the cells were washed once with 1.5 ml PBS, and the medium replaced with low serum (0.1% fcs) containing growth medium (starvation medium) After a second overnight incubation, the medium was replaced with 0.5 ml/well of starvation medium. Some assays were also conducted in normal growth medium (7% fcs. PC-3, or 10% fcs, MDA-468) Cells were treated with vehicle control (DMSO) or drug at a final DMSO concentration of 1% v/v (a 5 µl addition per 0.5 ml medium), and cells were allowed to incubate for the stated times. The incubations were terminated by aspiration of the medium, washing the wells with 1.0 ml PBS, and lysis in 0.1 ml MPER reagent, supplemented with protease inhibitors (Halt reagent) and phosphatase inhibitors (1 mM NaF, 1 mM sodium vanadate). Cell lysates were briefly centrifuged to remove insoluble debris, and aliquots were taken for protein (BCA) and Western blot analysis. For Western analysis, lysates were combined with Laemmli SDS sample buffer, boiled, and loaded onto 10% Tris-Glylcine gels, normalizing for the amount of protein loaded in each lane. Electrophoresed gels were transferred onto nitrocellulose paper, blocked with 5% milk in Tris-buffered saline containing 0.1% Tween-20, and incubated overnight with the primary antibody (phospho-AKT-Thr308 @ 1:657, phospho-AKT-Ser473 @ 1:1000, phospho-S6 kinase @ 1:1000). Blots were washed three times with blocking buffer and incubated one hour with anti-rabbit IgG-HRP @ 1:2000. Washed blots were developed using the Supersignal Western Chemiluminescent detection system. Films were scanned using a Bio Rad CCD camera, and phospho-protein bands were quantitated using Bio Rod Quantity-One software.

Soft agar efficacy assays: PC-3 and MDA-468 cells were grown in soft agar over a period of 2 weeks. Culture plates (Corning 35 mm×10 mm) were prepared with a bottom layer of 0.5% agar in growth medium, 2 ml/well. Cells were trypsinized, dispersed into single cells with a 21-gauge needle, and seeded in a top layer of 0.3% agar/growth medium, 1.5 ml/plate, containing 4500 cells per plate. On the following day, the first vehicle or drug treatment was added, in a volume of 1.0 ml of 0.3% agar/growth medium, containing 1% DMSO. Drug concentrations were adjusted to reflect the total volume of agar in the plates. The cells were allowed to grow for seven days and treated a second time (adding an additional 1 ml of 0.3% agar). Colonies were visually inspected for growth and viability every few days.

On day 12-14, nitroblue tetrazolium (0.5 mg/ml PBS) was added, 0.3 ml per plate, and the viable colonies were allowed to develop color for 1-2 days. Plates were scanned using a Bio Rad CCD camera, and the colonies were quantitated for only number, and for total stained area, using ImagePro software.

AKT2 and PDK-1 Expression and Purification pHisAKT2 was constructed by cloning AKT2 into pBlueBacHis2A (Invitrogen Corp.) through the BamH1 and Bgl2 restriction sites, forming a fusion protein behind a 38 amino acid N-terminal His tag sequence derived from the vector. The new N-terminal sequence+first 10 residues of AKT2 is as follows: MPRGSHHHHHHGMASMTG-GQQMGRDLYDDDDKDRWGS<u>MNEVSVIKEG</u> (AKT2 is undedined and is in bold His-6) Similarly, pHisPdK-1 was constructed by cloning PDK1 into pBlueBacHis2A (Invitrogen Corp.) at EcoR1 cloning site, forming a fusion protein behind an N-terminal His tag (preceding sequence of . . . ICSWYHGIL<u>DMARTTSQLYD</u> . . . (PDK1 sequence underlined). The new N terminal sequence+first 10 residues of PDK1 is as follows, MPRGSHHHHHHGMASMTG-GQQMGRDIYDDDDKDRWGSELEICSWYHGILD <u>MARTTSQLYD</u> . . . (PDK-1 is underlined and His-6 is in bold).

Recombinant baculovirus containing either His-tagged AKT2 or His-tagged PDK-1 cDNAs were prepared by the following method. pHisAKT2 or pHisPDK 1 were cotransfected with Bac-N-Blue (Invitrogen) vial DNA info SF-21 cells and after 3-4 days, viral supernatant were isolated and recombinant viruses were plaque purified. His-tagged AKT2 (HisAKT-V) or His-tagged PDK-1 (HisPDK-1-V) cDNA expressing clones were selected and expanded as a stock for use in the expression of recombinant proteins described below.

To express His-tagged AKT2 and PDK-1, a 10 liter suspensions of SF-21 insect cells were infected with recombinant viruses (i.e., either HisPDK-1-V or HisAKT2-V) and cells were harvested 3-4 days post infection and frozen. To purity recombinant His-tagged AKT2 and PDK-1, cell pellets were thawed, homogenized (in phosphate buffered saline (PBS), supplemented with 10% Triton X-100, 0.5 M NaCl, 2 g/l NaF, 2.5 µg/ml aprotinin, 5 µg/ml leupeptin, 1.25 µg/ml pepstatin, 0.1% beta-mecaptoethanol, and 1 mM vanidate, 10 mM imidizole and adjusted to pH 7.6) and were purified using two sequential rounds of Ni2+ affinity chromatography followed by gel filtration. Enzymes were frozen in small aliquots and stored at −80□C in 50 mM Tris-HCl, pH 7.5, 150 mM NaCl, pH 7.5, 0.1 mM EGTA, 0.1 mM EDTA, 0.2 µM benzamidine, 0.1% beta-mercaptoethanol and 0.25 M sucrose.

Enzyme Assays

PDK-1-dependent activation and subsequent enzymatic activity of AKT2: Purified human AKT2 activity was routinely measured in an assay in which the enzyme was first activated by PDK-1 in the presence of phosphatidylinositol-4,5-bisphosphate (PIP2). Once activated, AKT2-dependent phosphorylation of a peptide substrate was measured by scintillation proximity assay (SPA).

Phospholipid vesicles were prepared as follows: 2.2 mg each of phosphatidylcholine (Sigma Cat # P-1287) and phosphatidylserine (Sigma Cat #P-6641) were transferred to a borosilicate glass test tube and dried down under nitrogen. 1 mg of $PIP_2$ (Biomol Cat #PH-106) was suspended in 9.5 ml of 10 mM HEPES, pH 7.5 and transferred to the dried lipids. The tube was vortexed until a milky suspension was produced. Then the tube was placed in a ice water-jacketed cup horn sonicator (Branson Instruments) and subjected to sonication for 20 min at medium power until a translucent phospholipid vesicle preparation was obtained. Aliquots of the vesicle suspension were frozen at −80□C until needed.

Assays were performed in 96-well polypropylene V-bottom plates. Incubations were carried out for 2 hr at room temperature. The assay mixture contained in a volume of 60 µL: 15 mM MOPS, pH 7.2, 1 mg/ml bovine serum albumin, 18 mM betaglycerolphosphate, 0.7 mM dithiothreitol, 3 mM EGTA, 10 mM MgOAc, 7.5 (M ATP, 0.2 µCi of [$\gamma$-$^{33}$P]ATP, 7.5 µM biotinylated peptide substrate (biotin-ARRRDGG-GAQPFRPRAATF), 0.5 µL of $PIP_2$-containing phospholipid vesicles, 60 pg of purified recombinant human PDK-1, and 172 ng of purified recombinant human AKT2. Test compounds were added from stock solutions in DMSO. The final concentration of DMSO was 2.5%. Following incubation, 10 µL of the assay mixture was transferred to a 96-well clear-bottom polystyrene plate (Wallac Isoplate) containing 0.33 mg of streptavidin-coated SPA beads (Amersham Cat. # RPNQ0007) suspended in 200 µL of phosphate-buffered saline, pH 7.4, containing 50 mM EDTA and 0.1% Triton X-100. After brief shaking, the SPA beads were allowed to settle to the bottom of the plate overnight at room temperature. Product formation, measured in a Wallac MicroBeta scintillation counter, was proportional to the time of incubation and to the amount of PDK-1 and inactive AKT2 added. PDK-1 was added at sub-optimal levels so that the assay could sensitively detect inhibitors of AKT2 activation as well as direct AKT2 kinase inhibitors. The z'-factor for the assay was greater than 0.7.

Phosphorylation of the peptide substrate on the threonine residue was shown to be dependent upon activated AKT2 produced during the incubation. No phosphorylation was observed in the absence of ATP, $Mg^{2+}$, PDK-1, AKT2, or $PIP_2$-Containing vesicles. Phosphorylation was readily observed, however, upon addition of purified activated human AKT1 (purchased from Upstate Biotechnology), independent of the presence or absence of added PDK-1 or $PIP_2$-containing vesicles.

Direct assay of PDK-1 activity: Recombinant human PDK-1 activity was directly measured using a filter binding protocol. Incubations were performed at room temperature for 4 hr in a final volume of 60 µL containing: 50 mM Tris-HCl, pH 7.5, 0.1 mM EGTA, 0.1 mM EDTA, 0.1% beta-mercaptoethanol, 1 mg/ml bovine serum albumin, 10 mM MgOAc, 10 µM ATP, 0.2 µCi of [$\gamma$-$^{33}$P]ATP, 7.5 µM of substrate peptide ($H_2$N-ARRRGVTTKTFCGT) and 60 ng of purified human PDK-1. The enzymatic reaction was stopped by addition of 25 mM EDTA. A portion of the reaction mixture was spotted on Whatman P81 phosphocellulose paper. The filter paper was washed 3 times with 0.75% phosphoric acid to remove unreacted [$\gamma$-$^{33}$P]ATP, and once with acetone. After drying, the filter-bound labeled peptide was quantitated using a Fuji Phosphoimager.

Results

Compounds, which preferentially inhibit Akt/Pdk activity are shown in the table designated Group 1 compounds.

An overview of the results of the inhibition $IC_{50}$ in nM are presented in the table 1 below:

TABLE 1

| Example | Akt-2 inhibition IC50 (nM) |
| --- | --- |
| 546 | 4 |
| 220 | 6 |
| 521 | 44 |
| 504 | 24 |
| 492 | 23 |
| 540 | 19 |

REFERENCES

Alessi, D. R., M. T. Kozlowski, et al. (1998). "3-Phosphoinositide-dependent protein kinase 1 (PDK 1) phosphorylates and activates the p70 S6 kinase in vivo and in vitro." Curr Biol 8(2)-69-81.

Besson, A., S. M. Robbins, et al. (1999). "PTEN/MMAC1/TEP1 in signal transduction and tumorigenesis." Eur J Biochem 263(3): 605-11.

Brognard, J., A. S. Clark, et al. (2001). "Akt/protein kinase B is constitutively active in non-small cell lung cancer cells and promotes cellular survival and resistance to chemotherapy and radiation." Cancer Res 61(10): 3986-97.

Cantrell, D. (2002). "Protein kinase B (Akt) regulation and function in T lymphocytes." Semin Immunol 14(1): 19-26.

Datta, S. R., A. Brunet, et al. (1999). "Cellular survival: a play in three Akts." Genes Dev 13(22): 2905-27.

Dimmeler, S. and A. M. Zeiher (2000). "Akt takes center stage in angiogenesis signaling." Circ Res 86(1): 4-5.

Holland, E. C., J. Celestino, et al. (2000). "Combined activation of Ras and Akt in neural progenitors induces glioblastoma formation in mice." Nat Genet 25(1): 55-7.

Inoki, K., Y. Li, et al. (2002). "TSC2 is phosphorylated and inhibited by Akt and suppresses mTOR signalling." Nat Cell Biol 12: 12.

Myers, M. P., I. Pass, et al. (1998). "The lipid phosphatase activity of PTEN is critical for its tumor supressor function." Proc Natl Acad Sci USA 95(23): 13513-8.

Page, C., H. J. Lin, et al. (2000). "Overexpression of Akt/AKT can modulate chemotherapy-induced apoptosis." Anticancer Res 20(1A): 407-16.

Potter, C. J., L. G. Pedraza, et al. (2002). "Akt regulates growth by directly phosphorylating Tsc2." Nat Cell Biol 12: 12.

Shiojima, I. and K. Walsh (2002). "Role of Akt signaling in vascular homeostasis and angiogenesis." Circ Res 90(12): 1243-50.

Stambolic, V., A. Suzuki, et al. (1998). "Negative regulation of PKB/Akt-dependent cell survival by the tumor suppressor PTEN." Cell 95(1): 29-39.

Testa, J. R. and A. Bellacosa (2001). "AKT plays a central role in tumorigenesis." Proc Natl Acad Sci USA 98(20): 10983-5.

Vanhaesebroeck, B. and D. R. Alessi (2000). "The PI3K-PDK1 connection: more than just a road to PKB." Biochem J 346(Pt 3): 561-76.

Vivanco, I. and C. L. Sawyers (2002). "The phosphatidylinositol 3-Kinase AKT pathway in human cancer." Nat Rev Cancer 2(7): 489-501.

Inhibition of Chk Kinase Activity

Gen ral Remarks

The compounds of this invention inhibit the cell cycle checkpoint kinases which are essential for the cellular response to DNA damage and for the coordination of the cell cycle. The DNA damage might be due to external or internal influence These influences involve—without being limited to them—replication errors, DNA base damages, DNA strand breaks and the exposition to irradiation or cytotoxic chemicals.

The inhibition of one or more of the cell cycle checkpoint kinases is the basis for the effect of the compounds of this invention e.g. against cancer, like solid tumours or leukemia, against other hyperproliferative diseases, e.g. HIV and viral infections, like e.g. cytomegalus-infections, herpes and hepatitis B and C and HIV.

The eukaryotic cell division cycle ensures the duplication of the genome and its correct distribution to the daughter cells by running through a coordinated and regulated sequence of events. The cell cycle is divided in four successive phases: the G1 phase represents the time before the DNA replication, during which the cell is growing and susceptible for external stimuli. During the S-phase the cell replicates its DNA, and in the G2 phase the cell prepares for the entry into the mitosis. During the mitosis (M-Phase) the replicated DNA is separated and the cell division is carried out.

Corresponding to the extraordinary relevance of the cell division cycle the passage through the cycle is strictly regulated and controlled. The enzymes needed for the progression through the cycle, the cyclin-dependent kinases, have to be activated at the right moment and have to be switched off as soon as the corresponding phase is finished. Checkpoint systems arrest the progression through the cell cycle if DNA damage is detected, the DNA replication is not completed or the building of the spindel apparatus is not completed (Hartwell et al., 1989). They do this by influencing the generation, activation or inactivation of the cyclin-dependent kinases.

Checkpoints permit the cell to track the ordered course of the individual phases of the cell cycle The most important checkpoints are at the transition from the G1 phase into the S phase and at the transition from the G2 phase into the M phase (for a review see Dasika et al. 1999). The G1 checkpoint ensures that the cell does not start the DNA synthesis if it is not sufficiently nourished or if it does not correctly interact with other cells or with the substrate or if the DNA of the cell is not intact The G2/M checkpoint ensures that the DNA is completely replicated and the mitotic spindle is build up before the cell enters the mitosis. The G1 checkpoint is controlled by the gene product of the tumour suppressor gene p53. p53 becomes activated after the detection of changes in the metabolism or the genomic integrity of the cell and p53 is able to initiate either a stop of the cell cycle program or apoptosis. For this the transcriptional activation of the expression CDK inhibiting protein p21 plays a crucial role.

A fundamental component of the G2/M checkpoint is the activation of the kinases ATM, Chk1 and Chk2 after a DNA damage and finally the phosphorylation and inactivation of the phosphatase Cdc25C. This results in a cell cycle arrest, as the inhibitory phosphorylation of the amino acids threonine-14 and tyrosine-15 of the cyclin dependent kinase 1 (CDK1) is not further removed by Cdc25C.

The loss of the regulation of the cell cycle and the loss of checkpoint control are characteristic features of tumour cells. p53, which is essential for the G1 checkpoint, is the gene most often mutated in human tumours (about 50%). In tumour cells expressing unmutated p53, it is often inactivated by an enhanced proteolytic degradation or the genes of other proteins involved in the G1 checkpoint are mutated or deregulated. Examples are the inactivation of the tumour suppressor genes Rb, $p16^{INK}4$ and $p19^{ARF}$ or the overexpression of the oncogenes HDM-2 and cyclin D (Levine, 1997). In consequence nearly all tumour cells do not have a functional G1 checkpoint which enables the to accumulate further mutations and to escape from a DNA damage induced apoptosis. This inactivation of the G1 checkpoint is an important factor for the genomic instability which drives the evolution of human tumours and crucially contributes to the resistance of tumour cells against chemotherapeutics and irradiation. On the other hand the inactivation of the G1 checkpoint enhances the dependence of the tumour cells on the second important barrier against the cell killing effect of DNA damages, the G2/M checkpoint, and makes the tumour cells especially vulnerable to an abrogation of the G2/M checkpoint (Hartwell und Kastan, 1994, O'Connor und Fan, 1996).

The cell cycle checkpoint kinase Chk1 is an important part of the G2/M checkpoint (Sanchez et al., 1997). Inactivation of Chk1 abrogates a DNA-damage induced G2/M arrest and thereby leads to a preferred killing of the resulting checkpoint deficient cells (Takai et al., 2000, Koniaras et al., 2001, Liu et al., 2000). The inactivation of Chk1 causes that Cdc25C stays active despite of the DNA damage and is able to activate Cdk1/CycB, the main effector of the entry into the mitosis. However, due to the persistent DNA damage the cell is not able to complete the M phase successfully and undergoes apoptosis instead ("mitotic catastrophe"). The cell cycle checkpoint kinase Chk2 is also activated by DNA damage (Matsuoka et al. 1998, Chaturvedi et al., 1999) and activated Chk2 phosphorylates and thereby inactivates Cdc25C. Cells without active Chk2 have a defect in their checkpoint response to DNA damage (Hirao et al., 2000).

The inactivation of Chk1 and Chk2 abrogates the G2/M arrest which is induced by damaged DNA and sensitises the resulting checkpoint deficient cells to the killing by DNA damaging events. As cancer cells are more sensitive towards the abrogation of the G2/M checkpoint than normal cells there is great interest in compounds, which inhibit Chk1, Chk2 or Chk1 and Chk2, as a result abrogate the G2/M checkpoint and improve the killing of cancer cells by DNA damaging events. Such DNA damaging events can be the direct damage of the DNA by irradiation or chemotherapeutics, e.g. strandbreaks inducing compounds, DNA-alkylating compounds or topoisomerase inhibitors, the exertion of influence on the building of the mitotic spindle apparatus, hypoxic stress due to limited supply of the tumour with blood—e.g. induced by anti-angiogenic drugs—or also endogenous DNA damages resulting from the genomic instability inherent to cancer cells.

EXPERIMENTAL PROCEDURE 2

Chk1 Kinase Assay

Recombinant Chk1-His$_6$-fusion protein, expressed in insect cells (Sf-9) and purified by Ni-NTA affinity chromatography was used as kinase. Alternatively, commercially available GST-Chk1-fusion protein (Upstate Biotechnology, Dundee, Scotland) can be used. As substrate for the kinase reaction the biotinylated peptide biotin-Arg-Ser-Gly-Leu-Tyr-Arg-Ser-Pro-Ser-Met-Pro-Glu-Asn-Leu-Asn-Arg-Pro-Arg-OH was used which can be purchased e.g. from the company Biosyntan GmbH (Berlin-Buch, Germany).

Chk1 (200 ng/measurement point) was incubated for 60 min at 22°C in the presence of different concentrations of test compounds (0 µM and concentrations in the range 0.001-30 µM) in 30 µl assay buffer [50 mM Hepes/NaOH pH7.5, 10 mM MgCl$_2$, 1 mM MnCl$_2$, 0.1 mM sodium ortho-vanadate, 1.0 mM dithiothreitol, 0.5 µM adenosine-tri-phosphate (ATP), 1.9 µM substrate peptide (Biotin-Arg-Ser-Gly-Leu-Tyr-Arg-Ser-ProSer-Met-Pro-Glu-Asn-Leu-Asn-Arg-Pro-Arg-OH), 6 nCi/measurement point $^{33}$P-gamma ATP, 0.008% NP40, 1.5% (v/v) dimethylsulfoxide]. The reaction was stopped by the addition of 20 µl of a suspension of streptavidine coated PVT-SPA-beads (0.15 mg/measurement point, from Amersham Biotech) in an aqueous EDTA/ATP-solution (20 mM EDTA, 50 µM ATP, 1% (v/v) Triton X-100 in PBS).

The resulting mixture was incubated further 16 h at 22° C. to allow the binding of the biotinylated peptide to the streptavidine coated PVT-SPA-beads and to allow the sedimentation of the beads. Subsequently the amount of 33P incorporated into the substrate peptide was evaluated by scintillation measurement in a Topcount NXT (Perkin-Elmer).

Chk2 Kinase Assay

Recombinant Chk2-His$_6$-fusion protein, expressed in insect cells (Sf-9) and purified by Ni-NTA affinity chromatography was used as kinase. Alternatively, commercially available GST-Chk2-fusion protein (Upstate Biotechnology, Dundee, Scotland) can be used. As substrate for the kinase reaction the biotinylated peptide biotin-Arg-Ser-Gly-Leu-Tyr-Arg-Ser-Pro-Ser-Met-Pro-Glu-Asn-Leu-Asn Arg-Pro-Arg-OH was used which can be purchased e.g. from the company Biosyntan GmbH (Berlin-Buch, Germany).

Chk2 (400 ng/measurement point) was incubated for 60 min at 22°C in the presence of different concentrations of test compounds (0 µM and concentrations in the range 0.001-30 µM) in 30 µl assay buffer [50 mM Hepes/NaOH pH7.5, 10 mM MgCl$_2$, 1 mM MnCl$_2$, 0.1 mM sodium ortho-vanadate, 1.0 mM dithiothreitol, 1.5 µM adenosine-tri-phosphate (ATP), 8 µM substrate peptide (Biotin-Arg-Ser-Gly-Leu-Tyr-Arg-Ser-Pro-Ser-Met-Pro-Glu-Asn-Leu-Asn-Arg-Pro-Arg-OH), 15 nCi/measurement point $^{33}$P-gamma ATP, 0.008% NP40, 1.5% (v/v) dimethylsulfoxide]. The reaction was stopped by the addition of 20 µl of a suspension of streptavidine coated PVT-SPA-beads (0.25 mg/measurement point, from Amersham Biotech) in an aqueous EDTA/ATP-solution (20 mM EDTA, 50 µM ATP, 1% (v/v) Triton X-100 in PBS).

The resulting mixture was incubated further 16 h at 22° C. to allow the binding of the biotinylated peptide to the streptavidine coated PVT-SPA-beads and to allow the sedimentation of the beads. Subsequently the amount of $^{33}$P incorporated into the substrate peptide was evaluated by scintillation measurement in a Topcount NXT (Perkin-Elmer).

FACS-Assay

Human HeLa (ATCC CCL-2) cervix adenocarcinoma cells were plate out to a density of 3000 cells/cm$^2$ in DMEM medium containing 10% FCS in 6-well plates After 48 h incubation the medium was exchange for DMEM medium supplemented with 10% FCS and 5 µg/ml bleomycine sulfate. After 18 h incubation the test compounds were added to final concentrations of 0.03 µM, 0.1 µM, 0.3 µM, 1 µM, 3 µM, 10 µM, or 30 µM. After a further incubation of 24 h or 48 h the cells were collected by trypsinisation, permeablelised and fixed in 70% ethanol. The DNA was stained with propidium iodide and the cellular DNA-content was measured by a Fluorescence Activated Cell Scan (FACS) The portion of cells with a cellular DNA-content corresponding to the G2 and M phases of the cell cycle was evaluated to judge the effect of the test compound on the bleomycine induced G2/M arrest of the cells.

Expression and purification of Chk1 and Chk2

The coding sequences were cloned by RT-PCR and nested PCR from commercially available polyA-RNA. The primers used for this purpose were designed according to the sequence information in Genebank (AF 016582 for Chk1, AF086904 for Chk2). In preparation for the C-terminal His6-fusion in the respective second PCRs 3'-primers were used, which removed the stop codon at the end of the coding sequence of Chk1 and Chk2 by mutation. Additional restriction sites were added to the primers (EcoRI-sites for the 5'-primers and HindIII-sites for the 3'-primers).

The cDNAs were cloned into the vector pT7-Blue T (Novagen). To introduce the His$_6$-sequence at the C-terminus of Chk1 and Chk2 EcoRI/HindIII fragments from these pT7-Blue plasmids were cloned into the bacterial expression vector pET23a. From these pET23a-Chk1 und pET23a-Chk1 vectors DNA fragments coding for Chk1-His6 or Chk2-His$_6$ were excised and inserted into the baculovirus-transfer-vector pVL1392.

The generated vectors were transfected into Sf-9 cells with AcNPV baculovirus genomic DNA (BaculoGold Transfection Kit, Pharmingen) The viruses produced by this procedure were plaque-purified and amplified for further infections Recombinant Chk1-His$_6$-fusion protein and recombinant Chk2-His$_6$-fusion protein were produced in Sf-9—Cells. The Sf-9—Cells were infected with the viruses at a MOI (Multiplicity of infectivity)=1 and subsequently cultivated for 3 days in TNM-FH-medium. After lysis of the cells and sedimentation of the cell debris by centrifugation (20000×g) the fusion proteins were purified from the supernatant by Ni-NTA affinity chromatography (Superflow from QIAGEN, Hilden, Germany) and dialysed into 50 mM Tris/HCl buffer (pH 7.5) containing 150 mM NaCl and 2 mM EDTA. The protein solution was shock frozen and stored at −80°C.

Results

Compounds, which preferentially inhibit Chk activity are shown in the table designated Group 2 compounds.

An overview of the results of the inhibition IC$_{50}$ in nM are presented in the table 2 below:

TABLE 2

| Example | Chk-1 IC$_{50}$ (nM) |
|---------|----------------------|
| 65      | 440                  |
| A16     | 300                  |
| A17     | 200                  |
| A18     | 80                   |
| 699     | 20                   |

REFERENCES

Chaturvedi, P et al. (1999), Oncogene 18, 4047-4054.
Dasika, G-K: et al. (1999), Oncogene 18, 7883-7899.
Hartwell, L. H. et al (1989), Science 246, 629-634.
Hatwell, L. H. und Kastan, M. B. (1994) Science 266, 1821-1828.
Hirao, A. et al. (2000), Science 287, 1824-1827.
Jackson, J. R et al. (2000), Cancer Res 60, 566-572
Koniaras, K. et al. (2001), Oncogene 20, 7453-7463.
Levine, A. J. (1997), Cell 88, 323-331.
Liu, Q. et al. (2000), Genes Dev. 14, 1448-1459.
Matsuoka, S. et al (1998), Science 282, 1893-1897.
O'Connor, P. M., und Fan, S. (1996). Prog. Cell Cycle Res. 2, 165-173.
Sanchez, Y. et al. (1997), Science 277, 1497-1501.
Takai, H. et al. (2000), Genes Dev. 14, 1439-1447.

Inhibition of KDR-kinase Activity

KDR Kinase Assay

Recombinant KDR-GST-fusion protein, expressed in insect cells (Sf-9) and purified by Glutathion affinity chrormatography was used as kinase. Alternatively, commercially available GST-KDR-fusion protein (Proqinase, Freiburg i.Brsg., Germany) can be used. As substrate for the kinase reaction the biotinylated copolymer poly-(Glu, Tyr-4:1) which can be purchased e.g. from the company Cisbiointernational (Marcoule, France).

In a black low volume 384 well microtiterplate (Greiner, Frickenhausen, Germany) KDR (enzyme amount depending on lot, adjusted to give an dF of about 300-400) was incubated for 20 min at 22° C. in the presence of different concentrations of test compounds (0 µM and concentrations in the range 0.001-30 µM) in 15 µl assay buffer [50 mM Hepes/NaOH pH7.0, 25 mM MgCl$_2$, 5 mM MnCl$_2$, 0.5 mM sodium orthovanadate, 1.0 mM dithiothreitol, 1 µM adenosine-tri-phosphate (ATP), 23.5 µg/ml substrate [biotinylated poly-(Glu, Tyr; 4:1)], 1.5% (v/v) dimethylsulfoxide]. The reaction was stopped by the addition of 5 µl of a solution of the detection reagents [0.3 µg/ml Eu-W1024-labeled antiphosphotyrosine antibody (PT66) (Perkin-Elmer) and 4.125 µg/ml SA-XL-655 (Cisbiointernational, Marcoule, France)] in an aqueous EDTA-solution (250 mM EDTA, 0.1% (w/v) bovine serum albumine in 100 mM HEPES/NaOH pH 7.0).

The resulting mixture was incubated further 2 h at 22° C. to allow the binding of the biotinylated substrate and product to the SA-XL-665 and the EU labeled anti-phosphotyrosine antibody. Subsequently the amount of phosphate incorporated into the substrate was evaluated by resonance energy transfer measurement in a HTRF reader (Discovery, Perkin-Elmer).

The IC$_{50}$ values are determined from the inhibitor concentration that is necessary to inhibit the phosphate incorporation to 50% of the uninhibited incorporation after removal of the blank reading (EDTA-stopped reaction).

Results:

Compounds, which preferentially inhibit Akt and Pdk and the VEGF-R activity are shown in the table designated Group 3 compound.

An overview of the results of the inhibition IC$_{50}$ in nM are presented in the table 3 below:

TABLE 3

| Example | VEGFR II (KDR) IC$_{50}$ (nM) |
|---------|-------------------------------|
| 389     | 330                           |
| 477     | 740                           |
| 473     | 400                           |
| 512     | 1400                          |
| 436     | 1600                          |
| 535     | 2.6                           |
| 546     | 4                             |
| 452     | 9.7                           |
| 539     | 10.6                          |
| 395     | 32                            |

Further, the invention is explained in more detail by the examples.

Group 1 compounds: preferred compounds inhibiting preferentially Akt, Pdk kinases Group 2 compounds: preferred compounds inhibiting preferentially Chk kinases Group 3 compounds: preferred compounds inhibiting preferentially Akt and/or Pdk and VEGF-R kinases Group 1 compounds:

| Example | structure |
|---------|-----------|
| 313     | 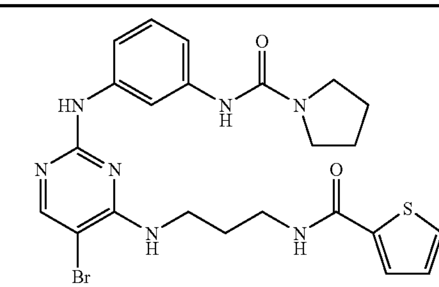          |
| 342     | 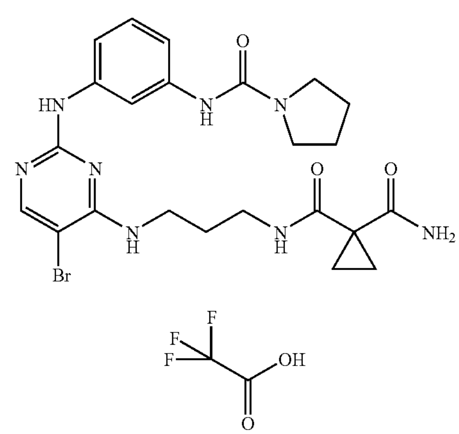          |

| Example | structure |
|---|---|
| 343 | 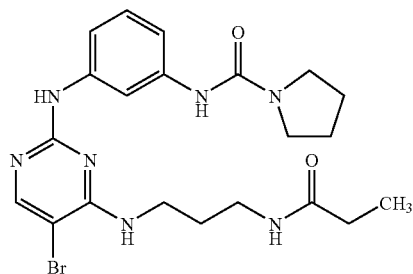 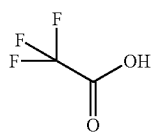 |
| 346 | 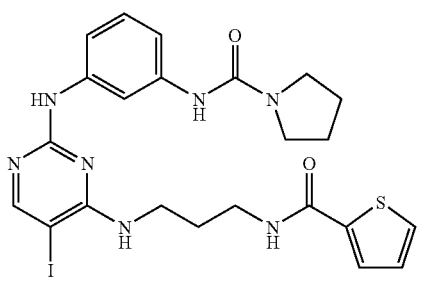 |
| 444 | Chiral 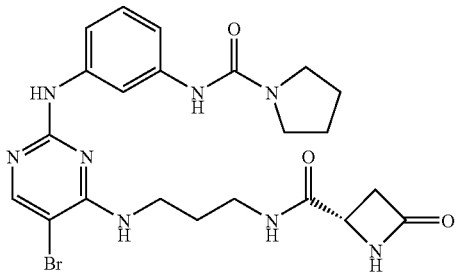 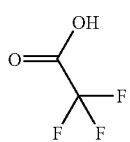 |
| 446 | 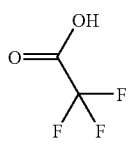 |
| Example | structure |
|---|---|
| | Chiral 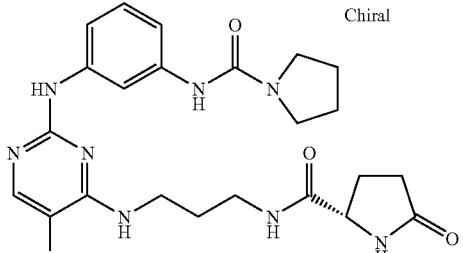 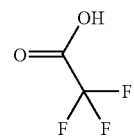 |
| 452 | Chiral 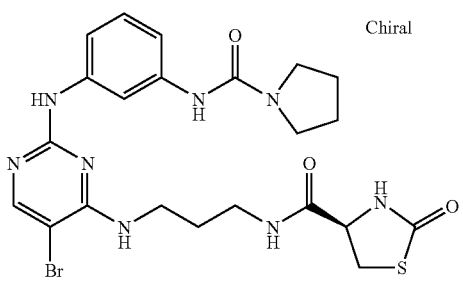 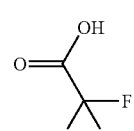 |
| 468 | 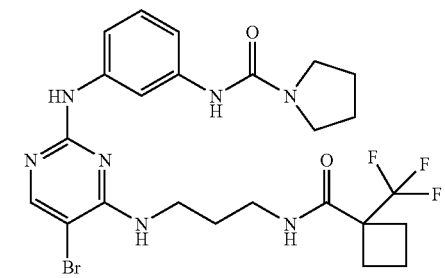 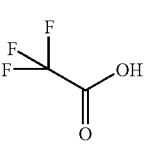 |
| 471 | 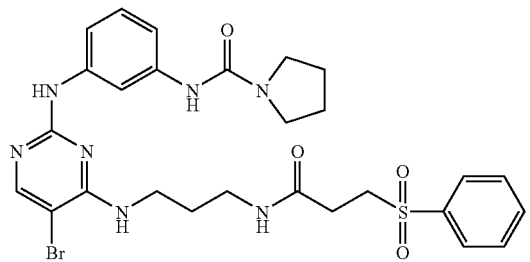 |

| Example | structure |
|---|---|
| | 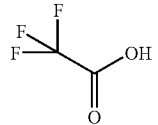 |
| 474 | 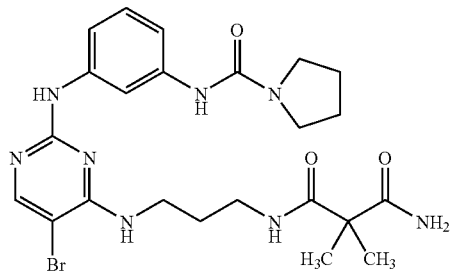 |
| | 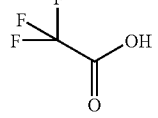 |
| 486 | 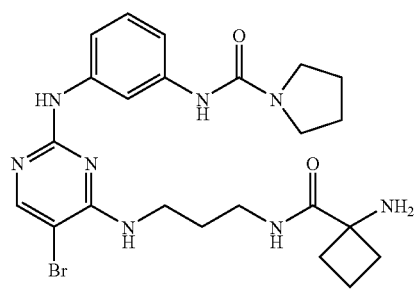 |
| | 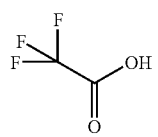 |
| | 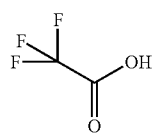 |
| 493 | 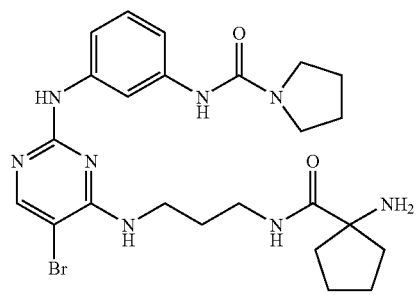 |
| Example | structure |
|---|---|
| | 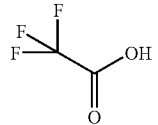 |
| | 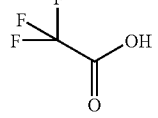 |
| 498 | 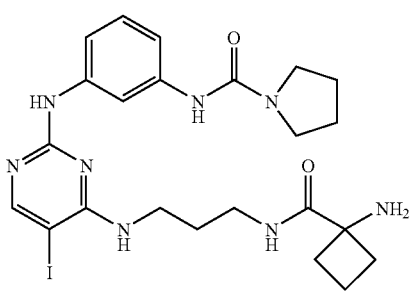 |
| | 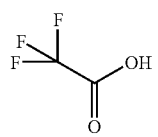 |
| | 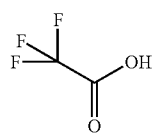 |
| 515 | 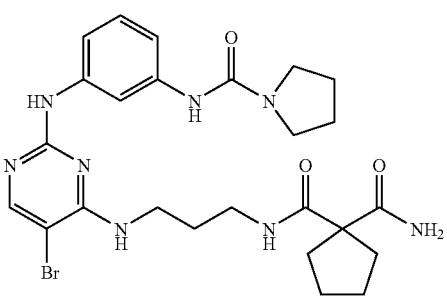 |
| | 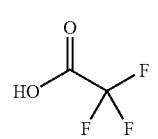 |
| | 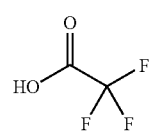 |

-continued
| Example | structure |
|---|---|
| 535 | 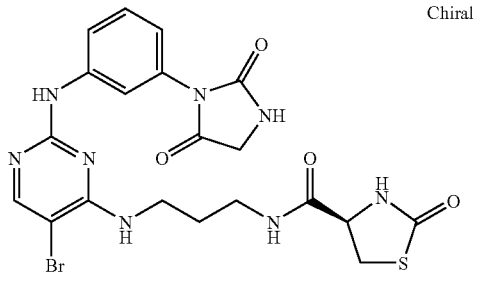 Chiral |
| 546 | 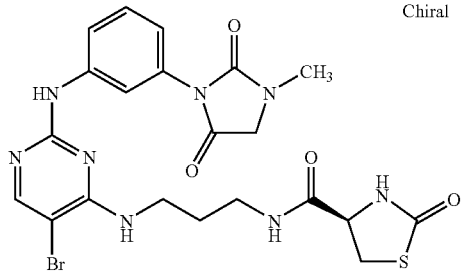 Chiral |
| 394 | 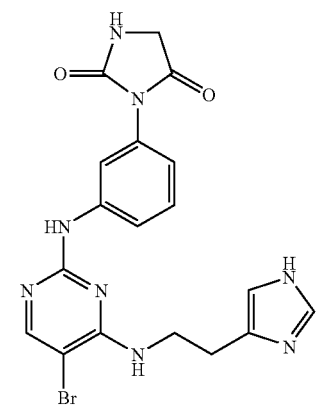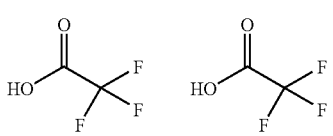 |
-continued
| Example | structure |
|---|---|
| 395 | 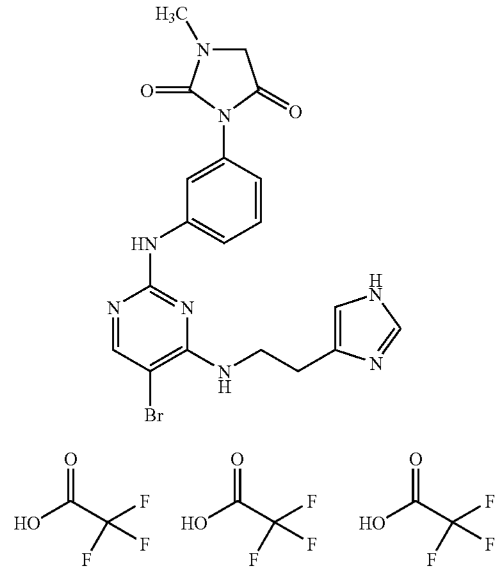 |
| 255 | 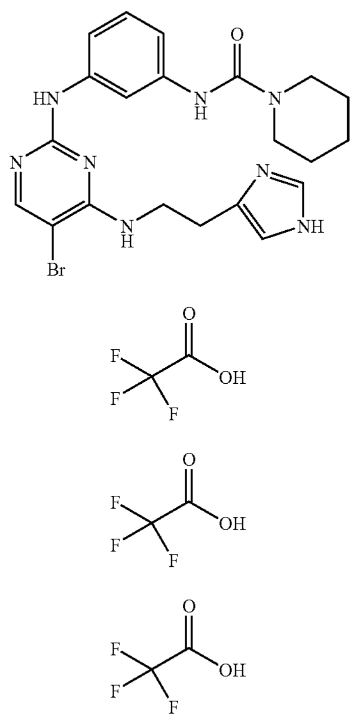 |
| 242 | 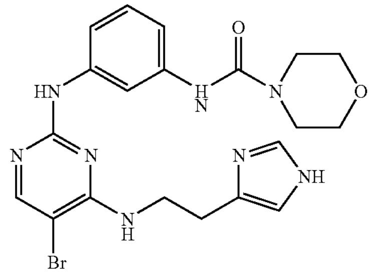 |
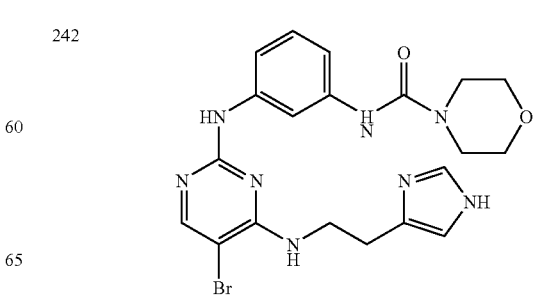

-continued
| Example | structure |
|---|---|
| | 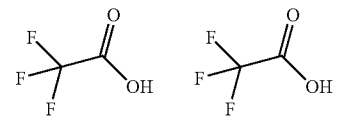 |
| 220 | 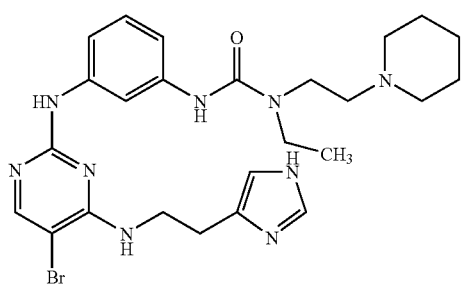 |
| 389 | 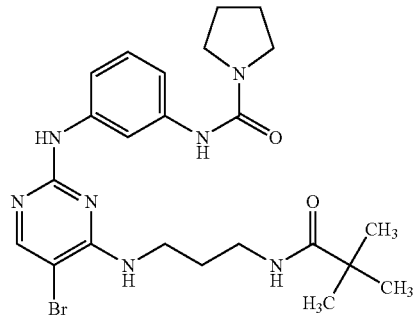 |
| | 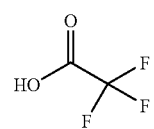 |
| 548 | |
-continued
| Example | structure |
|---|---|
| 533 | Chiral 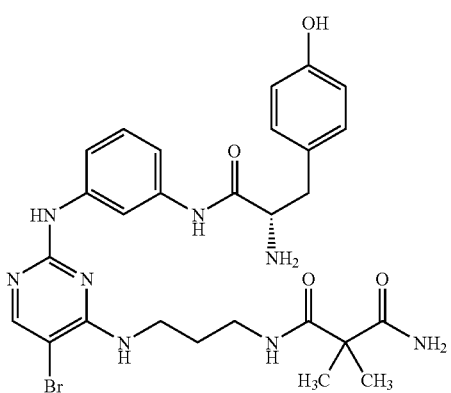 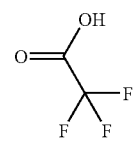 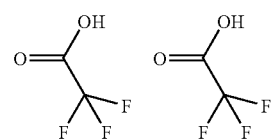 |
| 524 | 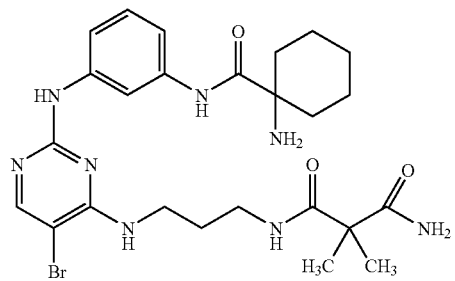 |
| | 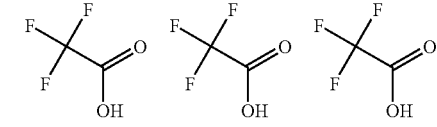 |
| 521 | 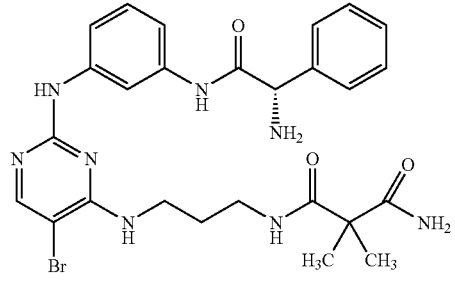 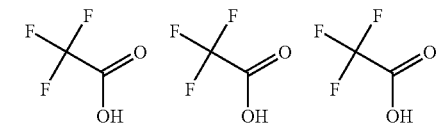 |

| Example | structure |
|---|---|
| 508 | 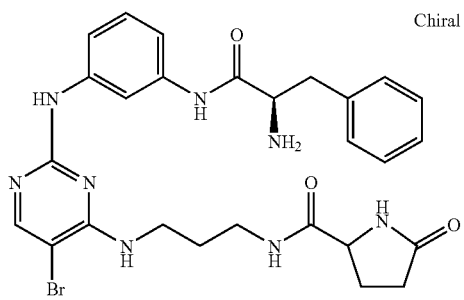 Chiral |
| 504 | 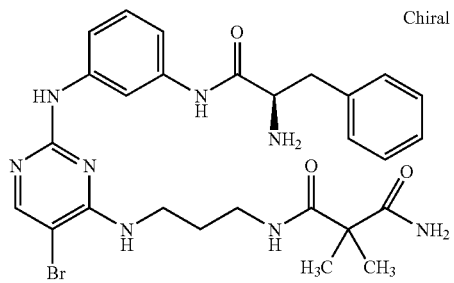 Chiral |
| 492 | 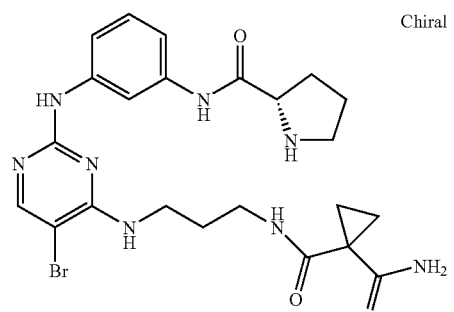 Chiral |
| Example | structure |
|---|---|
| 540 | 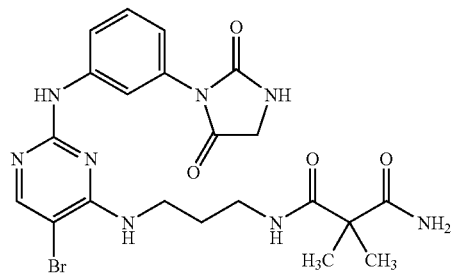 |
| Example | structure |
|---|---|
| 509 | 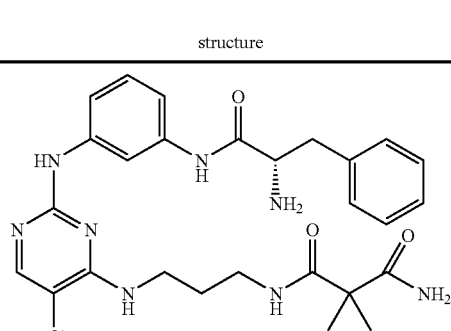 |
| 516 | 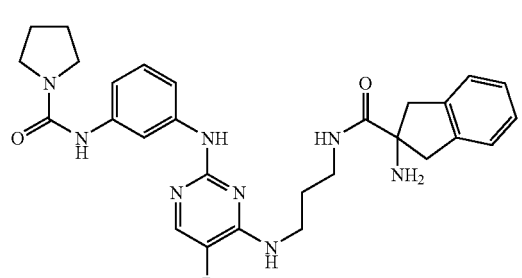 |
| 505 | 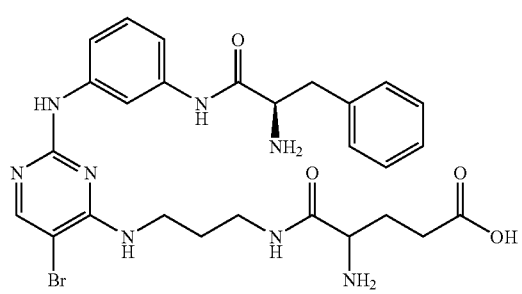 |

-continued
| Example | structure |
|---|---|
| 504 | 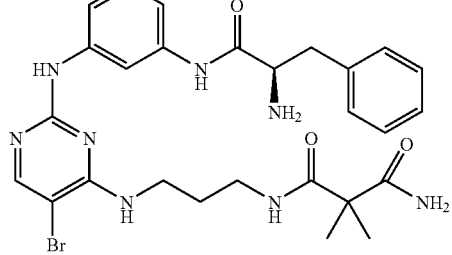 |
| 410 | 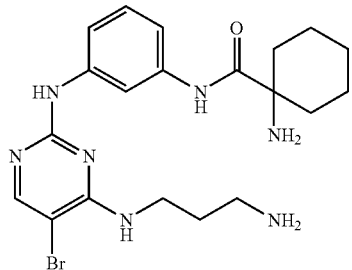 |
| 490 | 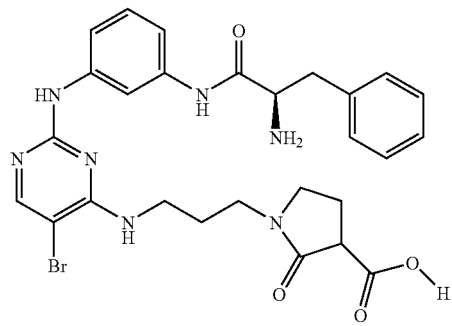 |
| 402 | 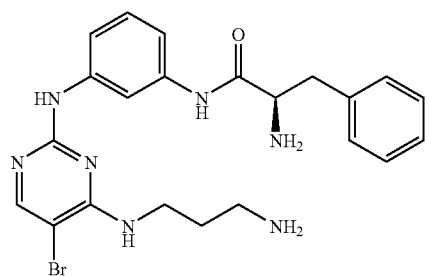 |
-continued
| Example | structure |
|---|---|
| 399 | 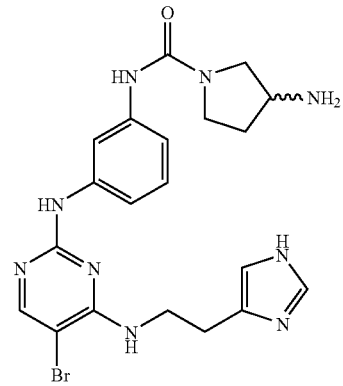 |
| 476 | 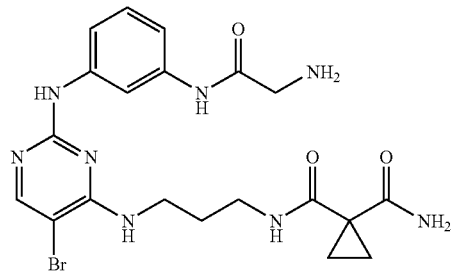 |
| 450 | 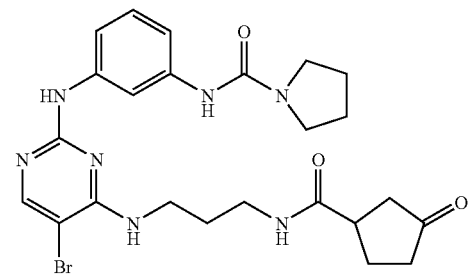 |
| 431 | 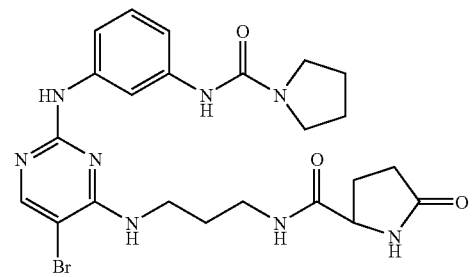 |
| 251 | 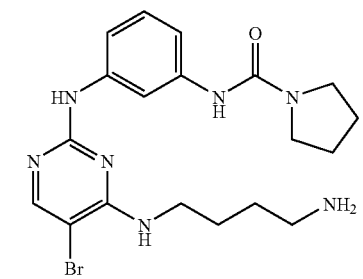 |

| Example | structure |
|---|---|
| 99 | 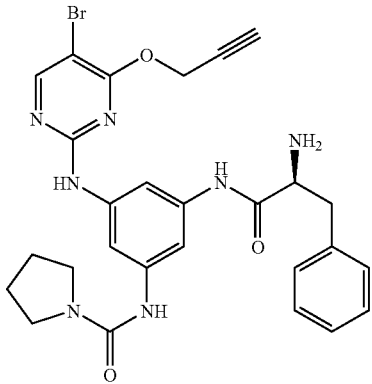 |
| A16 | 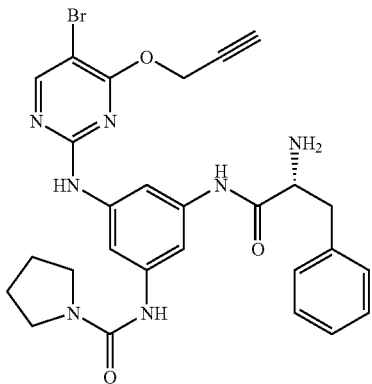 |
| A17 | 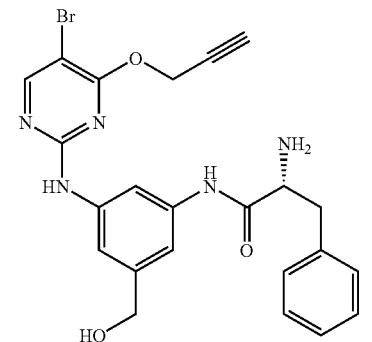 |
| A18 | 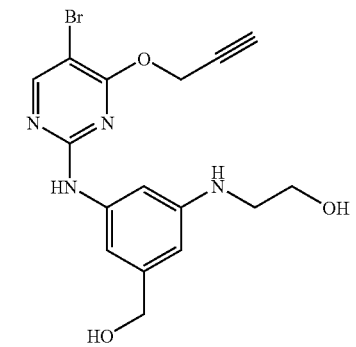 |
| Example | structure |
|---|---|
| 103 | 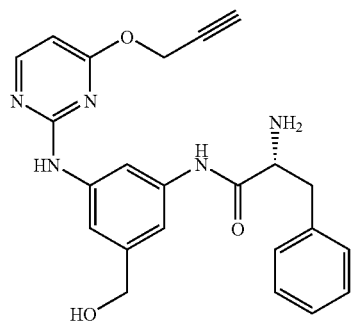 |
| 104 | 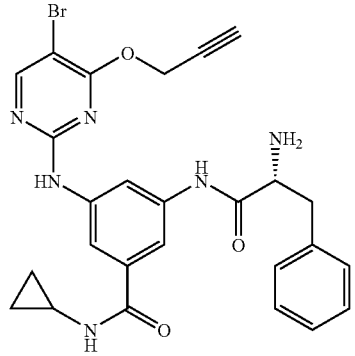 |
| 105 | 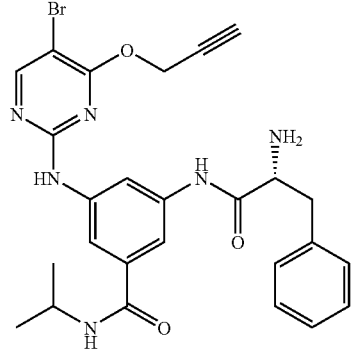 |
| A19 | 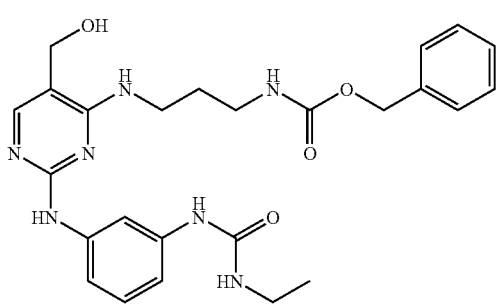 |

| Example | structure |
|---|---|
| 108 | 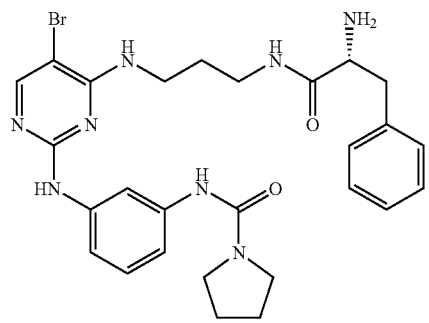 |
| 109 | 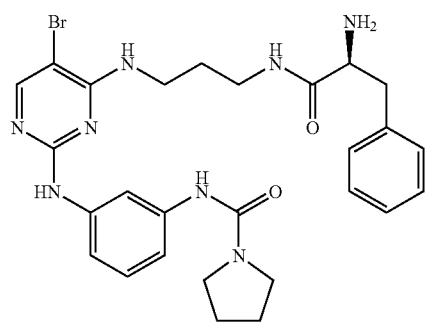 |
| 111 | 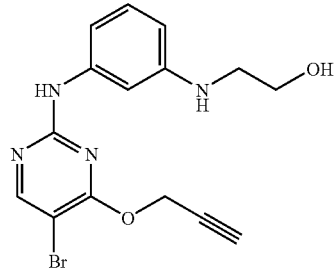 |
| 114 | 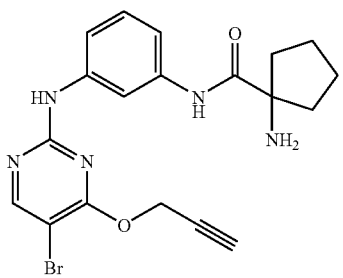 |
| 115 | 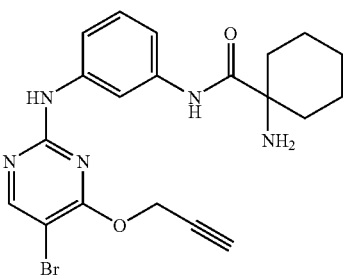 |
| Example | structure |
|---|---|
| 118 | 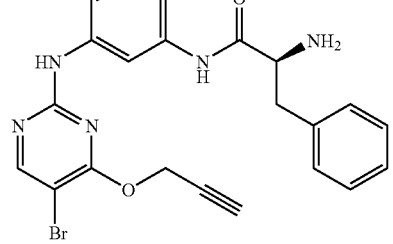 |
| 119 | 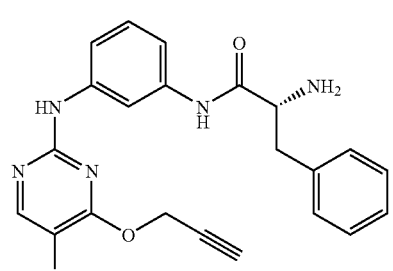 |
| 121 | 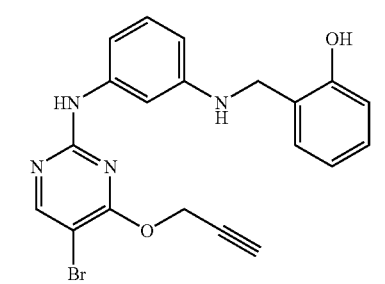 |
| 123 | 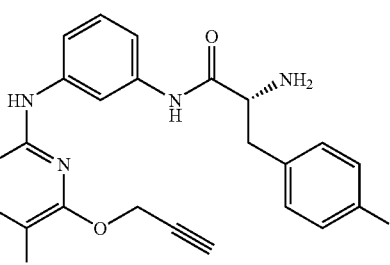 |
| 124 | 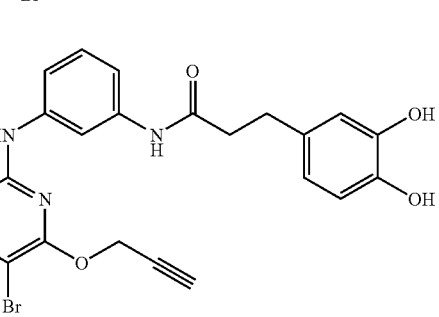 |

| Example | structure |
|---|---|
| 125 | 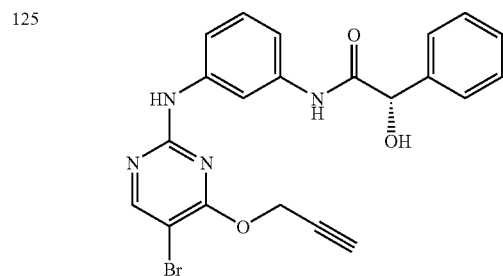 |
| 126 | 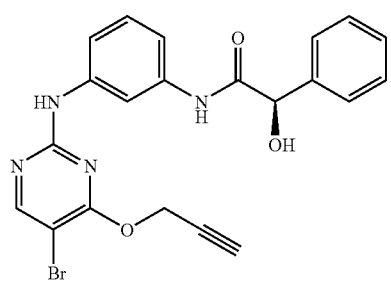 |
| 127 | 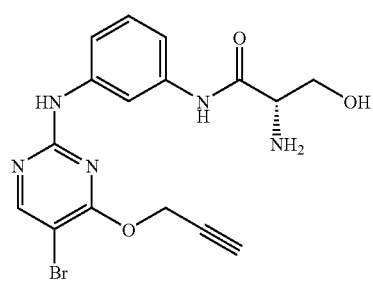 |
| 129 | 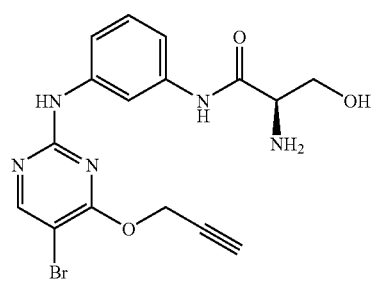 |
| 130 | 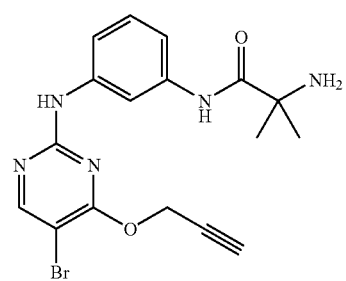 |
| Example | structure |
|---|---|
| 131 | 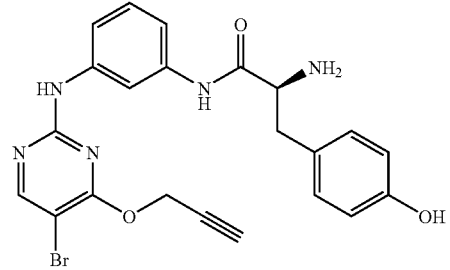 |
| 132 | 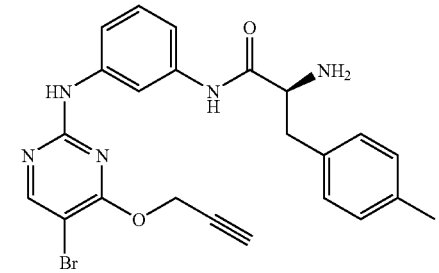 |
| 133 | 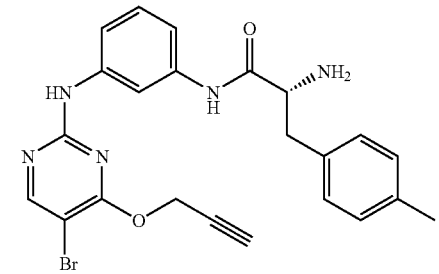 |
| 699 | 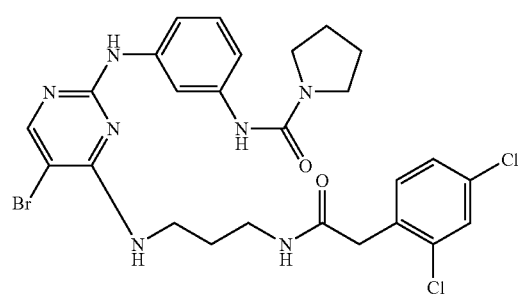 |
| 700 | 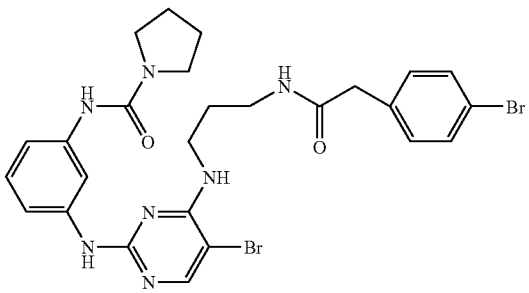 |

-continued
| Example | structure |
|---|---|
| 701 | 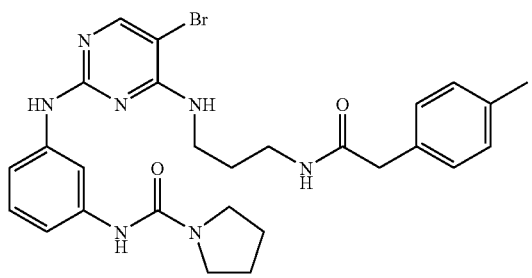 |
| 702 | 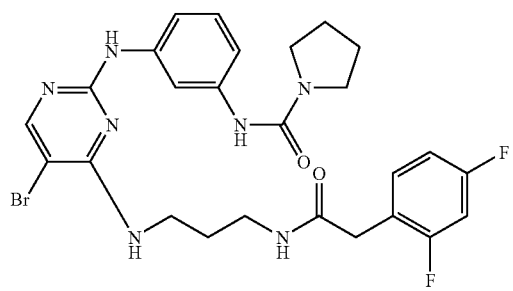 |
| 703 | 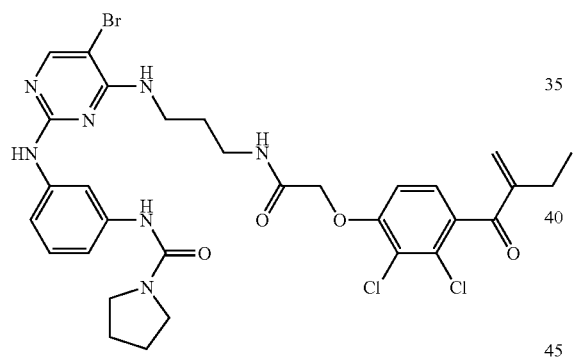 |
| 704 | 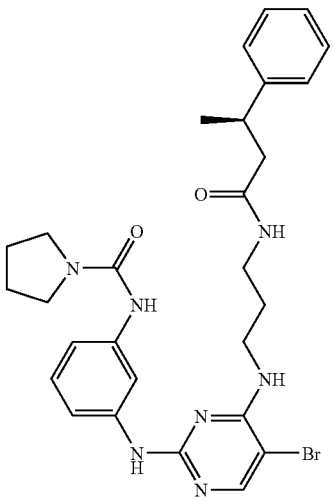 |
-continued
| Example | structure |
|---|---|
| 705 | 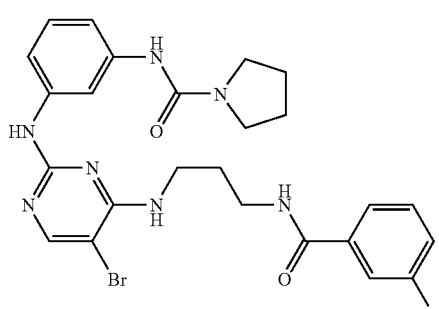 |
| Example | structure |
|---|---|
| 200 | 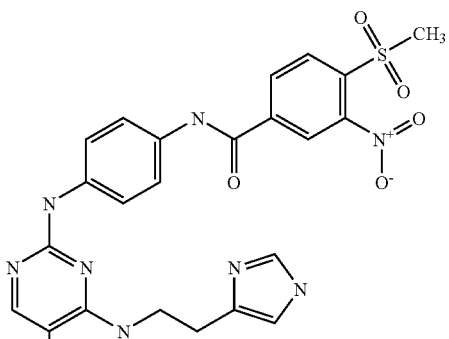 |
| 207 | |
| 222 | 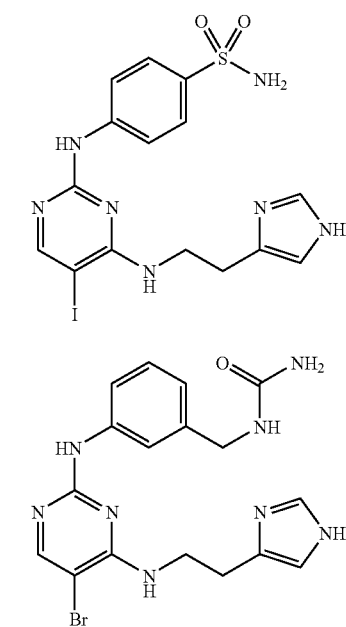 |

-continued

| Example | structure |
|---------|-----------|
| 230 | 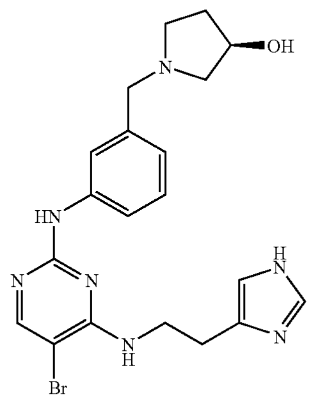 |
| 233 | 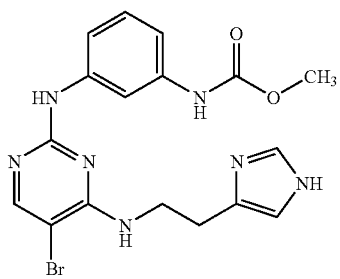 |
| 239 | 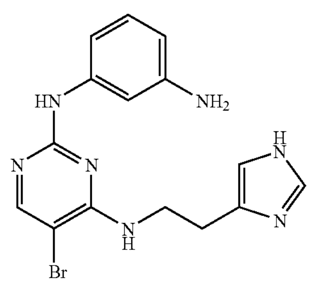 |
| 241 | 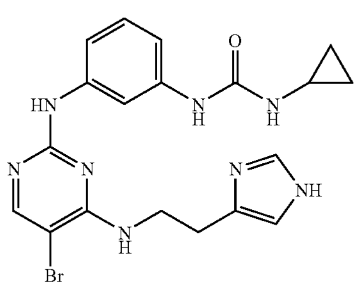 |
| 242 | 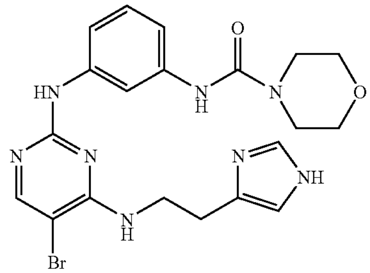 |

-continued

| Example | structure |
|---------|-----------|
| 246 | 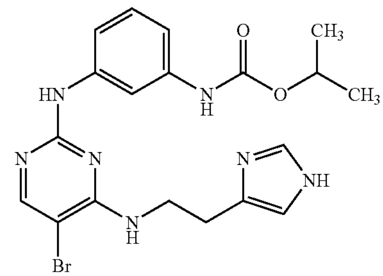 |
| 254 | 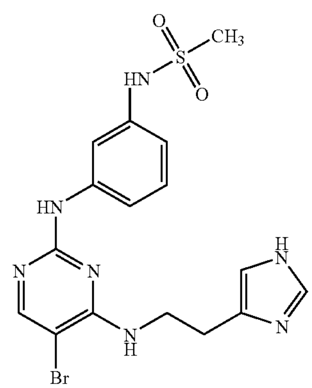 |
| 259 | 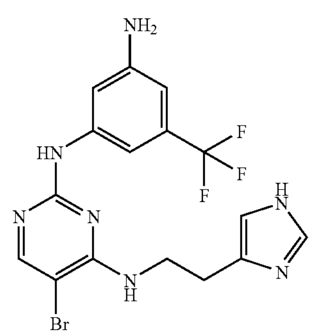 |
| 261 | 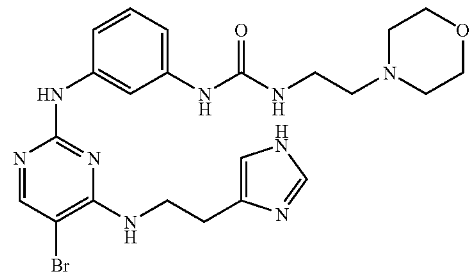 |

-continued
| Example | structure |
|---|---|
| 274 | 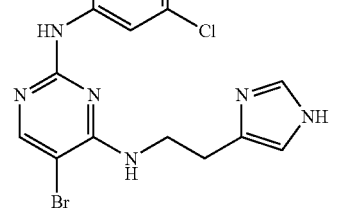 |
| 275 | 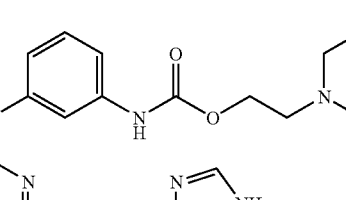 |
| 289 | 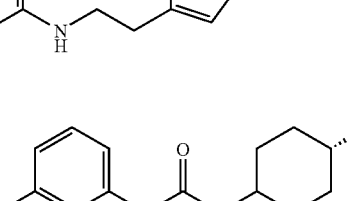 |
| 297 | 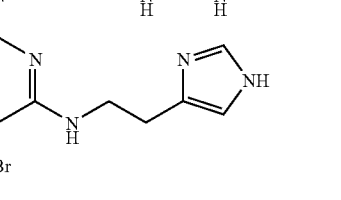 |
| 298 | 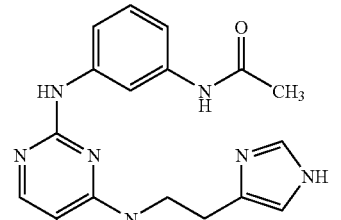 |
-continued
| Example | structure |
|---|---|
| 452 | 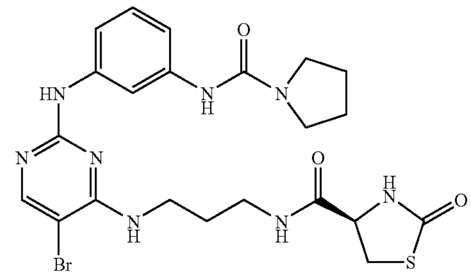 |
| 394 | 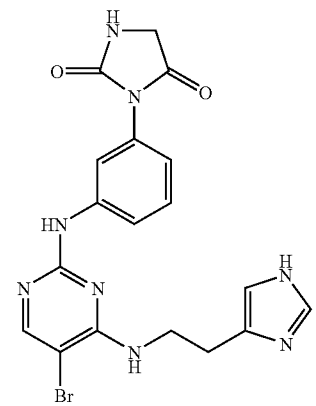 |
| 395 | 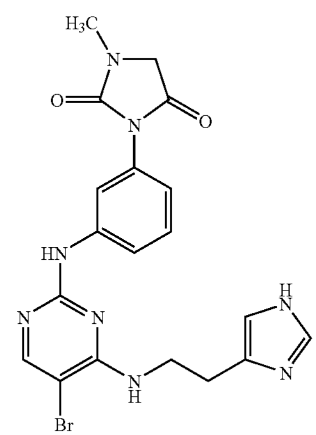 |
| 490 | 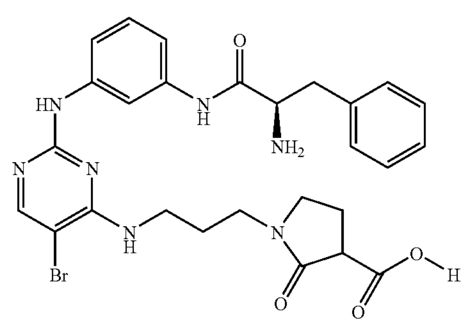 |

-continued
| Example | structure |
|---|---|
| 502 | 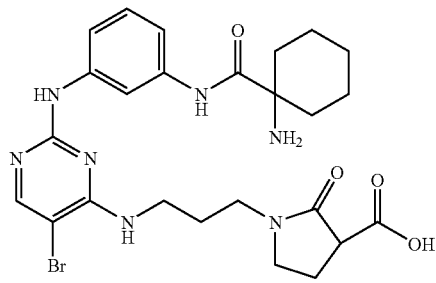 |
| 508 | 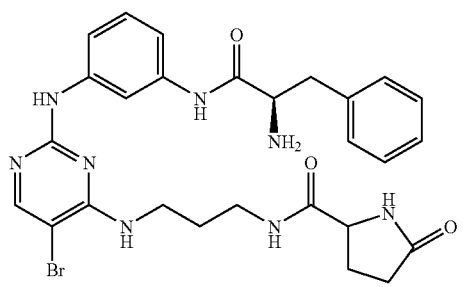 |
| 509 | 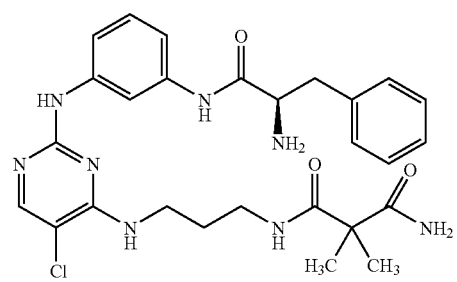 |
| 411 | 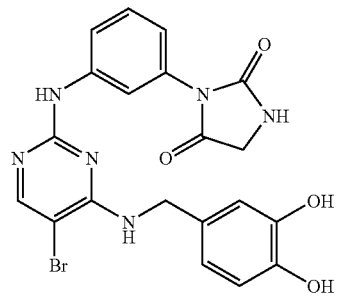 |
| 414 | 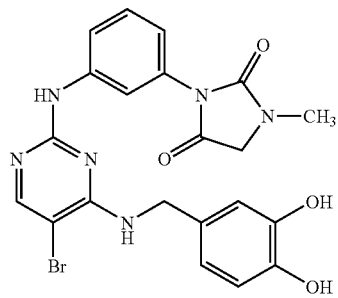 |
-continued
| Example | structure |
|---|---|
| 535 | 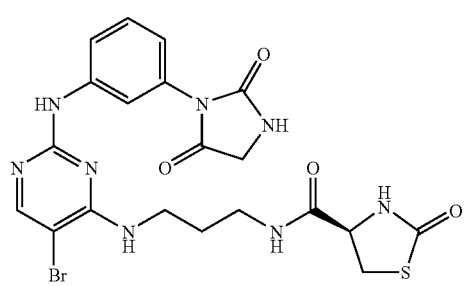 |
| 539 | 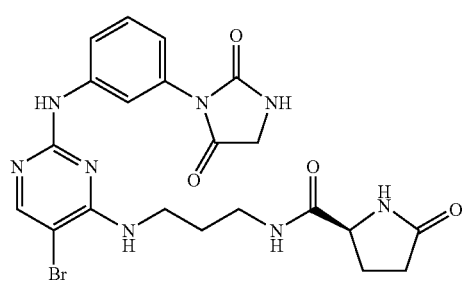 |
| 540 | 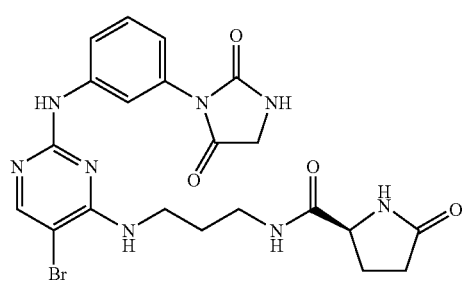 |
| 520 | 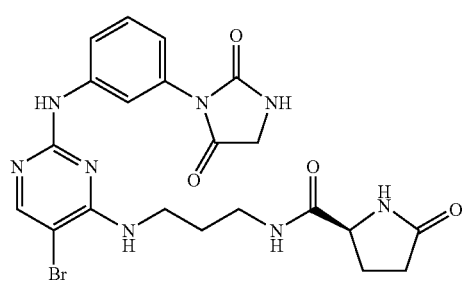 |
| 546 | 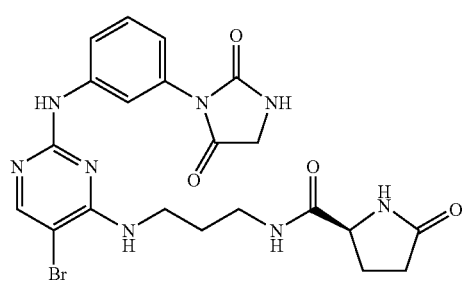 |

-continued
| Example | structure |
|---------|-----------|
| 547 | 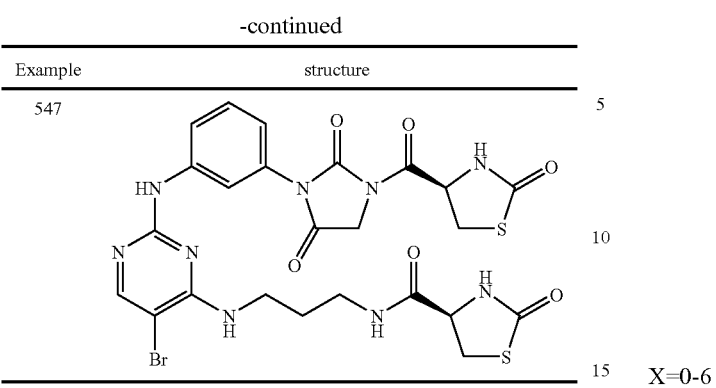 |
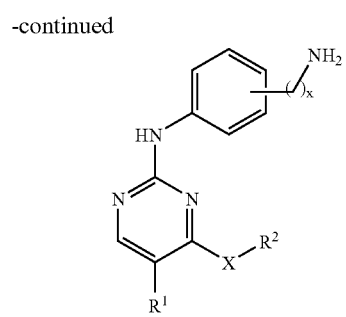
X=0-6
The following examples demonstrate the feasibility of the disclosed invention, without restricting the invention to these disclosed examples.
Synthetic Schemes
Scheme 1:
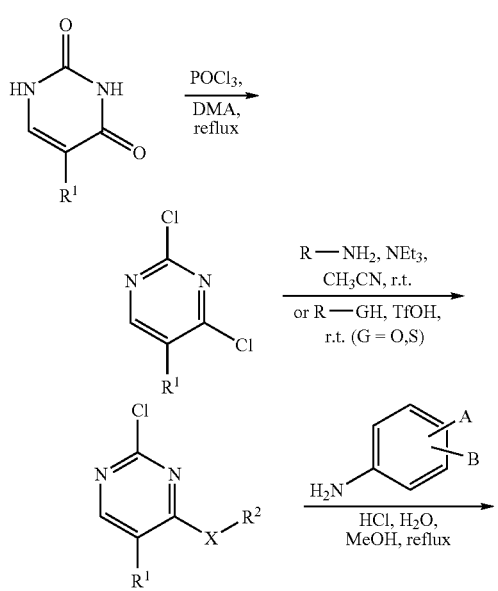
Scheme 2:
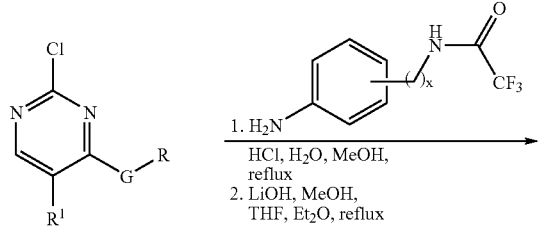
Scheme 3:
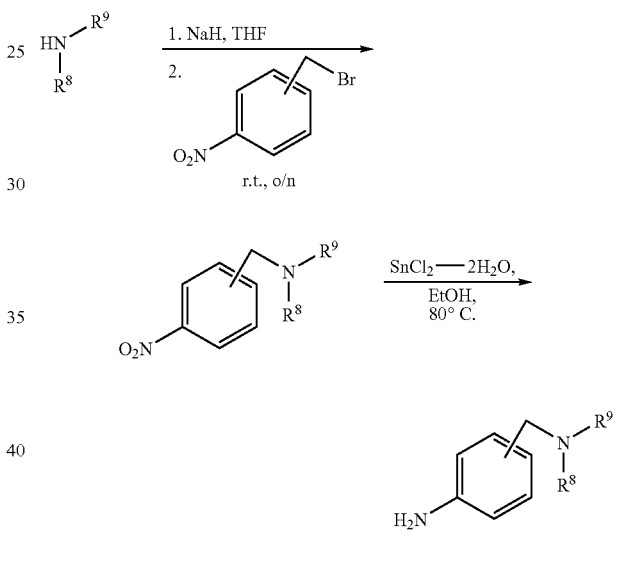
Scheme 4:
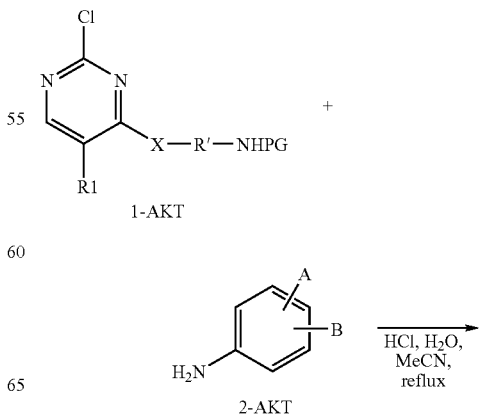

-continued
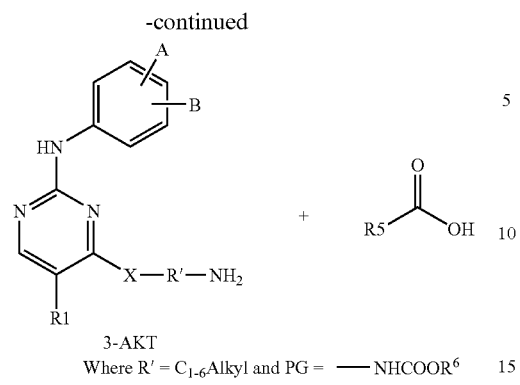
3-AKT
Where R' = C₁₋₆Alkyl and PG = —NHCOOR⁶
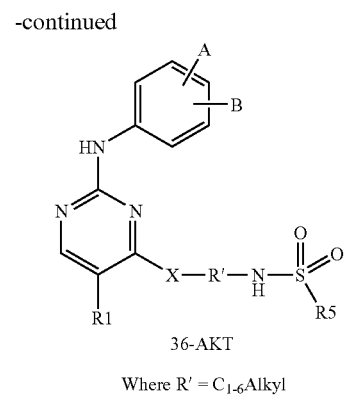
36-AKT
Where R' = C₁₋₆Alkyl
Scheme 4A
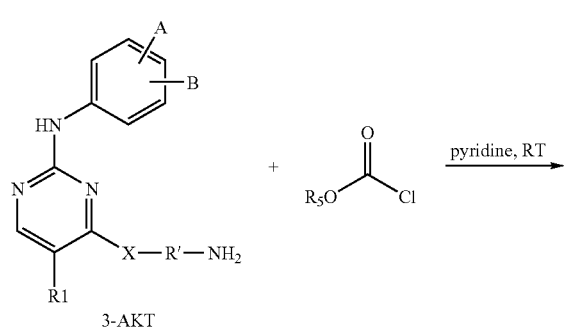
3-AKT
Scheme 4C
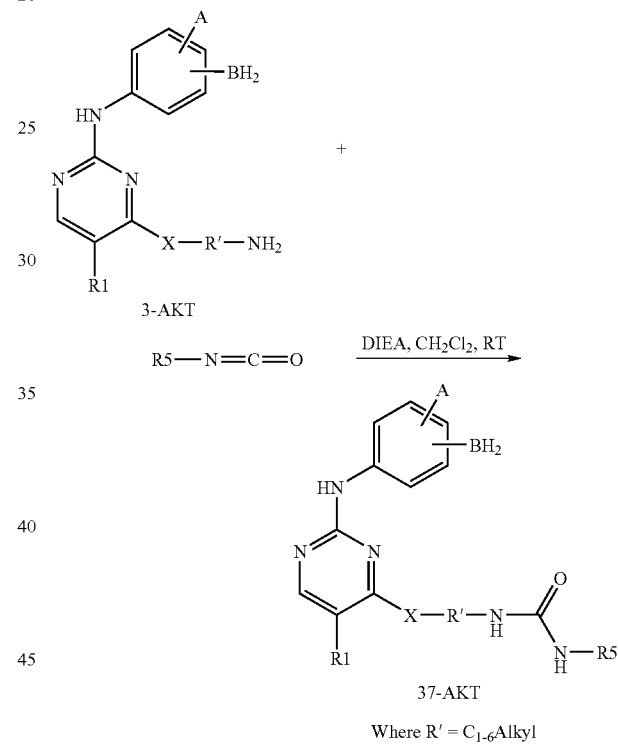
Scheme 4B
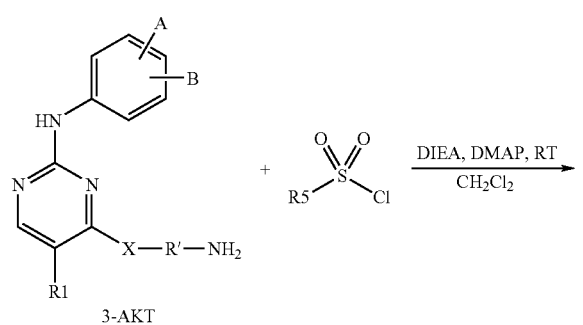
3-AKT
Scheme 4D
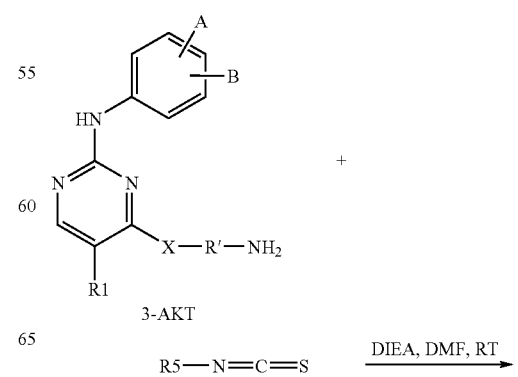

-continued
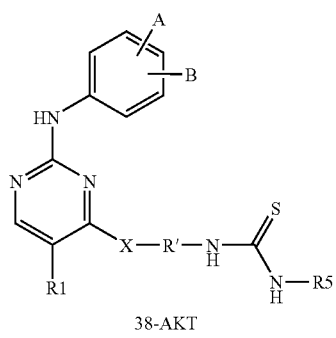
38-AKT
Where R' = C$_{1-6}$Alkyl
Scheme 4E
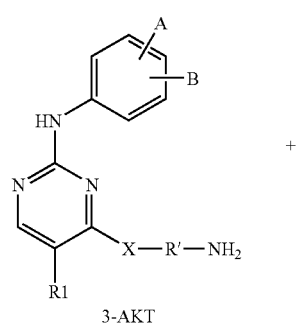
3-AKT
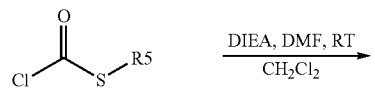
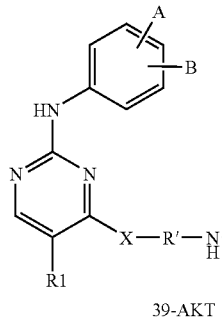
39-AKT
Where R' = C$_{1-6}$Alkyl
Scheme 4F
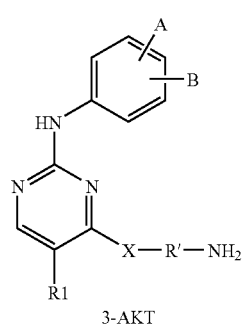
3-AKT
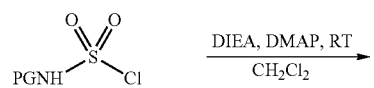
-continued
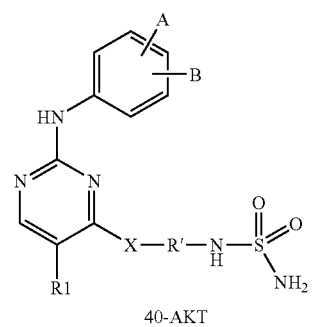
40-AKT
Where R' = C$_{1-6}$Alkyl and PG = —NHCOOR$^6$
Scheme 5
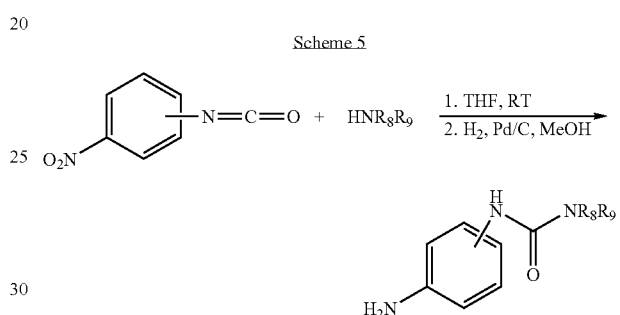
6-AKT
Where R$^8$ and R$^9$ are as described in the claims.
Scheme 6
O$_2$N—⟨⟩—N=C=O + HOR$_6$ → (1. THF, RT, o/n; 2. H$_2$, Pd/C, MeOH)
8-AKT
Where R$^5$ is as described in the claims.
Scheme 7
HN(R')—CH$_2$—C(O)OMe
9-AKT
+ O$_2$N—⟨⟩—N=C=O → (THF, RT, o/n)

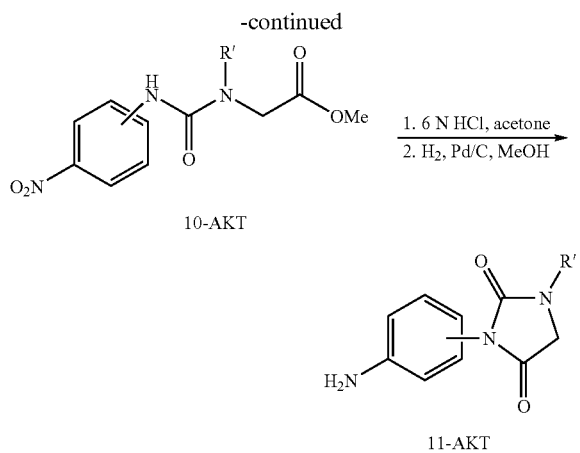
Where R' is hydrogen or methyl.
Scheme 8
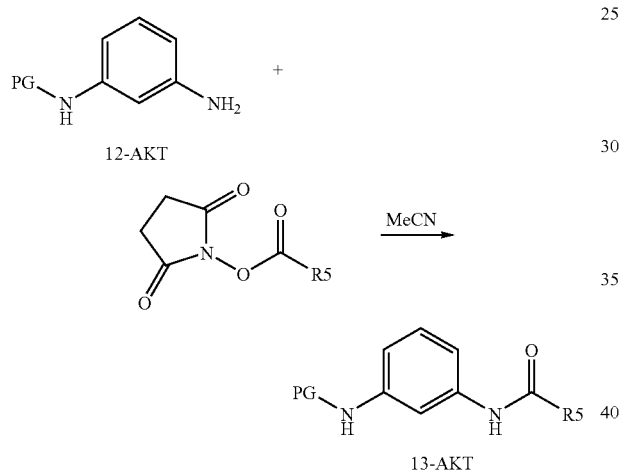
Where $R^5$ is as described in the claims and PG=—NH-COOR$^6$
Scheme 9
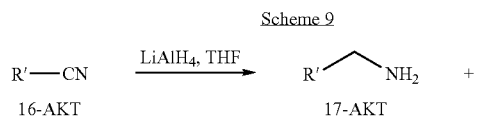
Where R' is $C_{1-6}$Aklylaryl or $C_{1-6}$Alkylheteroaryl.
Scheme 10
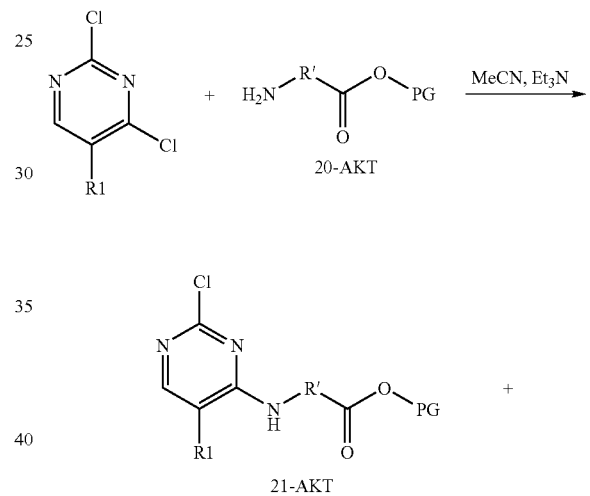
Where R' is $C_{1-6}$Alkyl, R'' is halogen, $R^8$ and $R^9$ are as described in the claims and PG=—NHCOOR$^6$.
Scheme 11
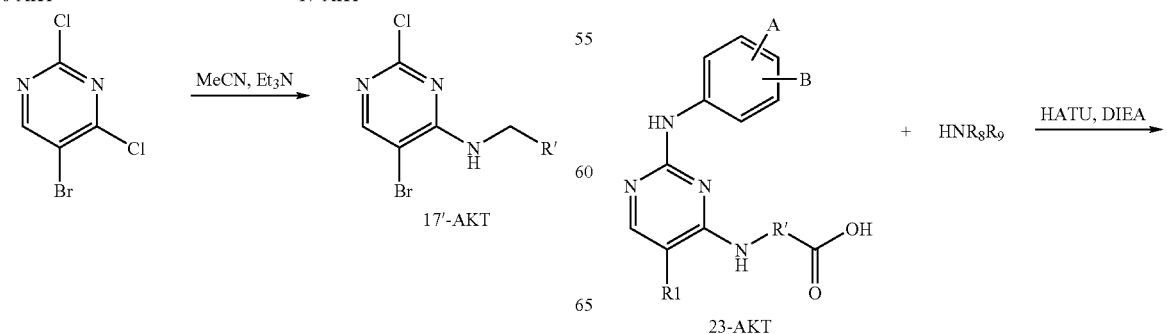

73

-continued

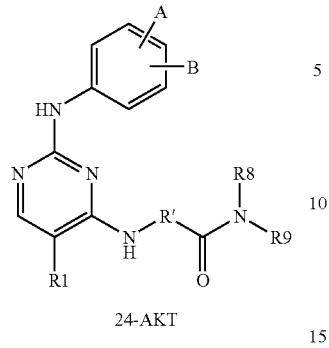

24-AKT

Where R' is $C_{1-6}$Alkyl; A, B, $R^8$, $R^9$ are as described in the claims and PG=$R^6$ as described in the claims.

Scheme 12

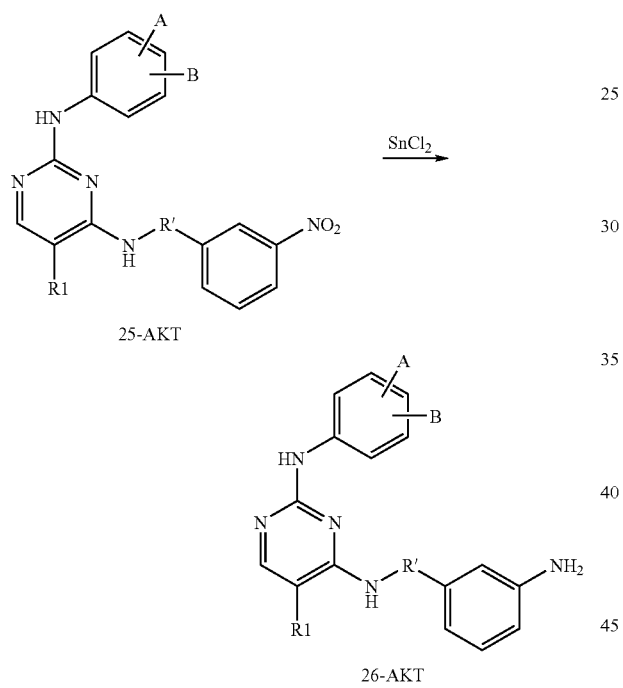

25-AKT

26-AKT

Where R' is $C_{1-6}$Alkyl; and $R^1$, A and B are as described in the claims.

Scheme 13

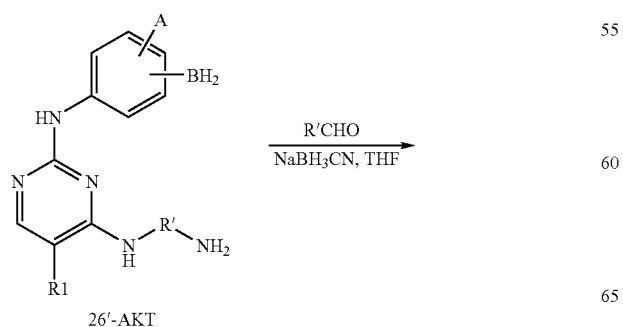

26'-AKT

74

-continued

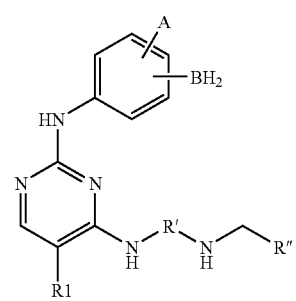

27-AKT

Where R' is $C_{1-6}$Alkyl and R" is cycloalkyl ring, heteroaryl or aryl; and $R^1$, A and B are as described in the claims.

Scheme 14

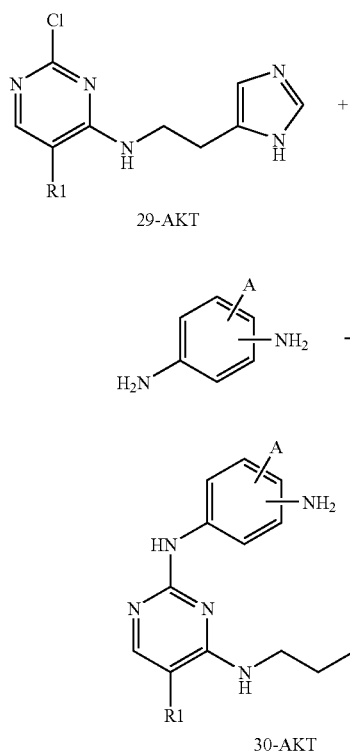

29-AKT

30-AKT

31-AKT

Where $R^1$ and A are as described in the claims.

Scheme 15

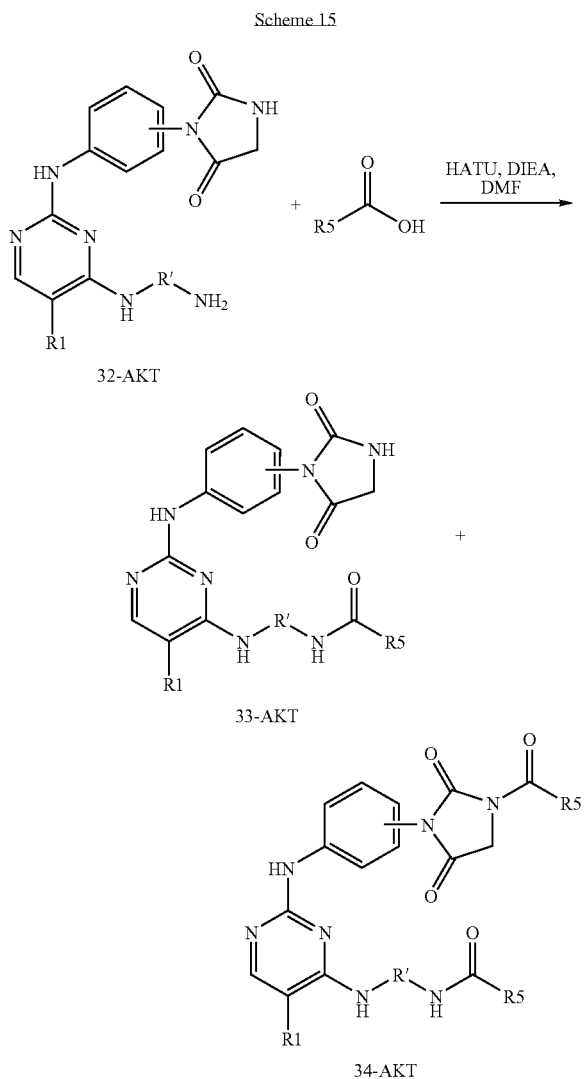

Where R' is $C_{1-6}$Alkyl and $R^1$ and $R^5$ are as described in the claims.

EXAMPLES

A. Synthesis of Compounds

The following Examples have been synthesized according to the above mentioned schemes.

A1 5-Bromo-4-(2-(1H-imidazol-4-yl)-ethylamino)-2-(4-pyrrolidin-1-ylmethyl-phenylamino)-pyrimidine 1a) 5-Bromo-2,4-dichloropyrimidine To 5-bromouracil (50 g) were sequentially added N,N-diethylaniline (60 mL) and phosphoryl chloride (120 mL), and the mixture was refluxed for 5 h. The volatiles were removed by distillation, the residue poured into ice water and the mixture extracted with methyl tert-butyl ether. The combined extracts were washed with brine, dried ($Na_2SO_4$) and filtered through Celite. Distillation of the crude product gave the title compound (63.4 g).

$^1$H NMR (300 MHz, $CDCl_3$): δ/ppm=8.69 (s, 1H).

1b) 5-Bromo-4-(2-(1H-imidazol-4-yl)-ethylamino)-2-chloro-pyrimidine

To a solution of 5-bromo-2,4-dichloropyrimidine (4.56 g) and triethylamine (3 mL) in acetonitrile (20 mL) 2-(1H-imidazol-4-yl)-ethylamine (2.45 g) was added portionwise at 0° C., and the suspension stirred at room temperature overnight. The reaction mixture was partitioned between ethyl acetate and brine, the aqueous phase extracted with additional ethyl acetate, the combined organic phases dried ($Na_2SO_4$) and evaporated, which gave, after chromatography on silica using dichloromethane/methanol, the title compound (4.41 g).

$^1$H NMR (300 MHz, $CD_3OD$): δ/ppm=2.91 (t, 2H, J=7 Hz), 3.73 (t, 2H, J=7 Hz), 6.87 (s, 1H), 7.61 (s, 1H), 8.11 (s, 1H).

1c) 4-Pyrrolidin-1-ylmethyl-phenylamin

To a suspension of sodium hydride (60% in oil, 220 mg) in THF (5 mL) pyrrolidine (391 mg) was added, the mixture stirred at r.t. for 6 h, a solution of 1-bromomethyl-4-nitrobenzene (1.08 g) in THF (8 mL) added and stirred overnight. The reaction was quenched with water and extracted with ethyl acetate, the organic phase dried ($Na_2SO_4$) and evaporated, which gave, after chromatography on silica using dichloromethane/methanol, 1-(4-nitro-benzyl)-pyrrolidine (690 mg).

$^1$H NMR (300 MHz, $CDCl_3$): δ/ppm=1.84 (m, 4H), 2.58 (m, 4H), 3.77 (s, 2H), 7.61 (dbr, 2H, J=9 Hz), 8.22 (dbr, 2H, J=9 Hz).

To a solution of 1-(4-nitro-benzyl)-pyrrolidine (1.37 g) in ethanol (66 mL) tin(II)-chloride dihydrate (9.0 g) was added portionwise and the resulting mixture refluxed for 2 h. The reaction mixture was partitioned between ethyl acetate and saturated aqueous sodium bicarbonate solution, the aqueous phase extracted with additional ethyl acetate, the combined organic phases dried ($Na_2SO_4$) and evaporated, which gave, after chromatography on silica using dichloromethane/methanol, the title compound (432 mg).

$^1$H NMR (300 MHz, $CD_3OD$): δ/ppm=1.85 (m, 4H), 2.65 (m, 4H), 3.61 (s, 2H), 6.72 (d, 2H, J=9 Hz), 7.11 (d, 2H, J=9 Hz).

1d) 5-Bromo-4-(2-(1H-imidazol-4-yl)-ethylamino)-2-4-pyrrolidin-1-ylmethyl-phenylamino)-pyrimidine A mixture of 5-bromo-4-(2-(1H-imidazol-4-yl)-ethylamino)-2-chloro-pyrimidine (60 mg), 4-pyrrolidin-1-ylmethyl-phenylamine (35 mg) and hydrochloric acid (37% in water, 40 μL) in methanol (2 mL) was refluxed overnight. The reaction mixture was partitioned between ethyl acetate and saturated aqueous sodium bicarbonate solution, the organic phase dried ($Na_2SO_4$) and evaporated, which gave, after chromatography on silica using dichloromethane/methanol, the title compound (4 mg).

$^1$H NMR (400 MHz, $CD_3OD$): δ/ppm=2.09 (m, 4H), 3.02 (t, 2H, J=7 Hz), 3.31 (m, 4H), 3.79 (t, 2H, J=7 Hz), 4.30 (s. 2H), 7.11 (s, 1H), 7.40 (d, 2H, J=9 Hz), 7.76 (d, 2H, J=9 Hz), 7.97 (s, 1H). 8.19 (s, 1H).

A2

2-(4-(Aminomethyl)-phenylamino)-4-(prop-2-ynylamino)-5-trifluoromethyl-pyrimidine 2a) 2,4-Dichloro-5-trifluoromethyl-pyrimidine To 5-trifluoromethyluracil (25 g) were sequentially added N,N-diethylaniline (25 g) and phosphoryl chloride (94 g), and the mixture was refluxed for 18 h. After cooling to r.t. the solution was poured onto ice (100 g), stirred for 10 min. and extracted with diethyl ether The combined organic phases were washed with saturated aqueous sodium carbonate solution and water, dried (Na$_2$SO$_4$), and filtered. After removal of most of the ether, distillation of the residue at 190° C. and 860 to 300 mbar gave the title compound (5.8 g).

$^1$H NMR (300 MHz, CDCl$_3$): δ/ppm=8.83 (s, 1H).

2b) 2-chloro-4-(prop-2-ynylamino)-5-trifluoromethyl-pyrimidine

To a solution of 2,4-dichloro-5-trifluoromethyl-pyrimidine (3-47 g) in acetonitrile (16 mL) a solution of propargylamine (1.76 g) in acetonitrile (16 mL) was added dropwise at 0° C., the mixture warmed to r.t. and stirred at r.t. for 48 h. The suspension was diluted with ethyl acetate, washed with brine, dried (Na$_2$SO$_4$), and evaporated. Purification by flash chromatography on silica using hexane/methyl tert-butyl ether gave the title compound (1.97 g).

$^1$H NMR (400 MHz, CDCl$_3$): δ/ppm=2.34 (t, 1H, J=1.5 Hz), 4.37 (dd, 2H, J=1.5/5 Hz), 5.53 (brs, 1H), 8.33 (s, 1H).

2c) 2-(4-(Aminomethyl)-phenylamino)-4(prop-2-ynylamino)5-trifluoromethyl-pyrimidine A mixture of 2-chloro-4-(prop-2-ynylamino)-5-trifluoromethyl-pyrimidine (235 mg), N-(4-aminobenzyl)-2,2,2-trifluoro-acetamide (410 mg) and hydrochloric acid (37% in water, 0.2 mL) in methanol (5 mL) was refluxed for 1 h. The reaction mixture was partitioned between ethyl acetate and saturated aqueous sodium bicarbonate solution, the aqueous phase extracted with ethyl acetate, the combined organic phases dried (Na$_2$SO$_4$), concentrated, filtered through silica using dichloromethane/methanol, and the filtrate evaporated. To a solution of the residue in methanol (9 mL), tetrahydrofuran (9 mL) and diethyl ether (4-5 mL) was added lithium hydroxide (150 mg) and the mixture was refluxed for 6 h, after which it was partitioned between ethyl acetate and saturated aqueous sodium bicarbonate solution. The aqueous phase was extracted with additional ethyl acetate, the combined organic phases dried (Na$_2$SO$_4$) and evaporated, which gave, after chromatography on silica using dichloromethane/methanol, the title compound (120 mg).

$^1$H NMR (300 MHz, CD$_3$OD): δ/ppm=2.55 (t, 1H, J=1.5 Hz), 4.07 (s, 2H), 4.26 (d, 2H, J=1.5 Hz), 7.39 (d, 2H, J=8 Hz), 7.86 (d, 2H, J=8 Hz).

A3

N-(3-((2-((4-(aminosulfonyl)phenyl)amino)-5-bromo-4-pyrimidinyl)amino)propyl)-1H-pyrrole-2-carboxamide 3a) (3-((5-bromo-2-chloro-4-pyrimidinyl)amino)propyl)-carbamic acid tert-butyl ester To a solution of 5-bromo-2,4-dichloro-pyrimidine (1.4 g) in acetonitrile (10 mL) at 0° C. was added triethylamine (0.94 mL) and 3-aminopropylcarbamic acid-1,1-dimethylethyl ester (1.0 g). After removing the cooling bath the reaction mixture was stirred overnight at room temperature. The reaction mixture was concentrated and to the residue water (20 mL) was added. The precipitate was collected, washed with water and ether to afford the title compound (1.8 g).

$^1$H NMR (400 MHz, DMSO-d$_6$): δ/ppm=1.34 (s, 9H), 1.62 (m, 2H), 2.93 (m, 2H), 3.36 (m, 2H), 6.78 (t, 1H), 7.64 (t, 1H), 8.22 (s, 1H).

3b) 4-((4-((3-aminopropyl)amino)5-bromo-2-pyrimidinyl)amino)-benzenesulfonamide hydrochloride To a solution of 4-aminobenzenesulfonamide (190 mg) in acetonitrile (20 mL), hydrochloric acid solution (4M in dioxane, 0.3 mL) and water (0.3 mL) was added (3-((5-bromo-2-chloro-4-pyrimidinyl)amino)propyl)-carbamic acid-1,1-dimethylethyl ester (360 mg). The resulting mixture was refluxed overnight. The precipitate was collected and washed with acetonitrile and methanol to afford the title compound (320 mg).

$^1$H NMR (400 MHz, DMSO-d$_6$): δ/ppm=1.86 (m, 2H), 2.78 (m, 2H), 3.51 (m, 2H), 7.23 (s, 2H), 7.75 (d, 2H), 7.79 (d, 2H), 7.96 (m, 3H), 8.19 (s, 1H), 10.38 (t, 1H).

3c) N-(3-((2-((4-(aminosulfonyl)phenyl)amino)-5-bromo-4-pyrimidinyl)amino)propyl)-1H-pyrrole-2-carboxamide trifluoroacetate 4-((4-((3-aminopropyl)amino)-5-bromo-2-pynmidinyl)amino)-benzenesulfonamide (120 mg) was suspended in dimethylformamide (5 mL). 2-Pyrrolecarboxylic acid (50 mg), O-(7-azabenzotriazol-1-yl)-N,N,N',N'-tetramethyluronium hexafluorophosphate (180 mg), and diisopropylethylamine (0.3 mL) were added and the resulting mixture was stirred at room temperature for 15 min. Purification by HPLC chromatography using acetonitrile/water gave the title compound (65 mg).

$^1$H NMR (400 MHz, DMSO-d$_6$): δ/ppm=1.78 (m, 2H), 3.27 (m, 2H), 3.44 (m, 2H), 6.03 (d, 1H), 6.71 (s, 1H), 6.80 (s, 1H), 7.14 (s, 2H), 7.42 (t, 1H), 7.68 (d, 2H), 7.83 (d, 2H), 8.04 (t, 1H), 8.11 (s, 1H), 9.78 (s, 1H), 11.39 (s, 1H).

A4

N-[3-[[(2R)-2-Amino-1 oxo-3-phenylpropyl]amino]-5-[[5-bromo-4-(prop-2-ynyloxy)pyrimidin-2-yl]amino]phenyl]pyrrolidine-1-carboxamid 4a) Methyl3-amino-5-[[5-bromo(prop-2-ynyloxy)pyrimidin 2yl]amino]benzoate A mixture of 5-bromo-2-chloro-4-(prop-2-ynyloxy)pyrimidine (15 g), methyl 3,5-diaminobenzoate (45 g) and concentrated hydrochloric acid (15 ml) in methanol (600 ml) was stirred at 65° C. for 8 h. After concentration to half the volume water was added and the precipitate collected by filtration. The precipitate then was treated with sodium hydroxide solution (1 n) and dichloromethane. The organic phase then was washed with water and brine, dried (Na$_2$SO$_4$) and evaporated to dryness to give the title compound (13.8 g).

Mp.: 207.5-209° C.

4b) Methyl 5-[[5-bromo-4-(prop-2-ynyloxy)pyrimidin-2-yl]amino]-3-[[(2R)-2-[[(1,1-dimethyletoxy)carbonyl]amino]-1-oxo-3-phenylpropyl]amino]benzoate N-BOC-D-phenylalanine (3-3 g), 1-hydroxy-1H-benzotriazole hydrate(1.9 g) and N-[3-(dimethylamino)propyl]-N'-ethylcarbodiimid hydrochloride (2.37 g) were stirred in DMF (30 ml) for 30 minutes. Then methyl 3-amino-5-[[5-bromro-4-(prop-2-ynyloxy)pyrimidin-2-yl]amino]benzoate (3.88 g) were added and the mixture stirred over night. Then ethyl acetate (500 ml) was added and the reaction mixture washed subsequently with hydrochloric acid (0.1 n), saturated NaHCO$_3$-solution, water and brine. After drying (Na$_2$SO$_4$) the organic phase was evaporated and the residue subjected to column chromatography (ethyl acetate/dichloromethane) to yield 5.36 g of the title compound.

ESI-MS: 624 and 626 (M+)

4c) 5-[[5-Bromo-4-(prop-2-ynyloxy)pyrimidin-2-yl]amino]-3-[[(2R)-2-[[(1,1-dimethylethoxy)carbonyl]amino]-1-oxo-3-phenylpropyl]amino]benzoic acid Methyl 5-[[5-bromo-4-(prop-2-ynyloxy)pyrimidin-2-yl]amino]-3-[[(2R)-2-[[(1,1-dimethylethoxy)carbonyl]amino]-1-oxo-3-phenylpropyl]amino]benzoate (1.0 g) was stirred in a mixture of tetrahydrofuran (20 ml), methanol (20 ml) and sodium hydroxide solution (2 n; 20 ml) for 48 h. After evaporation water (50 ml) was added to the residue. On neutralisation with hydrochloric acid (1 n) a precipitate formed. The precipitate was subjected to chromatography on silica gel (hexanes/ethyl acetate/methanol) to yield the title compound (450 mg).

ESI-MS: 610 and 612 (M+)

4d) 1,1-Dimethylethoxy[(1R)-2-[[3-[[5-bromo-4-(prop-2-ynyloxy)pyrimidin-2-yl]amino]-5-[[(pyrrolidin-1-yl)carbonyl]amino]phenyl]amino]-2-oxo-1-(phenylmethyl)ethyl]carbamate 5-[[5-Bromo-4-(prop-2-ynyloxy)pyrimidin-2-yl]amino]-3-[[(2R)-2-[[(1,1-dimethylethoxy)carbonyl]amino]-1-oxo-3-phenylpropyl]amino]benzoic acid (200 mg), diphenylphosphorylazide (0.75 ml) and triethylamine (0.67 ml) were refluxed in toluene (40 ml) for 1.5 h. Then pyrrolidine (0.26 ml) was added and the mixture refluxed for additional 2 h. After cooling the reaction mixture was diluted with ethyl acetate (50 ml) and subsequently washed with saturated NaHCO$_3$-solution, water and brine. After drying (Na$_2$SO$_4$) and evaporation the residue was subjected to chromatography on silica gel (hexanes/ethyl acetate) to yield the title compound (126 mg).

ESI-MS: 678 and 680 (M+)

4e) N-[3-[[(2R)-2-Amino-1-oxo-3-phenylpropyl]amino]-5[[5-bromo-4-prop-2-ynyloxy)pyrimidin-2-yl]amino]phenyl]pyrrolidine-1-carboxamide 1,1-Dimethylethoxy[(1R)-2-[[3-[[5-bromo-4-(prop-2-ynyloxy)pyrimidin-2-yl]amino]-5-[[(pyrrolidin-1-yl)carbonyl]amino]phenyl]amino]-2-oxo-1(phenylmethyl)ethyl]carbamate (105 mg) and sulfuric acid (0.5 ml; 2 n) were stirred in dioxane (5 ml) at 85° C. for 3.5 h. After cooling and dilution with water saturated NaHCO$_3$-solution was added and the resulting precipitate collected by filtration yielding the title compound (76 mg).

ESI-MS: 578 and 580 (M+)

A4A

Synthesis of [3-[[5-bromo-2-[[3-[(1-pyrrolidinylcarbonyl)amino]phenyl]amino]-4-pyrimidinyl]amino]propyl]-carbamic acid ethyl ester To a solution of N-(3-((4-((3-aminopropyl)amino)-5-bromo-2-pyrimidinyl)amino)phenyl)-1-pyrrolidinecarboxamide (150 mg, 0.30 mmol) in pyridine (5 mL) was added ethyl chloroformate (38.5 mg, 0.35 mmol) at 0° C. under N$_2$. The resulting reaction mixture was stirred at 0° C. for 1 h and then was stirred at room temperature overnight. The mixture was washed with water (3×50 mL). Then the reaction mixture was concentrated. Purification by HPLC chromatography using acetonitrile/water gave the title compound (10 mg).

$^1$H NMR (400 MHz, DMSO-d$_6$): δ/ppm=0.79(t 3H), 1.38 (t. 2H), 1.48 (m, 4H), 2.65 (m, 2H), 3.00 (m, 4H), 3.19 (m, 2H), 3.59 (m, 2H), 6.78 (m, 1H), 6.85 (m, 2H), 7.57 (s, 1H), 7.82 (m, 2H), 8.23 (m, 1H), 10.08 (s, 1H)

A4B

Synthesis of N-[3-[[5-bromo-4-[[3-[(propylsulfonyl)amino]propyl]amino]-2-pyrimidinyl]amino]phenyl]-1-pyrrolidinecarboxamide To a solution of N-(3-((4-((3-aminopropyl)amino)-5-bromo-2-pyrimidinyl)amino)phenyl)-1-pyrrolidinecarboxamide (150 mg, 0.30 mmol) in dichloromethane (4 mL) was added DIEA (0.16 mL, 0.92 mmol) and DMAP (1.4 mg, 0.011 mmol) at 0° C., then a solution of 1-propanesulfonyl chloride (51 mg, 0.36 mmol) in dichloromethane (5 mL) was added. The resulting reaction mixture was stirred at 0° C. for 1 h and at room temperature overnight. The reaction mixture was concentrated. Purification by HPLC using acetonitrile/water gave the title compound (67 mg).

$^1$H NMR (400 MHz, DMSO): δ/ppm=0.82 (t, 3H), 1.61 (m, 2H), 1.76 (m, 2H), 1.79 (m, 4H), 2.80 (m, 2H), 2.90 (m, 2H), 3.31 (m, 4H), 3.51 (m, 2H), 7.09 (m, 1H), 7.18 (m, 2H), 7.89 (s, 1H), 8.11 (s, 2H), 8.50 (m, 1H), 10.31 (s, 1H).

A4C

Synthesis of N-[3-[[5-bromo-4-[[3-[[(phenylamino)carbonyl]amino]propyl]amino]-2-pyrimidinyl]amino]phenyl]-1-pyrrolidinecarboxamide To a suspension of N-(3-((4-((3-aminopropyl)amino)-5-bromo-2-pyrimidinyl)amino)phenyl)-1-pyrrolidinecarboxamide (100 mg, 0.2 mmol) and DIEA (0.14 mL, 0.8 mmol) in 1,4-dioxane (5 mL) was added phenyl isocyanate (35 mg, 0.3 mmol). The resulting solution was stirred overnight and concentrated. The crude residue was directly purified by prep HPLC using acetonitrile/water to give the title compound (68 mg).

$^1$H NMR (400 MHz, DMSO-d$_6$), δ/ppm=1.71 (m, 2H), 1.84 (m, 4H), 3.09 (m, 2H), 3.36 (m, 4H), 3.48 (m, 2H), 6.21 (t, 1H), 6.83 (t, 1H), 7.05 (m, 1H), 7.19 (m, 4H), 7.36 (m, 2H), 7.84 (br s, 1H), 7.92 (s, 1H), 8.16 (s, 2H), 8.47 (s, 1H), 9.71 (s, 1H).

A4D

Synthesis of N-[3-[[5-bromo-4-[[3-[[(ethylamino)thioxomethyl]amino]propyl]amino]-2-pyrimidinyl]amino]phenyl]-1-pyrrolidinecarboxamide A solution of N-(3-((4-((3-aminopropyl)amino)-5-bromo-2-pyrimidinyl)amino)phenyl)-1-pyrrolidinecarboxamide (100 mg, 0.20 mmol) and DMF (5 mL) was treated with DIEA (0.1 mL, 0.6 mmol, 3eq) and ethylthioisocyanate (15 mg, 0.17 mmol, 0.9 eq). The resulting mixture was stirred at RT for 2 hr. Then the crude mixture was purified by HPLC using acetonitrile/water to afford the title compound (82 mg).

$^1$H NMR (400 MHz, DMSO-d$_6$): δ/ppm=1.02 (t, 3H). 1.74 (m, 2H), 1.82 (m, 4H), 3.30-3.48 (m, 8H), 7.04-7.16 (m, 3H), 7.37 (m, 2H), 7.88 (s, 1H), 8.08 (m, 2H).

A4E

Synthesis of [3-[[S-bromo-2-[[3-[(1-pyrrolidinylcarbonyl)amino]phenyl]amino]-4-pyrimidinyl]amino]propyl]-carbamothioic acid S-ethyl ester A solution of N-(3-((4-((3-aminopropyl)amino)-5-bromo-2-pyrimidinyl)amino)phenyl)-1-pyrrolidinecarboxamide (150 mg, 0.30 mmol), DMF (1.5 mL) and dichloromethane (5 mL) was treated with DIEA (0.2 mL, 1.15 mmol, 4 eq.) and the was treated dropwise with a solution of ethyl chlorothioformate (41 mg, 0.33 mmol, 1.1eq) and dichloromethane (1 mL). The resulting mixture was stirred at rt. for 30 mins. Then the reaction mixture was diluted with dichloromethane (30 mL), washed with water (3×20 mL) and concentrated. The crude product was purified by chromatography on SiO$_2$ using ethyl acetate/methanol to afford the titile compound (112 mg).

¹H NMR (400 MHz, DMSO-d₆): δ/ppm=1.14 (t, 3H), 1.68 (m, 2H), 1.82 (m, 4H), 2.74 (q, 2H), 3.13 (m, 2H), 3.35 (m, 4H), 3.42 (m, 2H), 6.89 (t, 1H), 6.94 (d, 1H), 7.05 (t, 1H), 7.23 (d, 2H), 7.86 (s, 1H), 7.95 (m, 2H), 8.12 (t, 1H), 9.06 (s, 1H).

A4F

Synthesis of N-[3-[[4-[[3-[(aminosulfonyl)amino]propyl]amino]-5-bromo-2-pyrimidinyl]amino]phenyl]-1-pyrrolidinecarboxamide Chloro[[(1,1-dimethylethoxy)carbonyl]amino]-sulfane dioxide was prepared by adding chlorosulfonyl isocyanate (32 mg, 0.23 mmol, 1.0 eq.) to a cooled solution of tert-butyl alcohol (17 mg, 0.23 mmol, 1.0eq.) and dichloromethane (2 mL) in an ice-water bath. The resulting mixture was stirred at 0-5° C. for 2-3 hr. The solution was then treated with a solution of N-(3-((4-((3-aminopropyl)amino)-5-bromo-2-pyrimidinyl)amino)phenyl)-1-pyrrolidinecarboxamide (100 mg, 0.20 mmol, 1eq.) and dichloromethane (5 mL). DMAP (20 mg, 0.16 mmol) was then added followed by the dropwise addition of DIEA (0.1 mL, 0.57 mmol). The mixture was stirred at RT for overnight. The reaction mixture was concentrated in vacuo. The residue was dissolved in TFA (2 mL), and purified by HPLC using acetonitrile/water to afford the title compound (30 mg).

¹H NMR (400 MHz, DMSO-d₆): δ/ppm=1.76 (m, 2H), 1.82 (m, 4H), 2.92 (m, 2H), 3.36 (m, 4H) 3.45 km, 2H), 6.48 (s, 2H), 7.04 (d, 1H), 7.14 (t, 1H), 7.21 (d, 2H), 7.82 (s, 1H), 8.05 (m, 2H).

A5

N-(3-aminophenyl)-urea (A5)

Ammonia was bubbled into a solution of 3-nitrophenylisocyanate (1.5 g, 9.1 mmol) for ten minutes. The reaction mixture was then concentrated and the resulting yellow solid was washed with ether (200 mL) to afford N-(3-nitrophenyl)-urea (1.35 g, 7.5 mmol).

A solution of N-(3-nitrophenyl)-urea (1.0 g, 5-5 mmol) and methanol (40 mL) was treated with 10% Pd/C (250 mg) and placed under H₂ (45 psi) for 2 h. The mixture was then filtered through celite and concentrated to afford N-(3-aminophenyl)-urea (828 mg, 5.5 mmol).

¹H NMR (400 MHz, DMSO): δ/ppm=4.90 (s, 2H), 5.66 (s, 2H), 6.08 (dm, J=8 Hz, 1H), 6.43 (dm, J=8 Hz, 1H), 6.70 (t, J=1.6 Hz, 1H), 6.80 (t, J=8 Hz, 1H), 8.13 (s, 1H).

A6

(3-aminophenyl)-2-(4-morpholinyl)-carbamic acid ethyl ester 6a) 2-(4-morpholinyl)-(3-nitrophenyl)-carbamic acid ethyl ester A solution of 3-nitrophenyl isocyanate (0.5 g, 3.0 mmol) and 4-(2-aminoethyl)morpholine (0.5 mL, 3.8 mmol, 1.3 equiv.) in tetrahydrofuran (20 mL) was stirred for 3 h. The reaction mixture was concentrated and purified by chromatography (SiO₂) using hexane/ethyl acetate to afford 2-(4-morpholinyl)-(0.3-nitrophenyl)-carbamic acid ethyl ester (0.5 g).

¹H NMR (400 MHz, CDCl₃): δ/ppm=2.52 (m, 4H), 2.58 (m, 2H), 3.39 (m, 2H), 3.76 (m, 4H), 5.35 (br s, 1H), 7.43 (t, 1H), 7.87 (m, 2H), 8.20 (m, 1H)

6b) (3-aminophenyl)-2-(4-morpholinyl)-carbamic acid ethyl ester

A solution of 2-(4-morpholinyl)-(3-nitrophenyl)-carbamic acid ethyl ester (0.5 g, 1.7 mmol) and methanol (50 mL) was treated with 10% Pd/C (150 mg) and placed under H₂ (50 psi) for 2 h. The mixture was then filtered through celite and concentrated to afford the title compound (320 mg).

¹H NMR (400 MHz, CDCl₃): δ/ppm=2.52 (m, 4H), 2.68 (m, 2H), 3.52 (br s, 2H), 3.74 (m, 4H), 4.31 (m, 2H), 6.39 (m, 1H), 6.58 (m, 1H), 6.68 (br s, 1H), 6.94 (br s, 1H), 7.09 (m, 1H).

A7

3-(3-Aminophenyl)-2,4-imidazolidinedione

7a) [[(3-nitrophenyl)amino]carbonyl]aminoacetic acid methyl ester

To a suspension of 3-nitrophenyl isocyanate (10 g, 61 mmol) and glycine methyl ester hydrochloride (8.4 g, 67 mmol, 1.1 equiv.) in dichloromethane (250 mL) was added triethylamine (10 mL, 72 mmol, 1.2 equiv.) at 0° C. The resulting solution was stirred at room temperature overnight. The resulting dark brown solution was concentrated and triturated in water to give a light yellow suspension. The suspension was filtered and the filter cake was washed with water and air-dried to give [[[(3-nitrophenyl)amino]carbonyl]aminoacetic acid methyl ester (15 g) in quantitative yield.

¹H NMR (400 MHz, DMSO-d₆): δ/ppm=3.64 (s, 3H), 3.89 (d, 2H), 6.67 (t, 1H), 7.52 (t, 1H), 7.68 (dd, 1H), 7.76 (dd, 1H), 8.51 (s, 1H), 9.38 (br s, 1H).

7b) 343-nitrophenyl)-2,4-imidazolidinedione

A suspension of [[[(3-nitrophenyl)amino]carbonyl]aminoacetic acid methyl ester (6.9 g, 27 mmol) in 6N aqueous hydrochloride solution (40 mL) and acetone (20 mL) was stirred at reflux overnight. The resulting solution was cooled and concentrated. The resulting yellowish suspension was filtered and the filter cake was washed with water (50 mL), aqueous sodium bicarbonate solution (50 mL), and air-dried to afford the title compound (4.4 g).

¹H NMR (400 MHz, DMSO-d₆): δ/ppm=4.09 (s, 2H), 7.78 (t, 1H), 7.89 (dd, 1H), 8.23 (dd, 1H), 8.31 (d, 1H) 8.49 (br s, ₁H).

7c) 3-(3-Aminophenyl)-2,4-imidazolidinedione

A solution of 3-(3-nitrophenyl)-2,4-imidazolidinedione (4.4 g, 20 mmol) and methanol (100 mL) was treated with 10% Pd/C (1.0 g) and placed under H₂ (40 psi) for 2 h. The mixture was then filtered through celite and concentrated to afford the title compound (3.8 g).

¹H NMR (400 MHz, DMSO-d₆): δ/ppm=4.02 (s, 2H), 5.23 (br s, 2H), 6.39 (d, 1H), 6.47 (s, 1H), 6.54 (d, 1H), 7.06 (t, 1H), 8.19 (br s, 1H).

A8

D-[2-[(3-Aminophenyl)amino]-2-oxo-1-(phenylmethyl)ethyl]-carbamic acid tert-butyl ester A solution of 1,3-phenylenediamine (1.0 g, 10 mmol, 2 equiv.) and N-tert-butoxycarbonyl-D-phenylalanine hydroxysuccinimide ester (1.8 g, 5 mmol, 1 equiv.) in acetonitrile (40 mL) was stirred overnight. The reaction mixture was concentrated and purified by chromatography (SiO₂) using dichloromethane/methanol to afford the title compound (1.2 g).

¹H NMR (400 MHz, CDCl₃): δ/ppm=1.43 (s, 9H). 3.14 (m, 2H), 3.71 (br s, 2H), 4.48 (br s, 1H), 5.21 (br s, 1H), 6.43 (m, 1H), 6.53 (br s, 1H), 7.04 (m, 2H), 7.29 (m, 5H) 7.74 (br s, 1H).

A9

5-bromo-2-chloro-N-[2-(4-thiazolyl)ethyl]4-pyrimidinamin

Lithium Aluminum hydride (95%) (1.1 g, 27.5 mmol) was suspended in dry THF (20 mL) and cooled with an ice-water bath. A solution of 1,3-thiazol-4-acetonitrile (1.0 g, 8.06 mmol) in THF (10 mL) was added dropwise. The resulting mixture was stirred at room temperature overnight. To the reaction mixture was added water (1 mL), 15% NaOH (1 mL) followed by water (3 mL). The precipitate inorganic solid was filtered, then washed with ethyl acetate (100 mL). The combined organic phase was dried ($Na_2SO_4$) and concentrate in vacuo to afford 4-thiazoleethanamine as a brown oil (400 mg, 3.12 mmol). The oil (400 mg, 3.12 mmol) was dissolved in $CH_3CN$ (10 mL), treated with $Et_3N$ (0.7 mL, 97.5 mmol) and cooled with an ice-water bath. 5-Bromo-2,4-dichloropyrimidine (800 mg, 3.51 mmol) was then added. The resulting mixture was stirred at room temperature overnight. The mixture was dried in vacuo, then purified by chromatograpy ($SiO_2$) using hexane/ethyl acetate to afford the titled compound (110 mg)

$^1$H NMR (400 MHz, $CDCl_3$): δ/ppm=3.13 (t, 2H), 3.86 (m, 2H). 6.74 (t, 1H), 7.11 (s 1H), 8.12 (s, 1H), 8.83 (s, 1H)

A10

[3-(2-thiazolylamino)propyl]-carbamic acid 1,1-dimethylethyl ester

To a solution of (3-bromopropyl)-carbamic acid 1,1-dimethylethyl ester (1.2 g, 5.0 mmol) and 2-aminothiazole (1.0 g, 10 mmol, 2 equiv.) in DMF 20 (mL) was added $Cs_2CO_3$ (2.5 g, 7.7 mmol, 1.5 equiv.). The resulting mixture was heated at 85° C. under $N_2$ overnight. The reaction mixture was diluted with ethyl acetate (200 mL), washed with water (3×200 mL), and brine (200 mL). The organic phase was dried over $Na_2SO_4$, then concentrated in vacuo to afford an oil. The crude product was purified by chromatography ($SiO_2$) using hexane/ethyl acetate to afford the title compound as a light yellow solid (300 mg).

$^1$H NMR (400 MHz, DMSO-d6): δ/ppm=1.37 (s, 9H), 1.65 (m, 2H), 2.95 (m, 2H), 3.14 (m, 2H), 6.57 (d, 1H), 6.83 (t, 1H), 6.98 (d, 1H), 7.46 (t, 1H)

A11

N-[3-[[5-bromo-4-[[3-oxo-3-(propylamino)propyl]amino]-2-pyrimidinyl]amino]phenyl]-1-pyrrolidinecarboxamide 11a) N-[5-bromo-2-[[3-[(1-pyrrolidinylcarbonyl)amino]phenyl]amino]-4-pyrimidinyl]-β-alanine To a solution of 5-bromo-2,4-dichloropyrimidine (1.0 g, 4.4 mmol, 1 equiv.) in acetonitrile (10 mL) at 0° C. was added triethylamine (0.672 mL, 4.8 mmol, 1.1 equiv.) and H-beta-Ala-OtBu HCl (0.8 g, 4.4 mmol, 1 equiv.). After removing the cooling bath the reaction mixture was stirred at room temperature overnight. The reaction mixture was concentrated and to the residue water (20 mL) was added. The precipitate was collected, washed with water and ether to afford N-(5-bromo-2-chloro-4-pyrimidinyl)-β-alanine 1,1-dimethylethyl ester (0.52 g).

To a solution of N-(5-bromo-2-chloro-4-pyrimidinyl)-□-alanine 1,1-dimethylethyl ester (348 mg, 1.2 mmol, 1 equiv.) in acetonitrile (10 mL) was added water (1.0 mL), 4.0M HCl in dioxane (1.0 mL) and N-(3-aminophenyl)-1-pyrrolidinecarboxamide (520 mg, 2.5 mmol, 2.1 equiv.). The resulting mixture was stirred at 80° C. overnight. The white suspension was filtered and washed with acetonitrile to afford the title compound (500 mg).

$^1$H NMR (400 MHz, DMSO): δ/ppm=2.15 (t, 4H), 2.79 (t, 2H), 3.55 (t, 4H), 3.89 (m, 2H), 7.45 (m, 3H), 8.10 (s, 1H), 8.40 (d, 2H). 8.80 (t, 1H), 10.65 (s, 1H).

11b) N-[3-[[5-bromo 4-[[3-oxo-3-(propylamino)propyl]amino]-2-pyrimidinyl]amino]phenyl]-1-pyrrolidinecarboxamide To a solution of N-[5-bromo-2-[[3-[(1-pyrrolidinylcarbonyl)amino]phenyl]amino]-4-pyrimidinyl]-□-alanine (200 mg, 0.45 mmol) in DMF (20 mL) was added O-(7-aza-benzotriazol-1-yl)-N,N,N',N'-tetramethyluronium hexafluorophosphate (243 mg, 0.64 mmol, 1.4 equiv.), diisopropylethylamine (0.46 mL, 2.64 mmo, 5.9 equiv.l) and propylamine (32 mg, 0.54 mmol, 1.2 equiv.). The resulting mixture was stirred at room temperature for 20 min. Purification by HPLC chromatography using acetonitrile/water gave the title compound (40 mg).

$^1$H NMR (400 MHz, DMSO-$d_6$): δ/ppm=0.50 (t, 3H), 1.07 (m, 2H), 1.54 (t, 4H), 2.16 (t, 2H), 2.70 (m, 2H), 3.08 (t, 4H), 3.45 (m, 2H), 6.80 (d, 1H), 6.92 (t, 1H), 7.02 (d, 1H), 7.63 (s, 1H), 7.69 (t, 1H), 7.91 (s, 1H), 7.96 (s, 1H), 8.39 (t, 1H), 10.13 (s, 1H)

A12

N-(3-((4-(((3-aminophenyl)methyl)amino)-5-bromo-2-pyrimidinyl)amino)phenyl)-1-pyrrolidinecarboxamide (ZK 822797/26-AKT) (SY)

N-(3-((5-bromo-4-(((3-nitrophenyl)methyl)amino)-2-pyrimidinyl)amino)phenyl)-1-pyrrolidinecarboxamide (350 mg, 0.68 mmol) was dissolved in methanol (5 mL) and ethyl acetate (15 mL), then tin(II) chloride dihydrate (1.0 g, 4.44 mmol) was added. The resulting mixture was heated to reflux for 2 hr. The reaction mixture was diluted with ethyl acetate (100 mL), then washed with 4N NaOH (60 mL) and brine (80 mL). The organic phase was dried over $Na_2SO_4$, then concentrated in vacuo to afford the titled compound (288 mg).

$^1$H NMR (400 MHz, DMSO-$d_6$): δ/ppm=1.76 (m, 4H), 3.28 (m, 4H), 4.47 (d, 2H), 4.93 (s, 2H), 6.35 (d, 1H), 6.44 (m, 2H), 6.88-7.00 (m, 3H), 7.19 (d, 1H), 7.34 (t, 1H), 7.72 (s, 1H), 7.92 (s, 1H), 7.97 (s, 1H), 9.05 (s, 1H).

A13

N-[3-[[5-bromo-4-[[3-[(3-thienylmethyl)amino]propyl]amino]-2-pyrimidinyl]amino]phenyl]-1-pyrrolidinecarboxamide To a solution of N-(3-((4-((3-aminopropyl)amino)-5-bromo-2-pyrimidinyl)amino)phenyl)-1-pyrrolidinecarboxamide (1.0 g, 1.97 mmol) in THF (30 mL) was added 2-thiophenecarboxaldehyde (184 mg, 1.64 mmol, 0.8 equiv.), triethylamine (362 mg, 3-6 mmol, 1.8 equiv.) and sodium triacetoxyborohydride (688 mg, 3.25 mmol, 1.6 equiv.). The resulting mixture was stirred overnight at room temperature under $N_2$. The reaction was quenched by satuarated sodium bicarbonate (30 mL) and was extracted with ethyl acetate (3×30 mL). The reaction mixture was concentrated. Purification by HPLC chromatography using acetonitrile/water gave the title compound (310 mg).

$^1$H NMR (400 MHz, DMSO): δ/ppm=1.81 (t, 2H), 1.87 (t, 4H), 2.88 (m, 2H), 3.32 (t, 4H), 3.54 (m, 2H), 4.30 (t, 2H), 7.04 (m, 2H), 7.17 (m, 3H), 7.59 (d, 1H), 7.92 (s, 1H), 8.20 (s, 1H), 8.26 (s, 1H), 8.62 (t, 1H), 8.82 (s, 2H), 10.48 (s, 1H)

A14

N²-(3-amino-5-(trifluoromethyl)phenyl)-5-bromo-N⁴-(2-(1H-imidazol-4-yl)ethyl)-2,4-pyrimidinediamine and N-(3-((5-bromo-4-((2-(1H-imidazol-4-yl)ethyl)amino)-2-pyrimidinyl)amino)-5-(trifluoromethyl)phenyl)-ethanimidamide To a suspension of 5-(trifluoromethyl)-1,3-diaminobenzene (105 mg, 0.6 mmol, 1.2 equiv.) in acetonitrile (10 mL), hydrogen chloride (4.0M in dioxane, 0.15 mL. 0.6 mmol) and water (0.15 mL) was added 5-bromo-2-chloro-N-[2-(1H-imidazol-4-yl)ethyl]4-pyrimidine (150 mg, 0.5 mmol, 1 equiv.). The resulting mixture was refluxed overnight. The resulting white suspension was cooled to room temperature and concentrated. The crude residue was purified by HPLC chromatography using acetonitrile/water to afford the title compounds, N²-(3-amino-5-(trifluoromethyl)phenyl)-5-bromo-N⁴-(1H-imidazol-4-yl)ethyl)-2,4-pyrimidinediamine (50 mg) and N-(3-((5-bromo-4-((2-(1H-imidazol-4-yl)ethyl)amino)-2-pyrimidinyl)amino)-5-(trifluoramethyl)phenyl)-ethanimidamide (22 mg).

N²-(3-amino-5-(trifluoromethyl)phenyl)-5-bromo-N⁴-(2-(1H-imidazol-4-yl)ethyl)-2,4-pyrimidinediamine: ¹H NMR (400 MHz, DMSO-d₆): δ/ppm=2.96 (t, 2H), 3.64 (t, 2H), 6.42 (s, 1H), 7.01 (s, 1H), 7.24 (br t 1H), 7.44 (d, 2H), 8.06 (s, 1H), 8.97 (s, 1H), 9.39 (s, 1H).

N-(3-((5-bromo-4-((2-(1H-imidazol-4-yl)ethyl)amino)-2-pyrimidinyl)amino)-5-(trifluoromethyl)phenyl)-ethanimidamide: ¹H NMR (400 MHz, DMSO-d₆): δ/ppm=2.32 (s, 3H), 2.97 (m, 2H), 3.68 (m, 2H), 7.18 (s, 1H), 7.32 (m, 1H), 7.43 (s, 1H), 7.79 (s, 1H), 8.13 (s, 1H), 8.36 (s, 1H), 8.71 (s, 1H), 8.99 (s, 1H), 9.56 (s, 1H), 9,92 (s, 1H), 11.34 (s, 1H).

A15

(4R)-N-[3-[[5-bromo-2-[[3-(2,5-dioxo-1-imidazolidinyl)phenyl]amino]-4-pyrimidinyl]amino]propyl]-2-oxo-4-thiazolidinecarboxamide and (4R)-N-[3-[[5-bromo-2-[[3-[2,5-dioxo-3-[[(4R)-2-oxo-4-thiazolidinyl]carbonyl]-1-imidazolidinyl]phenyl]amino]-4-pyrimidinyl]amino]propyl]-2-oxo-4-thiazolidinecarboxamide To a solution of 3-[3-[[4-[(3-aminopropyl)amino]-5-bromo-2-pyrimidinyl]amino]phenyl]-2,4-imidazolidinedione hydrogen chloride salt (6.9 g, 13.9 mmol), (−)-2-oxo-4-thiazolidinecarboxylic acid (2.5 g, 17 mmol, 1.2 equiv.) and N,N-diisopropylethylamine (10 mL, 57.4 mmol, 4.1 equiv.) in dimethylformamide (150 mL) was added O-(7-azabenzotriazol-1-yl)-N,N,N',N'-tetramethyluronium hexafluorophosphate (6.5 g, 17.1 mmol, 1.2 equiv.) at 0° C. The resulting solution was warmed to room temperature and stirred overnight. The reaction mixture was concentrated under reduced pressure to remove dimethylformamide. The crude residue was triturated in water to give a suspension. The suspension was filtered and the filter cake was washed with water and air-dried (ca. 8 g). The solid was purified by HPLC chromatography using acetonitrile/water to afford the title compounds, (4R)-N-[3-[[5-bromo-2-[[3-(2,5-dioxo-1-imidazolidinyl)phenyl]amino]-4-pydmidinyl]amino]propyl]-2-oxo-4-thiazolidinecarboxamide (2.8 g) and (4R)-N-[3-[[5-bromo-2-[[3-[2,5-dioxo-3-[[(4R)-2-oxo-4-thiazolidinyl]carbonyl]-1-imidazolidinyl]phenyl]amino]-4-pyrimidinyl]amino]propyl]-2-oxo-4-thiazolidinecarboxamide (72 mg).

N-[3-[[5-bromo-2-[[3-(2,5-dioxo-1-imidazolidinyl)phenyl]amino]-4-pyrimidinyl]amino]propyl]-2-oxo-4-thiazolidinecarboxamide: ¹H NMR (400 MHz, DMSO-d₆): δ/ppm=1.71 (m, 2H), 3.14 (m, 2H), 3.36 (m, 1H), 3.42 (m, 2H), 3.64 (t, 1H), 4.04 (s, 2H), 4.23 (m, 1H), 6.99 (d, 1H), 7.01 (t, 1H), 7.59 (d, 1H), 7.72 (s, 1H), 7.81 (br s, 1H), 8.16 (m. 2H), 8.29 (s, 1H), 8.34 (s, 1H), 9.99 (brs, 1H).

(4R)-N-[3-[[5-bromo-2-[[3-[2,5-dioxo-3-[[(4R)-2-oxo-4-thiazolidinyl]carbonyl]-1-imidazolidinyl]phenyl]amino]-4-pyrimidinyl]amino]propyl]-2-oxo-4-thiazolidinecarboxamide: ¹H NMR (400 MHz, DMSO-d₆): δ/ppm=1.64 (m, 2H), 3.12 (m, 2H), 3,38 (m, 4H), 3.79 (m, 2H), 4.02 (s, 2H), 5.04 (d, 2H), 5.12 (d, 2H), 6.94 (d, 1H), 7.34 (t, 1H), 7.56 (d, 1H), 7.69 (s, 1H), 8.08 (s, 1H), 8.18 (s, 1H), 8.26 (s, 1H), 8.37 (s, 1H), 9.79 (br s, 1H).

Scheme 16

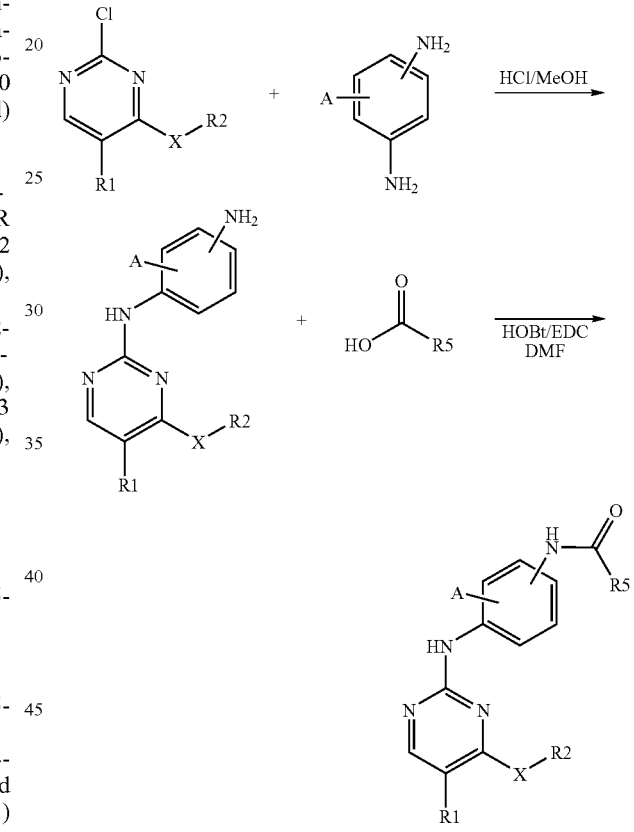

Where R¹, R² and R⁵ are as described in the claims.

Scheme 17

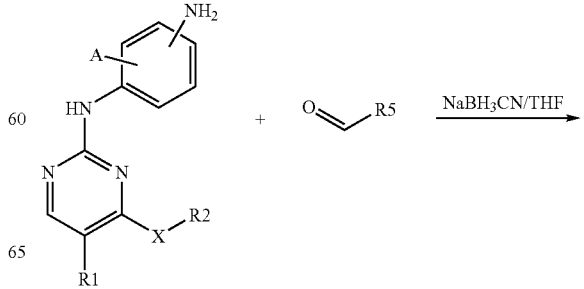

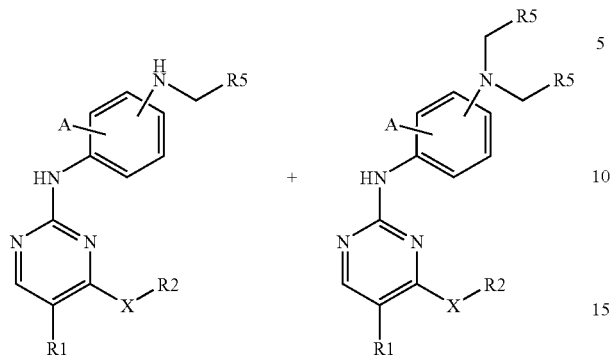
Where $R^1$, $R^2$ and $R^5$ are as described in the claims.
Scheme 18
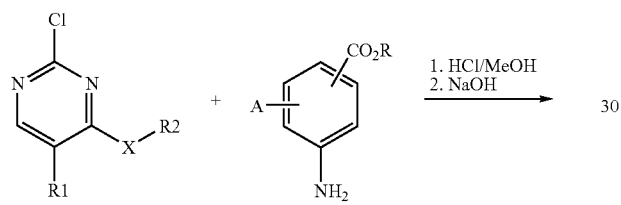
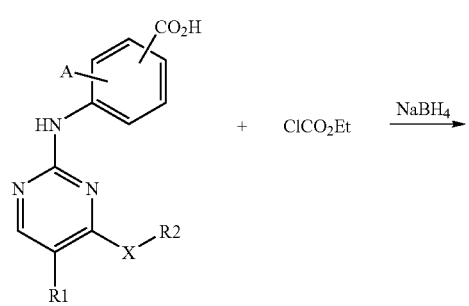
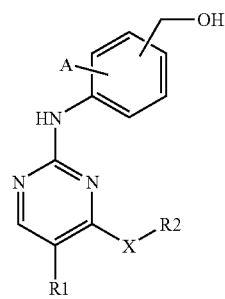
Where R is C1-C4 Alkyl and $R^1$, $R^2$ and $R^5$ are as described in the claims.
Scheme 19
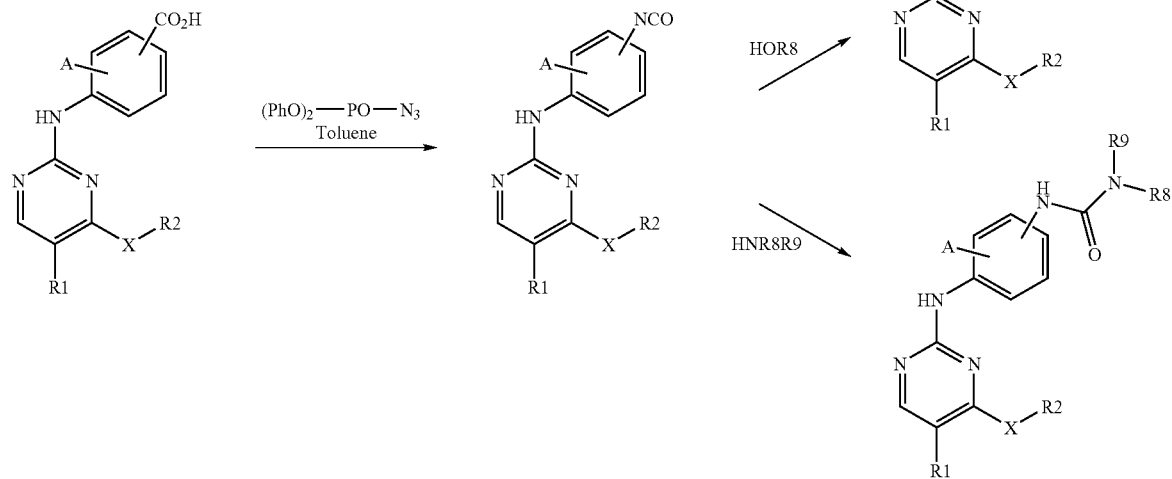

Where $R^1$, $R^2$ and $R^5$ are as described in the claims. $R^8$ and $R^9$ are as described in the claims but not representing —$R^{10}$.
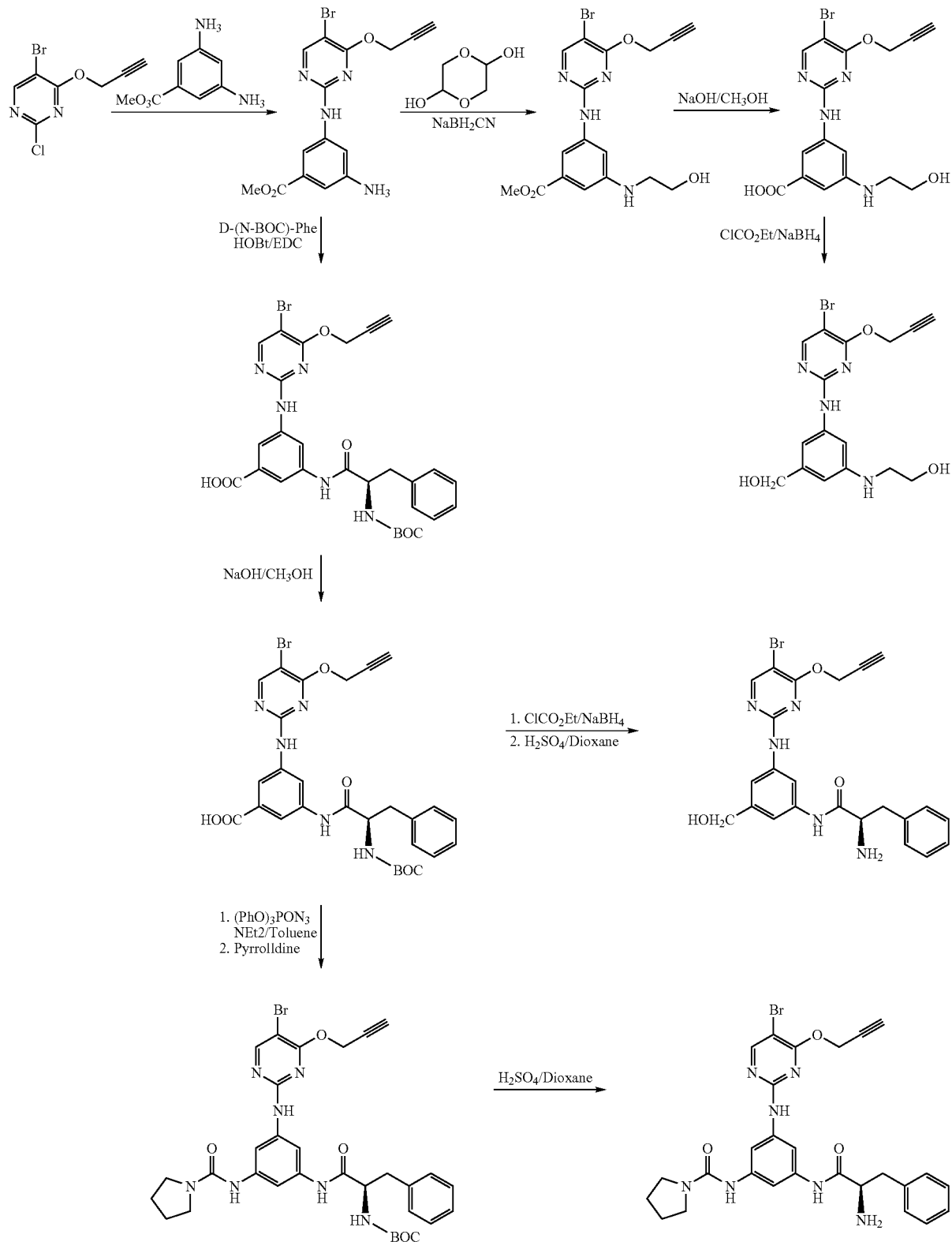
Schema 19a Scheme 20

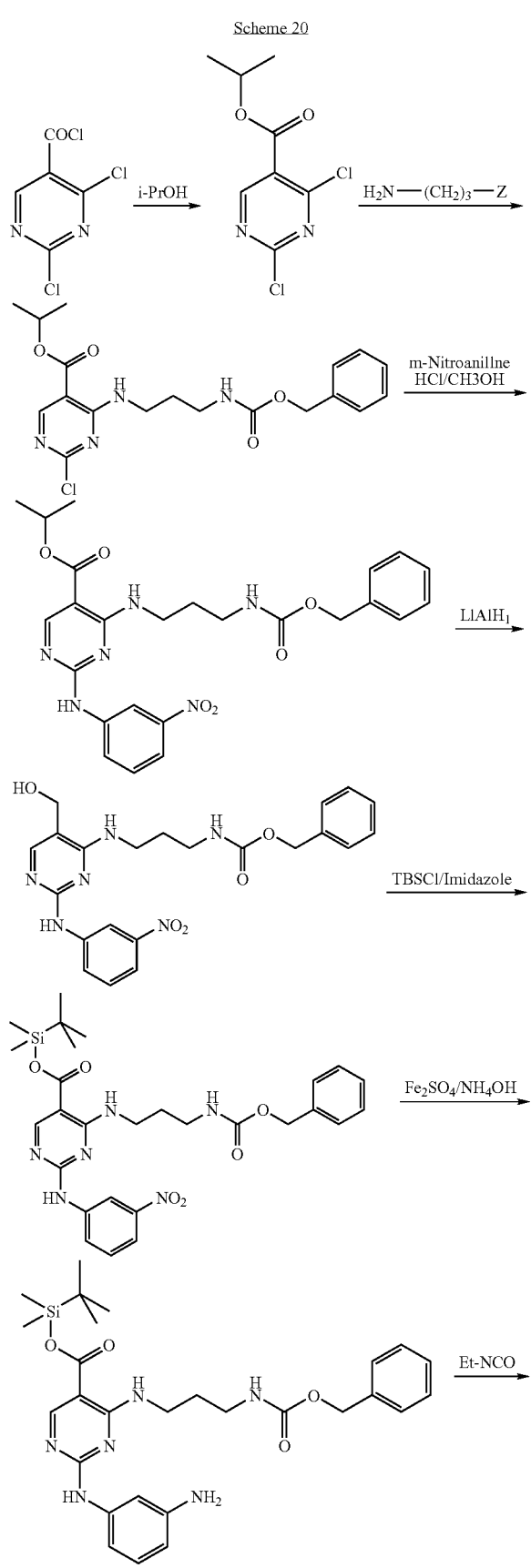

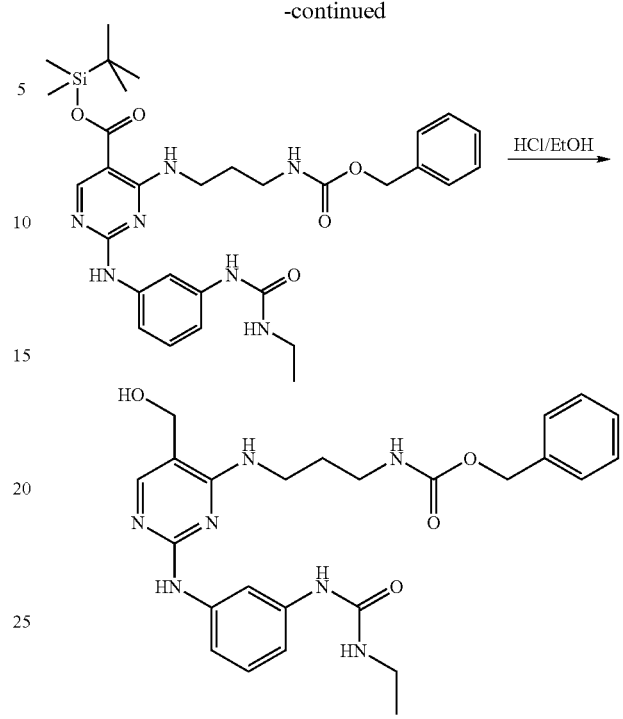

The following Examples have been synthesized according to the above mentioned schemes.

A16

N-[3-[[(2R)-2-Amino-1-oxo-3-phenylpropyl]amino]-5-[[5-bromo-4-prop-2-ynyloxy)pyrimidin-2-yl]amino]phenyl]pyrrolidine-1-carboxamide 16a) Methyl 3-amino-5-[[5-bromo-4-(prop-2-ynyloxy)pyrimidin-2-yl]amino]benzoate A mixture of 5-bromo-2-chloro-4-(prop-2-ynyloxy)pyrimidine (15 g), methyl 3,5-diaminobenzoate (45 g) and concentrated hydrochloric acid (15 ml) in methanol (600 ml) was stirred at 65° C. for 8 h. After concentration to half the volume water was added and the precipitate collected by filtration. The precipitate then was treated with sodium hydroxide solution (1 n) and dichloromethane. The organic phase then was washed with water and brine, dried ($Na_2SO_4$) and evaporated to dryness to give the title compound (13.8 g).

Mp.: 207.5-209° C.

16b) Methyl 5-[[5-bromo-4-(prop-2-ynyloxy)pyrimidin-2-yl]amino]-3-[[(2R)-2-[[(1,1-dimethylethoxy)carbonyl]amino]-1-oxo-3-phenylpropyl]amino]benzoate N-BOC-D-phenylalanine (3.3 g), 1-hydroxy-1H-benzotriazole hydrate(1.9 g) and N-[3-(dimethylamino)propyl]-N'-ethylcarbodiimid hydrochloride (2.37 g) were stirred in DMF (30 ml) for 30 minutes Then methyl 3-amino-5-[[5-bromo-4-(prop-2-ynyloxy)pyrimidin-2-yl]amino]benzoate (3.88 g) were added and the mixture stirred over night. Then ethyl acetate (500 ml) was added and the reaction mixture washed subsequently with hydrochloric acid (0.1 n), saturated $NaHCO_3$-solution, water and brine. After drying ($Na_2SO_4$) the organic phase was evaporated and the residue subjected to column chromatography (ethyl acetate/dichloromethane) to yield 5.36 g of the title compound.

ESI-MS: 624 and 626 (M+)

16c) 5-[[5-Bromo-4-(prop-2-ynyloxy)pyrimidin-2-yl]amino]-3-[[(2R)-2-[[(1,1-dimethylethoxy)carbonyl]amino]-1-oxo-3-phenylpropyl]amino]benzoic acid Methyl5-[[5-bromo-4-(prop-2-ynyloxy)pyrimidin-2-yl]amino]-3-[[(2R)-2-[[(1,1-dimethylethoxy)carbonyl]amino]-1-oxo-3-phenylpropyl]amino]benzoate (1.0 g) was stirred in a mixture of tetrahydrofuran (20 ml), methanol (20 ml) and sodium hydroxide solution (2 n; 20 ml) for 48 h. After evaporation water (50 ml) was added to the residue. On neutralisation with hydrochloric acid (1 n) a precipitate formed. The precipitate was subjected to chromatography on silica gel (hexanes/ethyl acetate/methanol) to yield the title compound (450 mg).

ESI-MS: 610 and 612 (M+)

16d) 1,1-Dimethylethoxy[(1R)-2-[[3-[[5-bromo-4-(prop-2-ynyloxy)pyrimidin-2-yl]amino]-5-[[(pyrrolidin-1-yl)carbonyl]amino]phenyl]amino]-2-oxo-1-(phenylmethyl)ethyl]carbamate 5-[[5-Bromo-4-(prop-2-ynyloxy)pyrimidin-2-yl]amino]-3-[[(2R)-2-[[(1,1-dimethylethoxy)carbonyl]amino]-1-oxo-3-phenylpropyl]amino]benzoic acid (200 mg), diphenylphosphorylazide (0.75 ml) and triethylamine (0.67 ml) were refluxed in toluene (40 ml) for 1.5 h. Then pyrrolidine (0.26 ml) was added and the mixture refluxed for additional 2 h. After cooling the reaction mixture was diluted with ethyl acetate (50 ml) and subsequently washed with saturated NaHCO₃-solution, water and brine. After drying (Na₂SO₄) and evaporation the residue was subjected to chromatography on silica gel (hexanes/ethyl acetate) to yield the title compound (126 mg).

ESI-MS: 678 and 680 (M+)

16e) N-3-[[(2R)-2-Amino-1-oxo-3-phenylpropyl]amino]-5-[[5-bromo-4-(prop-2-ynyloxy)pyrimidin-2-yl]amino]phenyl]pyrrolidine-1-carboxamide 1,1-Dimethylethoxy[(1 R)-2-[[3-[[5-bromo-4-(prop-2-ynyloxy)pyrimidin-2-yl]amino]-5-[[(pyrrolidin-1-yl)carbonyl]amino]phenyl]amino]-2-oxo-1-(phenylmethyl)ethyl]carbamate (105 mg) and sulfuric acid (0.5 ml; 2 n) were stirred in dioxane (5 ml) at 85° C. for 3.5 h. After cooling and dilution with water saturated NaHCO₃-solution was added and the resulting precipitate collected by filtration yielding the title compound (76 mg).

ESI-MS: 578 and 580 (M+)

A17

(αR)-α-Amino-N-[3-[[5-bromo-4-(prop-2-ynyloxy)pyrimidin-2-yl]amino]-5-(hydroxymethyl)phenyl]benzenepropanamide 17a) 1,1-Dimethylethoxy [(1R)-2-[[3-[[5-bromo-4-(prop-2-ynyloxy)pyrimidin-2-yl]amino]-5-(hydroxymethyl)phenyl]amino]-2-oxo-1-(phenylmethyl)ethyl]carbamate To a mixture of 5-[[5-bromo-4-(prop-2-ynyloxy)pyrimidin-2-yl]amino]-3-[[(2R)-2-[[(1,1-dimethylethoxy)carbonyl]amino]-1-oxo-3-phenylpropyl]amino]benzoic acid (100 mg) and triethylamine (25 µl) in tetrahydrofuran (2 ml) was added ethyl chloroformiate (16 µl) at −10° C. After stirring for 15 minutes at 0° C. sodium borohydride (19 mg) and methanol (1.6 ml) were added and stirring continued over night at room temperature. After dilution with water the reaction mixture was extracted with ethyl acetate and the organic layer subsequently washed with saturated NaHCO₃-solution and brine. After drying (Na₂SO₄) and evaporation the residue was subjected to chromatography on silica gel (hexanes/ethyl acetate) to yield the title compound (40 mg).

ESI-MS: 596 and 598 (M+)

17b) (αR)-α-Amino-N-[3-[[5-bromo-4-(prop-2-ynyloxy)pyrimidin-2-yl]amino]-5-(hydroxymethyl)phenyl]benzenepropanamide 1,1-Dimethylethoxy[(1R)-2-[[3-[[5-bromo-4-(prop-2-ynyloxy)pyrimidin-2-yl]amino]-5-(hydroxymethyl)phenyl]amino]-2-oxo-1-(phenylmethyl)ethyl]carbamate (22 mg) and sulfuric acid (0.3 ml; 2 n) were stirred in dioxane (3 ml) at 100° C. for 2.5 h. After cooling and dilution with water saturated NaHCO₃-solution was added and the resulting preticipate collected by filtration yielding the title compound (10 mg).

A18

3-[[5-Bromo-4-(prop-2-ynyloxy)pyrimidin-2-yl]amino]-5-[(2-hydroxyethyl)amino]benzenemethanol 18a) Methyl3-[[5-bromo-4-(prop-2-ynyloxy)pyrimidin-2-yl]amino]-[(2-hydroxy ethyl)amino]benzoate Methyl3-amino-5-[[5-bromo-4-(prop-2-ynyloxy)pyrimidin-2-yl]amino]benzoate (2 g), glycolaldehyde dimer (0-7 g), sodium cyanoborohydride (0.49 g) and acetic acid (0.3 ml) were stirred in methanol (100 ml) for 24 h. After evaporation halfconcentrated NaHCO₃-solution and ethyl acetate were added to the residue. The organic layer then was washed with water and brine, dried (Na₂SO₄), filtered and evaporated. The residue was chromatographed on silica gel (dichloromethane/methanol) to yield the title compound (1.1 g).

ESI-MS: 421 and 423 (M+)
Mp.: 179-179.5° C.

18b) 3-[[5-Bromo-4-(prop-2-ynyloxy)pyrimidin-2-yl]amino]-5-[(2-hydroxyethyl)amino]benzoic acid Methyl3-[[5-bromo-4-(prop-2-ynyloxy)pyrimidin-2-yl]amino]-5-[(2-hydroxyethyl)amino]benzoate (350 mg) in a mixture of tetrahydrofuran (6 ml) and sodium hydroxide solution (2 n; 6 ml) was stirred for 48 h at room temperature. After evaporation the residue was diluted with water and acidified until the product precipitated Filtration and drying yielded the title compound (340 mg).

MS: 406 and 408 (M+)

18c) 2-[3-(5-Bromo-4-prop-2-ynyloxy-pyrimidin-2-ylamino)-5-hydroxymethyl-phenylamino]ethanol To a mixture of 3-[[5-bromo-4-(prop-2-ynyloxy)pyrimidin-2-yl]amino]-5-[(2-hydroxyethyl)amino]benzoic acid and triethylamine (57 µl) in tetrahydrofuran (4 ml) was added ethyl chloroformiate (37 µl) at −10° C. After stirring for 15 minutes at 0° C. sodium borohydride (44 mg) and methanol (3.6 ml) were added and stirring continued over night at room temperature. After dilution with water the reaction mixture was extracted with ethyl acetate and the organic layer subsequently washed with saturated NaHCO₃-solution and brine After drying (Na₂SO₄) and evaporation the residue was subjected to chromatography on-silica gel (hexanes/ethyl acetate) to yield the title compound (59 mg).

CI-MS: 393 and 395 (M+)

A19

Phenylmethyl[3-[[2-[[3-[[(ethylamino)carbonyl]amino]phenyl]amino]-5-(hydroxymethyl)pyrimidin-4-yl]amino]propyl]carbamate 19a) 1-Methylethyl 2,4-dichloropyrimidine-5-carboxylate To a precooled solution (−40° C.) of 2,4-dichloropyrimidine-5-carbonyl chloride (5 ml) in tetrahydrofuran (20 ml) isopropanol (2.6 ml) was added dropwise. Then the reaction mixture was allowed to come to room temperature and stirred for 2h. After evaporation the residue was chromatographed on silica gel (dichloromethane/ethyl acetate) to yield the title compound (8.2 g).

1H NMR (300 MHz, CDCl$_3$): σ/ppm=1.40 (d, 6H, J=7 Hz), 5.31 (m, 1H), 9.0 (s, 1H)

19b) 1-Methylethyl2-chloro-4-[[3-[[(phenylmethoxy)carbonyl]amino]propyl]amino]pyrimidine-5-carboxylate To a solution of 1-methylethyl 2,4-dichloropyrimidine-5-carboxylate (4.7 g) and ethyldiisopropylamine (3.4 ml) in acetonitrile (250 ml) phenylmethyl [3-aminopropyl]carbamate (4.2 g) was added at 0° C. Subsequently the reaction mixture was stirred over night at room temperature. After evaporation the residue was chromatographed on silica gel (dichloromethane/isopropanol) to yield the title compound (5.9 g).

ESI-MS: 407 and 409 (M+)

19c) 1-Methylethyl2-[(3-nitrophenyl)amino]-4-[[3-[[(phenylmethoxy)carbonyl]amino]propyl]amino]pyrimidine-5-carboxylate 1-Methylethyl-2-chloro-4-[3-[[(phenylmethoxy)carbonyl]amino]propyl]-amino]pyrimidine-5-carboxylate (3 g) and 3-nitroaniline (1 g) were added to a mixture of dioxane (150 ml) and hydrochloric acid in dioxane (4 n, 25 ml). After stirring at 85° C. for 3.5 h the reaction mixture was poured into halfconcentrated NaHCO$_3$-solution. The title compound precipitated and was isolated by filtration-(3.5 g).

ESI-MS: 509 (M+)

19d) Phenylmethyl[3-[[5-hydroxymethyl)-2-[(3-nitrophenyl)amino]pyrimidin-4-yl]amino]propyl]carbamate To a solution of 1-Methylethyl 2-[(3-nitrophenyl)amino]-4-[[3-[[(phenylmethoxy)carbonyl]amino]propyl]amino]pyrimidine-5-carboxylate (1.7 g) in tetrahydrofuran (100 ml) LiAlH$_4$ (410 mg) was added in portions at 0° C. After 6 h at 0° C. the reaction was quenched by addition of saturated ammonium chloride solution. Ethyl acetate was added and the mixture filtered. After evaporation of the filtrate the residue was partitioned between water and dichloromethane. The organic layer was washed with brine, dried (Na$_2$SO$_4$), filtered and evaporated. Chromatography of the residue on silica gel (dichloromethane/methanol)) yielded the title compound (650 mg).

ESI-MS: 453 (M+)

19e) Phenylmethyl[3-[[5-[[[(1,1-dimethylethyl)dimethylsilyl]oxy]methyl]-2-[(3-nitrophenyl)amino]pyrimidin-4-yl]amino]propyl]carbamate A DMF solution (5 ml) of phenylmethyl [3-[[5-(hydroxymethyl)-2-[(3-nitrophenyl)amino]pyrimidin-4-yl]amino]propyl]carbamate (250 mg), chloro(1,1-dimethylethyl)dimethylsilane (190 mg) and 1H-imidazole (170 mg) was stirred at room temperature (48 h). After addition of ice water the mixture was extracted with ethyl acetate. The organic layer was washed with water, brine, dried (Na$_2$SO$_4$), filtered and evaporated. Trituration of the residue with diethyl ether yielded the title compound (300 mg).

ESI-MS: 567 (M+)

19f) Phenylmethyl[3-[[2-[(3-aminophenyl)amino]-5-[[[(1,1-dimethylethyl)dimethylsilyl]oxy]methyl]pyrimidin-4-yl]amino]propyl]carbamate Phenylmethyl[3-[[5-[[[(1,1-dimethylethyl)dimethylsilyl]oxy]methyl]-2-[(3-nitrophenyl)amino]pyrimidin-4-yl]amino]propyl]carbamate (244 mg), dissolved in ethanol (30 ml), was slowly added to a mixture of FeSO$_4$ heptahydrate (1.25 g), concentrated ammonia solution (25%; 1.25 ml) and water (5 ml). After refluxing for 3 h the mixture was filtered and the filter cake washed with ethyl acetate. The filtrate was washed with water and brine, dried (Na$_2$SO$_4$), filtered and evaporated to yield the crude title compound (230 mg), which was used in the next step without further purification.

19g) Phenylmethyl [3-[[5-[[[(1,1-dimethylethyl)dimethylsilyl]oxy]methyl]-2-[[3-[[(ethylamino)carbonyl]amino]phenyl]amino]pyrimidin-4-yl]amino]propyl]carbamate To a solution of phenylmethyl [3-[[2-[(3-aminophenyl)amino]-5-[[[(1,1-dimethylethyl)dimethylsilyl]oxy]methyl]pyrimidin-4-yl]amino]propyl]carbamate (225 mg) in acetonitrile (5 ml) ethyl isocyanate (33 µl) was added and the mixture stirred for 18 h at room temperature. Then 5 drops of ammonia solution (25%) were added and the precipitated title compound isolated by filtration (158 mg).

ESI-M5-608 (M+)

19h) Phenylmethyl [3-[[2-[[3-[[(ethylamino)carbonyl]amino]phenyl]amino]-5-(hydroxymethyl)pyrimidin-4-yl]amino]propyl]carbamate Phenylmethyl[3-[[5-[[[(1,1-dimethylethyl)dimethylsilyl]oxy]methyl]-2-[[3[[(ethylamino)carbonyl]amino]phenyl]amino]pyrimidin-4-yl]amino]propyl]carbamate (145 mg) were stirred in a mixture of ethanol (10 ml) and hydrochloric acid (4 n; 1 ml) for 3 h at room temperature. Then halfconcentrated NaHCO$_3$-solution and ethyl acetate were added.

The organic phase was washed with water and brine, dried (Na$_2$SO$_4$), filtered and evaporated to yield the title compound (120 mg).

ESI-MS: 494 (M+)

20A 1-(4-{5-Bromo-4-[2-(3H-imidazol-4-yl)-thylamino]-pyrimidin-2-ylamino}-phenyl)-3-cyclopropyl-thiourea 20a) 2,2,2-TrifluoroN-(4-nitro-phenyl-acetamide 4-Nitroaniline (50 g) was dissolved in pyridine (500 ml) and cooled to 0° C. Trifluoroacetic acid anhydride (52.2 ml) was added slowly at 0° C. and allowed to stir at room temperature overnight. The pyridine was distilled off under reduced pressure and the solid partitioned between ethyl acetate and water. The organic phase was seperated, dried over magnesium sulfate and the solvent was removed. The crude product was recrystallized from diisopropyl ether to yield 82 g (97%) of 2,2,2-Trifluoro-N-(4-nitro-phenyl)-acetamide which was directly used without purification in the next step.

20b) 2,2,2-TrifluoroN-(4-amino-phenyl)-acetamide 2,2,2-Trifluaro-N-(4-nitro-phenyl)-acetamide (30 g) was dissolved in ethyl acetate (500 ml) and Pd/C (10%, 3 g) was added. After hydrogenation (1 bar, room temperature) for 3 h the catalyst was filtered off and the solvent was removed under reduced pressure. The crude product was recrystallized from diisopropyl ether to yield 20.6 g (79%) of 2,2,2-TrifluoroN-(4-amino-phenyl)-acetamide. ESI-MS: 205

20c) N-(4-{5-Bromo-4-[2-(3H-imidazol-4-yl)ethylamino]-pyrimidin-2ylamino}-phenyl)-trifluoro acetamide 5-Bromo-4-[2-(1H-imidazol-4-yl)-ethylamino-2-chloro pyrimidine (5 g, prepared according to procedure 1b) was dissolved in acetonitrile (100 ml), 2,2,2-TrifluoroN-(4-amino-phenyl)-acetamide (3.37 g) and a solution of HCl in dioxane (4 M, 10 ml) were added and the reaction mixture was heated under reflux overnight. The reaction was cooled to room temperature and the precipitate was filtered and washed with acetonitrile. Yield of N-(4-{5-Bromo-4-[2-(3H-imidazolyl)-4-yl)-ethylamino]-pyrimidin-2-ylamino)phenyl}-trifluoro acetamide: 7.6 g (90%). ESI-MS: 471.

20d) N2-(4-Amino-phenyl)-5-bromo-N-4-[2-(3H-imidazol-4-yl)-ethyl]-pyrimidine-2,4-diamine N-(4-{5-Bromo-4-[2-(3H-imidazol-4-yl)-ethylamino]-pyrimidin-2-ylamino}-phenyl)-trifluoro acetamide (1 g, 1.9 mmole) was dissolved in THF (10 ml), MeOH (10 ml) and water (5 ml) and LiOH (455 mg) was added in one portion at room temperature. The reaction mixture was stirred at room temperature for two days, the solvent removed under reduced pressure. The residue was dissolved in ethyl acetate and water and extracted with ethyl acetate (3×). The combined organic layers were combined and dried over magnesium sulfate. After evaporation of the solvent one obtains 350 mg of N2-(4-Amino-phenyl)-5-bromo-N4-[2-(3H-imidazol-4-yl)ethyl]pyrimidine-2,4-diamine. ESI-MS: 375.

20e) 1-(4-{5-Bromo-4-[2-(3H-imidazol-4-yl)ethylamino]-pyrimidin-2-ylamino}-phenyl)-3-cyclopropyl-thiourea Cyclopropyl amine (0.275 mmole) was dissolved in THF (2 ml) and thiocarbonyl diimidazole (0.28 mmole) was added. The reaction was stirred at room temperature overnight and N2-(4-Amino-phenyl)-5-bromo-N4-[2-(3H-imidazol-4-yl)-ethyl]-pyrimidine-2,4-diamine (0.26 mmole) was added as a solution in THF (3 ml) and DMF (1 ml) and the reaction was stirred overnight. After removal of the solvents under reduced pressure the crude product was purified by flashmaster chromatography (dichloromethane: MeOH 9:1) to yield 12.5 mg of 1-(4-{5-Bromo-4-[2-(3H-imidazol-4-yl)-ethylamino]-pyrimidin-2-ylamino}-phenyl)-3-cyclopropyl-thiourea. ESI-MS: 474.

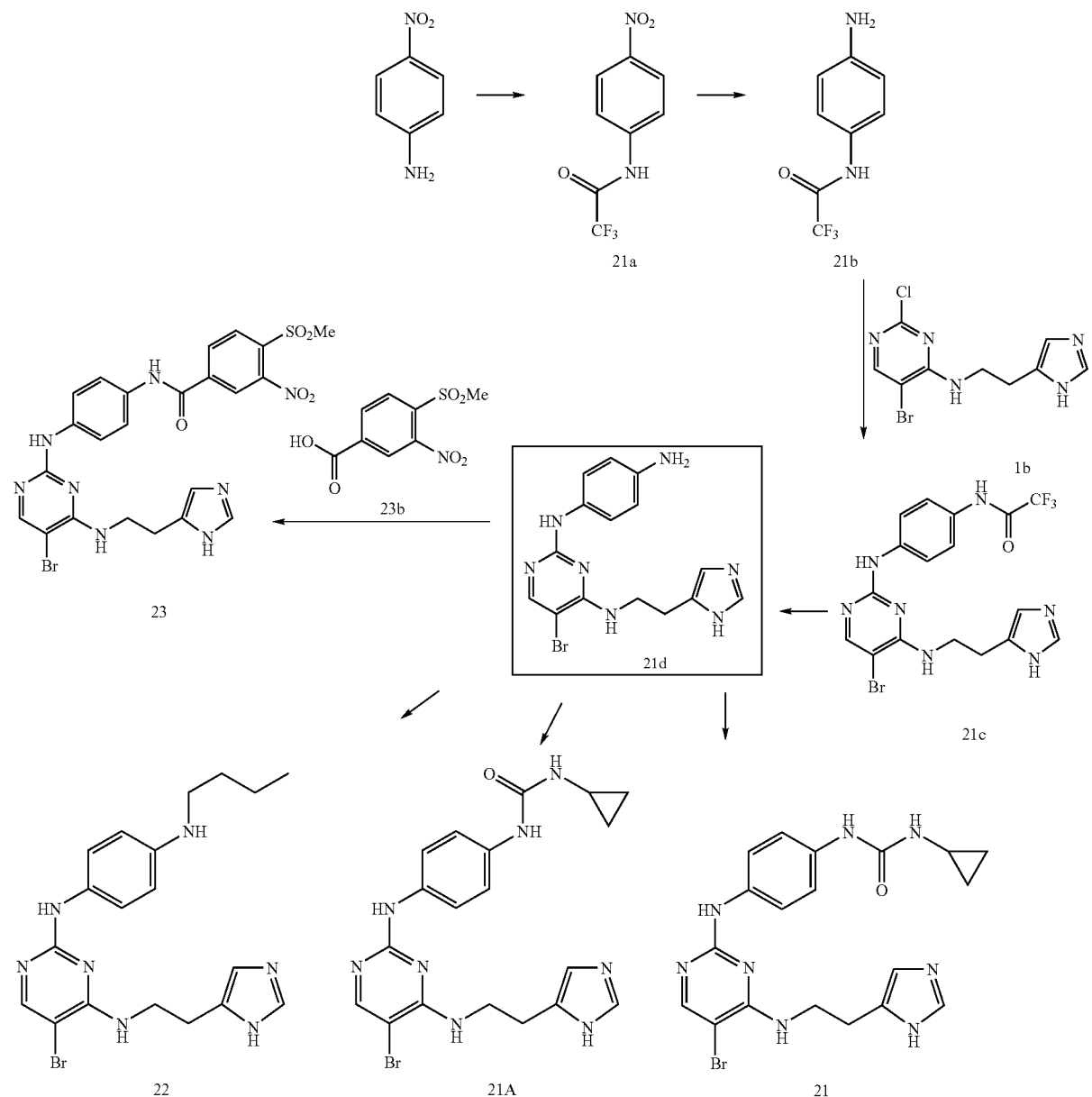

Scheme 22

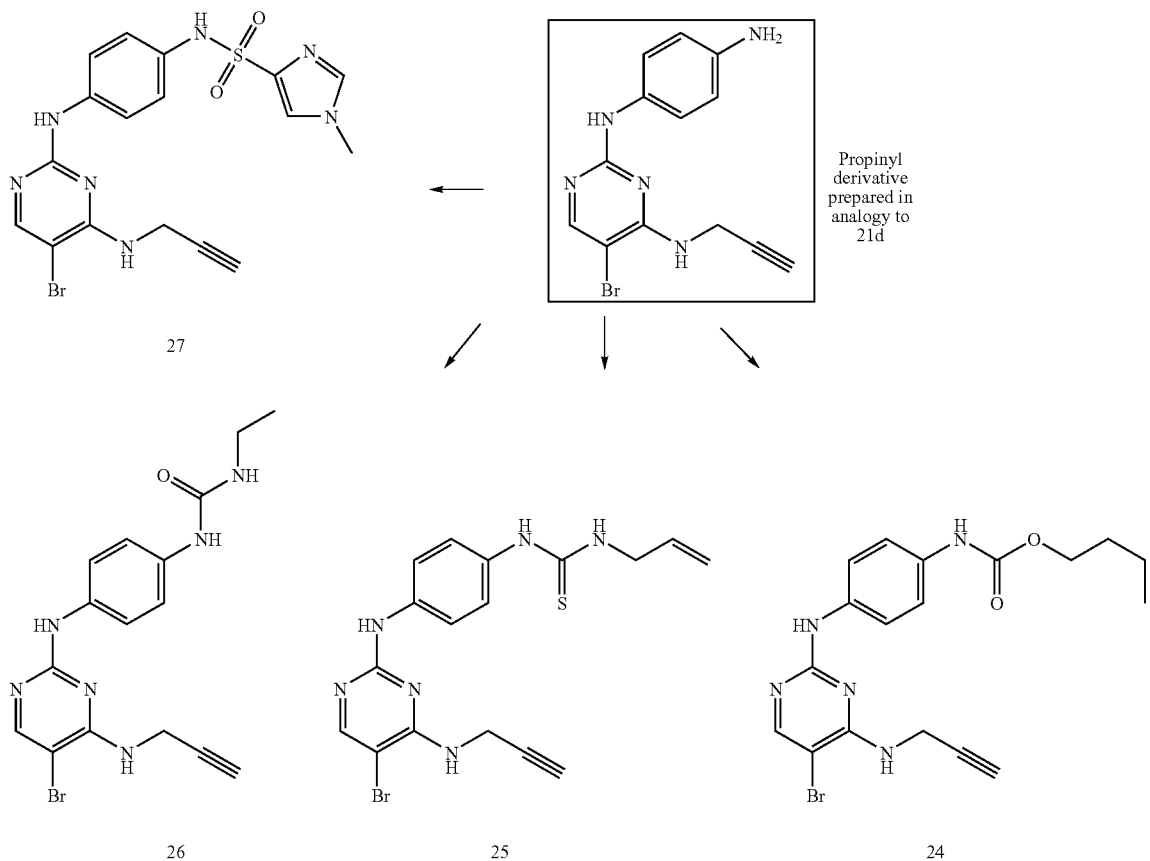

The following Examples have been synthesized according to the above mentioned schemes.

A21

1-(4-{5-Bromo-4-[2-(3H-imidazol-4-yl)-ethylamino]-pyrimidin-2-ylamino}-phenyl)-3-cyclopropyl-thiourea 21a) 2,2,2-TrifluoroN-(4-nitro-phenyl)-acetamide 4-Nitroaniline (50 g) was dissolved in pyridine (500 ml) and cooled to 0° C. Trifluoroacetic acid anhydride (52.2 ml) was added slowly at 0° C. and allowed to stir at room temperature overnight The pyridine was distilled off under reduced pressure and the solid partitioned between ethyl acetate and water. The organic phase was seperated, dried over magnesium sulfate and the solvent was removed. The crude product was recrystallized from diisopropyl ether to yield 82 g (97%) of 2,2,2-Trifluoro-N-(4-nitro-phenyl)-acetamide which was directly used without purification in the next step.

21b) 2,2,2-TrifluoroN-(4-amino-phenyl)-acetamide 2,2,2-Trifluoro-N-(4-nitro-phenyl)-acetamide (30 g) was dissolved in ethyl acetate (500 ml) and Pd/C (10%, 3 g) was added. After hydrogenation (1 bar, room temperature) for 3 h the catalyst was filtered off and the solvent was removed under reduced pressure The crude product was recrystallized from diisopropyl ether to yield 20.6 g (79%) of 2,2,2-TrifluoroN-(4-amino-phenyl)-acetamide. ESI-MS: 205

21c) N-(4-{5-Bromo-4-[2-(3H-imidazolyl-4-yl)ethylamino]pyrimidin-2-ylamino}-phenyl)-trifluoro acetamide 5-Bromo-4-[2-(1H-imidazol-4-yl)-ethylamino-2-chloro pyrimidine (5 g, prepared according to procedure 1b) was dissolved in acetonitrile (100 ml), 2,2,2-TrifluoroN-(4-amino-phenyl)-acetamide (3.37 g) and a solution of HCl in dioxane (4 M, 10 ml) were added and the reaction mixture was heated under reflux overnight. The reaction was cooled to room temperature and the precipitate was filtered and washed with acetonitrile. Yield of N-(4-{5-Bromo-4-[2-(3H-imidazol-4-yl)-ethylamino]pyrimidin-2-ylamino}phenyl)-trifluoro acetamide: 7.6 g (90%) ESI-MS: 471.

21d) N2-(4-Amino-phenyl)-5-bromo-N4-[2-(3H-imidazol-4-yl)-ethyl]-pyrimidin-2,4-diamine N-(4-{5-Bromo-4-[2-(3H-imidazol-4-yl)-ethylamino]-pyrimidin-2-ylamino}-phenyl)-trifluoro acetamide (1 g, 1.9 mmole) was dissolved in THF (10 ml), MeOH (10 ml) and water (5 ml) and LiOH (455 mg) was added in one portion at room temperature. The reaction mixture was stirred at room temperature for two days, the solvent removed under reduced pressure The residue was dissolved in ethyl acetate and water and extracted with ethyl acetate (3×). The combined organic layers were combined and dried over magnesium sulfate. After evaporation of the solvent one obtains 350 mg of N2-(4-Amino-phenyl)-5-bromo-N4-[2-(3H-imidazol-4-y)-ethyl]-pyrimidine-2,4-diamine. ESI-MS: 375.

21e) 1-(4-{5-Bromo-4-[2-(3H-imidazol-4-yl)ethylamino]-pyrimidin-2-ylamino}-phenyl)-3-cyclopropyl-thiourea Cyclopropyl amine (0.275 mmole) was dissolved in THF (2 ml) and thiocarbonyl diimidazole (0.28 mmole) was added. The reaction was stirred at room temperature overnight and N2-(4-Amino-phenyl)-5-bromo-N4-[2-(3H-imidazol-4-yl)-ethyl]-pyrimidine-2,4-diamine (0.26 mmole) was added as a solution in THF (3 ml) and DMF (1 ml) and the reaction was stirred overnight. After removal of the solvents under reduced pressure the crude product was purified by flashmaster chromatography (dichloromethane:MeOH 9:1) to yield 12.5 mg of 1-(4-{5-Bromo-4-[2-(3H-imidazol-4-yl)-ethylamino]-pyrimidin-2-ylamino}-phenyl)-3-cyclopropyl-thiourea. ESI-MS; 474.

A21A 1-(4-{5-Bromo-4-[2-(3-imidazol-4-yl)-ethylamino]-pyrimidin-2-ylamino}-phenyl)-3-cyclopropyl-urea Cyclopropyl amine (0.275 mmole) was dissolved in THF (2 ml) and carbonyl diimidazole (0.28 mmole) was added. The reaction was stirred at room temperature overnight and N2-(4-Amino-phenyl)-5-bromo-N4-[2-(3H-imidazol-4-yl)-ethyl]-pyrimidine-2,4-diamine (0.26 mmole, prepared according to procedure 21) was added as a solution in THF (3 ml) and DMF (1 ml) and the reaction was stirred overnight, After removal of the solvents under reduced pressure the crude product was purified by flashmaster chromatography (dichloromethane MeOH 9:1) to yield 23 mg (19%) of 1-(4-(5-Bromo-4-[2-(3-imidazol-4-yl)-ethylamino]pyrimidin-2-ylamino]phenyl)-3-cyclopropyl-urea. ESI-MS: 458.

A22

5-Bromo-N2-(4-butylamino-phenyl)-N4-[2-(3H-imidazol-4-yl)ethyl]-pyrimidine-2,4-diamine N2-(4-Amino-phenyl)-5-bromo-N4-[2-(3H-imidazol-4-yl)-ethyl]-pyrimidine-2,4-diamine (1 g, 2.6 mmole, prepared according to procedure 21) was dissolved in MeOH (10 ml), butanal (2.6 ml, 2.9 mmole) was added at room temperature and the reaction mixture was stirred at room temperature for 20 minutes. Sodium cyanoborohydride (266 mg, 3.6 mmole) was added and the reaction mixture was stirred at room temperature overnight. After extraction with ethylacetate/bicarbonate solution (3×) the combined organic layers were washed with saturated NaCl-solution, dried over magnesium sulfate and evaporated. The crude product was purified by flashmaster chromatography (dichloromethane:MeOH 95:5) to provide 5-Bromo-N2-(4-butylamino-phenyl)-N4-[2-(3H-imidazol-4-yl)-ethyl]-pyrimidine-2,4-diamine (130 mg). ESI-MS: 431.

A23

N-(4-{5-Bromo-4-[2-(3H-imidazol-4-yl)-ethylamino]-pyrimidin-2-ylamino}-phenyl)4-methanesulfonyl-3-nitro-benzamide 23a) 4-Methylsulfanyl-3-nitro-benzoic acid 4-chloro-3-nitrobenzoic acid (10 g) were suspended in ethanol (50 ml) and water (50 ml) and sodium bicarbonate (4.16 g) was added in portions. The reaction mixture was heated at reflux for 5 minutes and NaSMe (6.95 g) was added in one portion at this temperature. The reaction was stirred under reflux for further 3 hours and then cooled to ambient temperature. The precipitate was collected by filtration to provide 4-Methylsulfanyl-3-nitro-benzoic acid (11 g, quantitative). This material was used without further purification for the following step (procedure 23b)

23b) 4-Methanesulfonyl-nitro-benzoic acid

4-Methylsulfanyl-3-nitro-benzoic acid (1 g, 4.69 mmole) was dissolved in methanol (25 ml) and cooled to 5° C. A solution of Oxone® (5.8 g) in water (20 ml) was added portionwise at the same temperature. The reaction mixture was allowed to stir overnight at ambient temperature, methanol was removed under reduced pressure. The suspension was diluted with water and the solid was filtered off and dried in vacuum to provide 4-Methanesulfonyl-3-nitro-benzoic acid in 89% yield (960 mg). ESI-MS: 246.

23c) N-(4-{5-Bromo-4-[2-(3H-imidazol-4-yl)-ethylamino]-pyrimidin-2-ylamino}-phenyl)4-methanesulfonyl-3-nitro-benzamide 4-Methanesulfonyl-3-nitro-benzoic acid (72 mg, 0.29 mmole) was dissolved in DMA (3 ml) and thionyl chloride (0.29 mmole) was added at ambient temperature. After the mixture was stirred for 5 minutes N2-(4-Amino-phenyl)-5-bromo-N4-[2-(3H-imidazol-4-yl)-ethyl]-pyrimidine-2,4-diamine (100 mg, 0.26 mmole, prepared according to procedure 21) was added and the reaction was allowed to stir overnight. After extraction with bicarbonate solution and ethyl acetate (3×) the combined organic layers were dried over magnesium sulfate and the solvent was removed under reduced pressure. The crude product was purified by flashmaster chromatography on silica gel to provide 37 mg of N-(4-{5-Bromo-4-[2-(3H-imidazol-4-yl)-ethylamino]-pyrimidin-2-ylamino}-phenyl}-4-methanesulfonyl-3-nitro-benzamide (23% yield). ESI-MS: 602.

A 24

[4-(5-Bromo-4-prop-2-ynylamino-pyrimidin-2-ylamino)-phenyl]-carbamic acid butyl ester N2-(4-Amino-phenyl)-5-bromo-N4-prop-2-ynyl-pyrimidine-2,4-diamine (0.31 mmol, prepared in analogy to procedure 21) was dissolved in THF (20 ml), triethyl amine (0.33 mmole) and butyl chloroformate (0.33 mmole) were added at room temperature and the reaction was stirred at this temperature until the starting material disappeared (TLC, 3 h). The reaction was poured into water and [4-(5-Bromo-4-prop-2-ynylamino-pyrimidin-2-ylamino)-phenyl]-carbamic acid butyl ester was isolated by filtration. Yield: 91 mg (70%). ESI-MS: 419.

A25

1-Allyl-3-[4-(5-bromo-4-prop-2-ynylamino-pyrimidin-2-ylamino)-phenyl]-thiourea

N2-(4-Amino-phenyl)-5-bromo-N4-prop-2-ynyl-pyrimidine-2,4-diamine (100 mg, 0.3 mmole, prepared in analogy procedure 21) was dissolved in acetonitrile (10 ml) and allyl isothiocyanate (1 ml) was added at room temperature. The reaction mixture was heated under reflux for 3 hours, the solvent removed under reduced pressure and 1-Allyl-3[4-(5-bromo-4-prop-2-ynylamino-pyrimidin-2-ylamino)-phenyl]-thiourea was crystallized from acetone/ethyl acetate/hexanes. Yield 37 mg. ESI-MS: 418.

A26

1-[4-(5-Bromo-4-prop-2-ynylamino-pyrimidin-2-ylamino)-phenyl]-3-ethyl-urea

N2-(4-Amino-phenyl)-5-bromo-N4-prop-2-ynyl-pyrimidine-2,4-diamine (100 mg, 0.3 mmole, prepared in analogy to procedure 21) was dissolved in acetonitrile (10 ml) and ethyl isocyanate (0.5 ml) was added at room temperature. The reaction mixture was heated under reflux for 5 hours and then cooled to room temperature and stirred overnight. The solid was filtered off and dried under high vacuum to provide 47 mg of 1-[4-(5-Bromo-4-prop-2-ynylamino-pyrimidin-2-ylamino)-phenyl]-3-ethyl-urea. ESI-MS: 390.

A27

1-Methyl-1H-imidazole-4-sulfonic acid [4-(5-bromo-4-prop-2-ynylamino-pyrimidin-2-ylamino)-phenyl]-amide N2-(4-Amino-phenyl)-5-bromo-N4-prop-2-ynyl-pyrimidine-2,4-diamine (100 mg, 0.3 mmole prepared in analogy to procedure 21) was dissolved in acetonitrile (10 ml) and triethylamine (1 ml) and 1-Methyl-1H-imidazole-4-sulfonyl chloride (120 mg, 0.66 mmole) was added at room temperature. The reaction mixture was stirred under reflux for 5 hours, the solvent was removed under reduced pressure and the crude product was purified by column chromatography on silica gel (ethyl acetate: hexanes 1:1). Yield 41 mg of 1-Methyl-1H-imidazole-4-sulfonic acid [4-(5-b bromo-4-prop-2-ynylamino-pyrimidin-2-ylamino)-phenyl]-amide. ESI-MS: 463.

The following examples were prepared in analogy to the compounds described above.

| Example | Structure | ESI-MS | Mol-Weight |
|---|---|---|---|
| 28 | 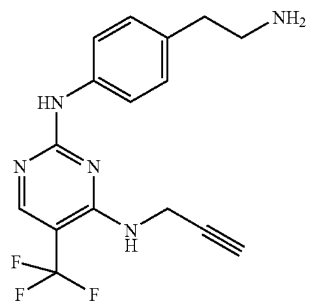 | 336 | |
| 29 | 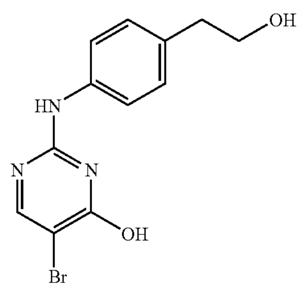 | 311 | |
| 30 | 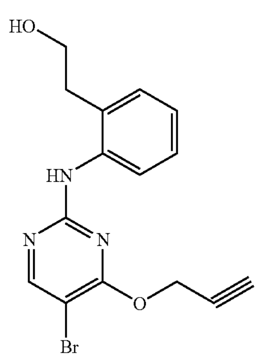 | 349 | |

-continued
| Example | Structure | ESI-MS | Mol-Weight |
|---|---|---|---|
| 31 | 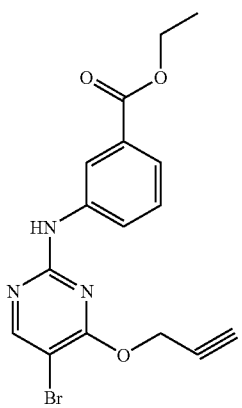 | 377 | |
| 32 | 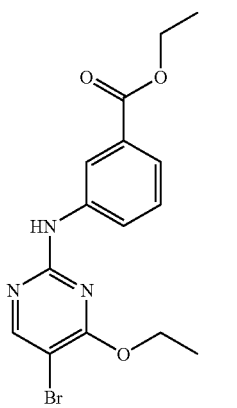 | 367 | |
| 33 | 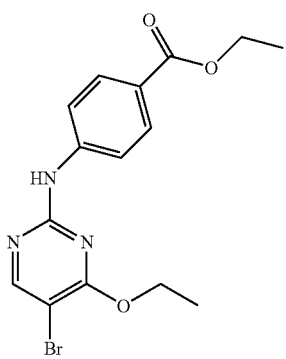 | 367 | |
| 34 | 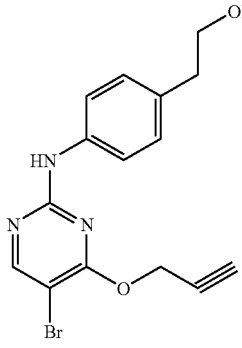 | 349 | |

-continued

| Example | Structure | ESI-MS | Mol-Weight |
|---|---|---|---|
| 35 | 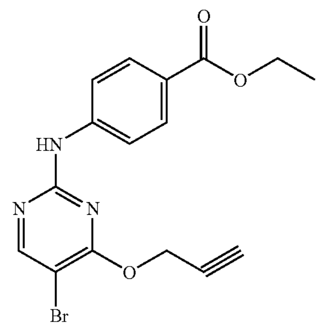 | | 377 |
| 36 | 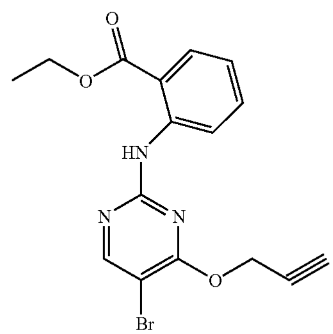 | | 377 |
| 37 | 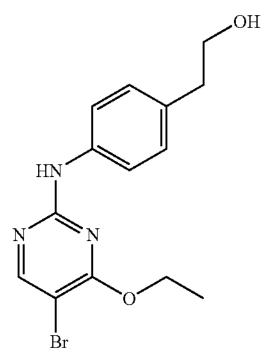 | | 339 |
| 38 | 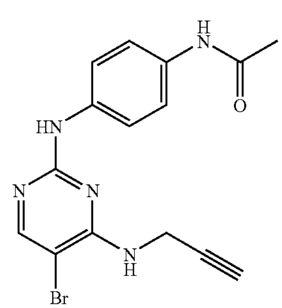 | | 361 |

-continued

| Example | Structure | ESI-MS | Mol-Weight |
|---|---|---|---|
| 39 | 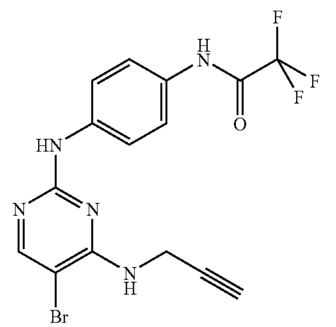 | 415 | |
| 40 | 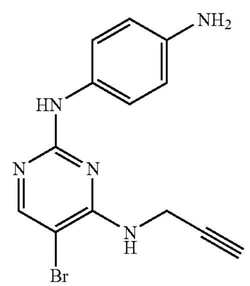 | 319 | |
| 41 | 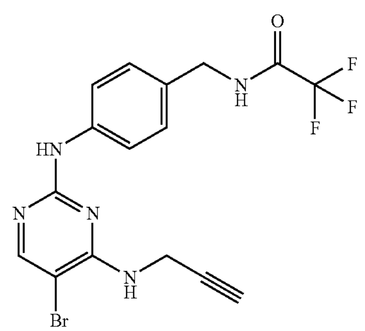 | 429 | |
| 42 | 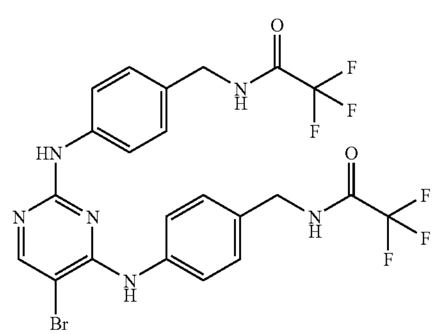 | 592 | |
| 43 | 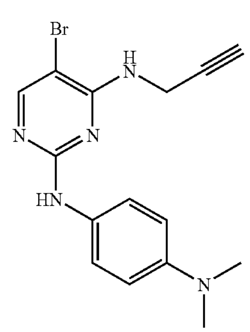 | 347 | |

-continued

| Example | Structure | ESI-MS | Mol-Weight |
|---|---|---|---|
| 44 | 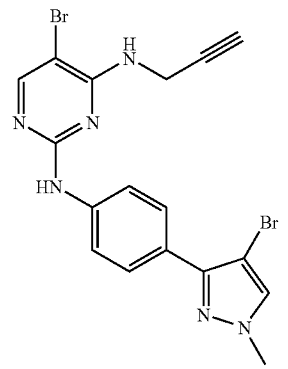 | 463 | |
| 45 | 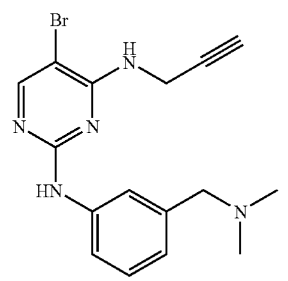 | 361 | |
| 46 | 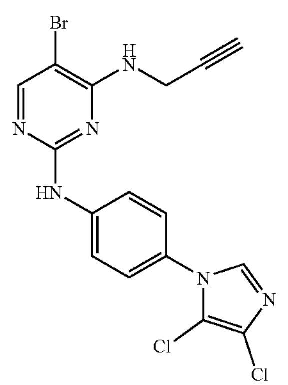 | 439 | |
| 47 | 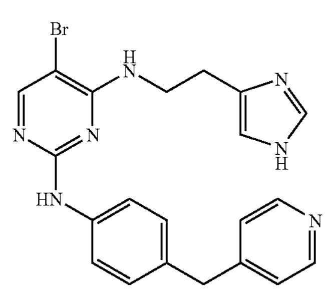 | 451 | |

-continued

| Example | Structure | ESI-MS | Mol-Weight |
|---------|-----------|--------|------------|
| 48 | 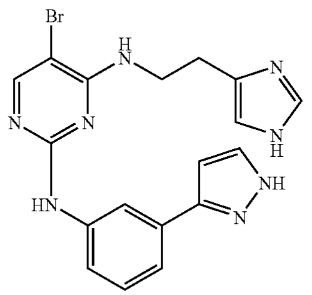 | 426 | |
| 49 | 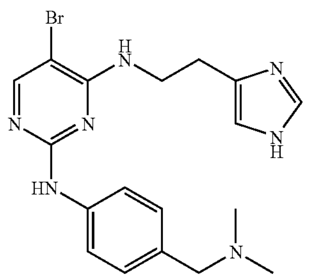 | 417 | |
| 50 | 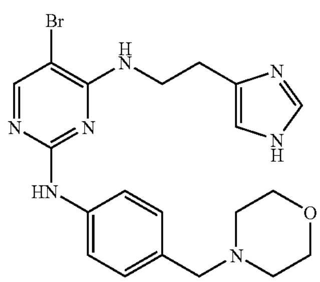 | 459 | |
| 51 | 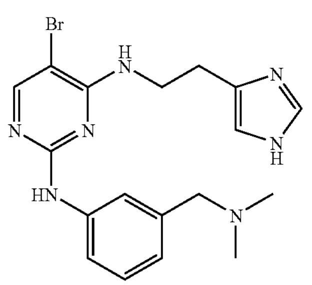 | 417 | |
| 52 | 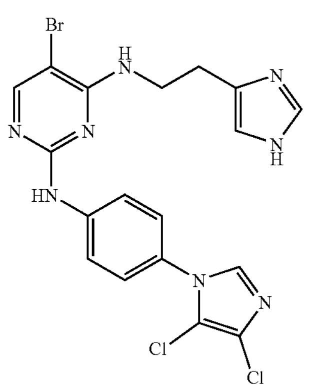 | 495 | |

-continued

| Example | Structure | ESI-MS | Mol-Weight |
|---|---|---|---|
| 53 | 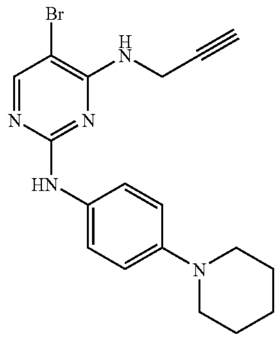 | | 387 |
| 54 | 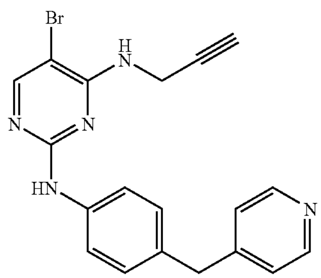 | | 395 |
| 55 | 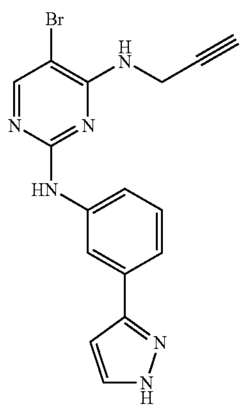 | | 370 |
| 56 | 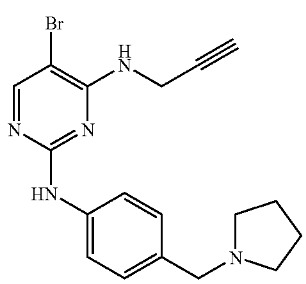 | | 387 |
| 57 | 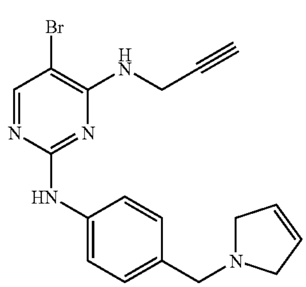 | | 385 |

-continued
| Example | Structure | ESI-MS | Mol-Weight |
|---|---|---|---|
| 58 | 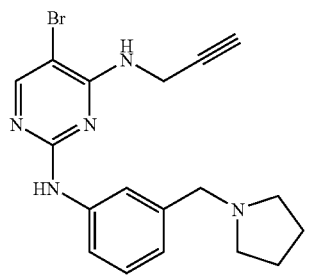 | 387 | |
| 59 | 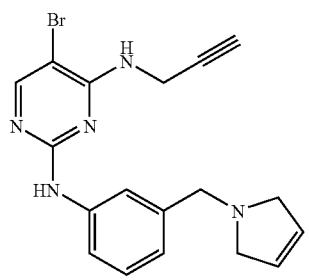 | 385 | |
| 60 | 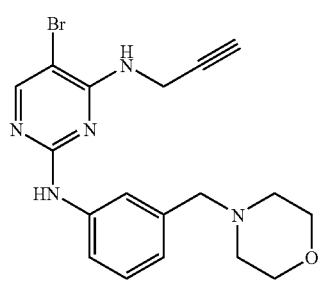 | 403 | |
| 61 | 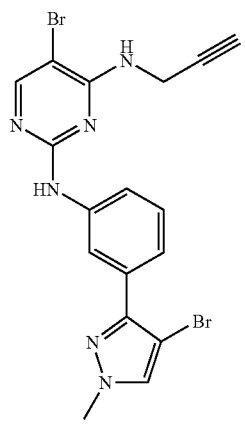 | 463 | |

-continued
| Example | Structure | ESI-MS | Mol-Weight |
|---|---|---|---|
| 62 | 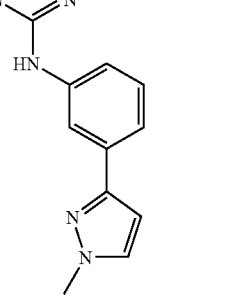 | | 384 |
| 63 | 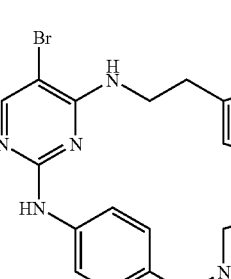 | | 441 |
| 64 | 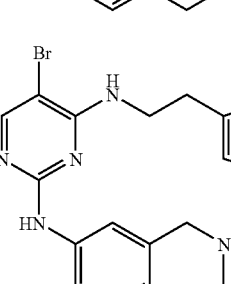 | | 443 |
| 65 | 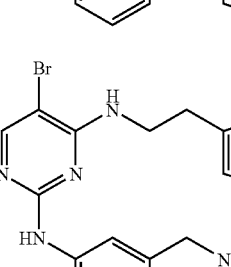 | | 441 |
| 66 | 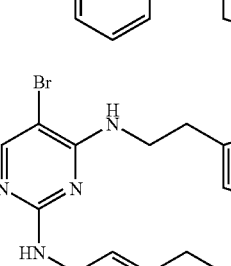 | | 459 |

-continued
| Example | Structure | ESI-MS | Mol-Weight |
|---|---|---|---|
| 67 | 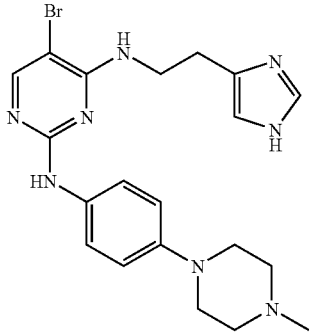 | 458 | |
| 68 | 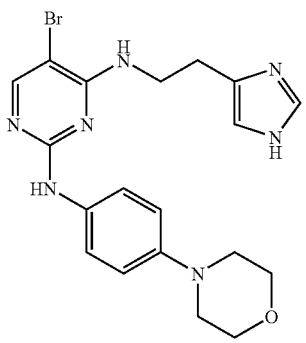 | 445 | |
| 69 | 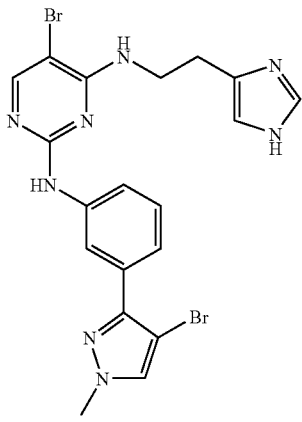 | 519 | |
| 70 | 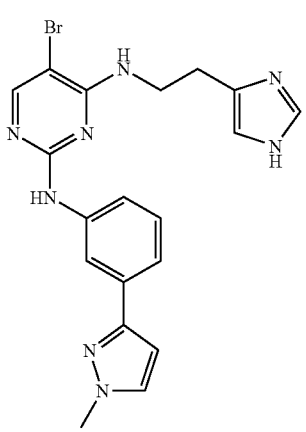 | 440 | |

-continued
| Example | Structure | ESI-MS | Mol-Weight |
|---|---|---|---|
| 71 | 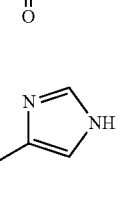 | 471 | |
| 72 | 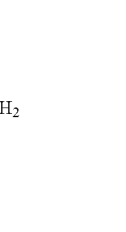 | 375 | |
| 73 | 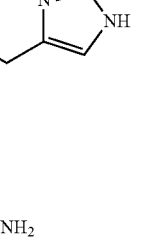 | 308 | |
| 74 | 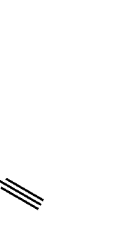 | 443 | |

-continued

| Example | Structure | ESI-MS | Mol-Weight |
|---|---|---|---|
| 75 | 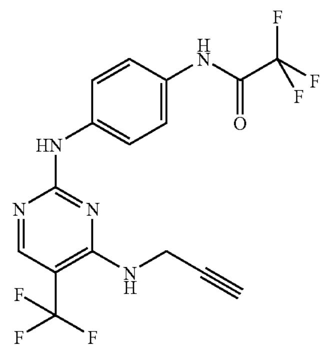 | 404 | |
| 76 | 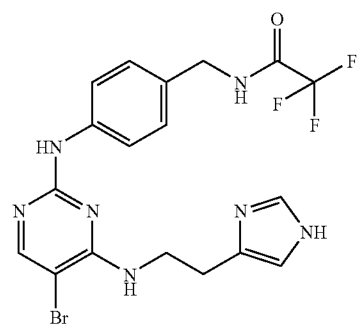 | 485 | |
| 77 | 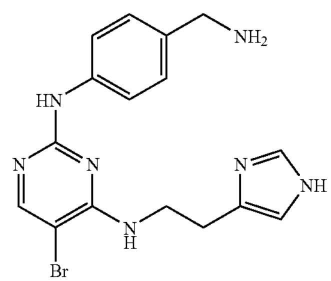 | 389 | |
| 78 | 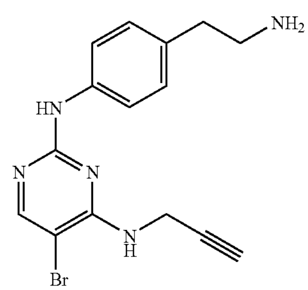 | 347 | |
| 79 | 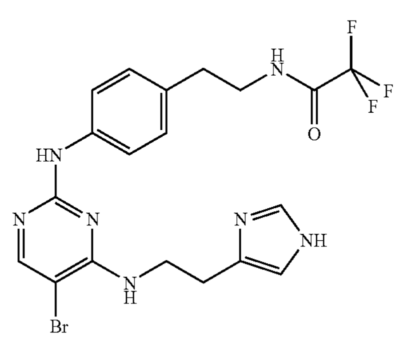 | 499 | |

-continued

| Example | Structure | ESI-MS | Mol-Weight |
|---|---|---|---|
| 80 | 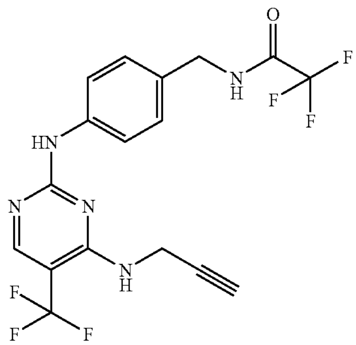 | | 418 |
| 81 | 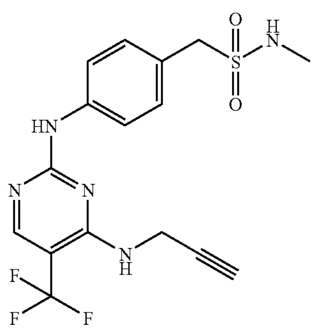 | | 400 |
| 82 | 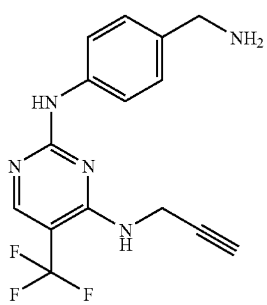 | | 322 |
| 83 | 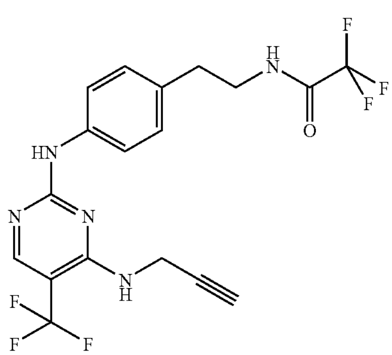 | | 432 |

| Example | Structure | ESI-MS | Mol-Weight |
|---|---|---|---|
| 84 | 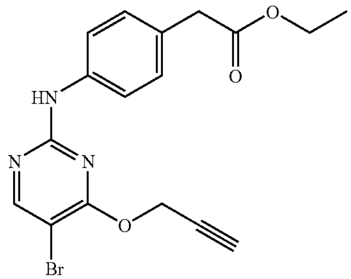 | 391 | |
| 85 | 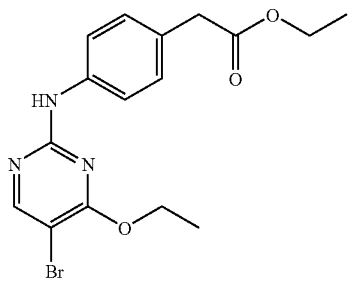 | 381 | |
| 86 | 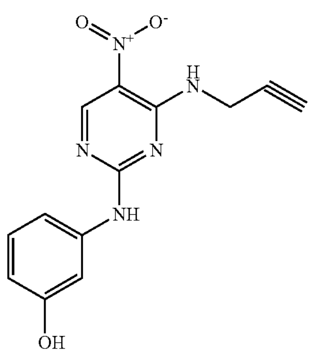 | 286 | 285.262 |
| 87 | 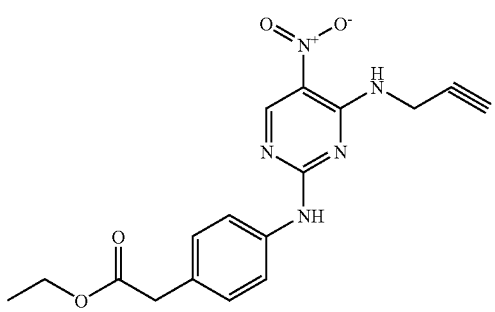 | 344 | 343.385 |
| 88 | 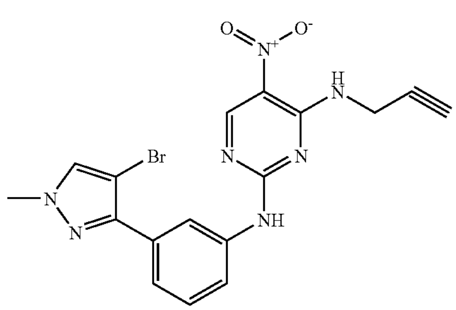 | 429 | 428.249 |

-continued

| Example | Structure | ESI-MS | Mol-Weight |
|---|---|---|---|
| 89 | 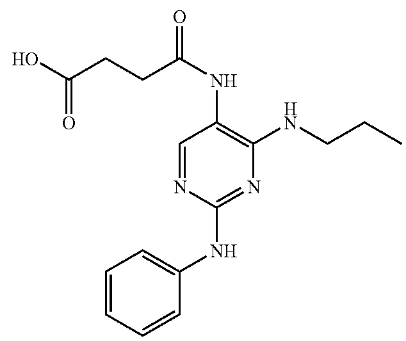 | 344 | 343.385 |
| 90 | 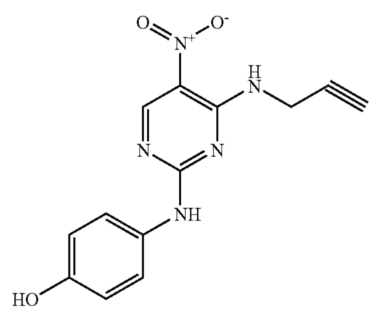 | 286 | 285.262 |
| 91 | 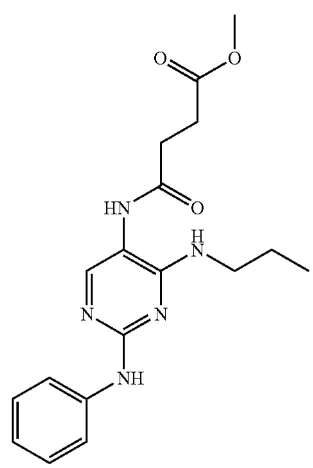 | 358 | 357.412 |
| 92 | 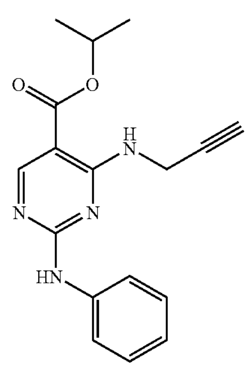 | 311 | 310.355 |

-continued

| Example | Structure | ESI-MS | Mol-Weight |
|---|---|---|---|
| 93 | 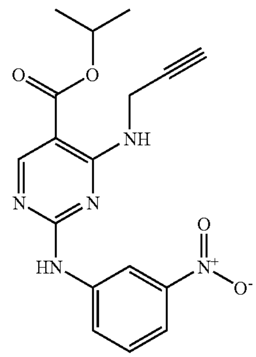 | 356 | 355.352 |
| 94 | 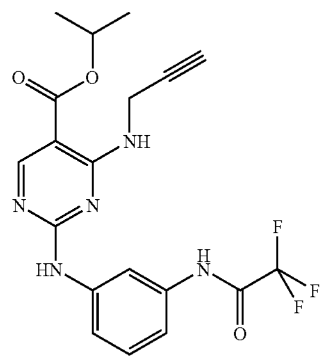 | 422 | 421.377 |
| 95 | 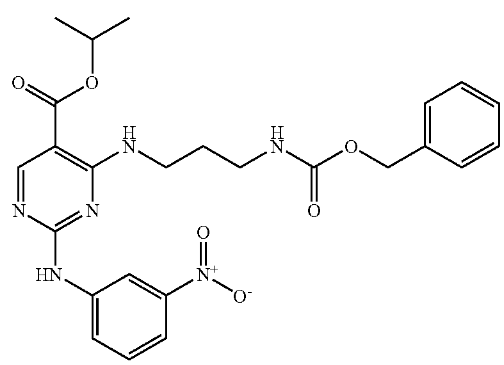 | 508 | 508.532 |
| 96 | 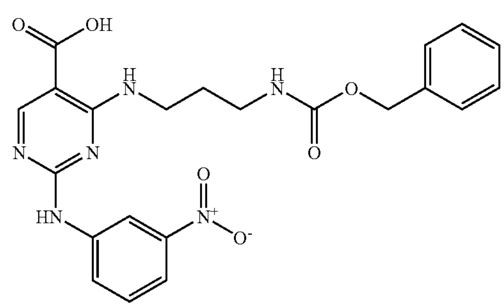 | 467 | 466.452 |

-continued

| Example | Structure | ESI-MS | Mol-Weight |
|---------|-----------|--------|------------|
| 97 | 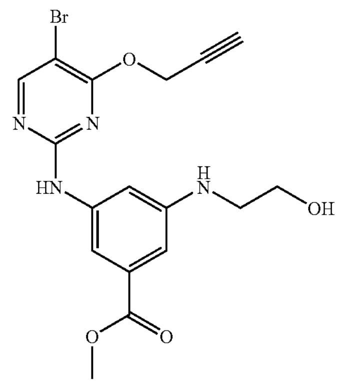 | 422 | 421.249 |
| 98 | 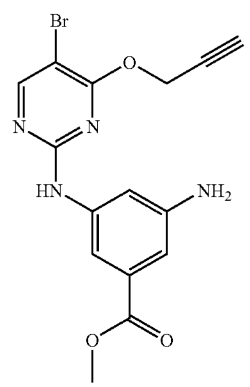 | 378 | 377.197 |
| 99 | 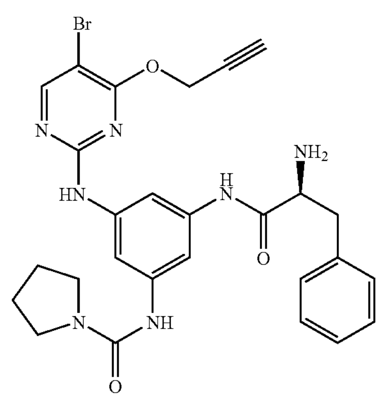 | 579 | 578.468 |
| 100 | 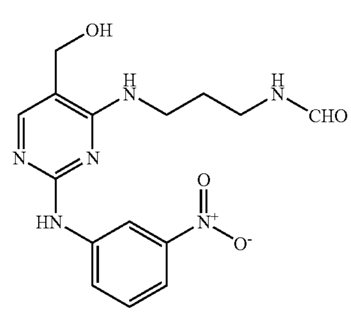 | 347 | 346.35 |

-continued

| Example | Structure | ESI-MS | Mol-Weight |
|---|---|---|---|
| 101 | 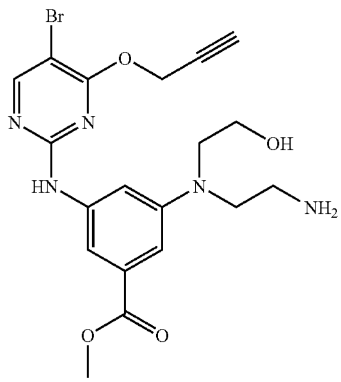 | 453 | 452.469 |
| 102 | 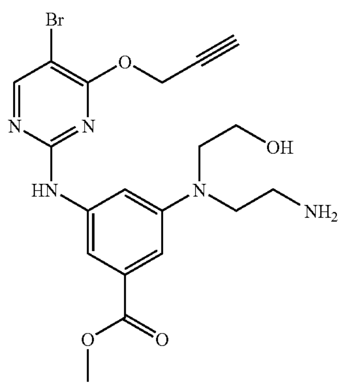 | 466 | 465.302 |
| 103 | 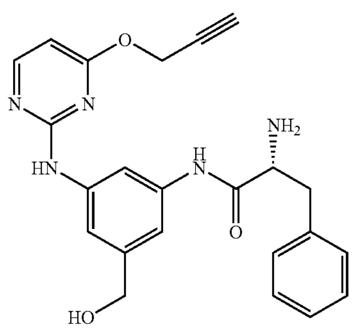 | 418 | 417.47 |
| 104 | 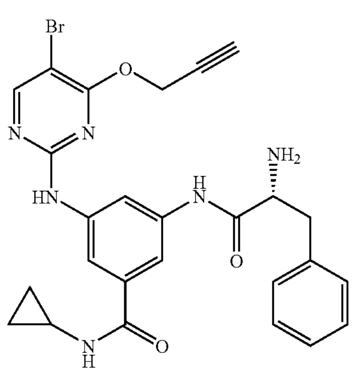 | 550 | 549.43 |

| Example | Structure | ESI-MS | Mol-Weight |
|---|---|---|---|
| 105 | 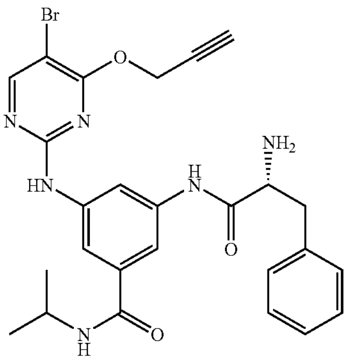 | 552 | 551.45 |
| 106 | 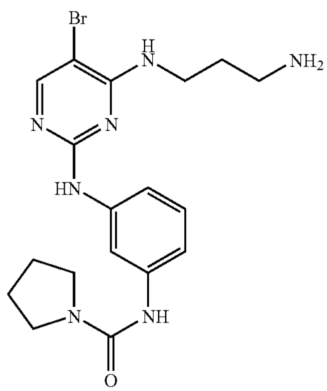 | 435 | 434.34 |
| 107 | 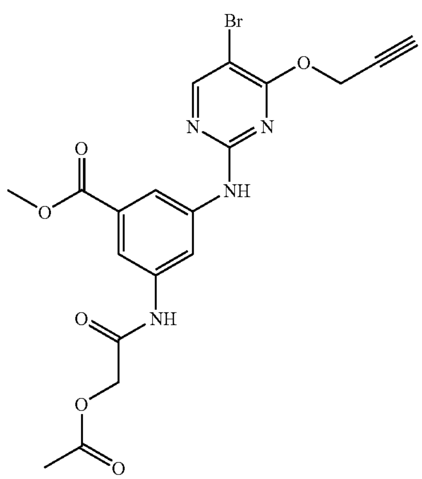 | 478 | 477.27 |
| 108 | 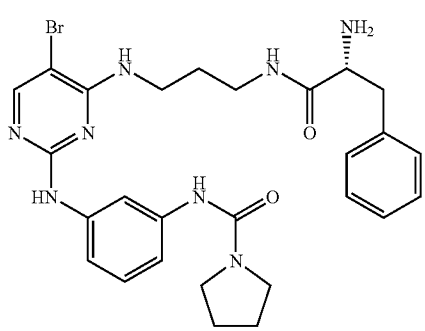 | 582 | 581.52 |

-continued

| Example | Structure | ESI-MS | Mol-Weight |
|---|---|---|---|
| 109 | 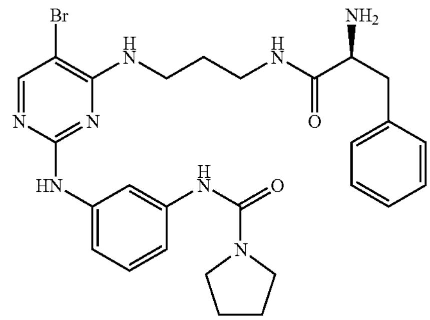 | 582 | 581.52 |
| 110 | 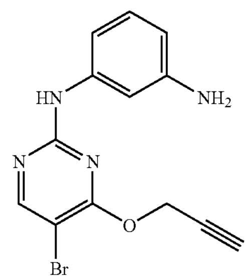 | 320 | 319.161 |
| 111 | 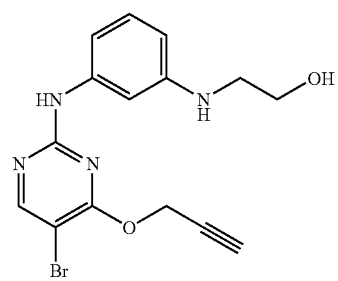 | 364 | 363.214 |
| 112 | 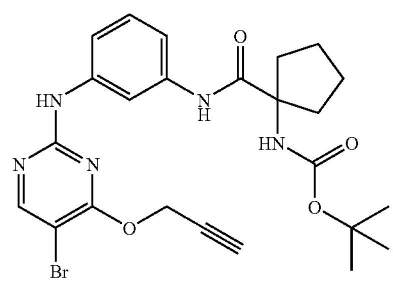 | 531 | 530.42 |
| 113 | 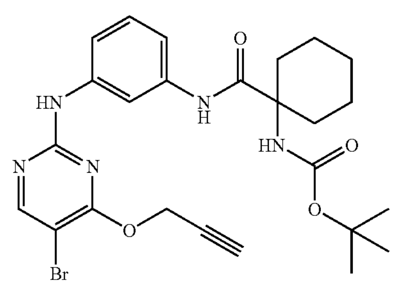 | 545 | 544.447 |

-continued
| Example | Structure | ESI-MS | Mol-Weight |
|---|---|---|---|
| 114 | 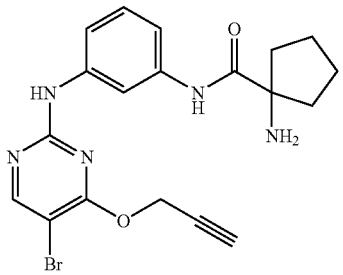 | 431 | 430.304 |
| 115 | 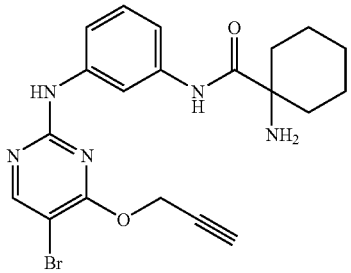 | 445 | 444.331 |
| 116 | 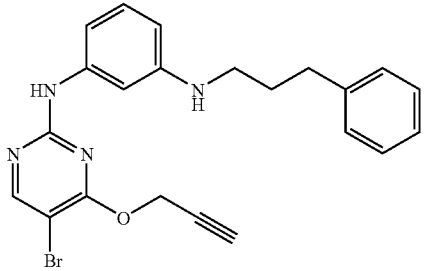 | 438 | 437.339 |
| 117 | 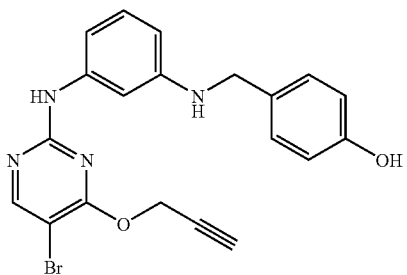 | 426 | 425.284 |
| 118 | 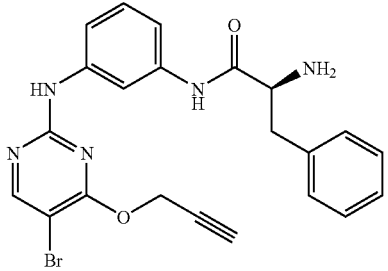 | 467 | 466.337 |

-continued

| Example | Structure | ESI-MS | Mol-Weight |
|---|---|---|---|
| 119 | 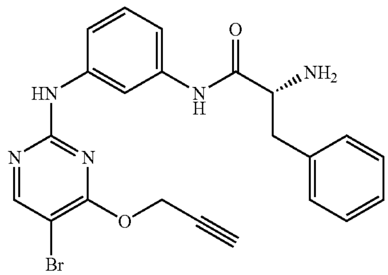 | 467 | 466.337 |
| 120 | 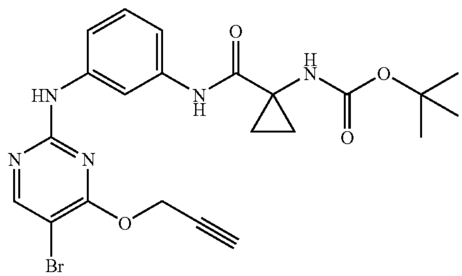 | 503 | 502.367 |
| 121 | 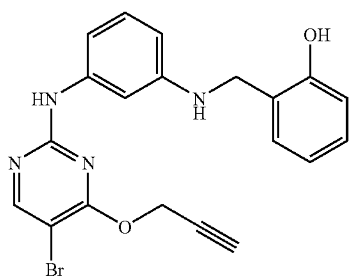 | 426 | 425.284 |
| 122 | 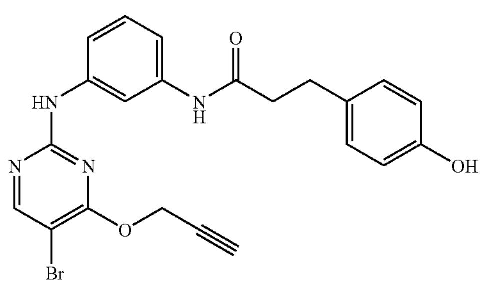 | 468 | 467.33 |
| 123 | 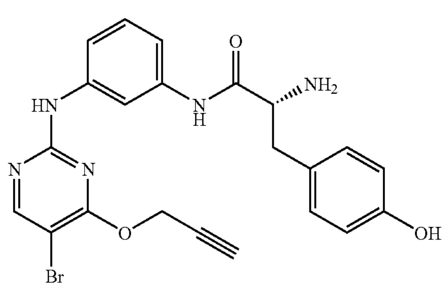 | 483 | 482.34 |

| Example | Structure | ESI-MS | Mol-Weight |
|---|---|---|---|
| 124 | 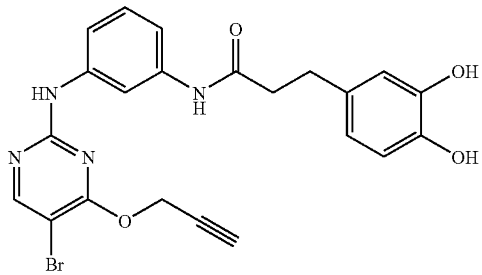 | 484 | 483.33 |
| 125 | 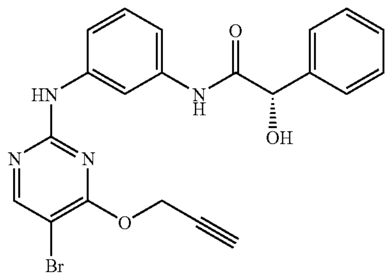 | 454 | 453.30 |
| 126 | 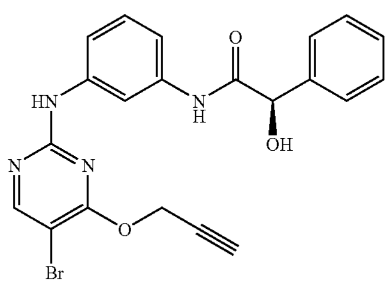 | 454 | 453.30 |
| 127 | 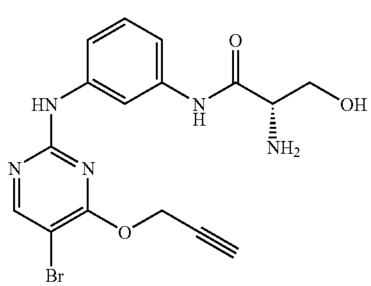 | 407 | 406.24 |
| 128 | 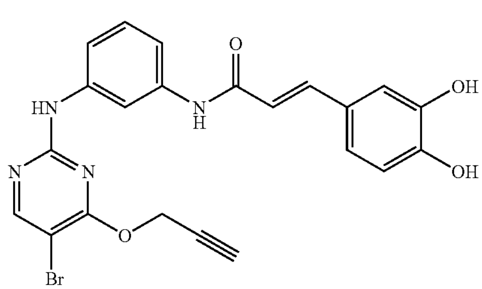 | 482 | 481.31 |

-continued

| Example | Structure | ESI-MS | Mol-Weight |
|---|---|---|---|
| 129 | 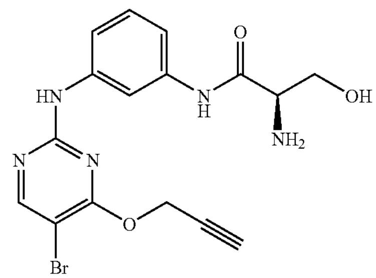 | 407 | 406.24 |
| 130 | 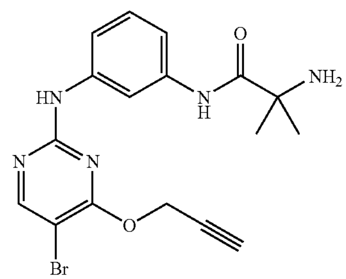 | 405 | 404.27 |
| 131 | 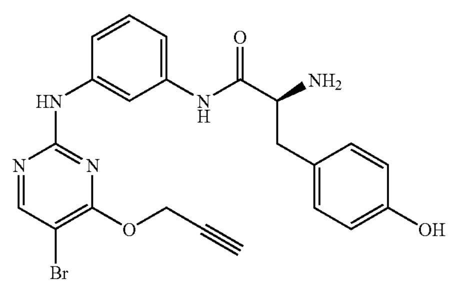 | 483 | 482.34 |
| 132 | 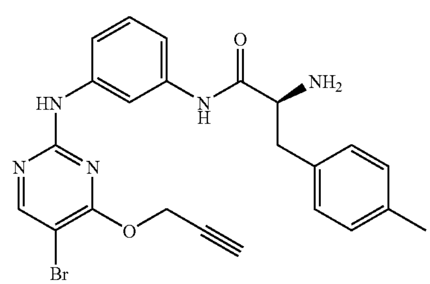 | 481 | 480.37 |
| 133 | 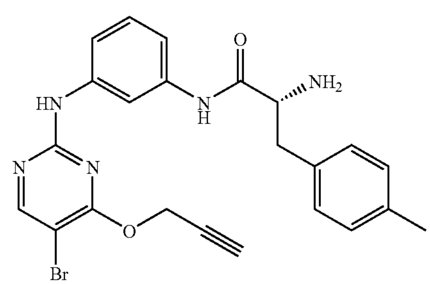 | 481 | 480.37 |

-continued

| Example | Structure | ESI-MS | Mol-Weight |
|---|---|---|---|
| 134 | 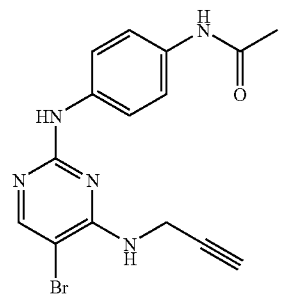 | 361 | 360.214 |
| 135 | 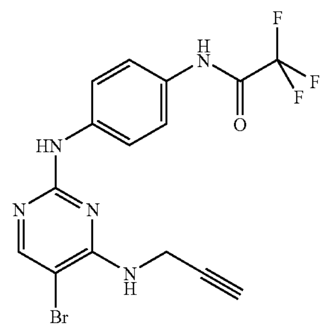 | 415 | 414.184 |
| 136 | 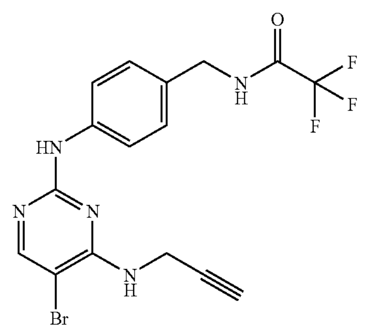 | 429 | 428.211 |
| 137 | 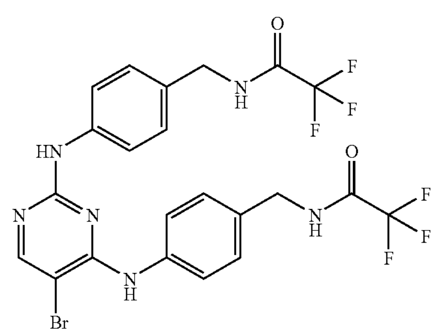 | 592 | 591.308 |
| 138 | 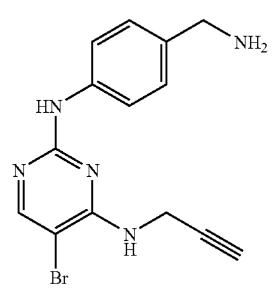 | 333 | 332.204 |

-continued

| Example | Structure | ESI-MS | Mol-Weight |
| --- | --- | --- | --- |
| 139 | 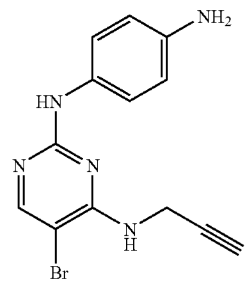 | 319 | 318.177 |
| 140 | 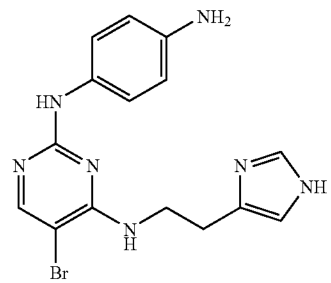 | 375 | 374.244 |
| 141 | 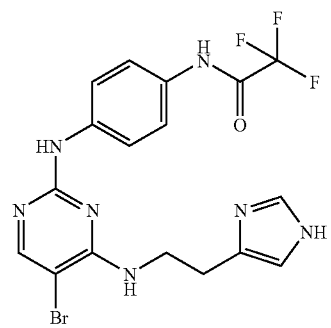 | 471 | 470.251 |
| 142 | 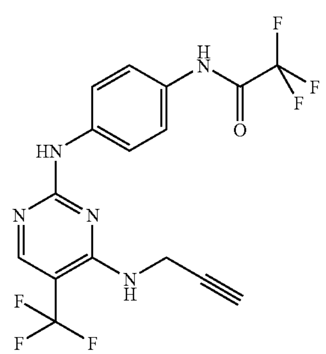 | 404 | 403.285 |
| 143 | 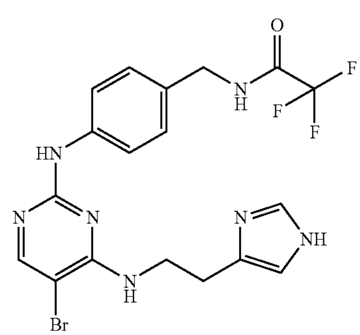 | 485 | 484.278 |

-continued

| Example | Structure | ESI-MS | Mol-Weight |
|---|---|---|---|
| 144 | 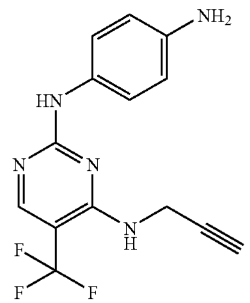 | 308 | 307.278 |
| 145 | 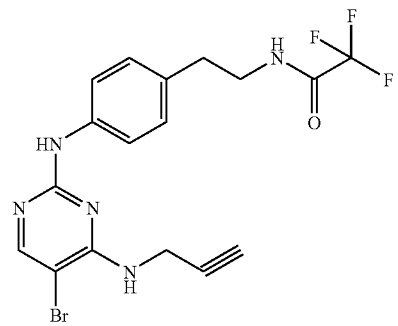 | 443 | 442.237 |
| 146 | 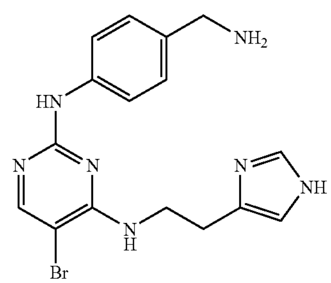 | 389 | 388.271 |
| 147 | 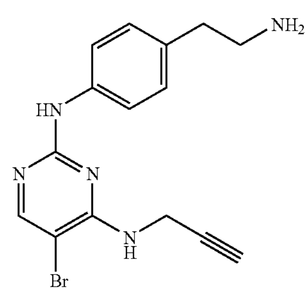 | 347 | 346.230 |
| 148 | 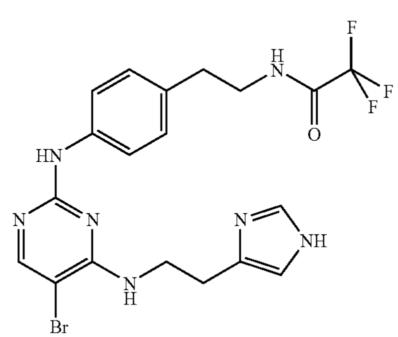 | 499 | 498.305 |

| Example | Structure | ESI-MS | Mol-Weight |
|---|---|---|---|
| 149 | 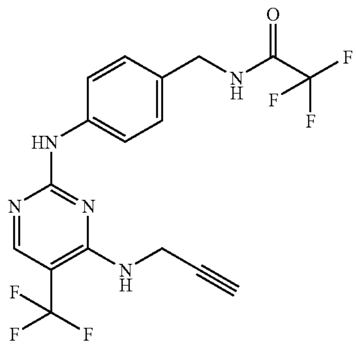 | 418 | 417.312 |
| 150 | 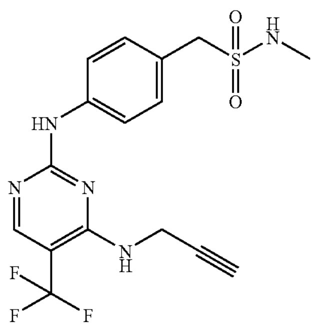 | 400 | 399.395 |
| 151 | 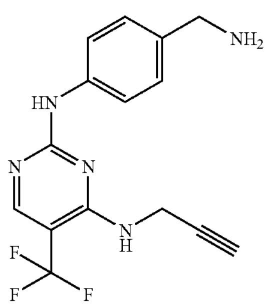 | 322 | 321.305 |
| 152 | 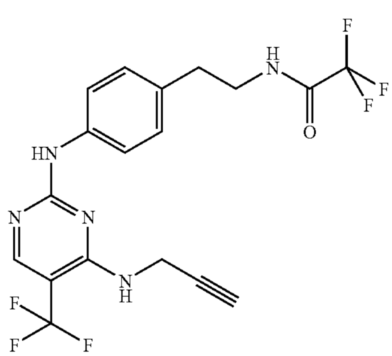 | 432 | 431.339 |

-continued
| Example | Structure | ESI-MS | Mol-Weight |
|---|---|---|---|
| 153 | 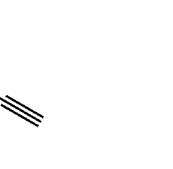 | 391 | 390.235 |
| 154 | 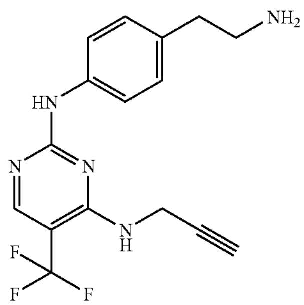 | 336 | 335.331 |
| 155 | 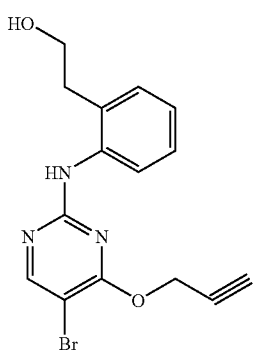 | 349 | 348.199 |
| 156 | 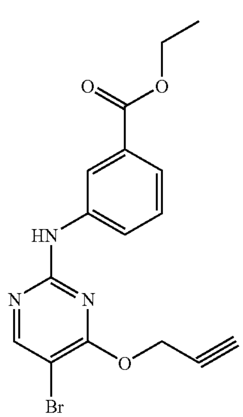 | 377 | 376.209 |

| Example | Structure | ESI-MS | Mol-Weight |
|---|---|---|---|
| 157 | 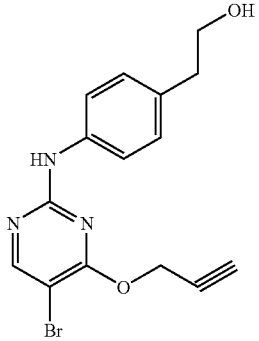 | 349 | 348.199 |
| 158 | 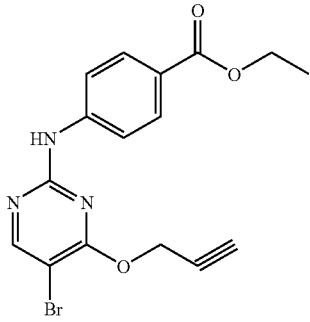 | 377 | 376.209 |
| 159 | 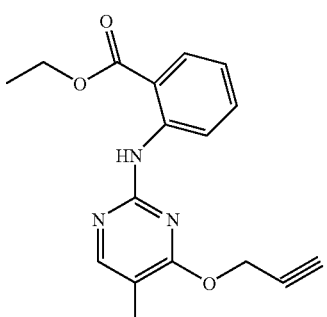 | 377 | 376.209 |
| 160 | 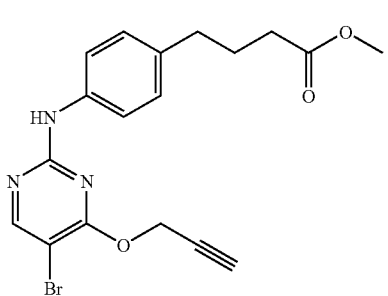 | 405 | 404.262 |

-continued
| Example | Structure | ESI-MS | Mol-Weight |
|---|---|---|---|
| 161 | 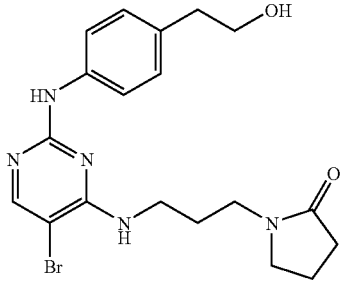 | 435 | 434.336 |
| 162 | 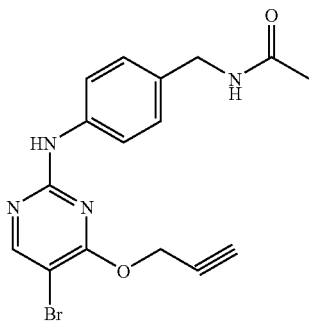 | 376 | 375.224 |
| 163 | 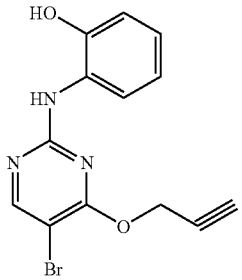 | 321 | 320.145 |
| 164 | 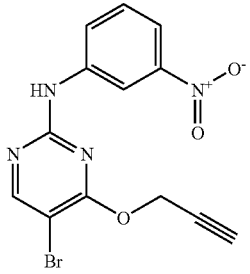 | 350 | 349.143 |
| 165 | 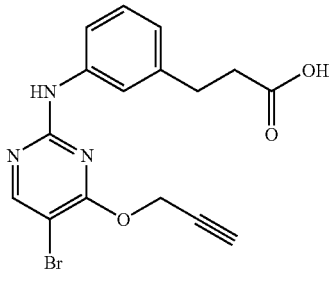 | 377 | 376.209 |

-continued

| Example | Structure | ESI-MS | Mol-Weight |
|---------|-----------|--------|------------|
| 166 | 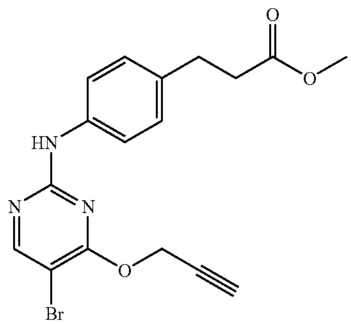 | 391 | 390.235 |
| 167 | 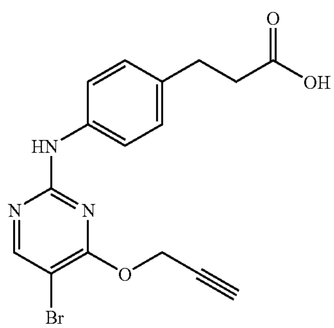 | 377 | 376.209 |
| 168 | 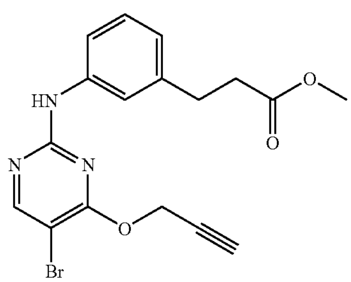 | 391 | 390.235 |
| 169 | 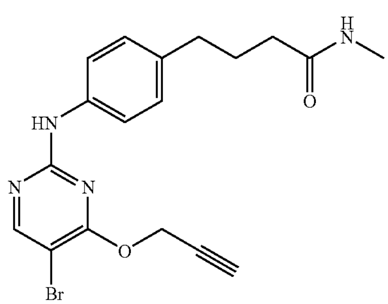 | 404 | 403.278 |
| 170 | 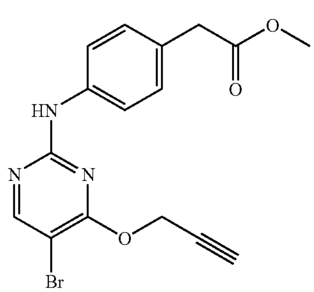 | 377 | 376.209 |

-continued

| Example | Structure | ESI-MS | Mol-Weight |
|---|---|---|---|
| 171 | 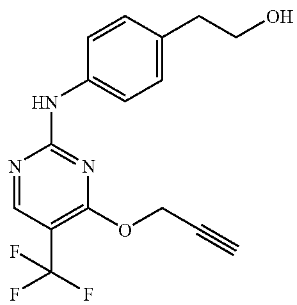 | 338 | 337.300 |
| 172 | 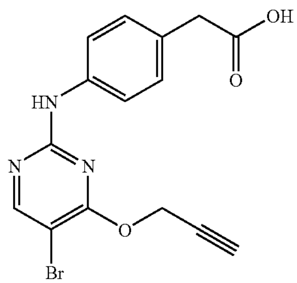 | 363 | 362.182 |
| 173 | 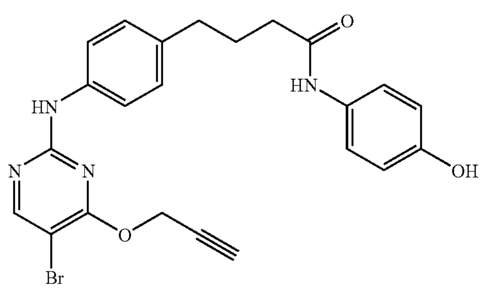 | 482 | 481.348 |
| 174 | 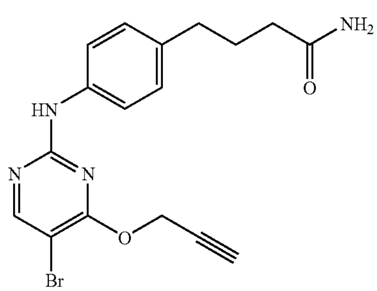 | 390 | 389.251 |
| 175 | 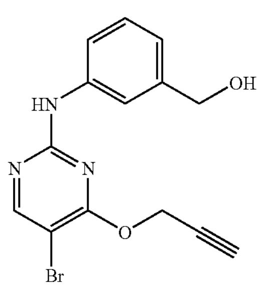 | 335 | 334.172 |

| Example | Structure | ESI-MS | Mol-Weight |
|---|---|---|---|
| 176 | 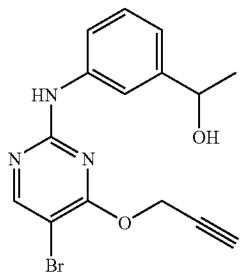 | 349 | 348.199 |
| 177 | 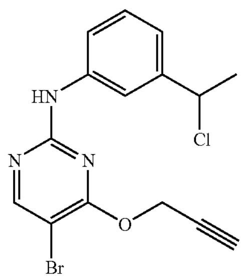 | 367 | 366.645 |
| 178 | 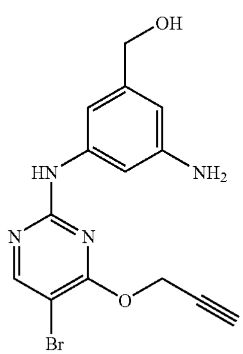 | 350 | 349.187 |
| 179 | 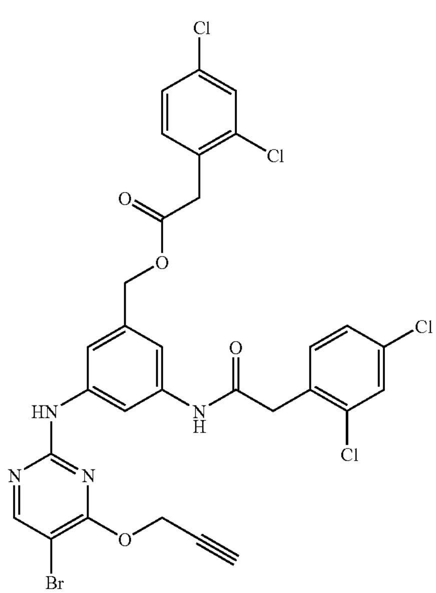 | 724 | 723.236 |

-continued

| Example | Structure | ESI-MS | Mol-Weight |
|---|---|---|---|
| 180 | 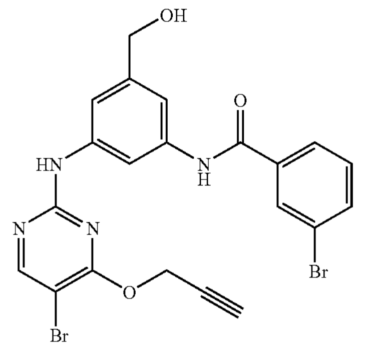 | 533 | 532.190 |
| 181 | 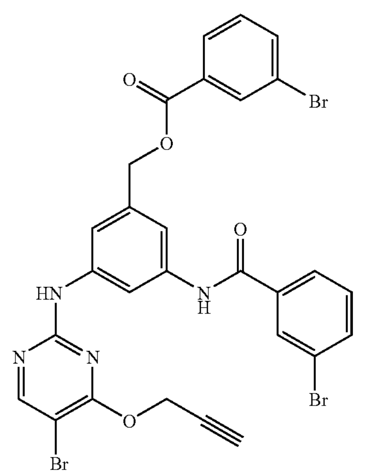 | 716 | 715.194 |
| 182 | 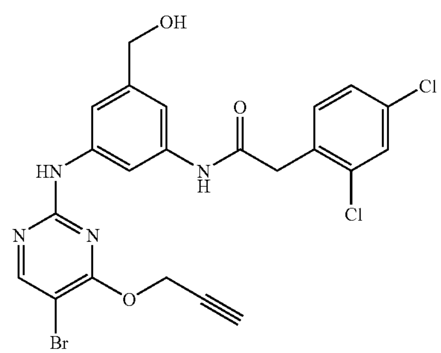 | 537 | 536.211 |
| 183 | 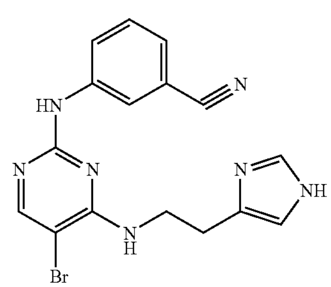 | 385 | 384.24 |

-continued

| Example | Structure | ESI-MS | Mol-Weight |
|---|---|---|---|
| 184 | 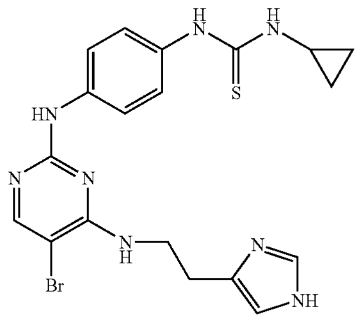 | 474 | 473.401 |
| 185 | 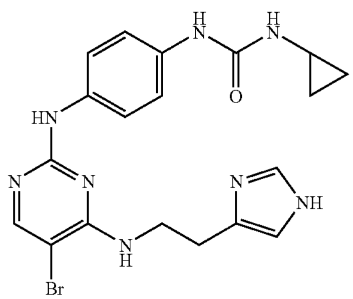 | 458 | 457.334 |
| 186 | 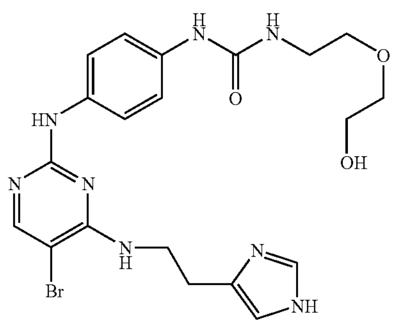 | 506 | 505.375 |
| 187 | 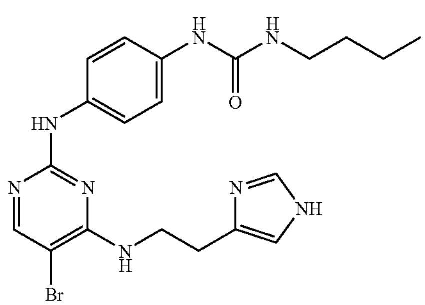 | 474 | 473.376 |
| 188 | 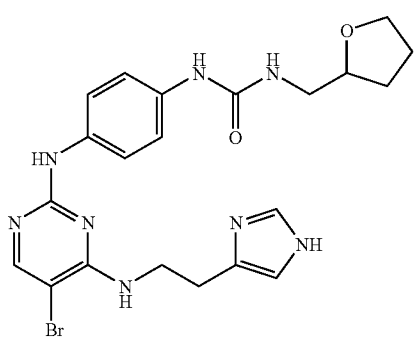 | 502 | 501.387 |

-continued

| Example | Structure | ESI-MS | Mol-Weight |
|---|---|---|---|
| 189 | 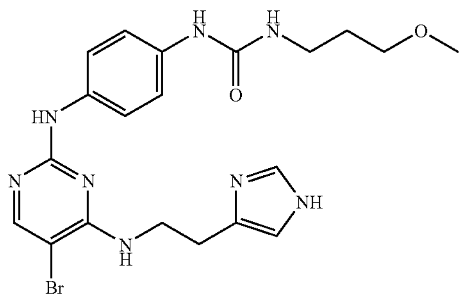 | 490 | 489.375 |
| 190 | 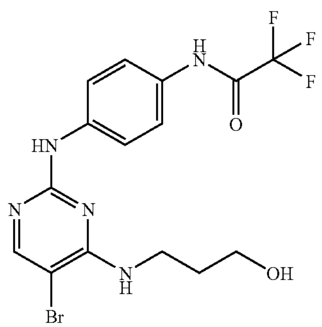 | 433 | 432.238 |
| 191 | 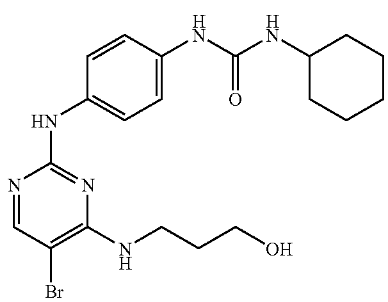 | 464 | 463.377 |
| 192 | 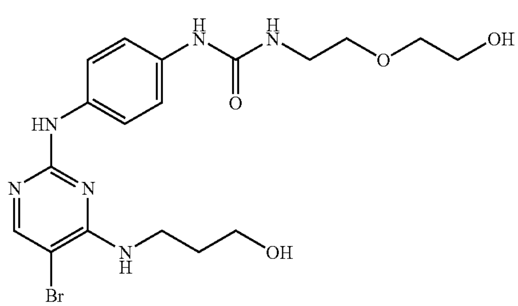 | 470 | 469.337 |
| 193 | 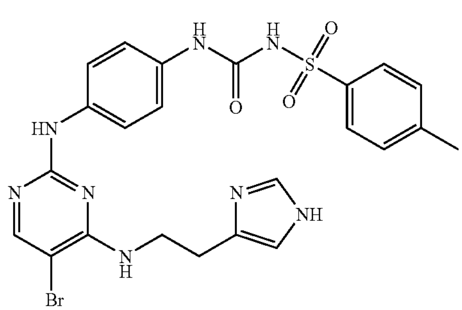 | 572 | 571.458 |

-continued

| Example | Structure | ESI-MS | Mol-Weight |
|---|---|---|---|
| 194 | 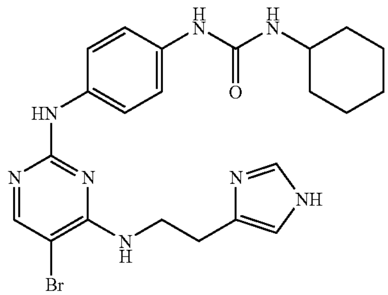 | 500 | 499.414 |
| 195 | 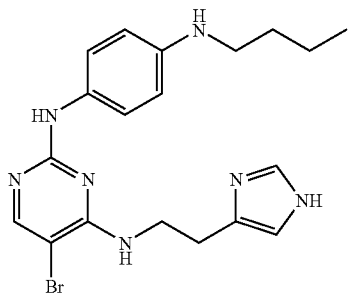 | 431 | 430.352 |
| 196 | 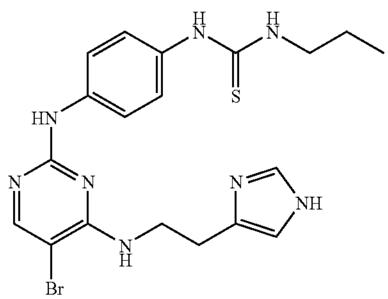 | 476 | 475.417 |
| 197 | 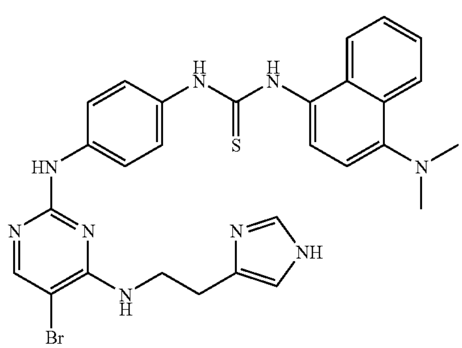 | 603 | 602.562 |
| 198 | 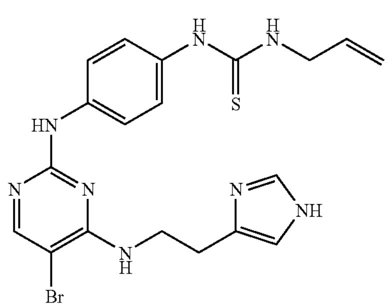 | 474 | 473.401 |

-continued

| Example | Structure | ESI-MS | Mol-Weight |
|---|---|---|---|
| 199 | 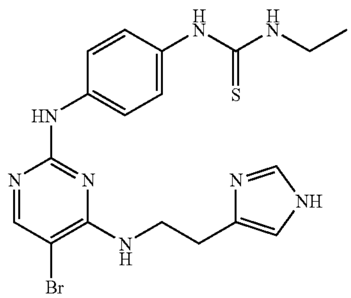 | 462 | 461.39 |
| 200 | 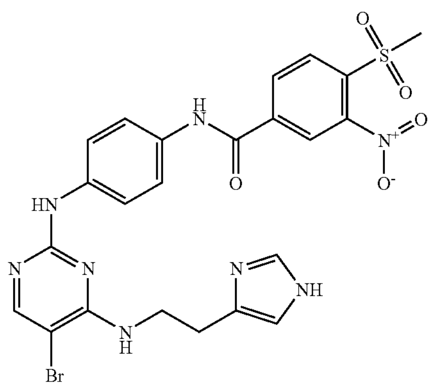 | 602 | 601.44 |
| 201 | 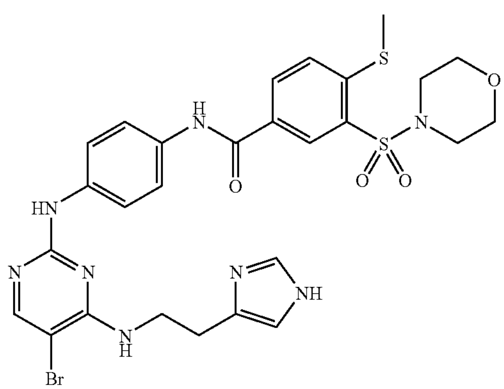 | 674 | 673.614 |
| 202 | 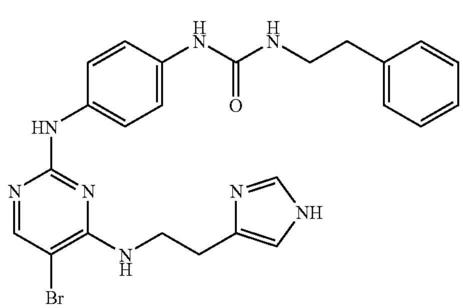 | 522 | 521.42 |

-continued
| Example | Structure | ESI-MS | Mol-Weight |
|---|---|---|---|
| 203 | 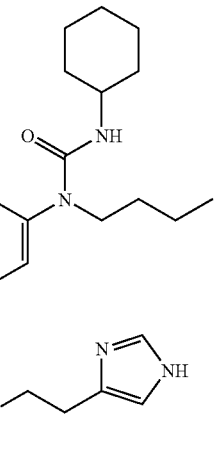 | 556 | 555.521 |
| 204 | 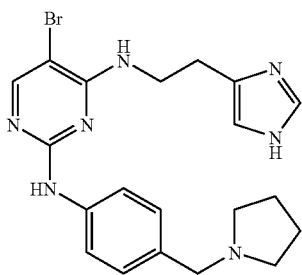 | 443 | |
| 205 | 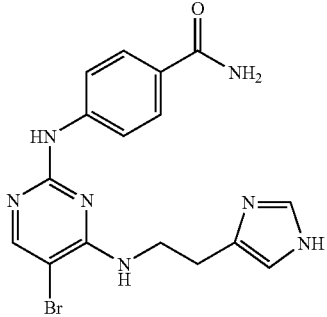 | 401 | |
| 206 | 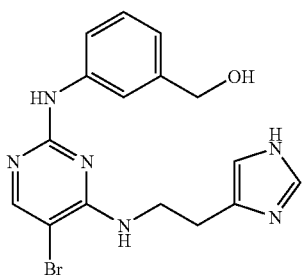 | 388 | |

-continued

| Example | Structure | ESI-MS | Mol-Weight |
|---------|-----------|--------|------------|
| 207 | 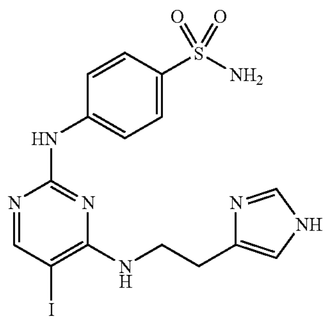 | 485 | |
| 208 | 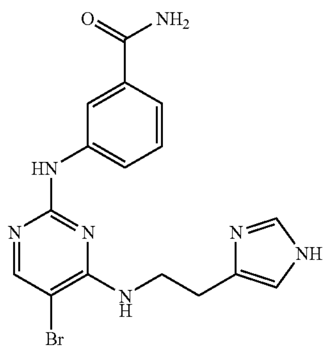 | 401 | |
| 209 | 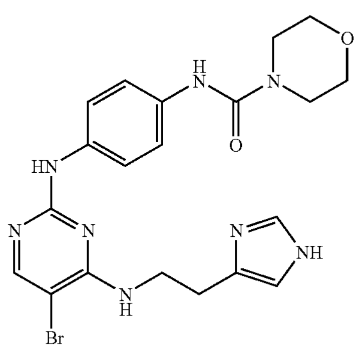 | 486 | |
| 210 | 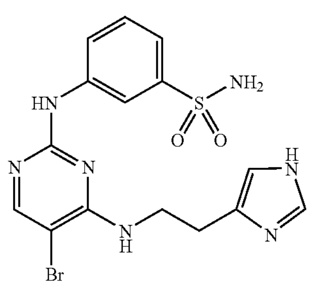 | 437 | |
| 211 | 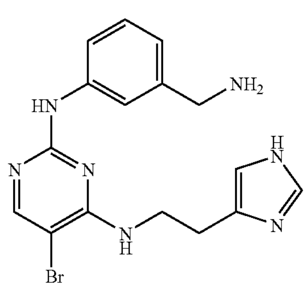 | 387 | |

| Example | Structure | ESI-MS | Mol-Weight |
|---|---|---|---|
| 212 | 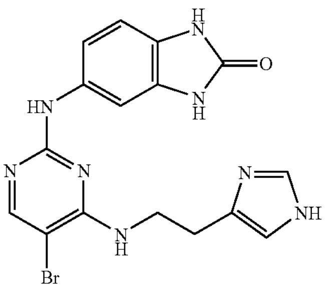 | | 414 |
| 213 | 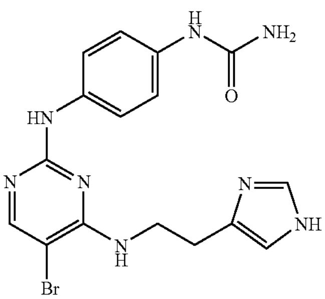 | | 416 |
| 214 | 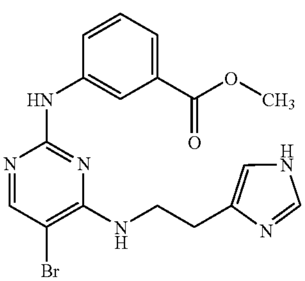 | | 416 |
| 215 | 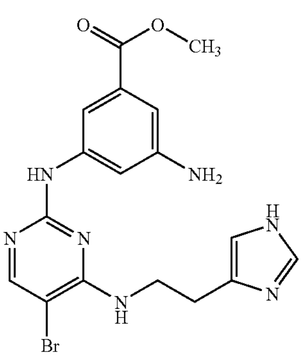 | | 431 |

-continued
| Example | Structure | ESI-MS | Mol-Weight |
|---|---|---|---|
| 216 | 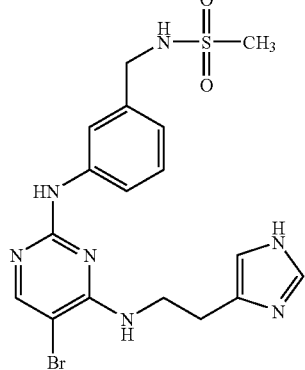 | 465 | |
| 217 | 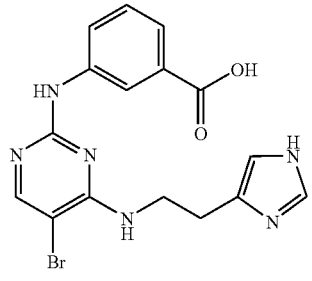 | 402 | |
| 218 | 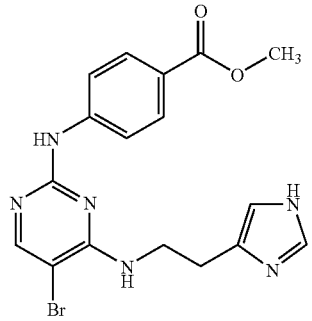 | 416 | |
| 219 | 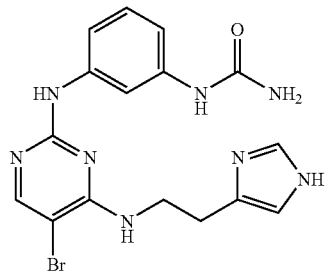 | 416 | |
| 220 | 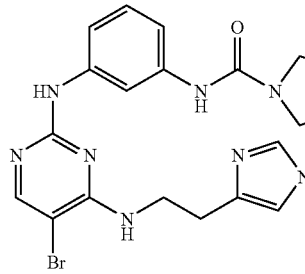 | 470 | |

-continued
| Example | Structure | ESI-MS | Mol-Weight |
|---|---|---|---|
| 221 | 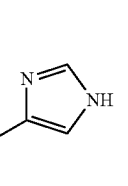 | 430 | |
| 222 | 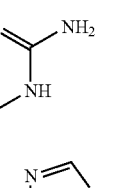 | 430 | |
| 223 | 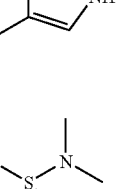 | 426 | |
| 224 | 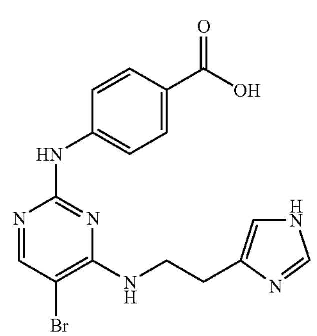 | 402 | |
| 225 | 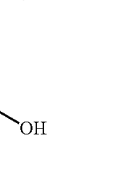 | 416 | |

-continued

| Example | Structure | ESI-MS | Mol-Weight |
|---|---|---|---|
| 226 | 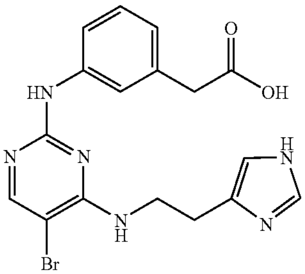 | 416 | |
| 227 | 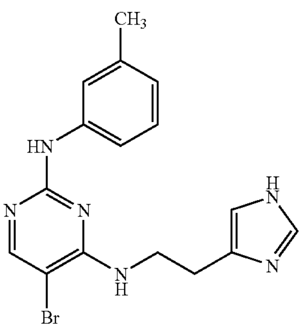 | 372 | |
| 228 | 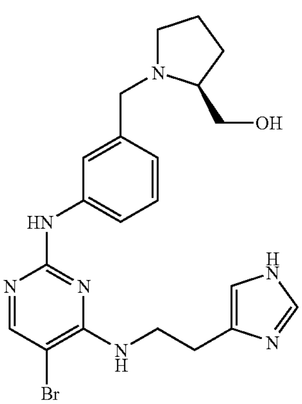 | 471 | |
| 229 | 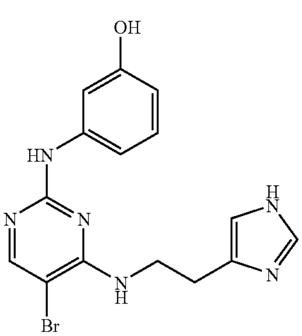 | 374 | |

-continued

| Example | Structure | ESI-MS | Mol-Weight |
|---|---|---|---|
| 230 | 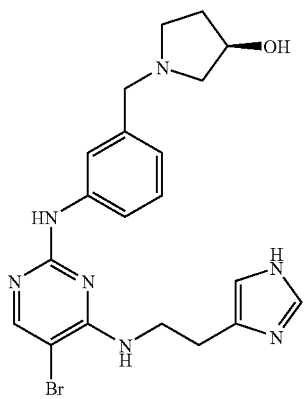 | 457 | |
| 231 | 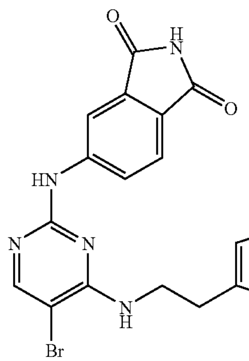 | 427 | |
| 232 | 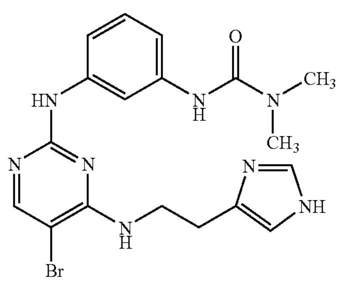 | 444 | |
| 233 | 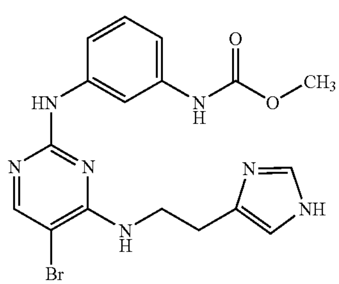 | 431 | |

-continued

| Example | Structure | ESI-MS | Mol-Weight |
|---|---|---|---|
| 234 | 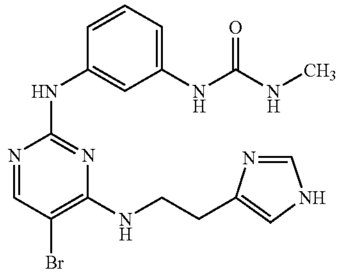 | 430 | |
| 235 | 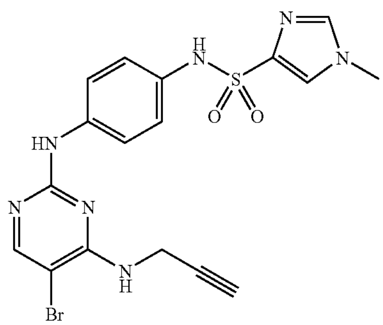 | 463 | |
| 236 | 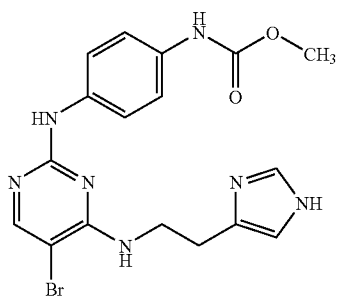 | 431 | |
| 237 | 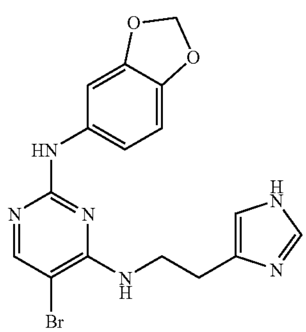 | 402 | |
| 238 | 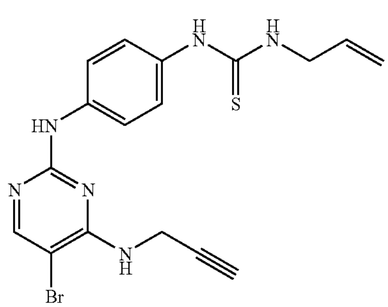 | 418 | |

| Example | Structure | ESI-MS | Mol-Weight |
|---|---|---|---|
| 239 | 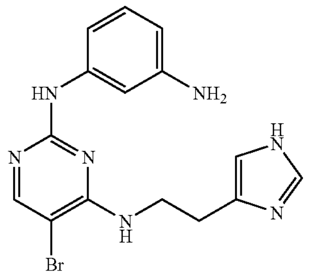 | 373 | |
| 240 | 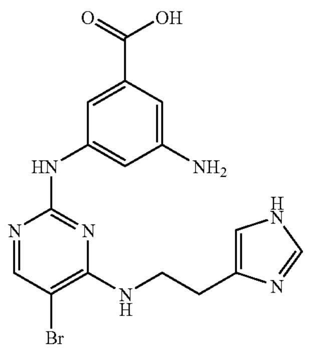 | 417 | |
| 241 | 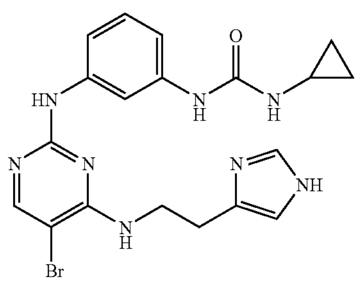 | 456 | |
| 242 | 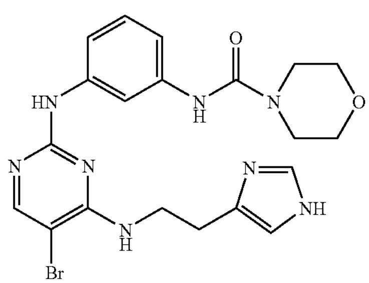 | 486 | |
| 243 | 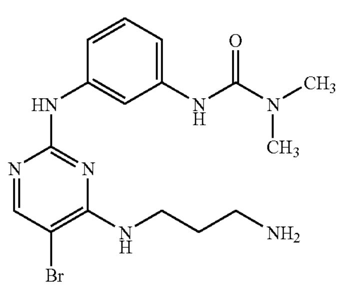 | 407 | |

-continued

| Example | Structure | ESI-MS | Mol-Weight |
|---|---|---|---|
| 244 | 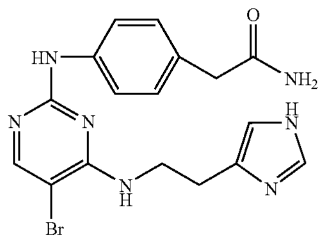 | 415 | |
| 245 | 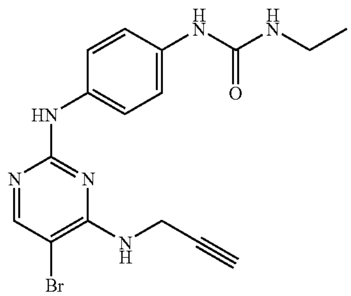 | 390 | |
| 246 | 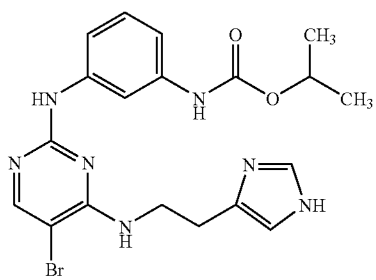 | 459 | |
| 247 | 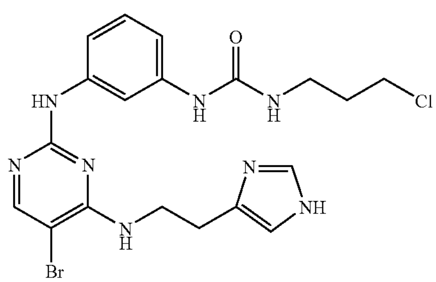 | 492 | |
| 248 | 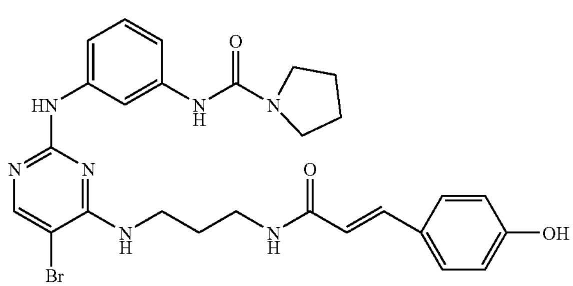 | 579 | |

-continued

| Example | Structure | ESI-MS | Mol-Weight |
|---|---|---|---|
| 249 | 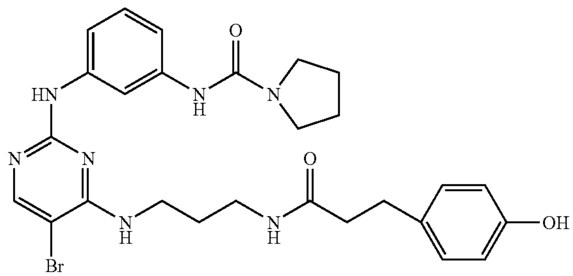 | 581 | |
| 250 | 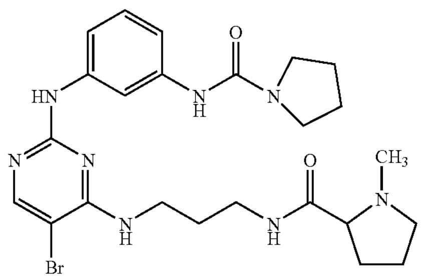 | 544 | |
| 251 | 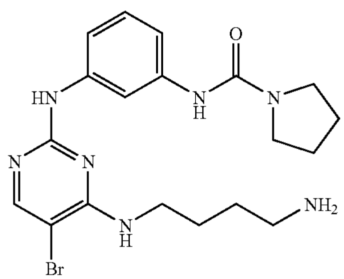 | 447 | |
| 252 | 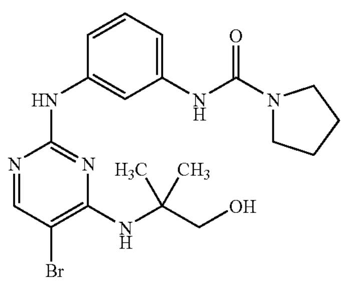 | 448 | |
| 253 | 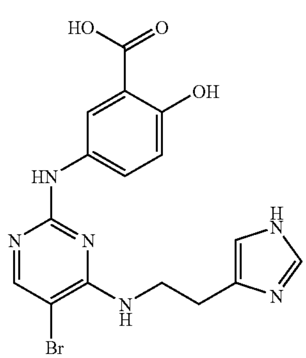 | 418 | |

-continued
| Example | Structure | ESI-MS | Mol-Weight |
|---|---|---|---|
| 254 | 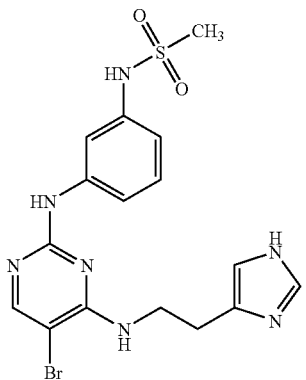 | 451 | |
| 255 | 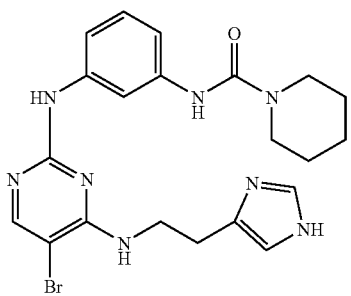 | 484 | |
| 256 | 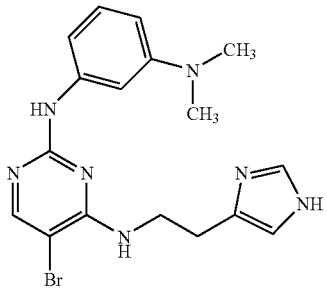 | 401 | |
| 257 | 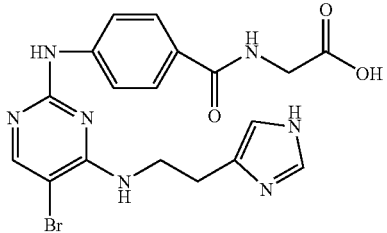 | 459 | |

-continued
| Example | Structure | ESI-MS | Mol-Weight |
|---|---|---|---|
| 258 | 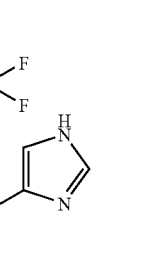 | 482 | |
| 259 | 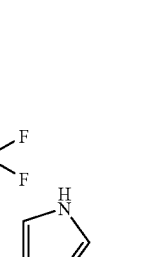 | 441 | |
| 260 | 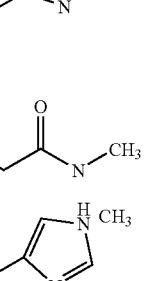 | 443 | |
| 261 | 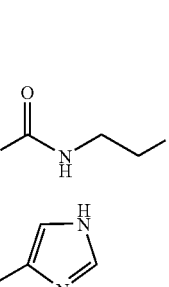 | 529 | |
| 262 | 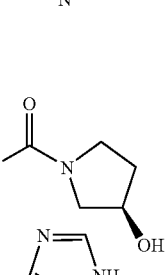 | 486 | |

-continued
| Example | Structure | ESI-MS | Mol-Weight |
|---------|-----------|--------|------------|
| 263 | 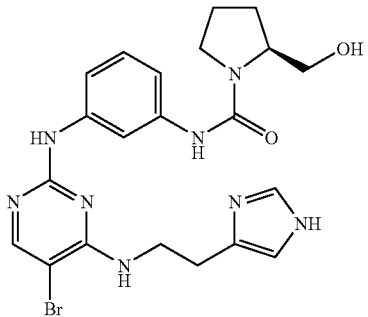 | 500 | |
| 264 | 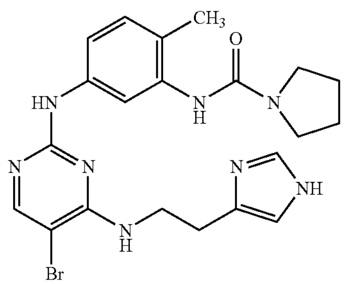 | 484 | |
| 265 | 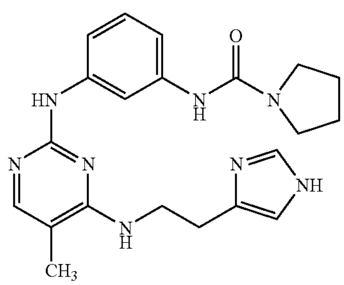 | 406 | |
| 266 | 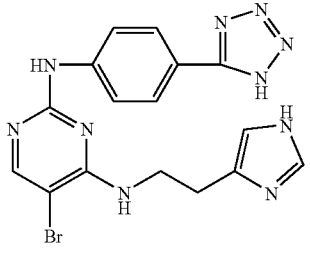 | 426 | |
| 267 | 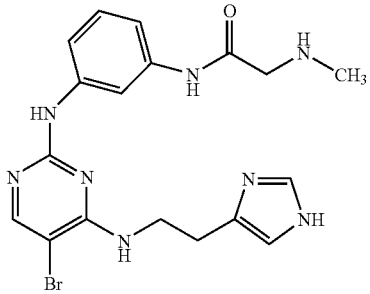 | 444 | |

-continued

| Example | Structure | ESI-MS | Mol-Weight |
|---|---|---|---|
| 268 | 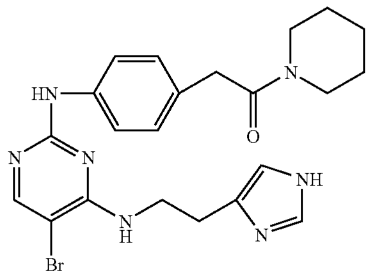 | 483 | |
| 269 | 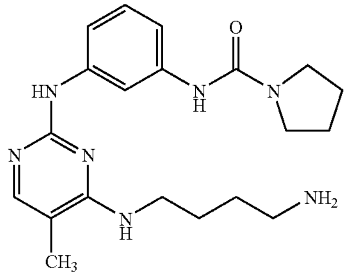 | 383 | |
| 270 | 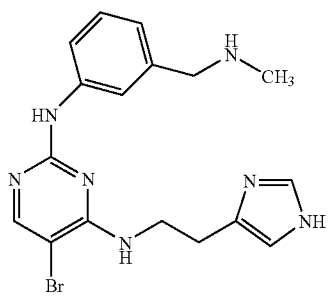 | 401 | |
| 271 | 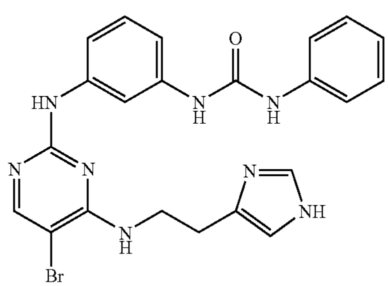 | 492 | |
| 272 | 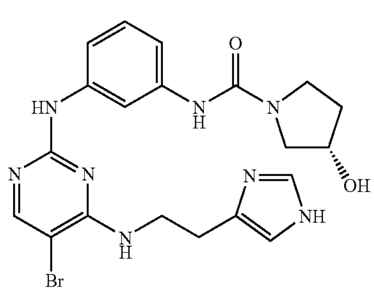 | 486 | |

-continued
| Example | Structure | ESI-MS | Mol-Weight |
|---|---|---|---|
| 273 | 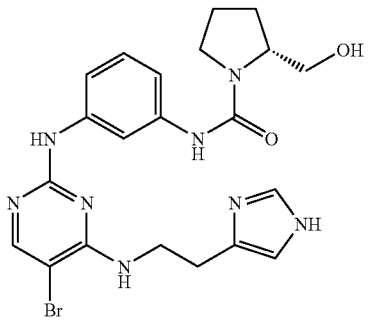 | 500 | |
| 274 | 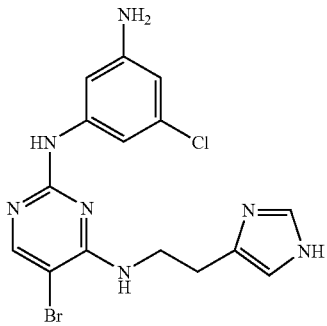 | 407 | |
| 275 | 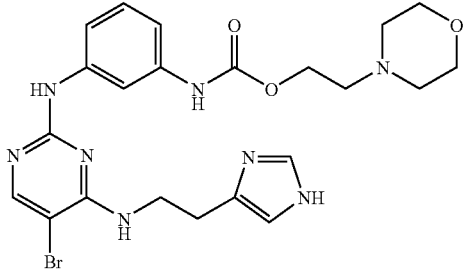 | 530 | |
| 276 | 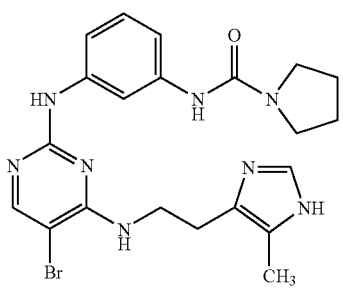 | 484 | |
| 277 | 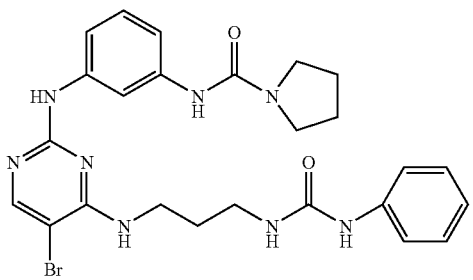 | 552 | |

-continued

| Example | Structure | ESI-MS | Mol-Weight |
|---|---|---|---|
| 278 | 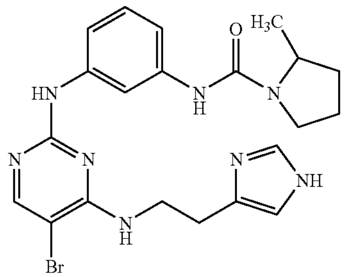 | 484 | |
| 279 | 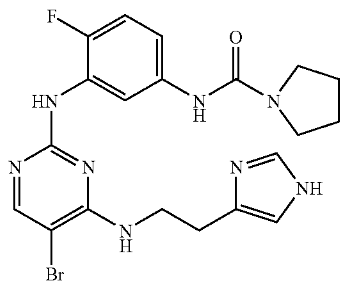 | 488 | |
| 280 | 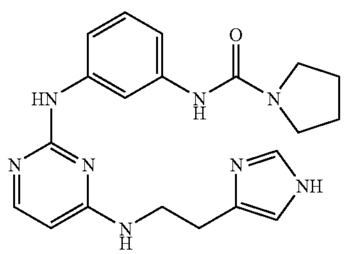 | 392 | |
| 281 | 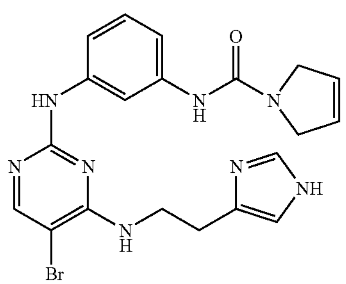 | 468 | |
| 282 | 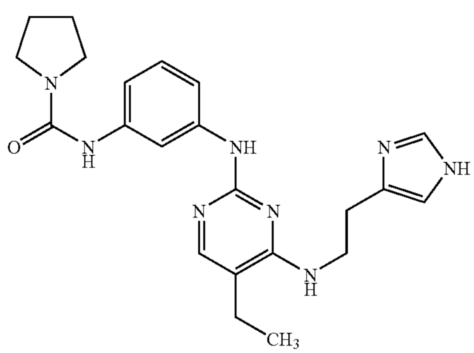 | 420 | |

| Example | Structure | ESI-MS | Mol-Weight |
|---------|-----------|--------|------------|
| 283 | 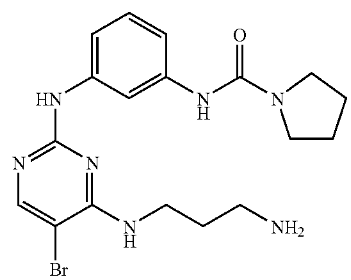 | 433 | |
| 284 | 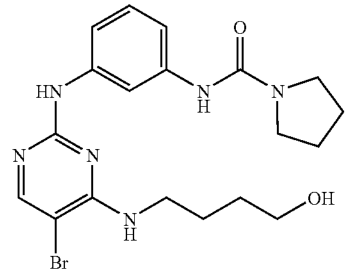 | 448 | |
| 285 | 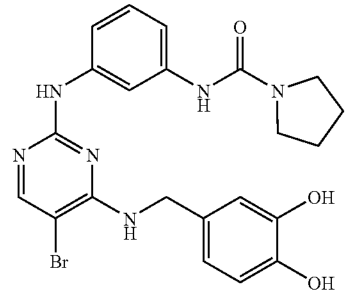 | 498 | |
| 286 | 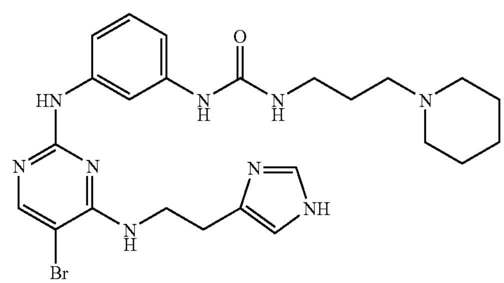 | 541 | |
| 287 | 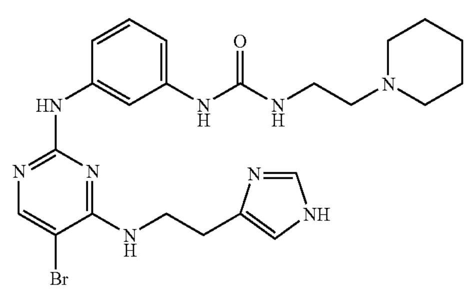 | 527 | |

-continued

| Example | Structure | ESI-MS | Mol-Weight |
|---|---|---|---|
| 288 | 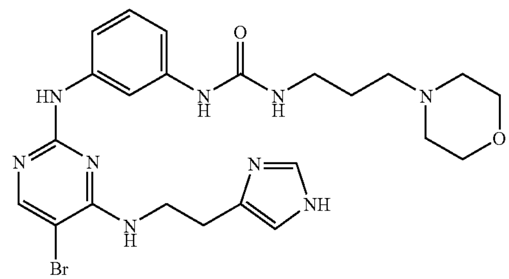 | 543 | |
| 289 | 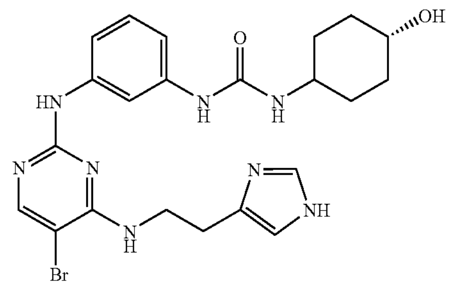 | 514 | |
| 290 | 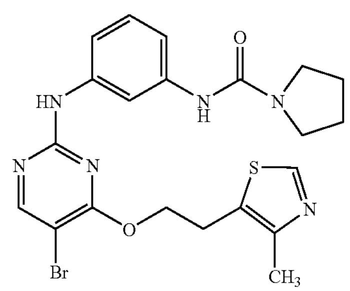 | 502 | |
| 291 | 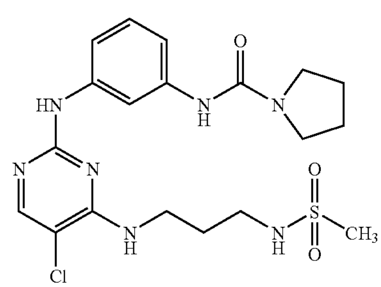 | 467 | |
| 292 | 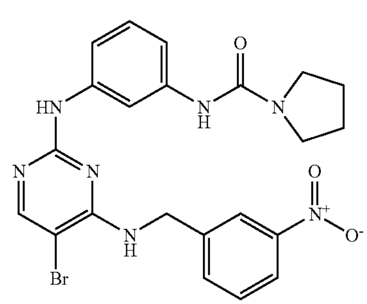 | 511 | |

|Example|Structure|ESI-MS|Mol-Weight|
|---|---|---|---|
|293| 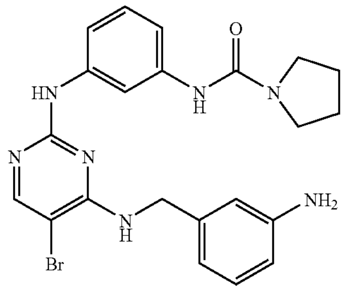 |481| |
|294| 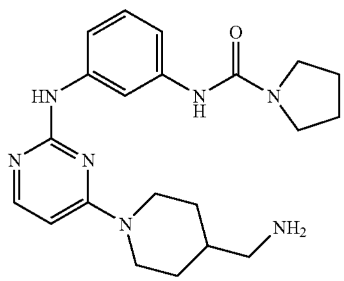 |395| |
|295| 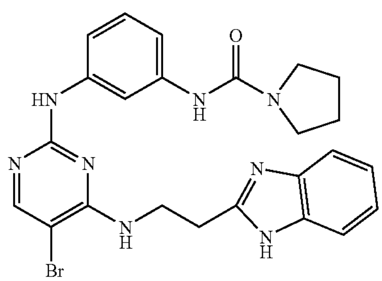 |520| |
|296| 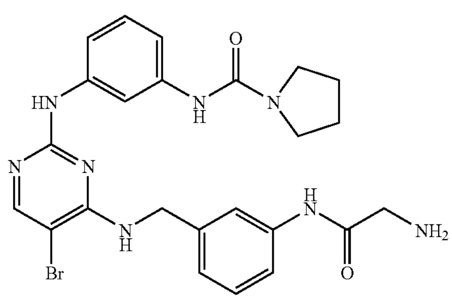 |538| |
|297| 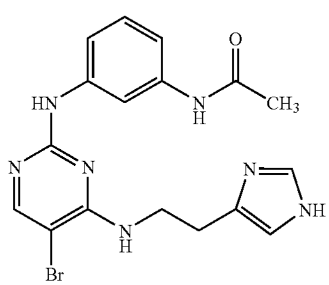 |415| |

-continued

| Example | Structure | ESI-MS | Mol-Weight |
|---|---|---|---|
| 298 | 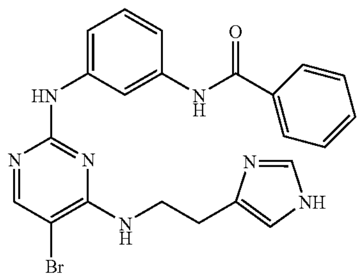 | 477 | |
| 299 | 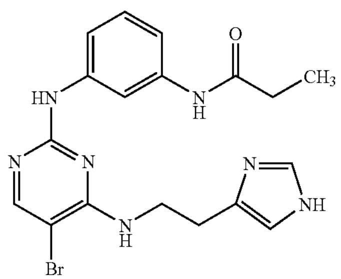 | 429 | |
| 300 | 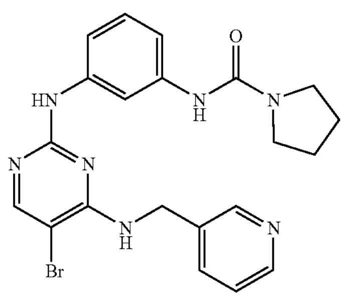 | 467 | |
| 301 | 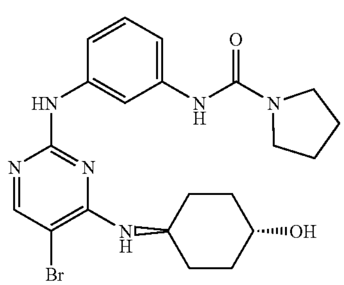 | 474 | |
| 302 | 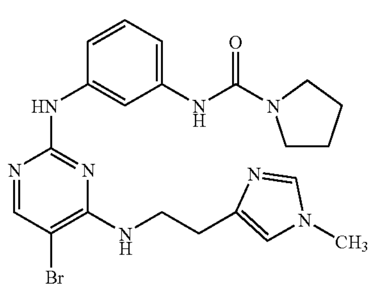 | 484 | |

-continued
| Example | Structure | ESI-MS | Mol-Weight |
|---------|-----------|--------|------------|
| 303 | 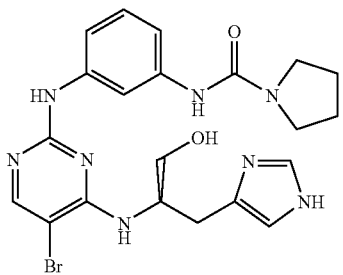 | 500 | |
| 304 | 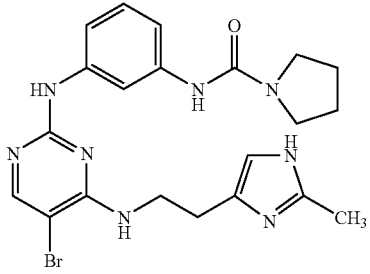 | 484 | |
| 305 | 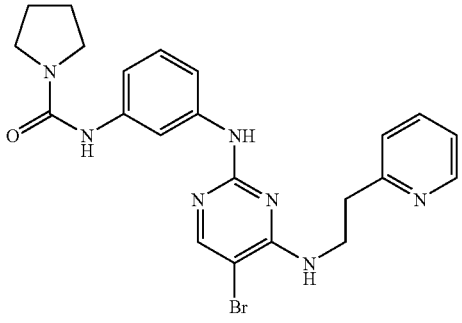 | 481 | |
| 306 | 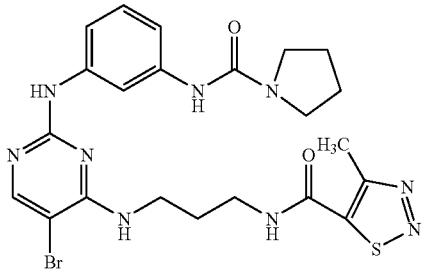 | 559 | |
| 307 | 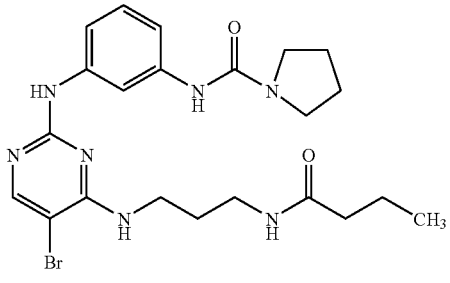 | 503 | |

-continued

| Example | Structure | ESI-MS | Mol-Weight |
|---|---|---|---|
| 308 | 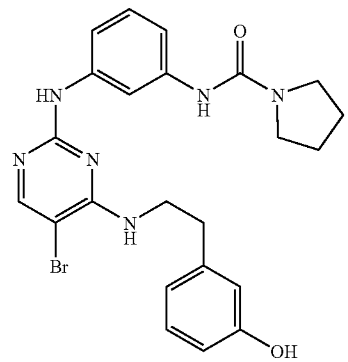 | 496 | |
| 309 | 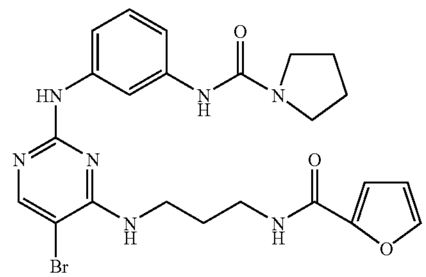 | 527 | |
| 310 | 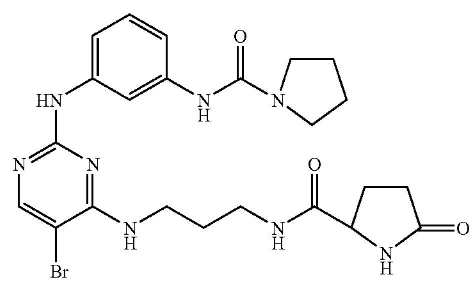 | 544 | |
| 311 | 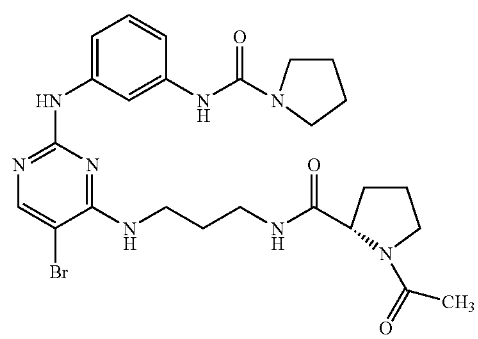 | 572 | |
| 312 | 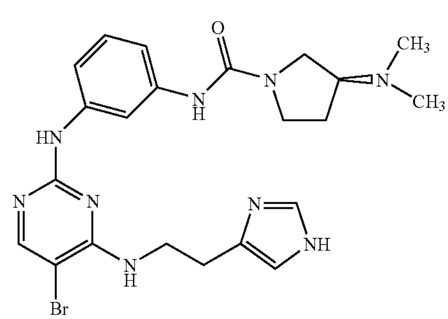 | 513 | |

| Example | Structure | ESI-MS | Mol-Weight |
|---|---|---|---|
| 313 | 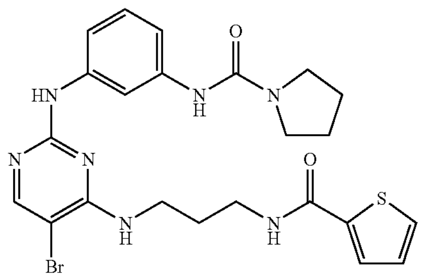 | 543 | |
| 314 | 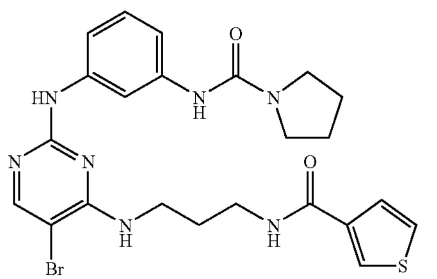 | 543 | |
| 315 | 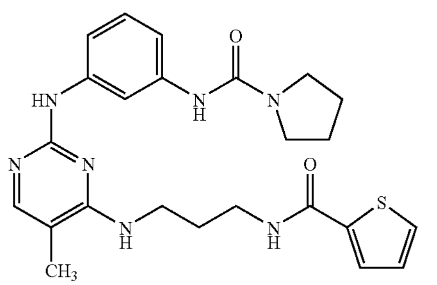 | 479 | |
| 316 | 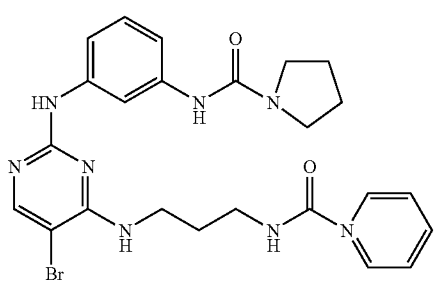 | 539 | |
| 317 | 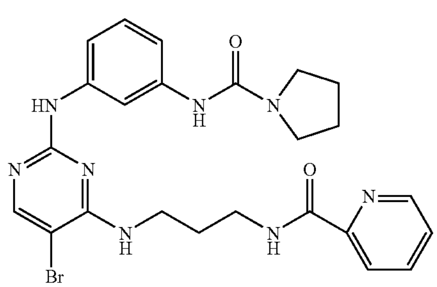 | 538 | |

-continued
| Example | Structure | ESI-MS | Mol-Weight |
|---|---|---|---|
| 318 | 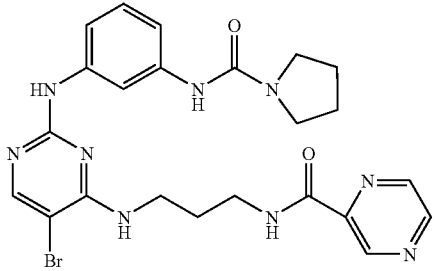 | 539 | |
| 319 | 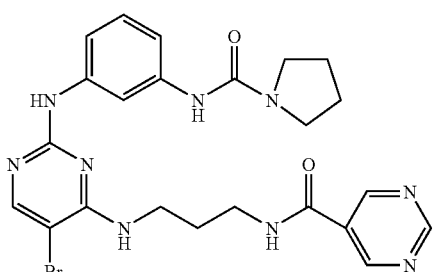 | 539 | |
| 320 | 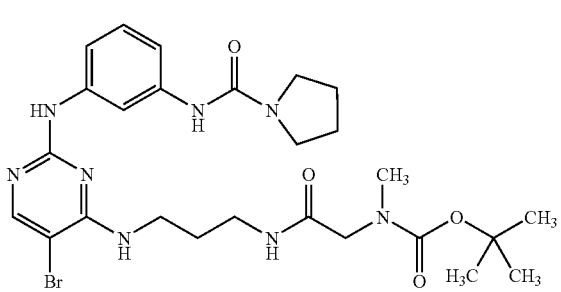 | 604 | |
| 321 | 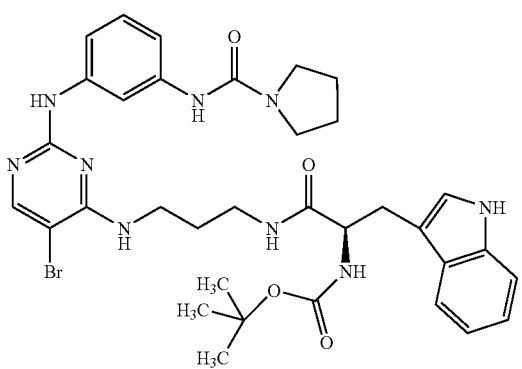 | 719 | |
| 322 | 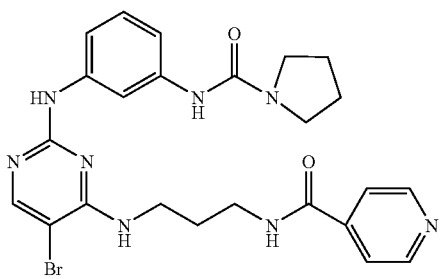 | 538 | |

| Example | Structure | ESI-MS | Mol-Weight |
|---|---|---|---|
| 323 | 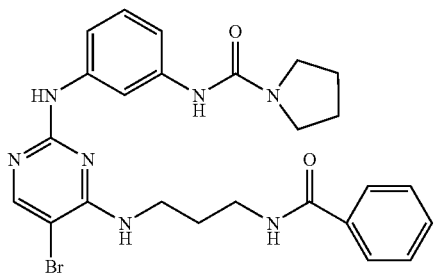 | 537 | |
| 324 | 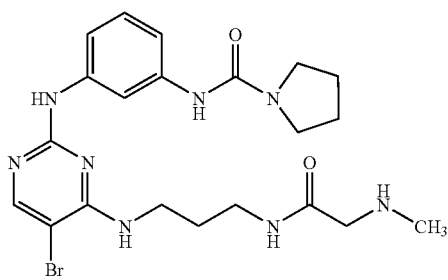 | 504 | |
| 325 | 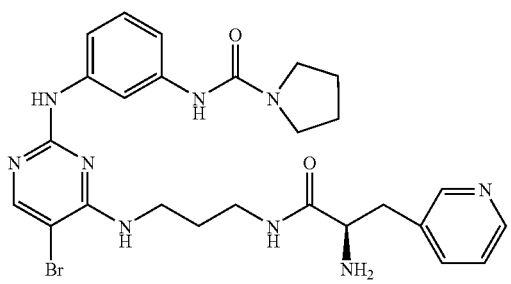 | 581 | |
| 326 | 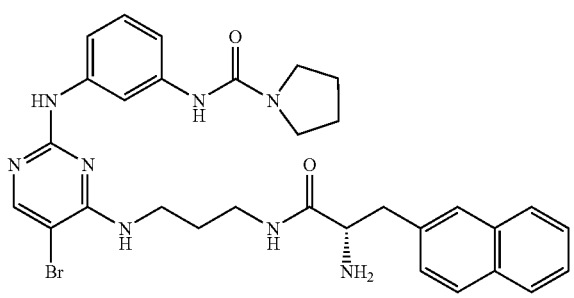 | 630 | |
| 327 | 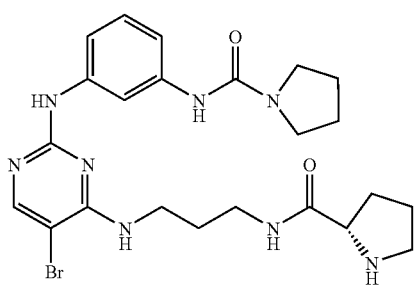 | 530 | |

-continued
| Example | Structure | ESI-MS | Mol-Weight |
|---|---|---|---|
| 328 | 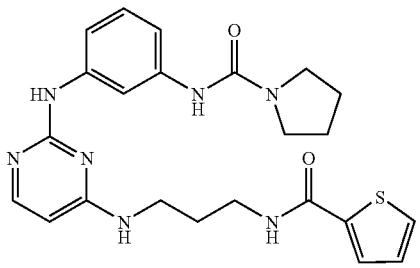 | | 465 |
| 329 | 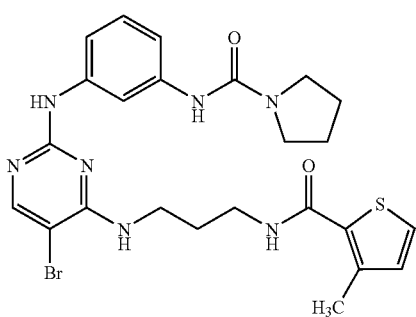 | | 557 |
| 330 | 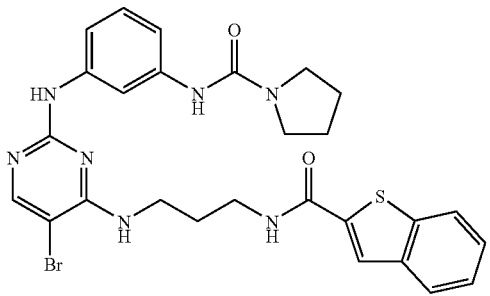 | | 593 |
| 331 | 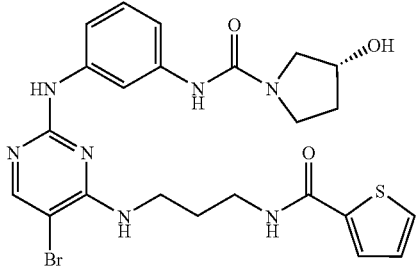 | | 559 |
| 332 | 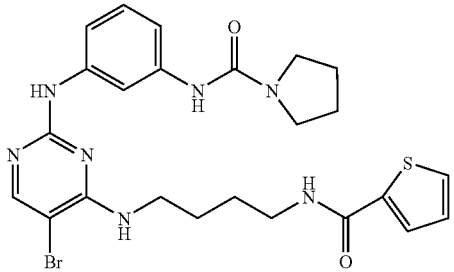 | | 557 |

-continued

| Example | Structure | ESI-MS | Mol-Weight |
|---|---|---|---|
| 333 | 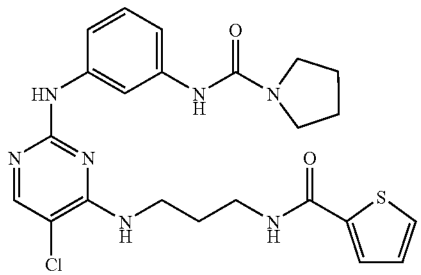 | 499 | |
| 334 | 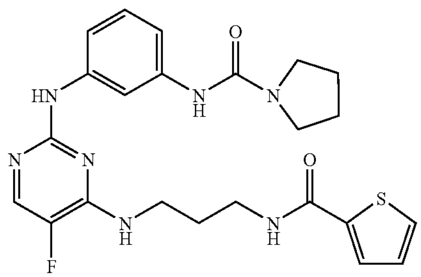 | 483 | |
| 335 | 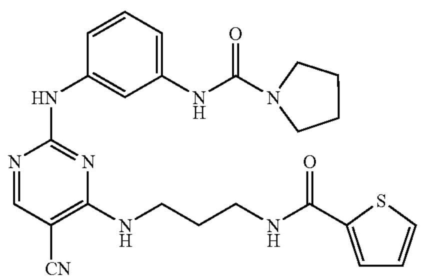 | 490 | |
| 336 | 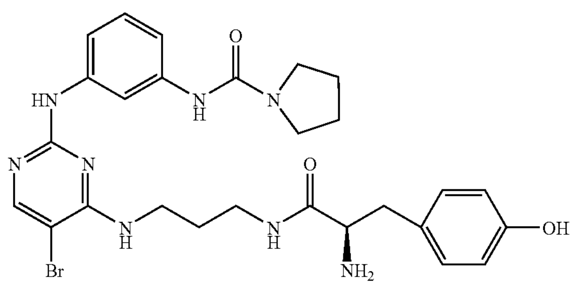 | 596 | |
| 337 | 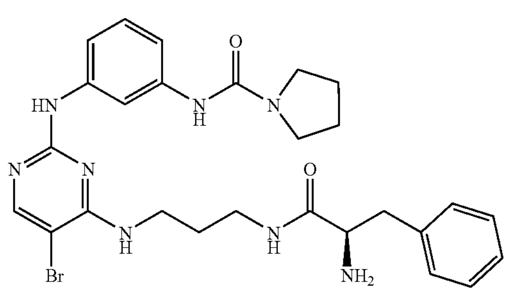 | 580 | |

| Example | Structure | ESI-MS | Mol-Weight |
|---|---|---|---|
| 338 | 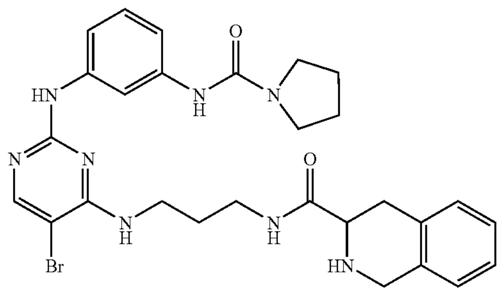 | 592 | |
| 339 | 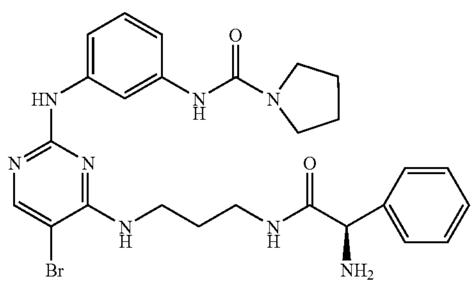 | 566 | |
| 340 | 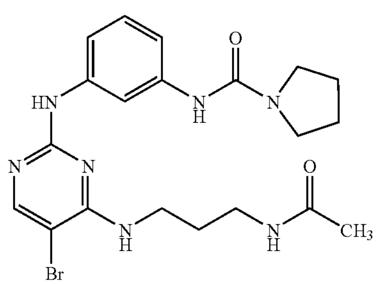 | 475 | |
| 341 | 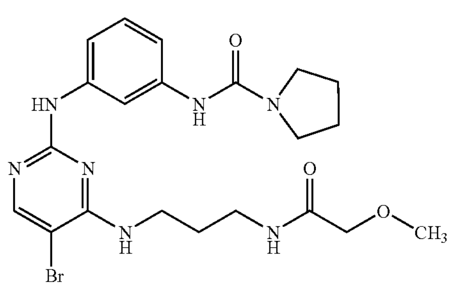 | 505 | |
| 342 | 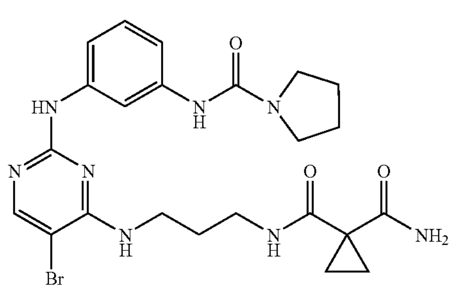 | 544 | |

-continued
| Example | Structure | ESI-MS | Mol-Weight |
|---|---|---|---|
| 343 | 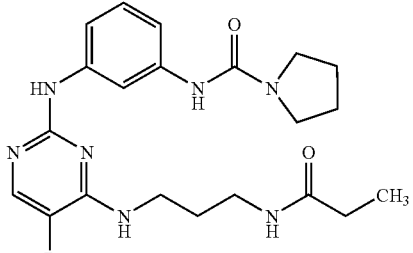 | 489 | |
| 344 | 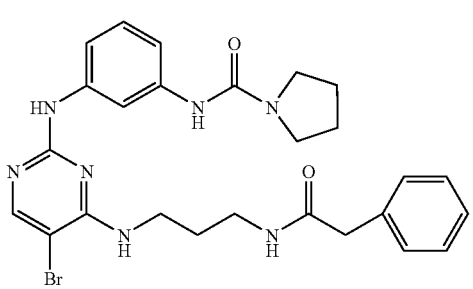 | 551 | |
| 345 | 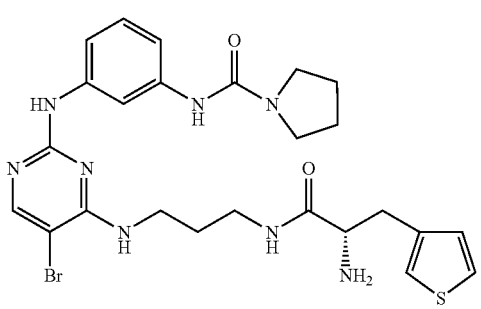 | 586 | |
| 346 | 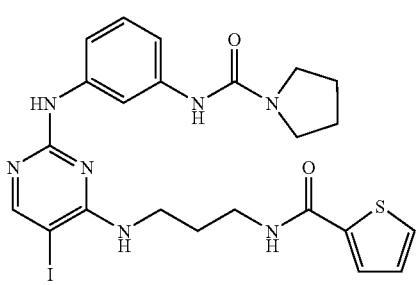 | 591 | |
| 347 | 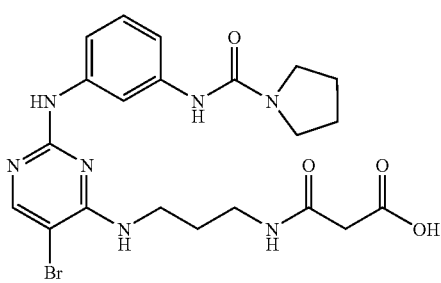 | 519 | |

-continued

| Example | Structure | ESI-MS | Mol-Weight |
|---------|-----------|--------|------------|
| 348 | 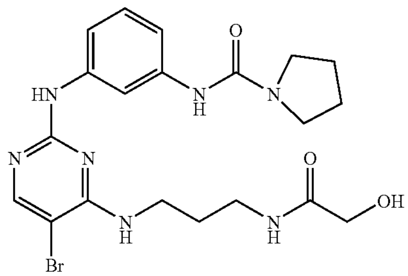 | | 491 |
| 349 | 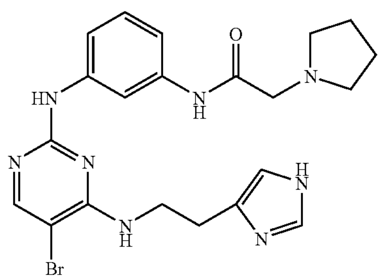 | | 484 |
| 350 | 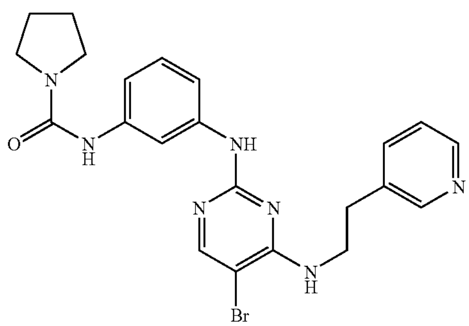 | | 481 |
| 351 | 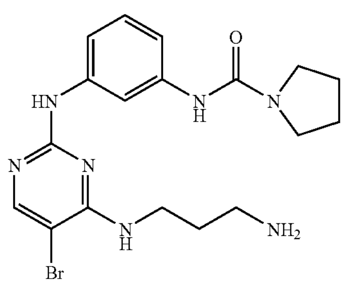 | | 433 |
| 352 | 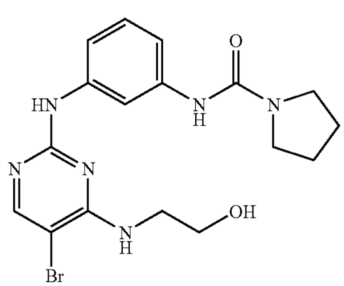 | | 420 |

| Example | Structure | ESI-MS | Mol-Weight |
|---|---|---|---|
| 353 | 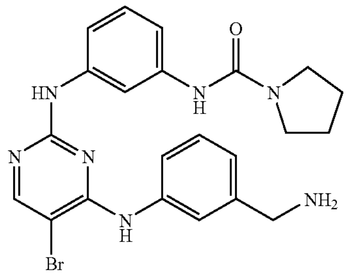 | 481 | |
| 354 | 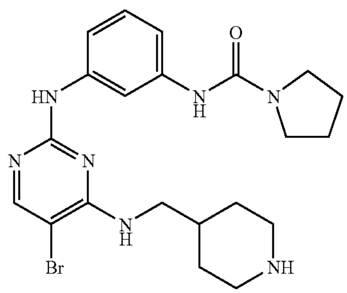 | 473 | |
| 355 | 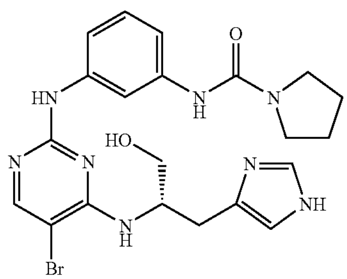 | 500 | |
| 356 | 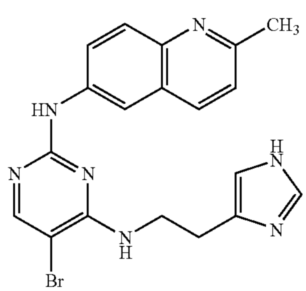 | 423 | |
| 357 | 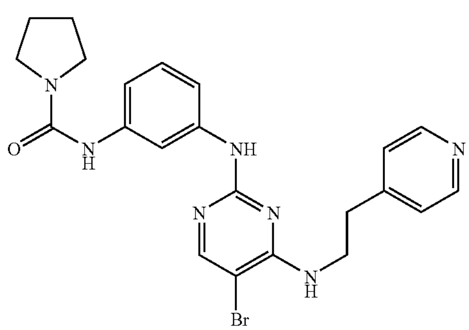 | 481 | |

-continued

| Example | Structure | ESI-MS | Mol-Weight |
|---|---|---|---|
| 358 | 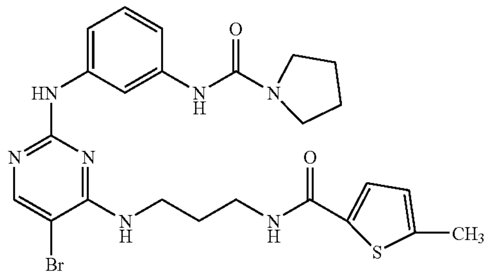 | 557 | |
| 359 | 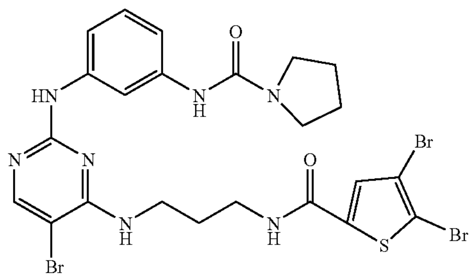 | 699 | |
| 360 | 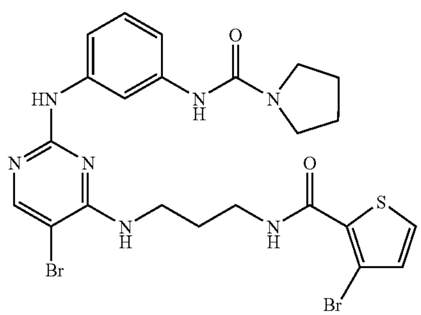 | 621 | |
| 361 | 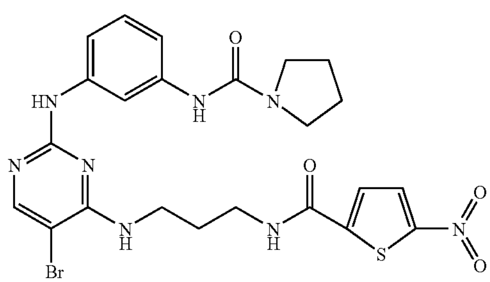 | 588 | |
| 362 | 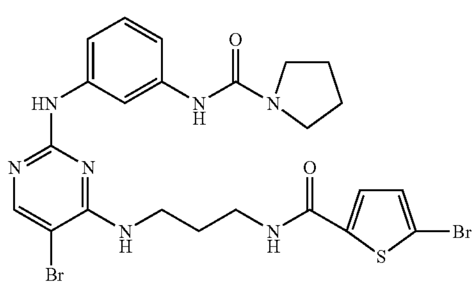 | 621 | |

-continued

| Example | Structure | ESI-MS | Mol-Weight |
|---|---|---|---|
| 363 | 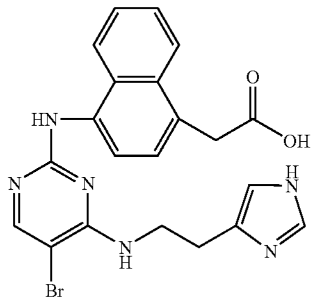 | | 466 |
| 364 | 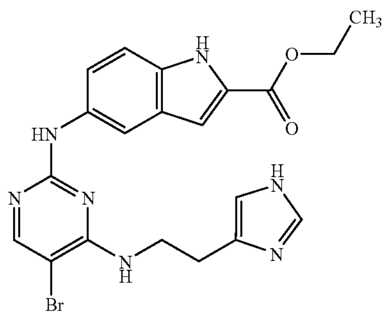 | | 469 |
| 365 | 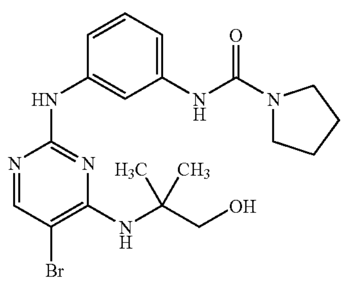 | | 448 |
| 366 | 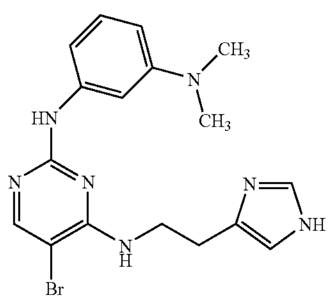 | | 401 |
| 367 | 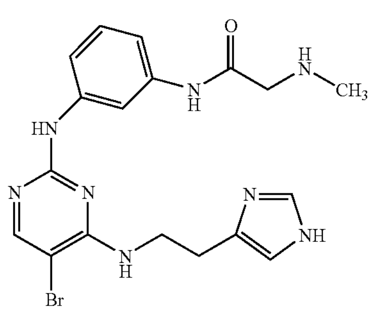 | | 444 |

-continued

| Example | Structure | ESI-MS | Mol-Weight |
|---------|-----------|--------|------------|
| 368 | 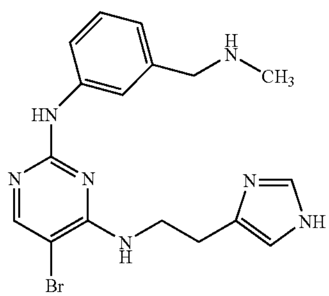 | 401 | |
| 369 | 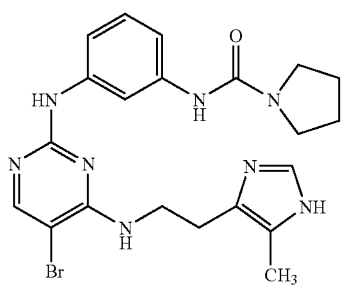 | 484 | |
| 370 | 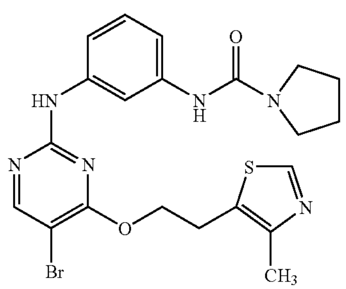 | 502 | |
| 371 | 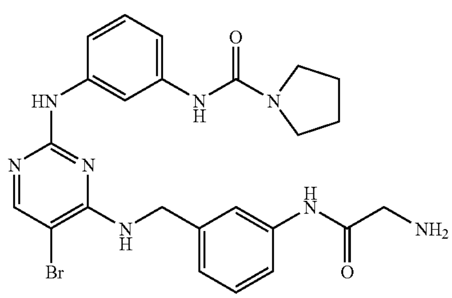 | 538 | |
| 372 | 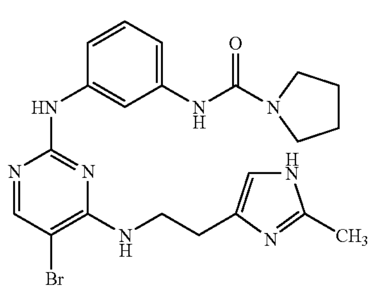 | 484 | |

| Example | Structure | ESI-MS | Mol-Weight |
|---|---|---|---|
| 373 | 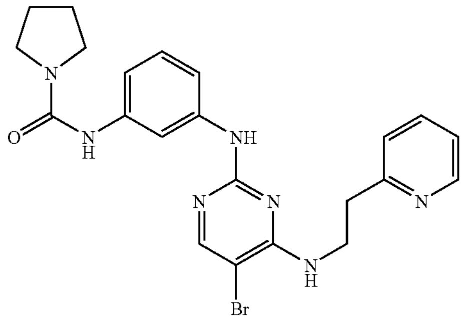 | 481 | |
| 374 | 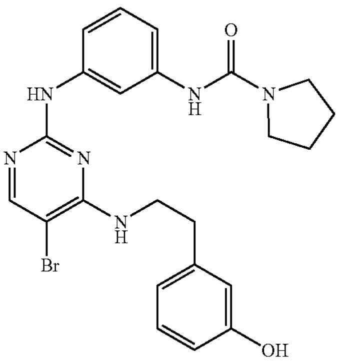 | 496 | |
| 375 | 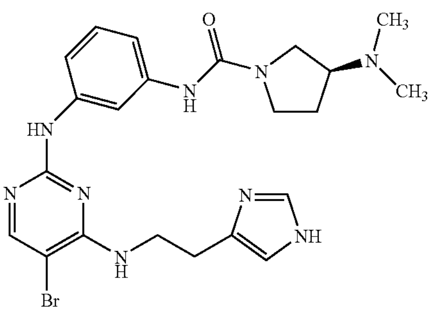 | 513 | |
| 376 | 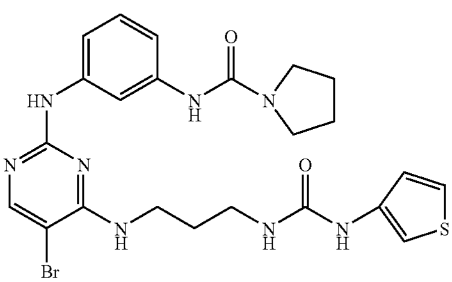 | 558 | |
| 377 | 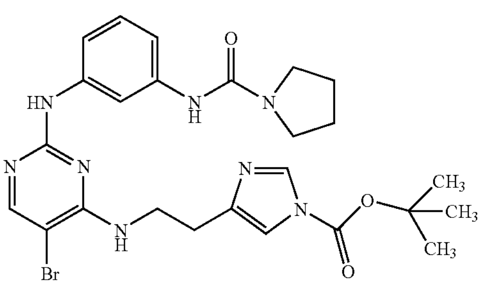 | 570 | |

| Example | Structure | ESI-MS | Mol-Weight |
|---|---|---|---|
| 378 | 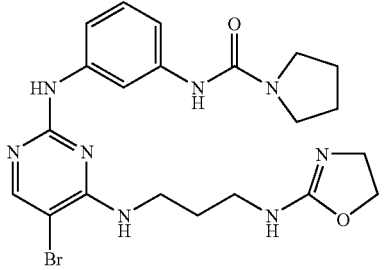 | 502 | |
| 379 | 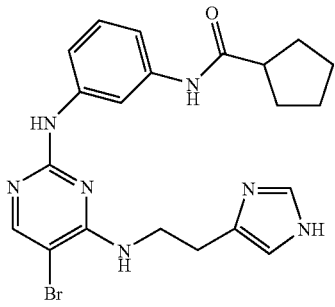 | 469 | |
| 380 | 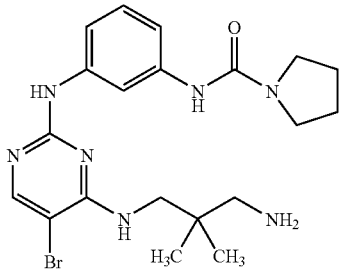 | 461 | |
| 381 | 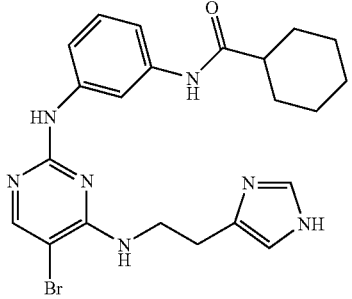 | 483 | |
| 382 | 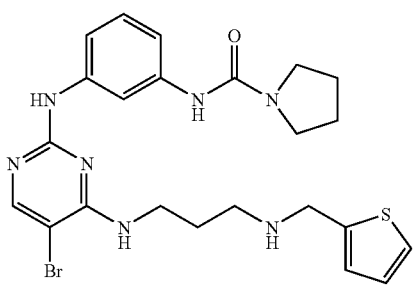 | 529 | |

| Example | Structure | ESI-MS | Mol-Weight |
|---|---|---|---|
| 383 | 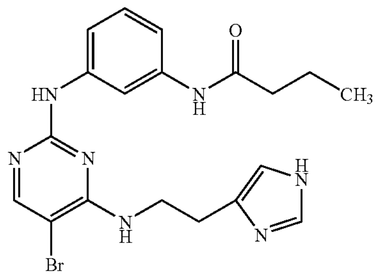 | 443 | |
| 384 | 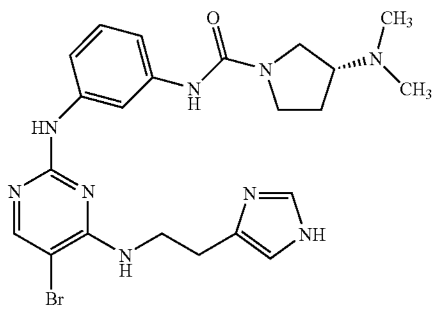 | 513 | |
| 385 | 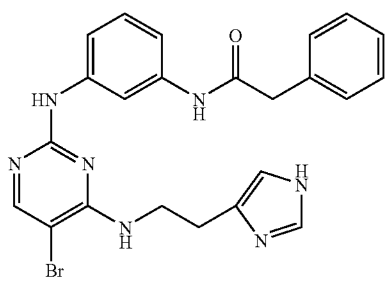 | 491 | |
| 386 | 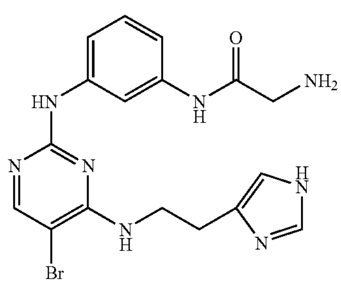 | 430 | |
| 387 | 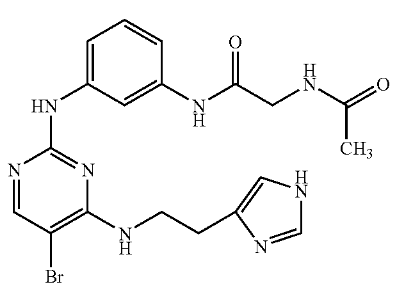 | 472 | |

-continued
| Example | Structure | ESI-MS | Mol-Weight |
|---|---|---|---|
| 388 | 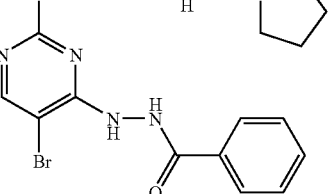 | 495 | |
| 389 | 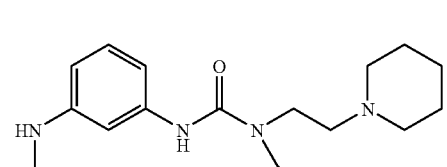 | 555 | |
| 390 | 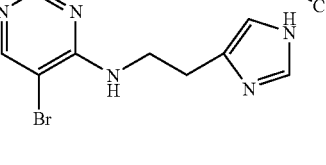 | 434 | |
| 391 | 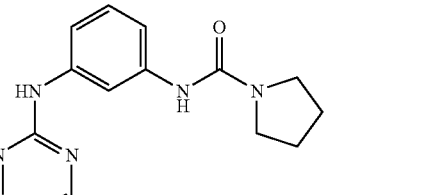 | 541 | |
| 392 | 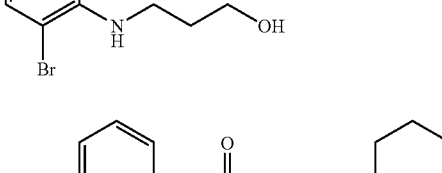 | 429 | |

| Example | Structure | ESI-MS | Mol-Weight |
|---|---|---|---|
| 393 | 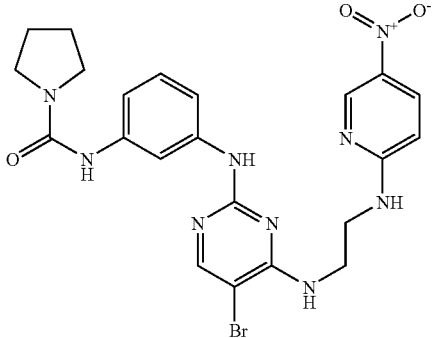 | | 541 |
| 394 | 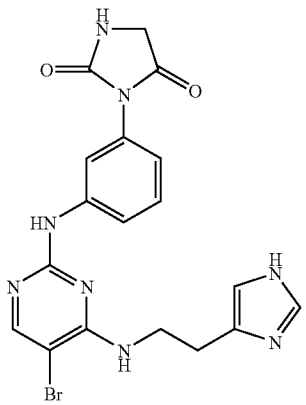 | | 456 |
| 395 | 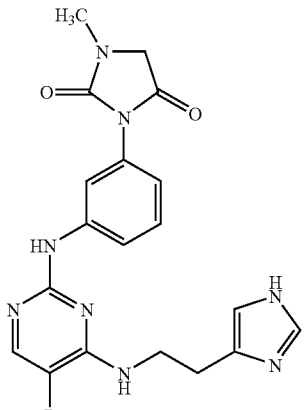 | | 470 |
| 396 | 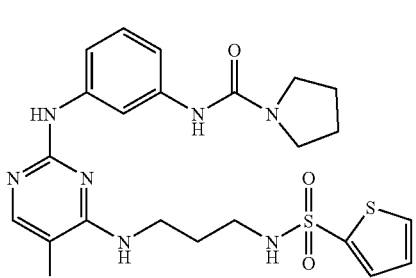 | | 579 |

-continued
| Example | Structure | ESI-MS | Mol-Weight |
|---|---|---|---|
| 397 | 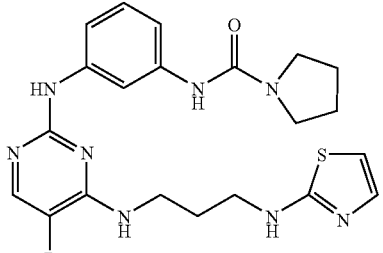 | 516 | |
| 398 | 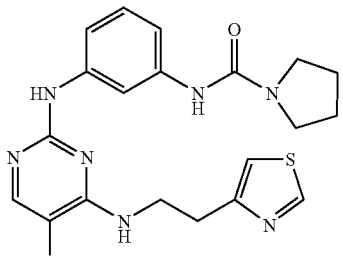 | 487 | |
| 399 | 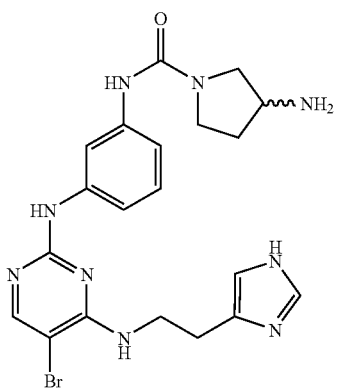 | 485 | |
| 400 | 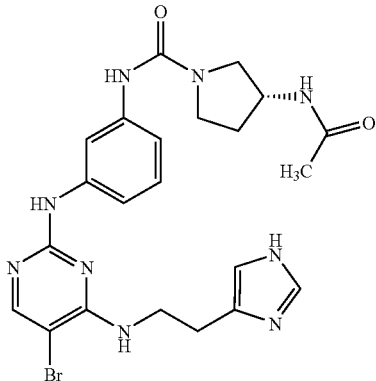 | 527 | |

-continued
| Example | Structure | ESI-MS | Mol-Weight |
|---|---|---|---|
| 401 | 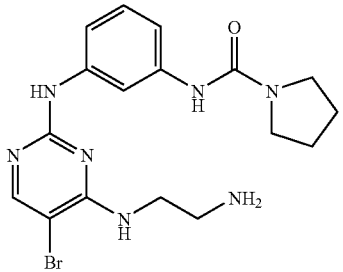 | | 419 |
| 402 | 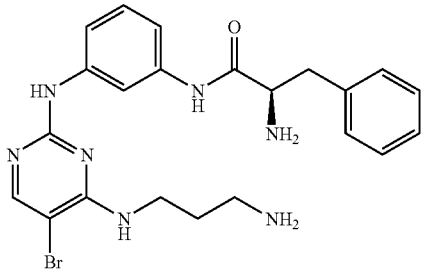 | | 483 |
| 403 | 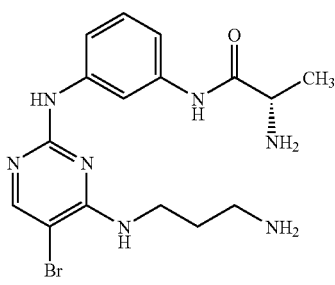 | | 407 |
| 404 | 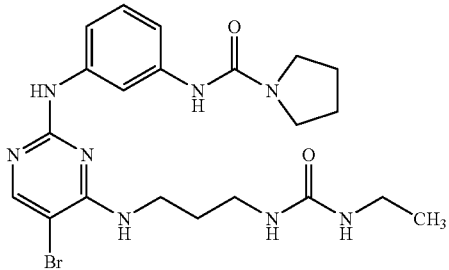 | | 504 |
| 405 | 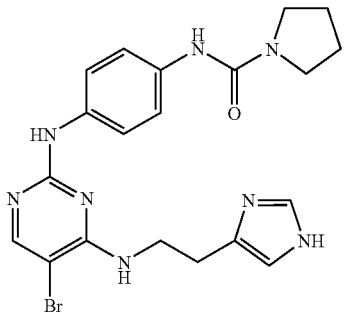 | | 470 |

-continued

| Example | Structure | ESI-MS | Mol-Weight |
|---------|-----------|--------|------------|
| 406 | 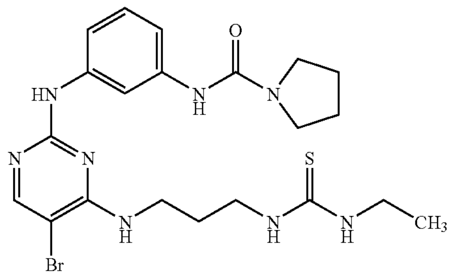 | 520 | |
| 407 | 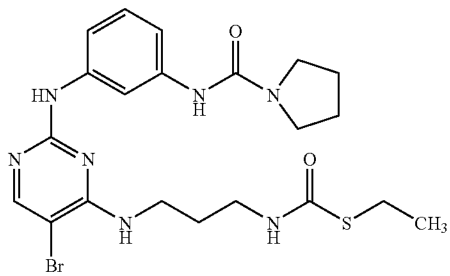 | 521 | |
| 408 | 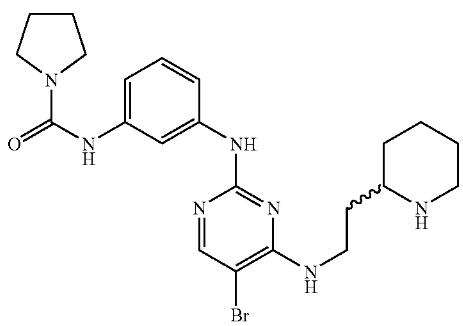 | 487 | |
| 409 | 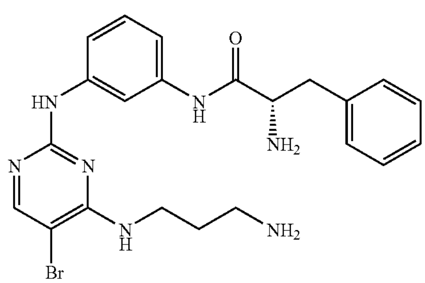 | 483 | |
| 410 | 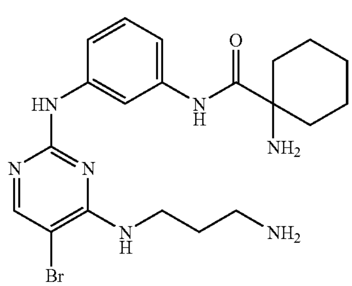 | 461 | |

-continued

| Example | Structure | ESI-MS | Mol-Weight |
|---|---|---|---|
| 411 | 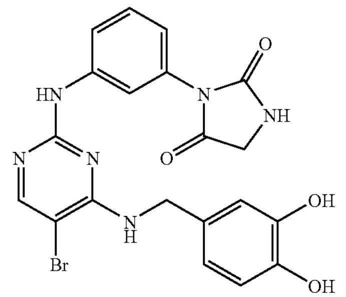 | 484 | |
| 412 | 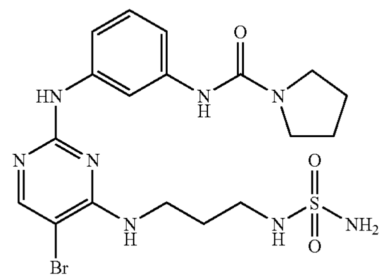 | 512 | |
| 413 | 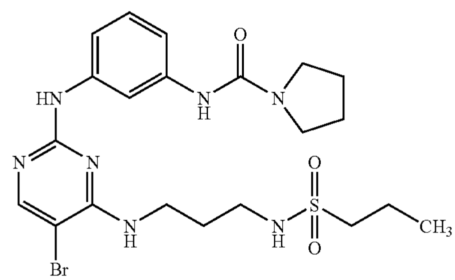 | 539 | |
| 414 | 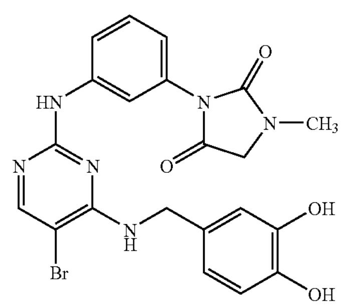 | 498 | |
| 415 | 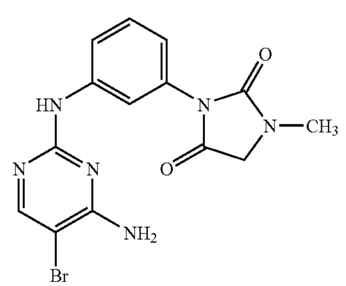 | 376 | |

-continued

| Example | Structure | ESI-MS | Mol-Weight |
|---------|-----------|--------|------------|
| 416 | 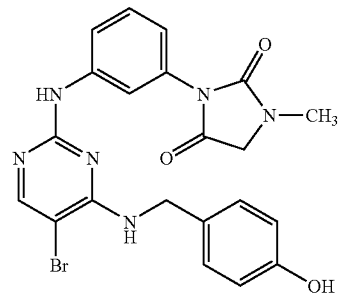 | 482 | |
| 417 | 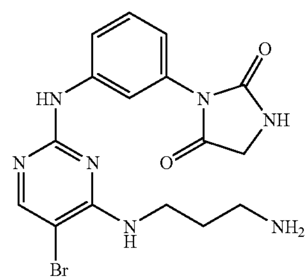 | 419 | |
| 418 | 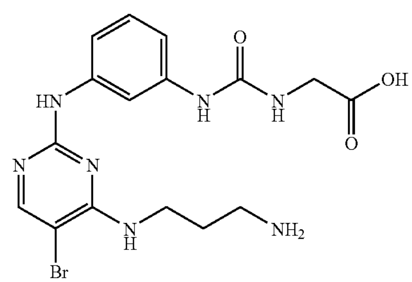 | 437 | |
| 419 | 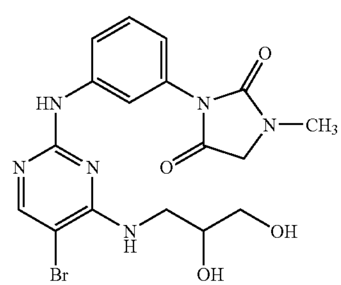 | 450 | |
| 420 | 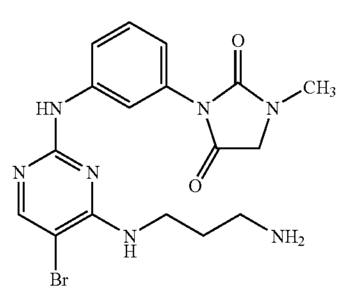 | 433 | |

-continued

| Example | Structure | ESI-MS | Mol-Weight |
|---------|-----------|--------|------------|
| 421 | 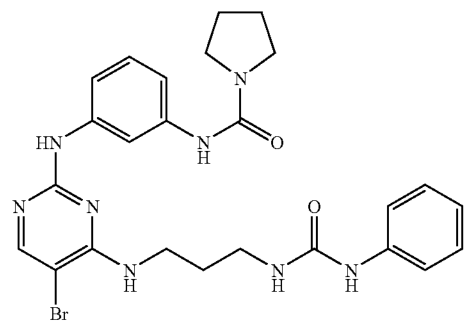 | 552 | |
| 422 | 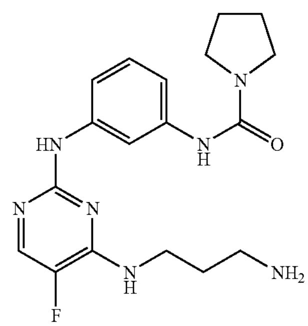 | 373 | |
| 423 | 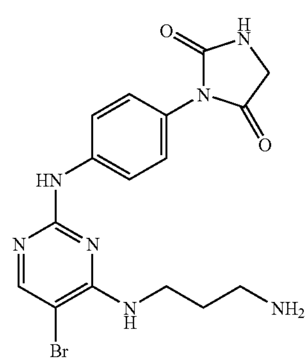 | 419 | |
| 424 | 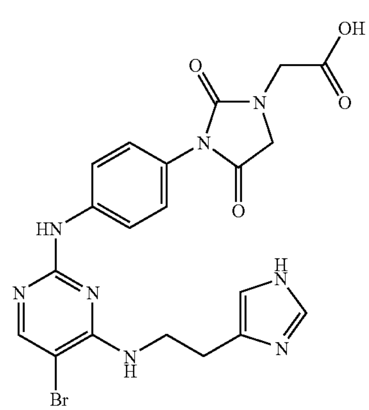 | 514 | |

-continued
| Example | Structure | ESI-MS | Mol-Weight |
|---|---|---|---|
| 425 | 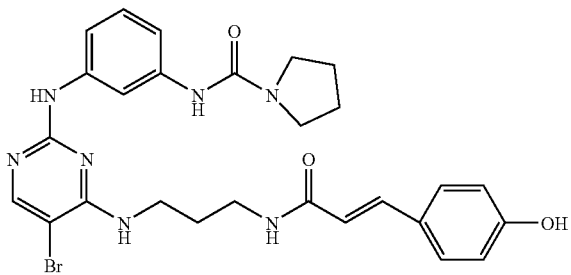 | 579 | |
| 426 | 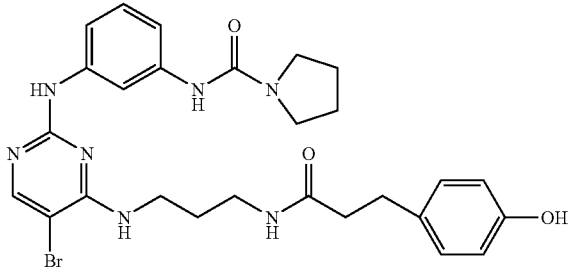 | 581 | |
| 427 | 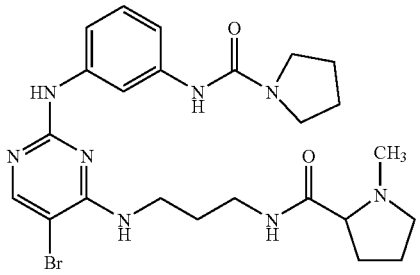 | 544 | |
| 428 | 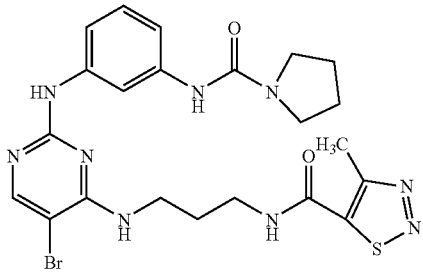 | 559 | |
| 429 | 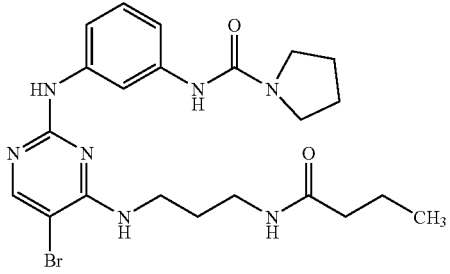 | 503 | |

-continued

| Example | Structure | ESI-MS | Mol-Weight |
|---------|-----------|--------|------------|
| 430 | 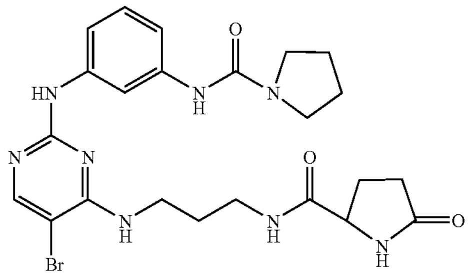 | 527 | |
| 431 | 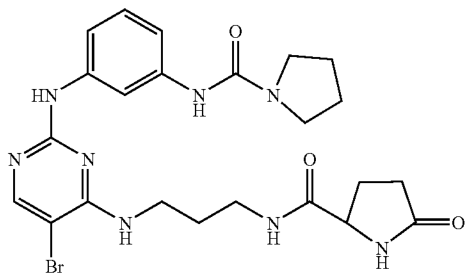 | 544 | |
| 432 | 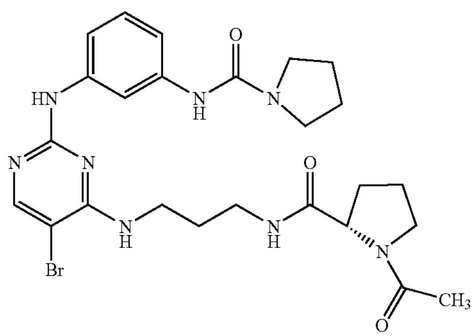 | 572 | |
| 433 | 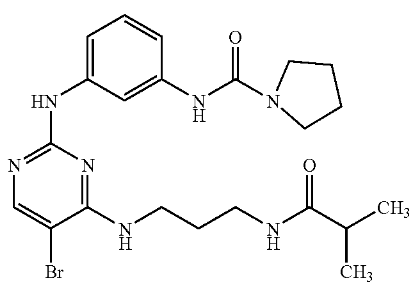 | 503 | |
| 434 | 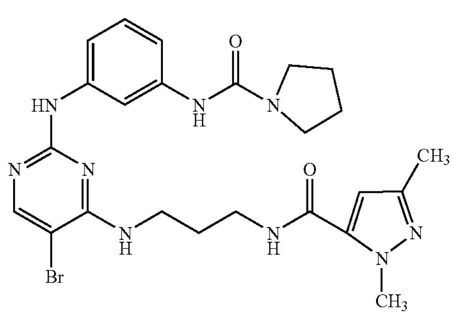 | 555 | |

-continued
| Example | Structure | ESI-MS | Mol-Weight |
|---------|-----------|--------|------------|
| 435 | 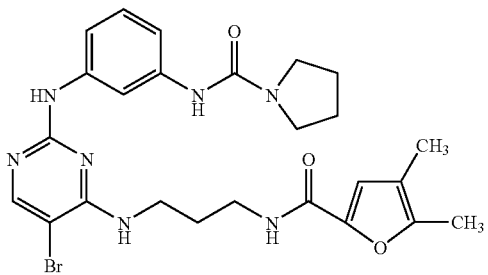 | 555 | |
| 436 | 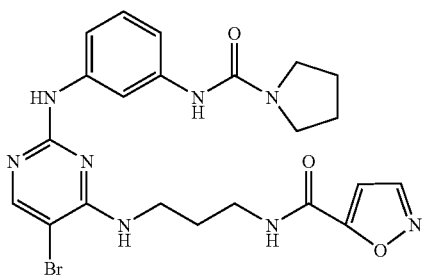 | 558 | |
| 437 | 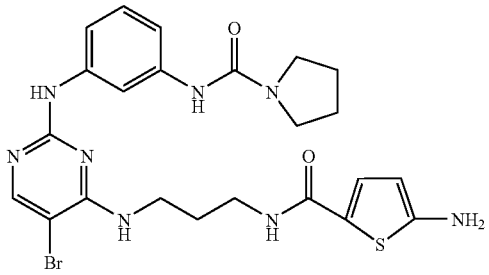 | 558 | |
| 438 | 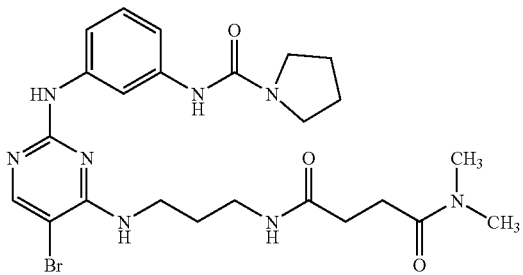 | 560 | |
| 439 | 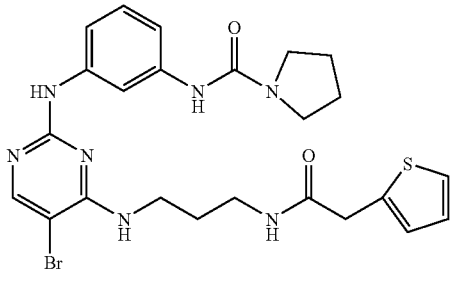 | 557 | |

-continued
| Example | Structure | ESI-MS | Mol-Weight |
|---|---|---|---|
| 440 | 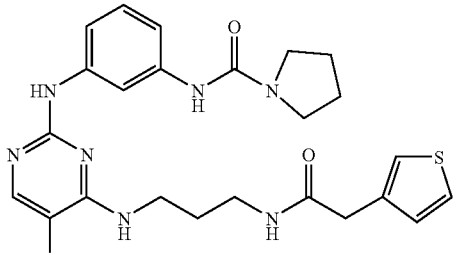 | 557 | |
| 441 | 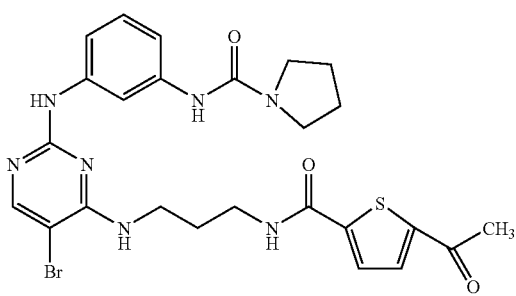 | 585 | |
| 442 | 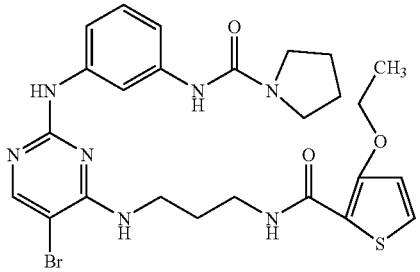 | 587 | |
| 443 | 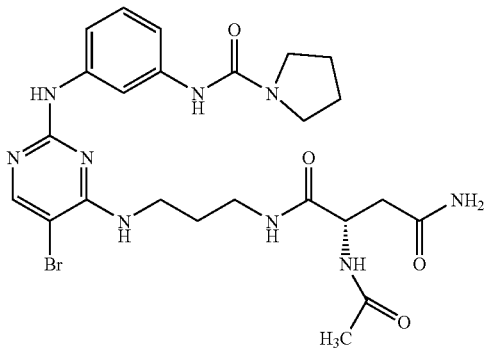 | 589 | |
| 444 | 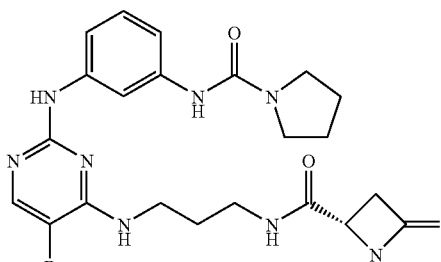 | 530 | |

-continued
| Example | Structure | ESI-MS | Mol-Weight |
|---|---|---|---|
| 445 | 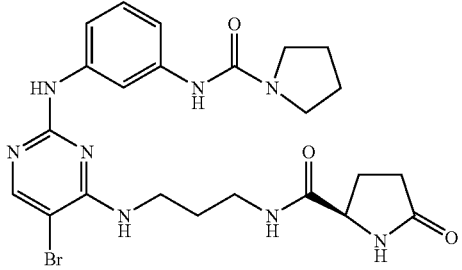 | 544 | |
| 446 | 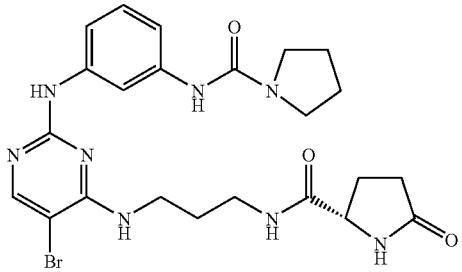 | 544 | |
| 447 | 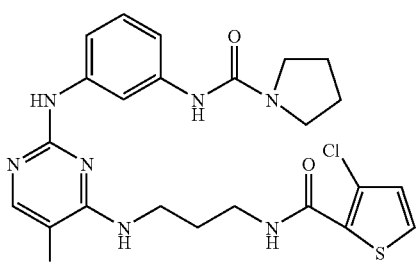 | 577 | |
| 448 | 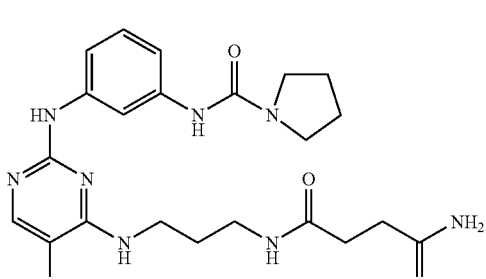 | 532 | |
| 449 | 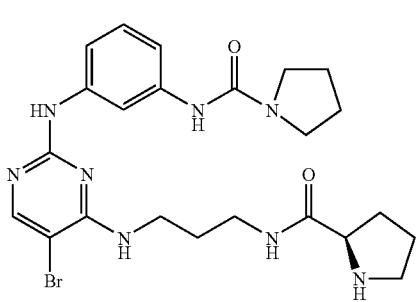 | 530 | |

-continued

| Example | Structure | ESI-MS | Mol-Weight |
|---|---|---|---|
| 450 | 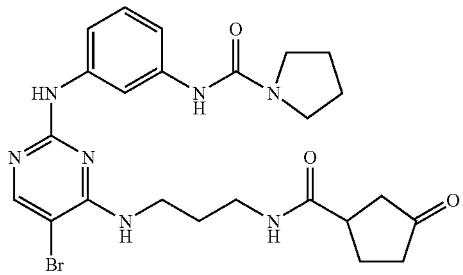 | 543 | |
| 451 | 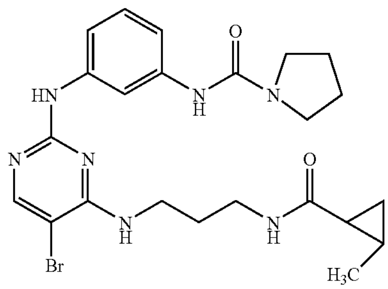 | 515 | |
| 452 | 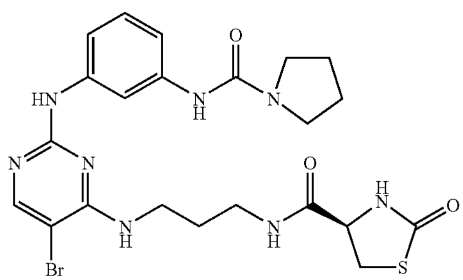 | 562 | |
| 453 | 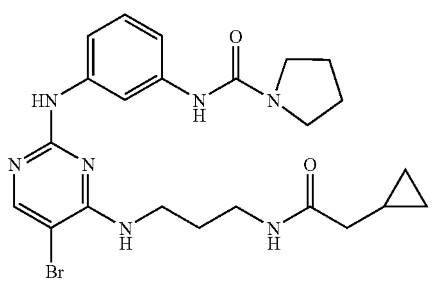 | 515 | |
| 454 | 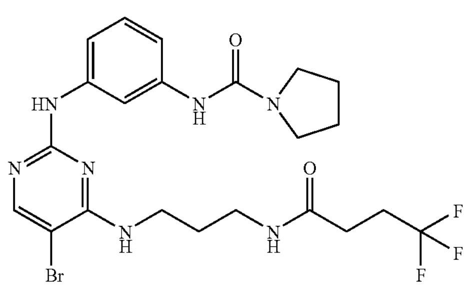 | 557 | |

-continued
| Example | Structure | ESI-MS | Mol-Weight |
|---|---|---|---|
| 455 | 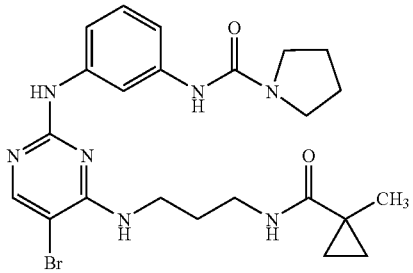 | 515 | |
| 456 | 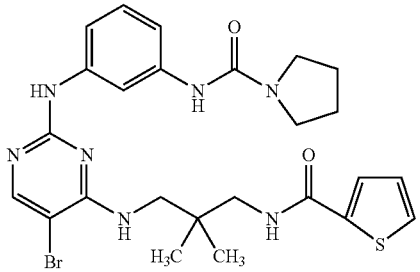 | 571 | |
| 457 | 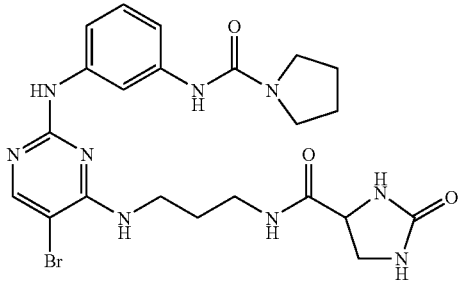 | 545 | |
| 458 | 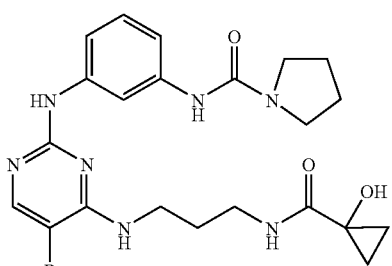 | 517 | |
| 459 | 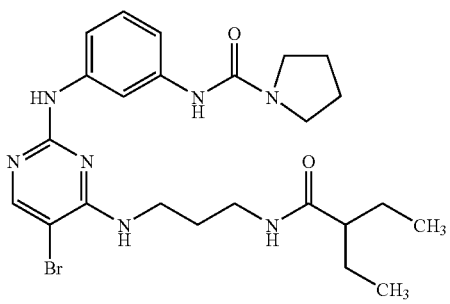 | 531 | |

-continued

| Example | Structure | ESI-MS | Mol-Weight |
|---|---|---|---|
| 460 | 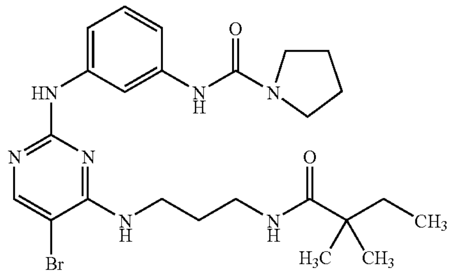 | 531 | |
| 461 | 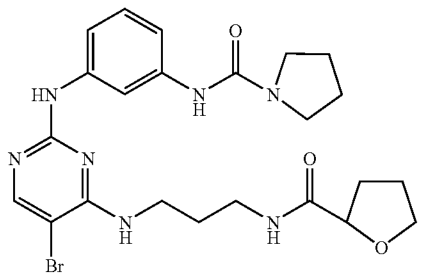 | 531 | |
| 462 | 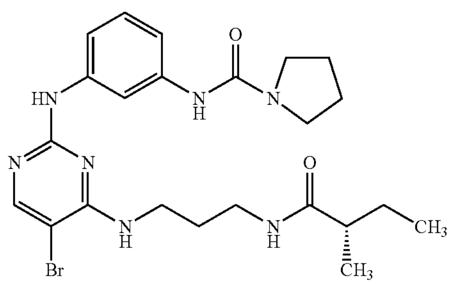 | 517 | |
| 463 | 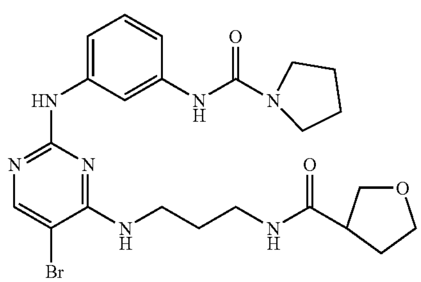 | 531 | |
| 464 | 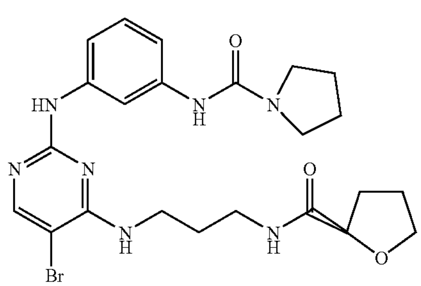 | 531 | |

-continued

| Example | Structure | ESI-MS | Mol-Weight |
|---|---|---|---|
| 465 | 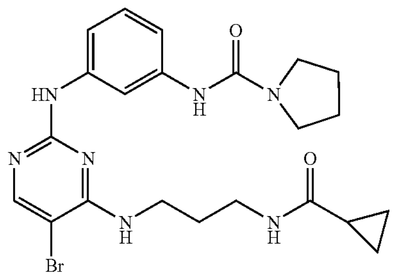 | 501 | |
| 466 | 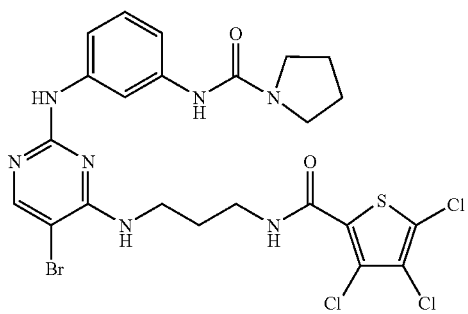 | 645 | |
| 467 | 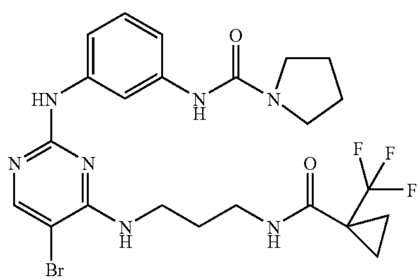 | 569 | |
| 468 | 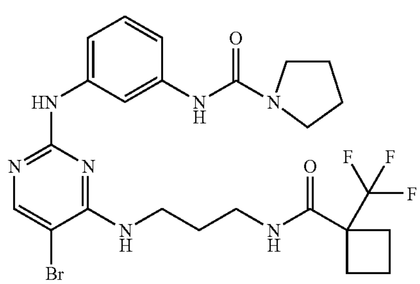 | 583 | |
| 469 | 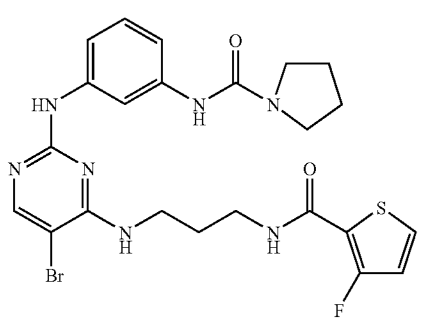 | 561 | |

-continued

| Example | Structure | ESI-MS | Mol-Weight |
|---|---|---|---|
| 470 | 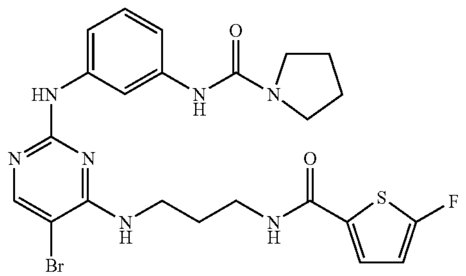 | 561 | |
| 471 | 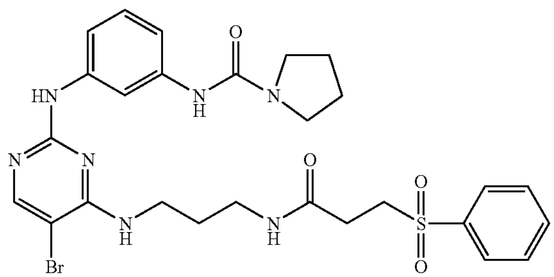 | 629 | |
| 472 | 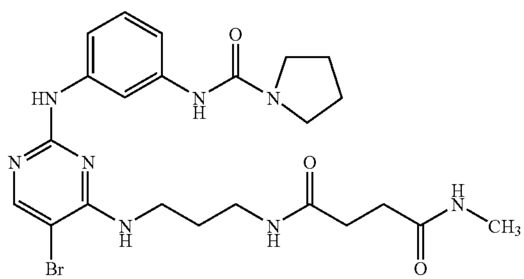 | 546 | |
| 473 | 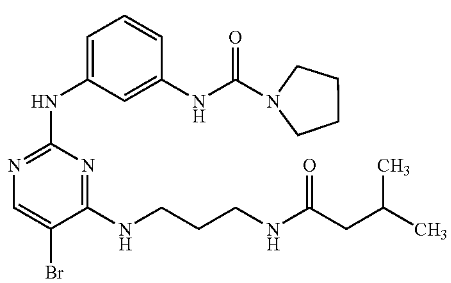 | 517 | |
| 474 | 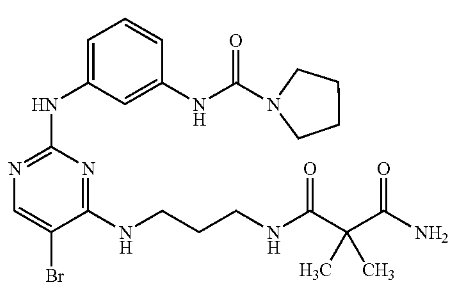 | 546 | |

-continued

| Example | Structure | ESI-MS | Mol-Weight |
|---|---|---|---|
| 475 | 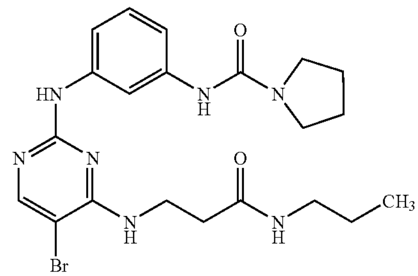 | 489 | |
| 476 | 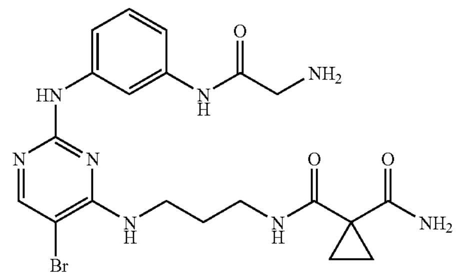 | 504 | |
| 477 | 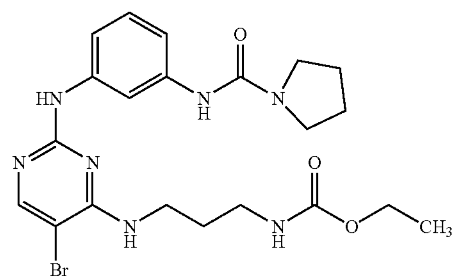 | 505 | |
| 478 | 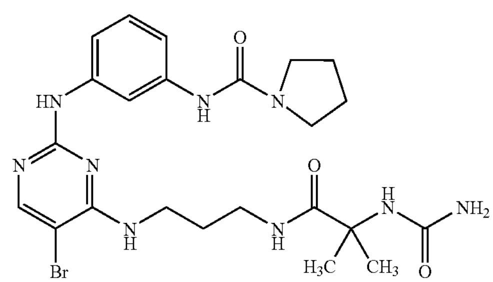 | 561 | |
| 479 | 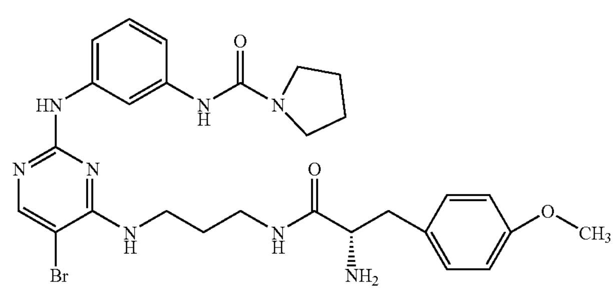 | 610 | |

-continued

| Example | Structure | ESI-MS | Mol-Weight |
|---|---|---|---|
| 480 | 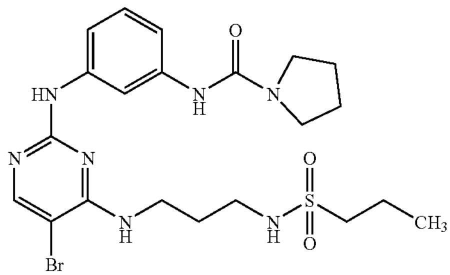 | 539 | |
| 481 | 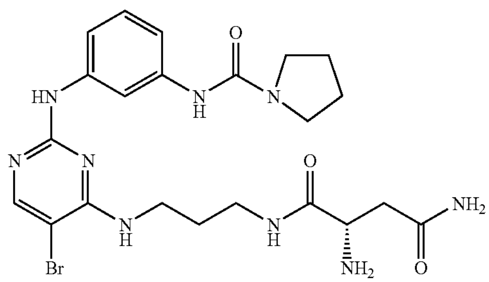 | 547 | |
| 482 | 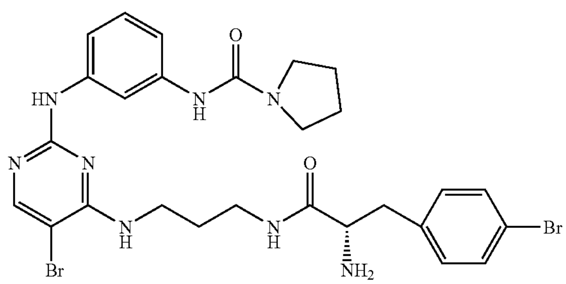 | 658 | |
| 483 | 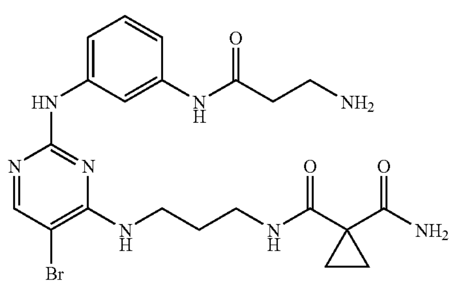 | 518 | |
| 484 | 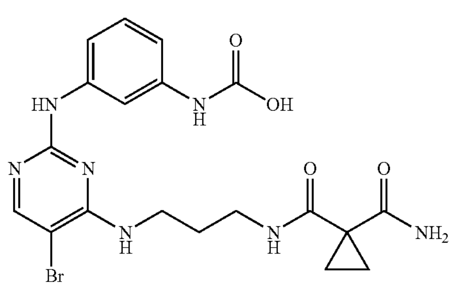 | 490 | |

-continued

| Example | Structure | ESI-MS | Mol-Weight |
|---|---|---|---|
| 485 | 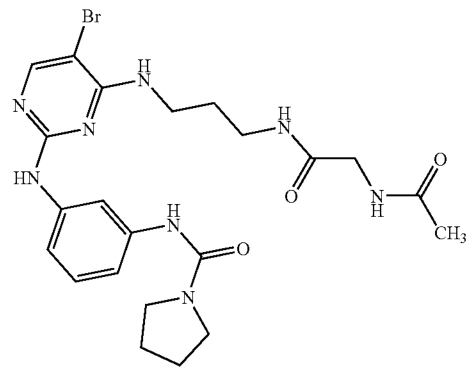 | 532 | |
| 486 | 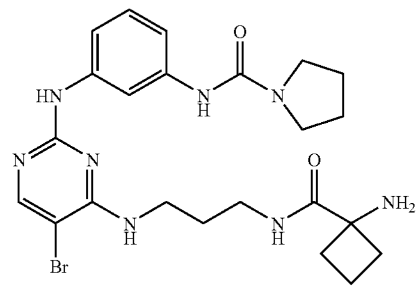 | 530 | |
| 487 | 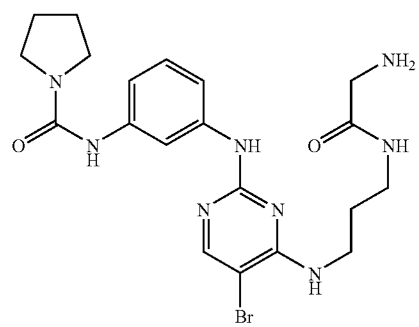 | 490 | |
| 488 | 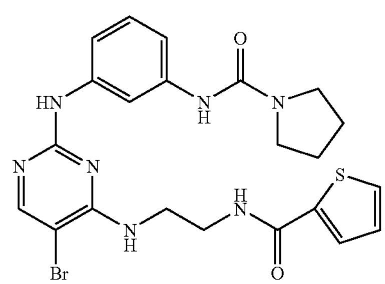 | 529 | |
| 489 | 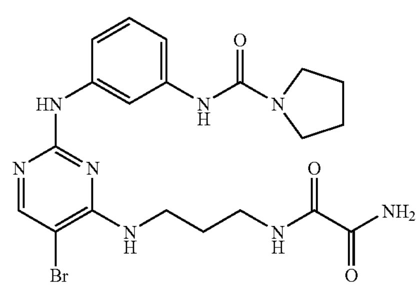 | 504 | |

-continued

| Example | Structure | ESI-MS | Mol-Weight |
|---|---|---|---|
| 490 | 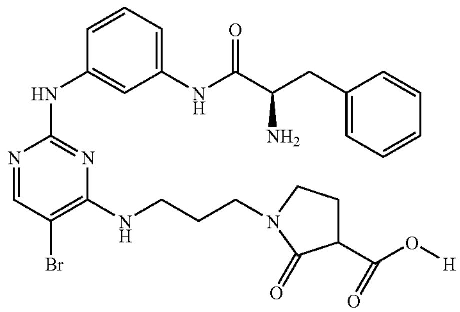 | 595 | |
| 491 | 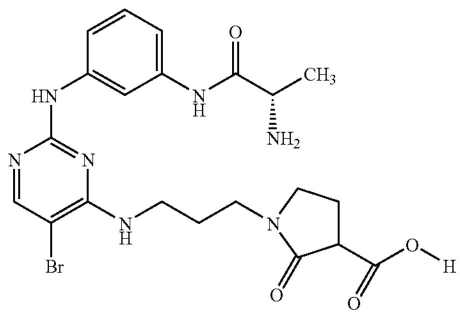 | 519 | |
| 492 | 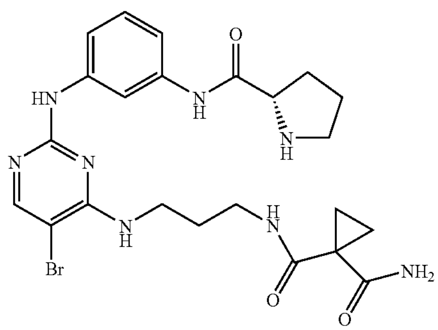 | 544 | |
| 493 | 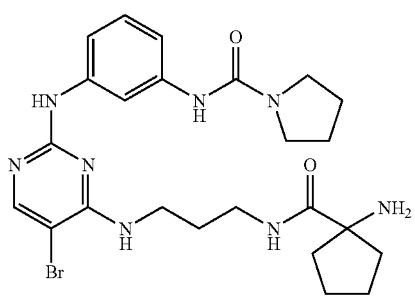 | 544 | |
| 494 | 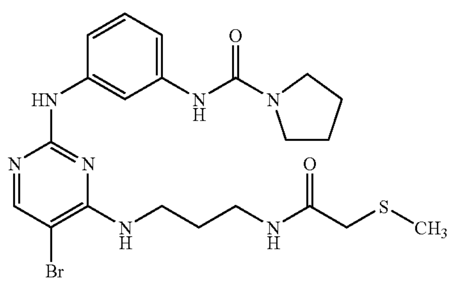 | 521 | |

| Example | Structure | ESI-MS | Mol-Weight |
|---|---|---|---|
| 495 | 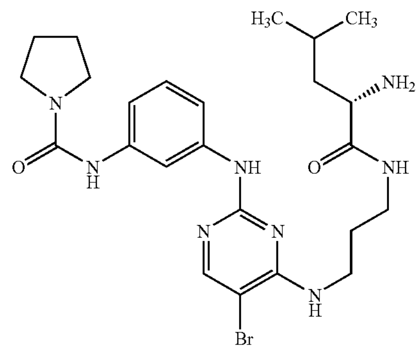 | 546 | |
| 496 | 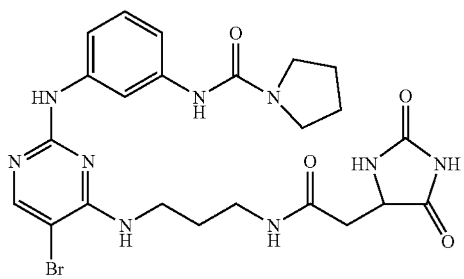 | 573 | |
| 497 | 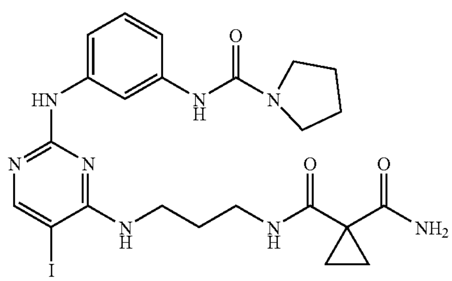 | 592 | |
| 498 | 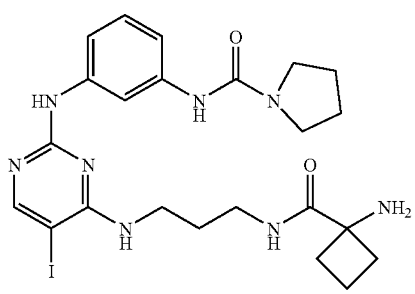 | 578 | |
| 499 | 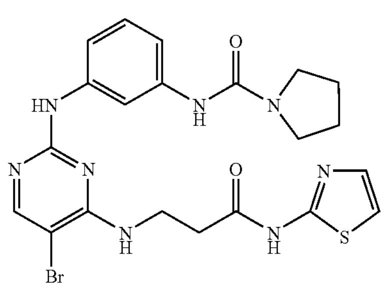 | 530 | |

| Example | Structure | ESI-MS | Mol-Weight |
|---|---|---|---|
| 500 | 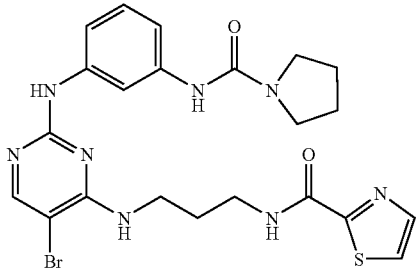 | | 544 |
| 501 | 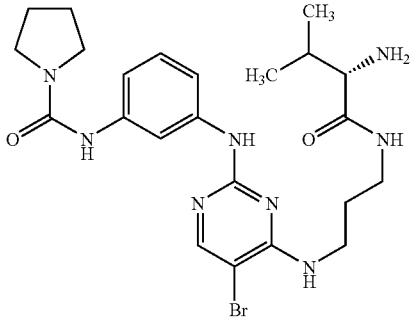 | | 532 |
| 502 | 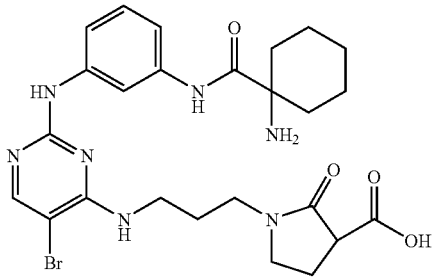 | | 573 |
| 503 | 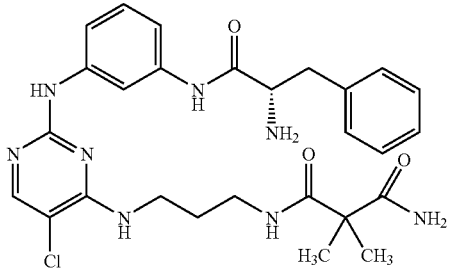 | | 552 |
| 504 | 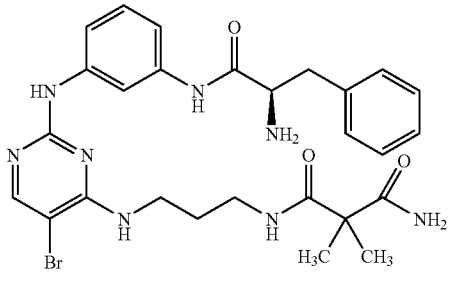 | | 596 |

-continued
| Example | Structure | ESI-MS | Mol-Weight |
|---|---|---|---|
| 505 | 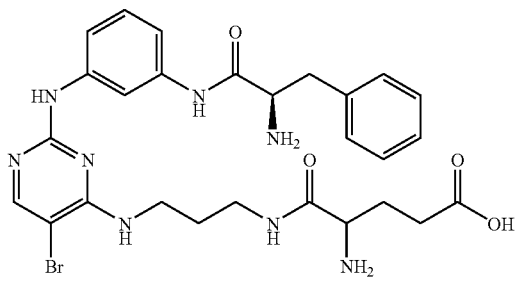 | 612 | |
| 506 | 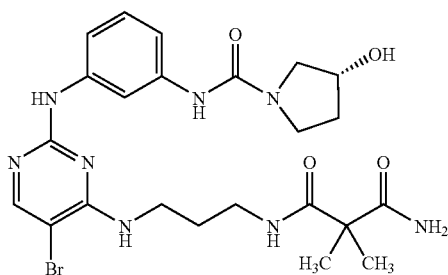 | 562 | |
| 507 | 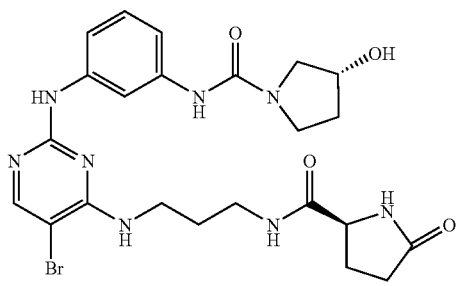 | 560 | |
| 508 | 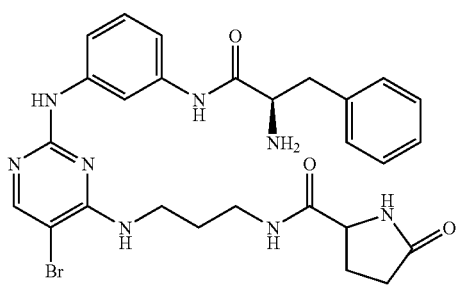 | 594 | |
| 509 | 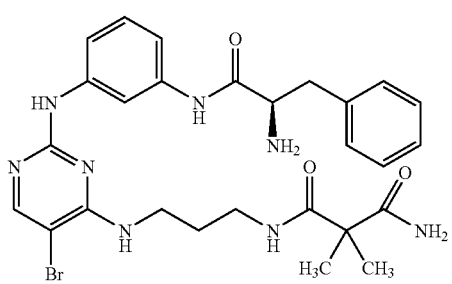 | 552 | |

-continued
| Example | Structure | ESI-MS | Mol-Weight |
|---|---|---|---|
| 510 | 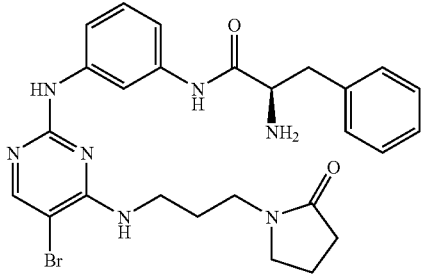 | 551 | |
| 511 | 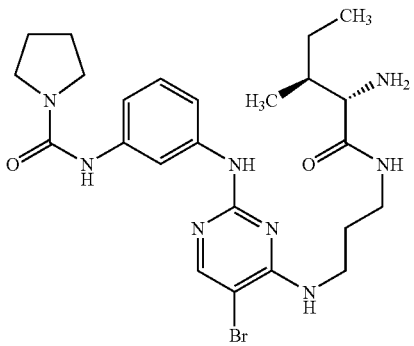 | 546 | |
| 512 | 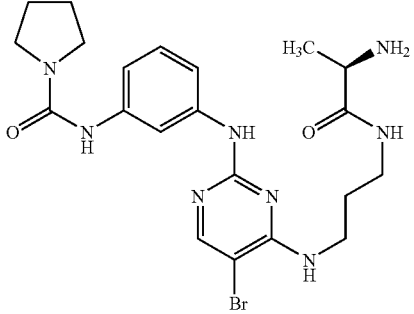 | 504 | |
| 513 | 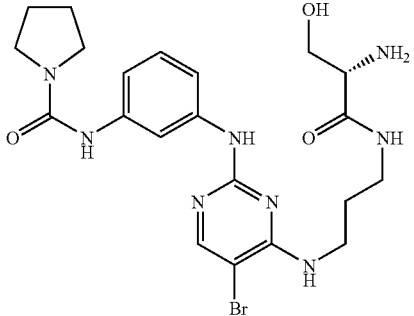 | 520 | |
| 514 | 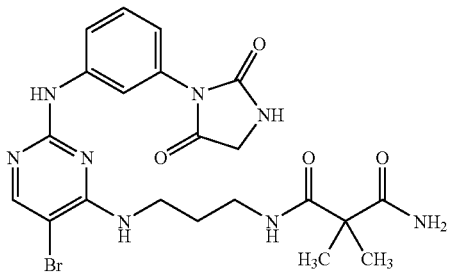 | 533 | |

-continued

| Example | Structure | ESI-MS | Mol-Weight |
|---|---|---|---|
| 515 | 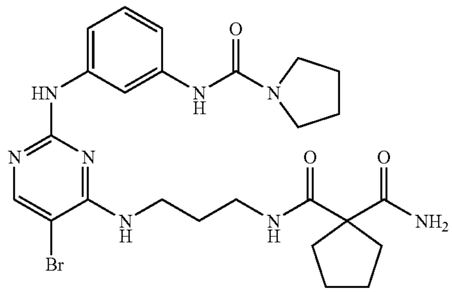 | 572 | |
| 516 | 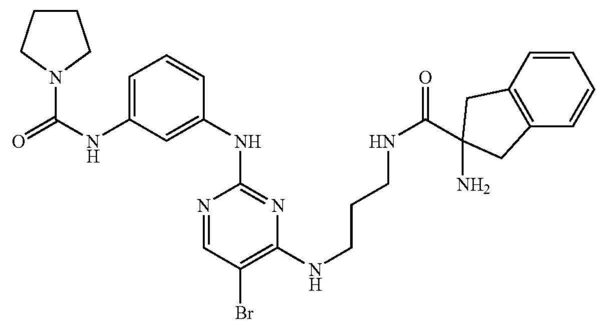 | 592 | |
| 517 | 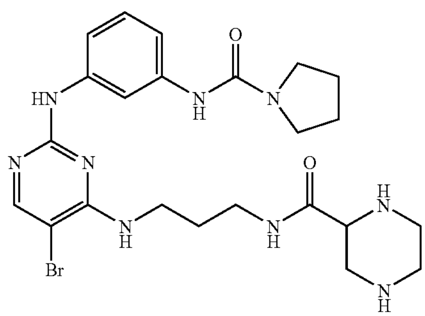 | 545 | |
| 518 | 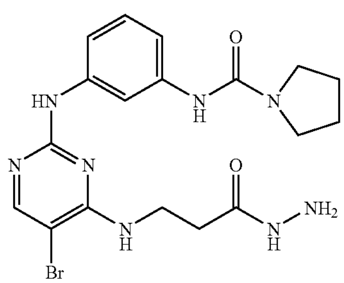 | 462 | |
| 519 | 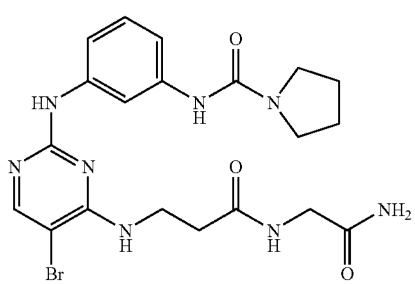 | 504 | |

-continued

| Example | Structure | ESI-MS | Mol-Weight |
|---|---|---|---|
| 520 | 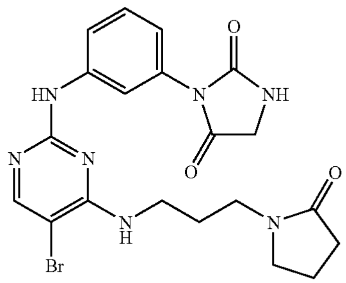 | | 487 |
| 521 | 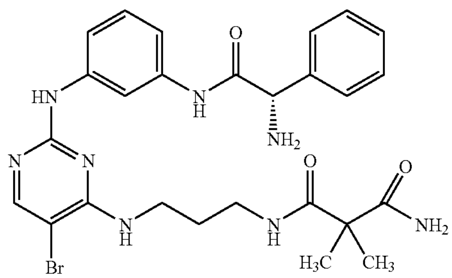 | | 582 |
| 522 | 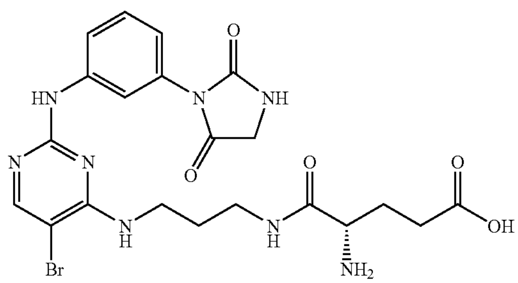 | | 548 |
| 523 | 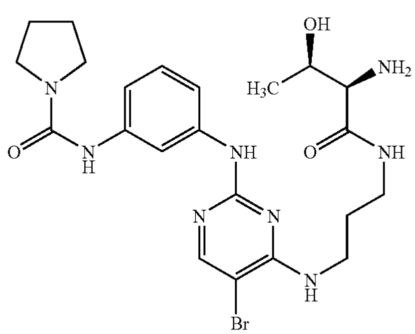 | | 534 |
| 524 | 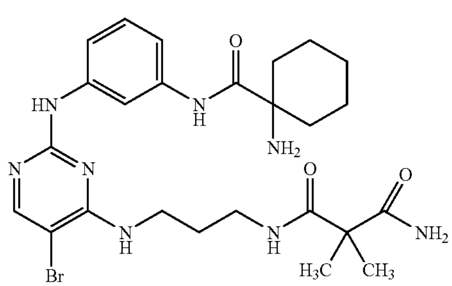 | | 574 |

-continued
| Example | Structure | ESI-MS | Mol-Weight |
|---|---|---|---|
| 525 | 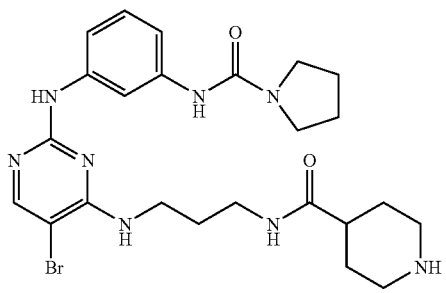 | | 544 |
| 526 | 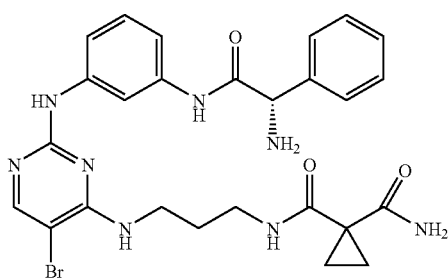 | | 580 |
| 527 | 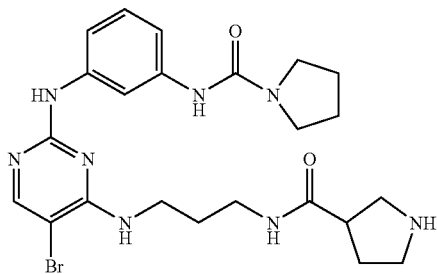 | | 530 |
| 528 | 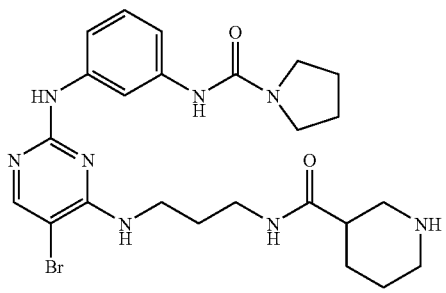 | | 544 |
| 529 | 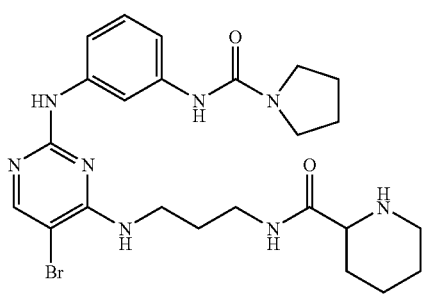 | | 544 |

| Example | Structure | ESI-MS | Mol-Weight |
|---|---|---|---|
| 530 | 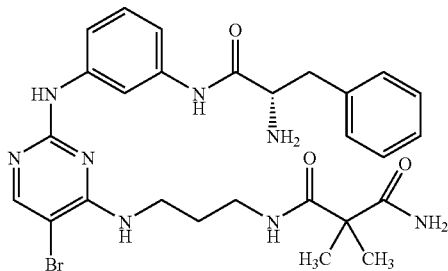 | | 596 |
| 531 | 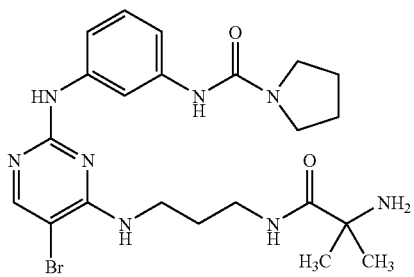 | | 518 |
| 532 | 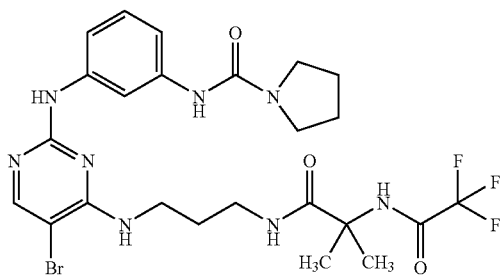 | | 614 |
| 533 | 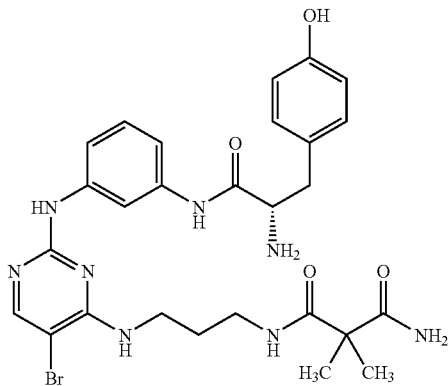 | | 612 |

-continued
| Example | Structure | ESI-MS | Mol-Weight |
|---|---|---|---|
| 534 | 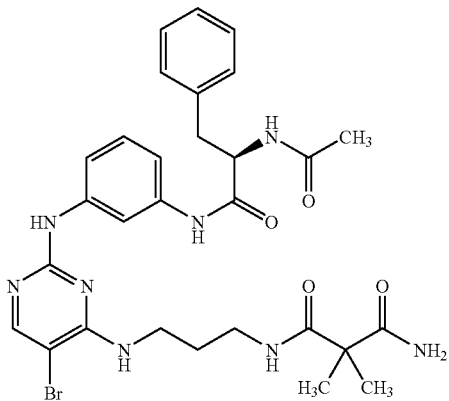 | 638 | |
| 535 | 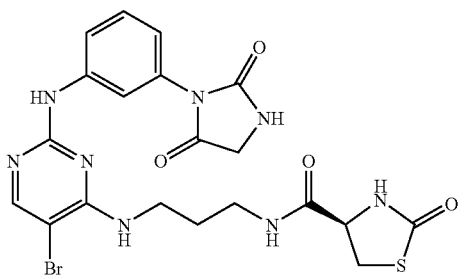 | 548 | |
| 536 | 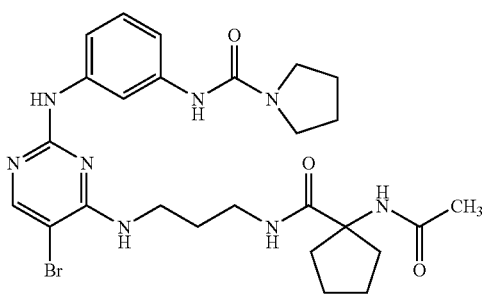 | 586 | |
| 537 | 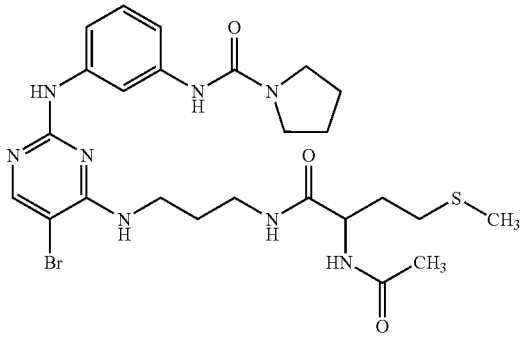 | 606 | |

-continued

| Example | Structure | ESI-MS | Mol-Weight |
|---|---|---|---|
| 538 | 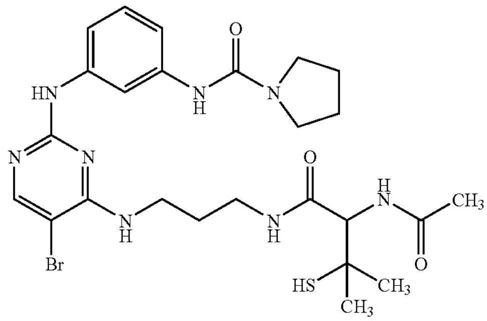 | 606 | |
| 539 | 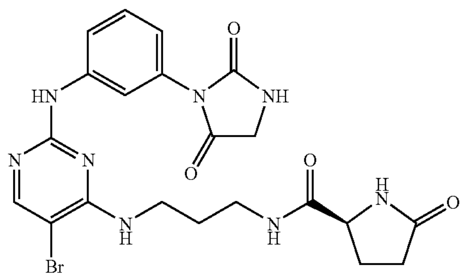 | 530 | |
| 540 | 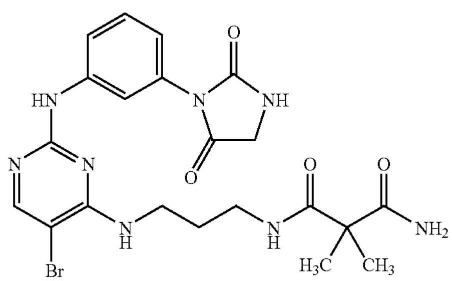 | 532 | |
| 541 | 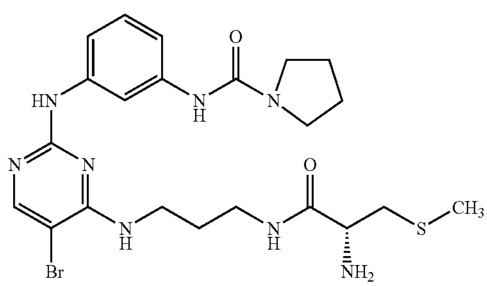 | 550 | |
| 542 | 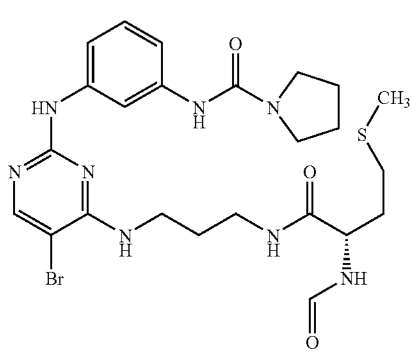 | 592 | |

| Example | Structure | ESI-MS | Mol-Weight |
|---|---|---|---|
| 543 | 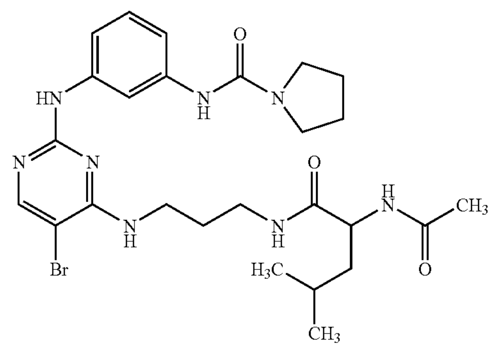 | 588 | |
| 544 | 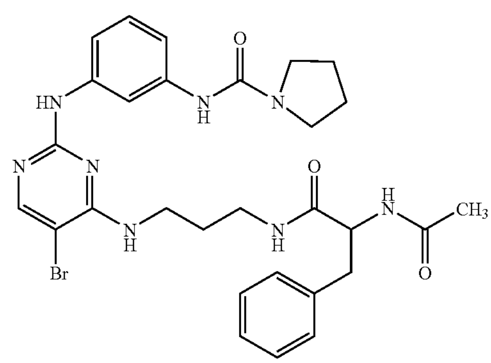 | 622 | |
| 545 | 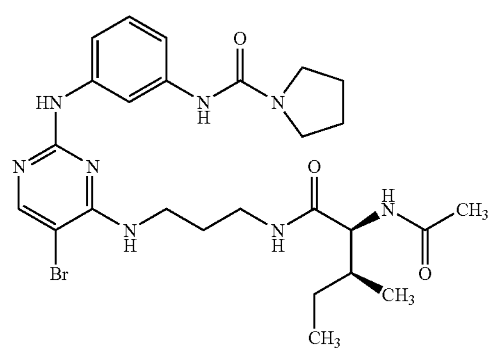 | 588 | |
| 546 | 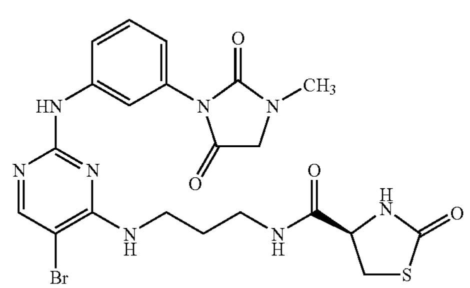 | 562 | |

-continued
| Example | Structure | ESI-MS | Mol-Weight |
|---|---|---|---|
| 547 | 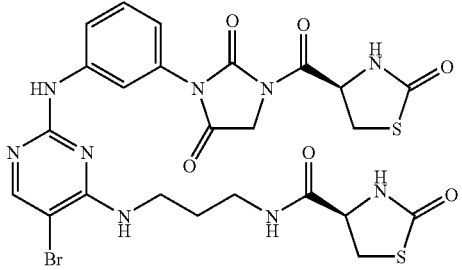 | | 677 |
| 548 | 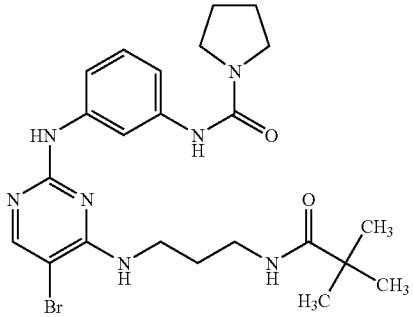 | | 517 |
| 549 | 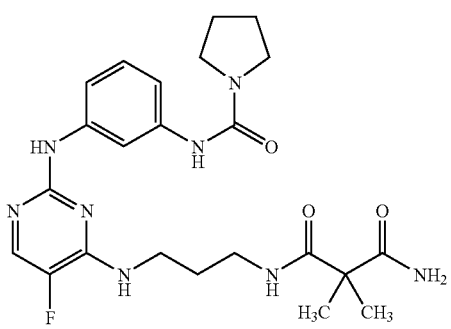 | | 486 |
| 550 | 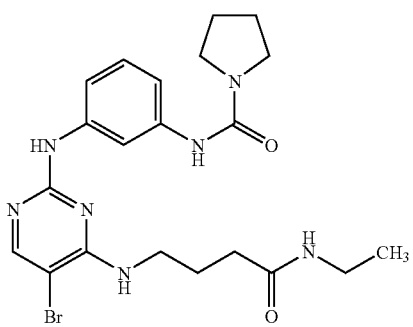 | | 489 |
| 551 | 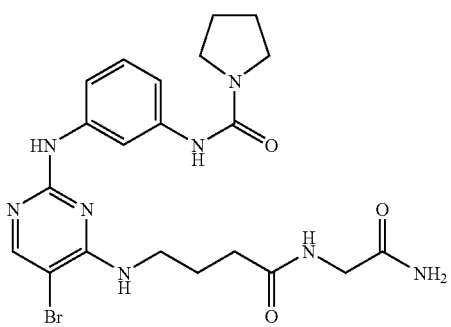 | | 518 |

-continued
| Example | Structure | ESI-MS | Mol-Weight |
|---|---|---|---|
| 552 | 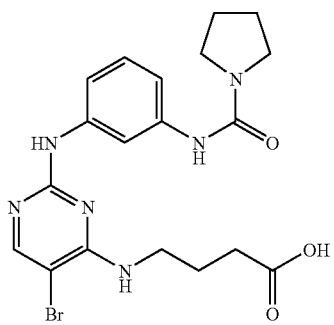 | | 462 |
| 553 | 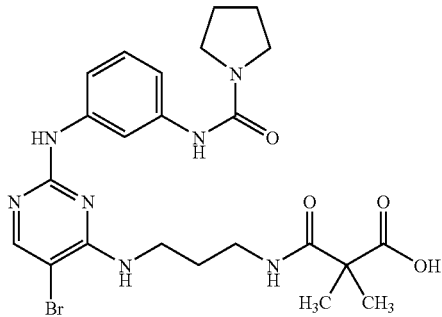 | | 547 |
| 554 | 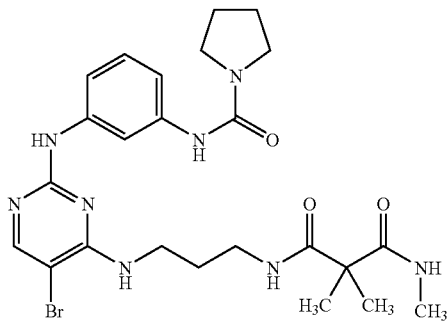 | | 560 |
| 555 | 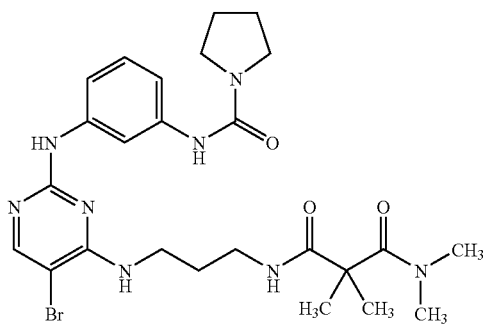 | | 574 |

| Example | Structure | ESI-MS | Mol-Weight |
|---|---|---|---|
| 556 | 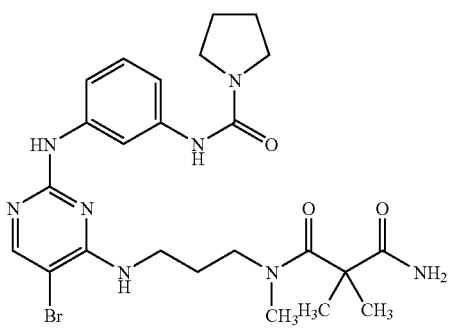 | 560 | |
| 557 | 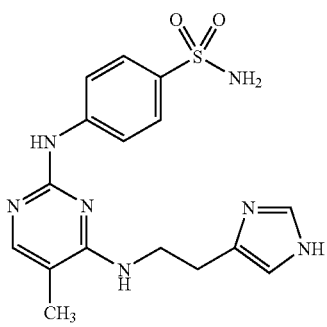 | 373 | |
| 558 | 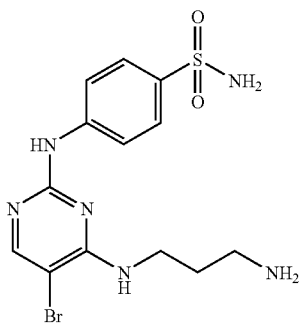 | 400 | |
| 559 | 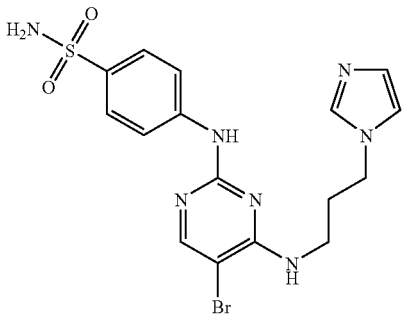 | 451 | |

-continued
| Example | Structure | ESI-MS | Mol-Weight |
| --- | --- | --- | --- |
| 560 | 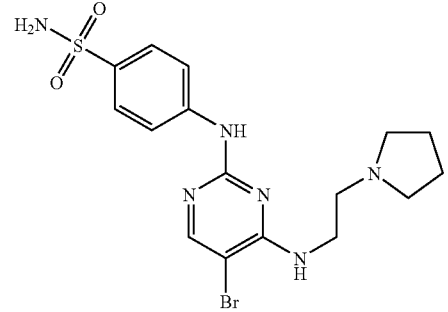 | | 440 |
| 561 | 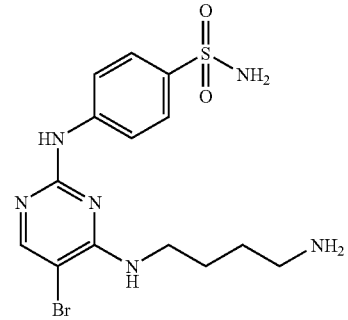 | | 414 |
| 562 | 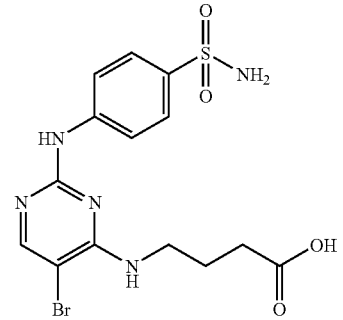 | | 429 |
| 563 | 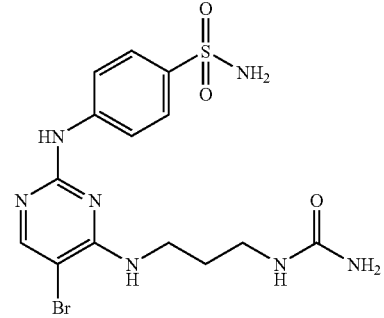 | | 443 |

-continued

| Example | Structure | ESI-MS | Mol-Weight |
|---------|-----------|--------|------------|
| 564 | 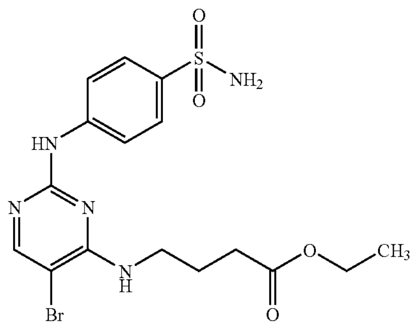 | 457 | |
| 565 | 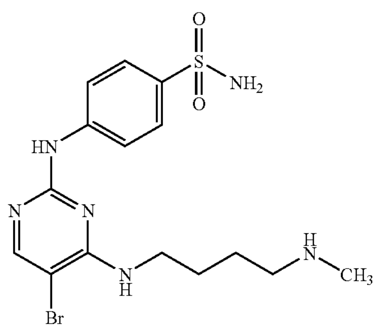 | 428 | |
| 566 | 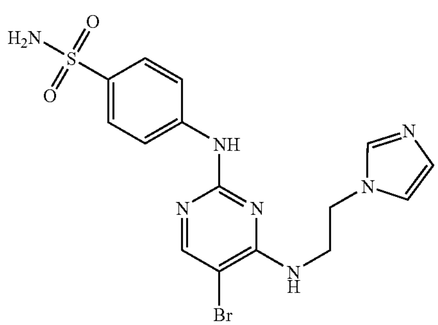 | 437 | |
| 567 | 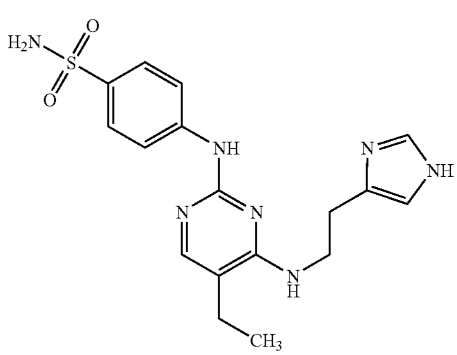 | 387 | |

| Example | Structure | ESI-MS | Mol-Weight |
|---|---|---|---|
| 568 | (structure) | 359 | |
| 569 | (structure) | 448 | |
| 570 | (structure) | 486 | |
| 571 | (structure) | 400 | |
| 572 | (structure) | 428 | |

| Example | Structure | ESI-MS | Mol-Weight |
|---------|-----------|--------|------------|
| 573 | 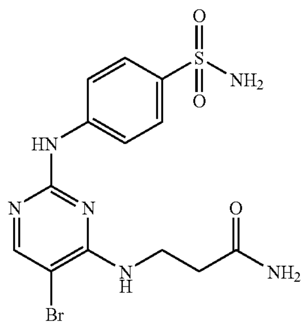 | | 414 |
| 574 | 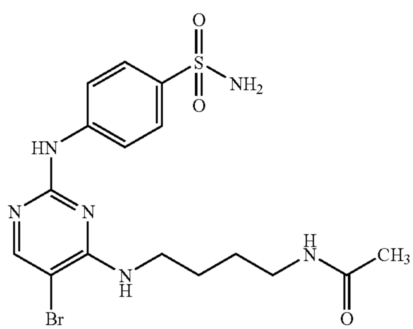 | | 456 |
| 575 | 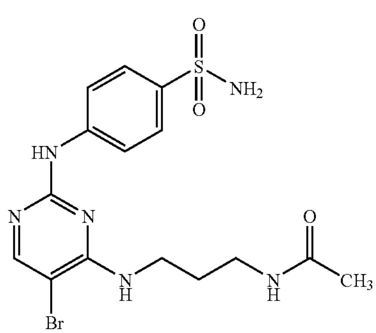 | | 442 |
| 576 | 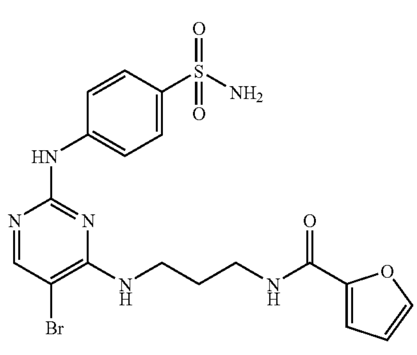 | | 494 |

-continued
| Example | Structure | ESI-MS | Mol-Weight |
|---|---|---|---|
| 577 | 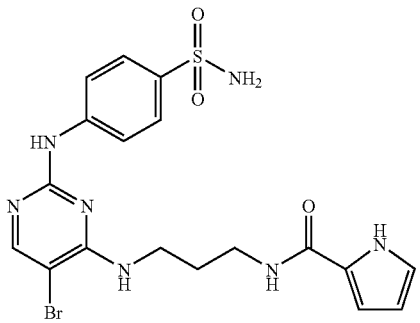 | | 493 |
| 578 | 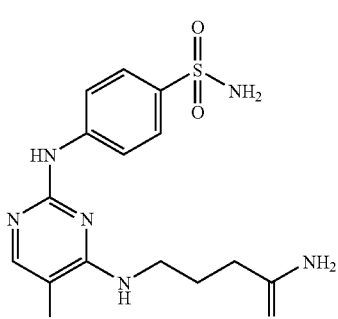 | | 428 |
| 579 | 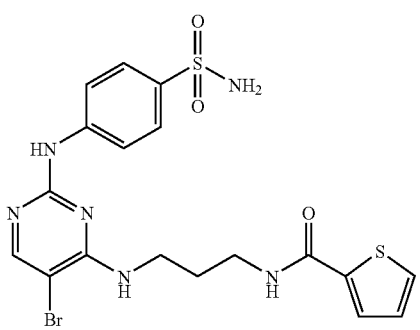 | | 510 |
| 580 | 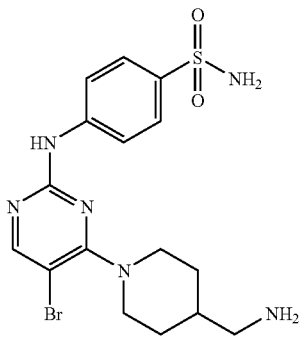 | | 440 |

-continued

| Example | Structure | ESI-MS | Mol-Weight |
|---|---|---|---|
| 581 | 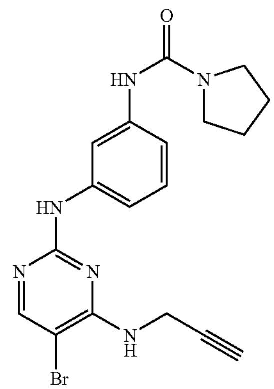 | 416 | 415.29 |
| 582 | 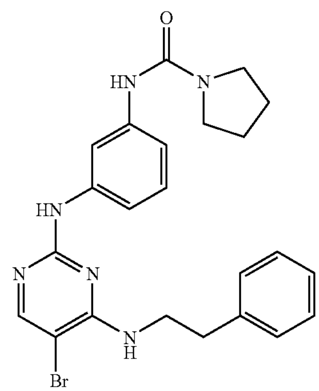 | 482 | 481.40 |
| 583 | 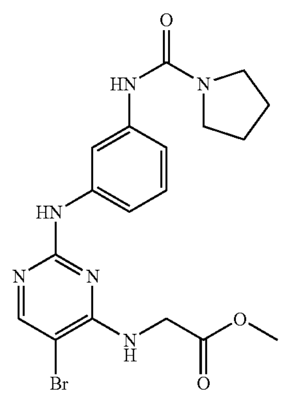 | 450 | 449.31 |
| 584 | 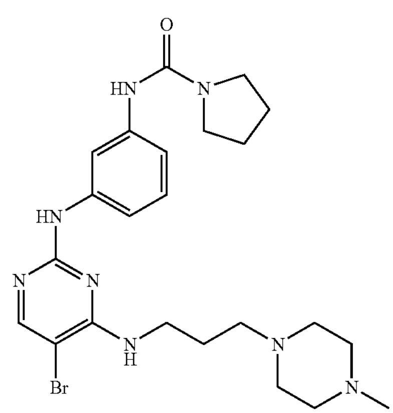 | 518 | 517.47 |

-continued

| Example | Structure | ESI-MS | Mol-Weight |
|---|---|---|---|
| 585 | 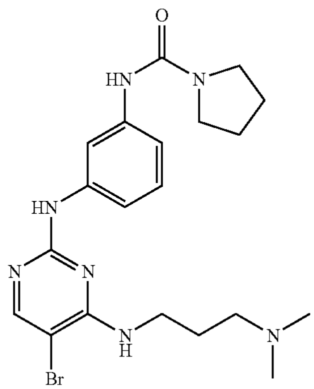 | 463 | 462.39 |
| 586 | 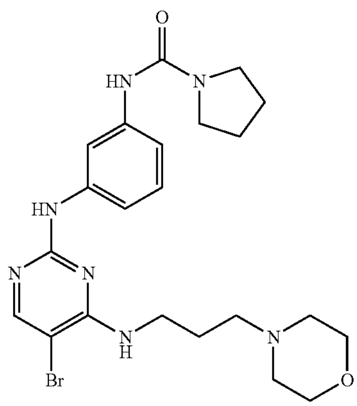 | 505 | 504.43 |
| 587 | 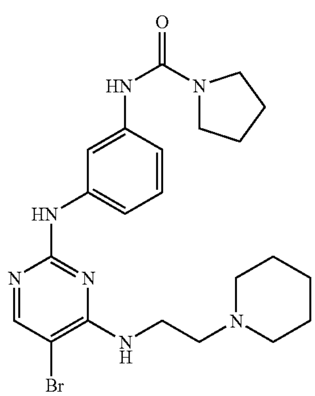 | 489 | 488.43 |
| 588 | 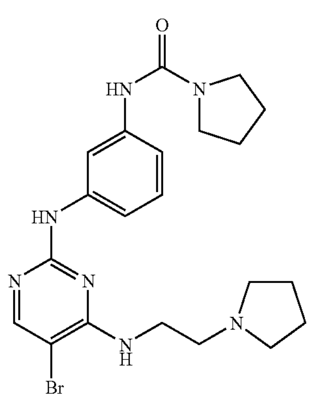 | 475 | 474.40 |

-continued

| Example | Structure | ESI-MS | Mol-Weight |
|---|---|---|---|
| 589 | 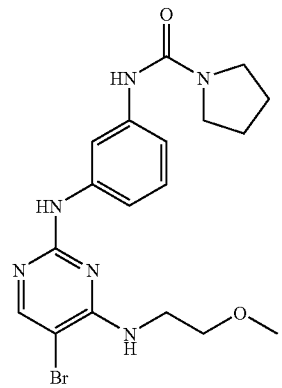 | 436 | 435.32 |
| 590 | 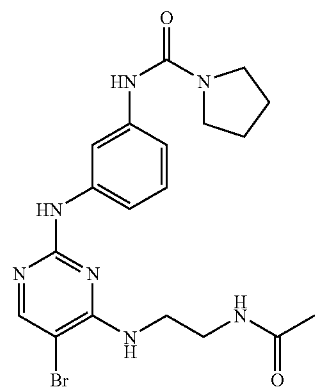 | 463 | 462.35 |
| 591 | 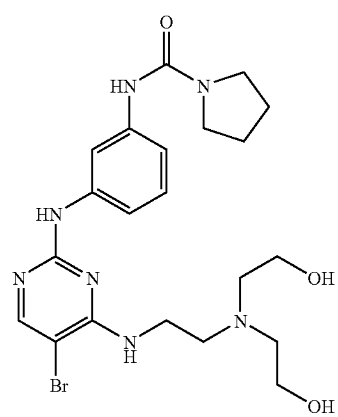 | 509 | 508.42 |
| 592 | 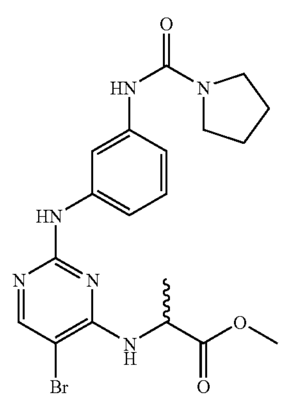 | 464 | 463.33 |

-continued

| Example | Structure | ESI-MS | Mol-Weight |
|---|---|---|---|
| 593 | 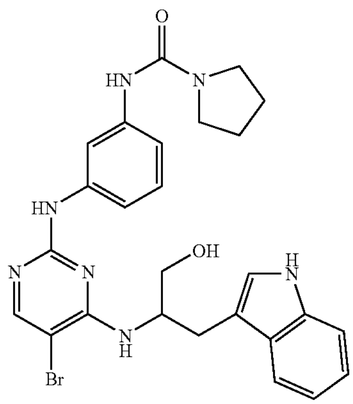 | 551 | 550.46 |
| 594 | 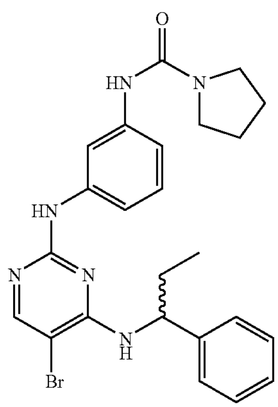 | 496 | 495.42 |
| 595 | 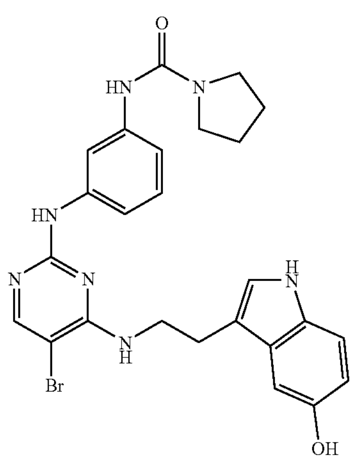 | 437 | 536.43 |

-continued

| Example | Structure | ESI-MS | Mol-Weight |
|---|---|---|---|
| 596 | 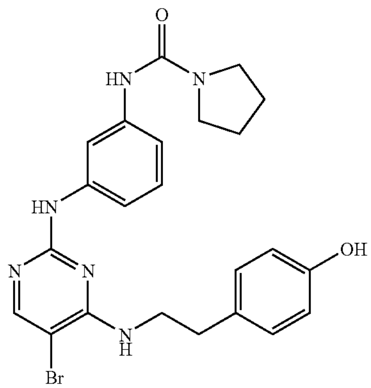 | 498 | 497.40 |
| 597 | 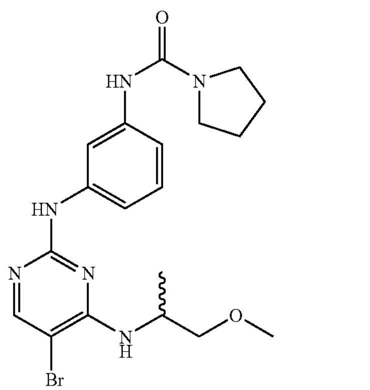 | 450 | 449.35 |
| 598 | 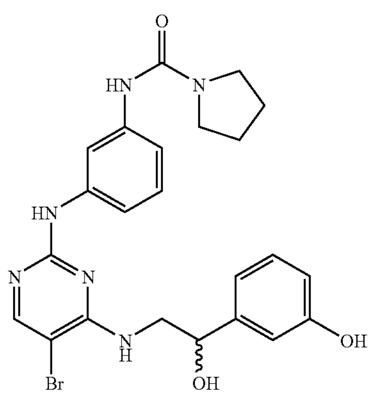 | 514 | 513.39 |
| 599 | 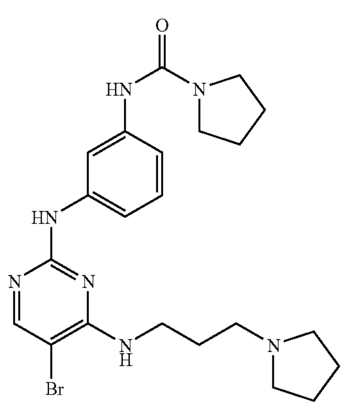 | 489 | 488.43 |

-continued

| Example | Structure | ESI-MS | Mol-Weight |
|---|---|---|---|
| 600 | 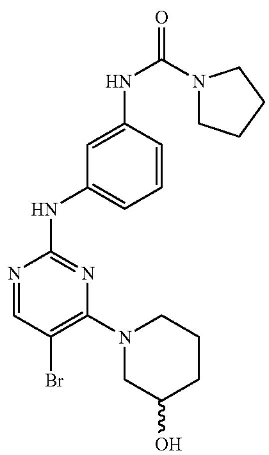 | 462 | 461.36 |
| 601 | 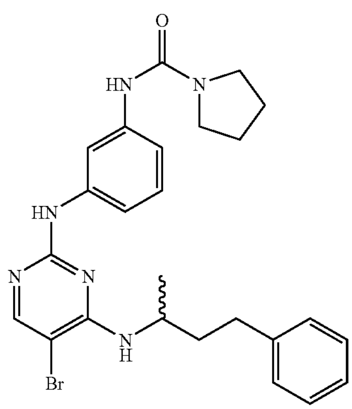 | 510 | 509.45 |
| 602 | 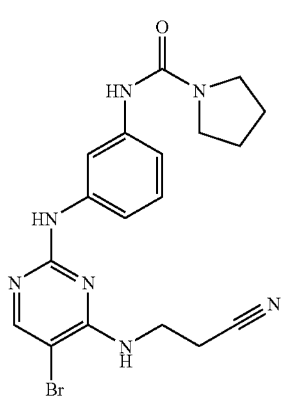 | 431 | 430.31 |

-continued
| Example | Structure | ESI-MS | Mol-Weight |
|---|---|---|---|
| 603 | 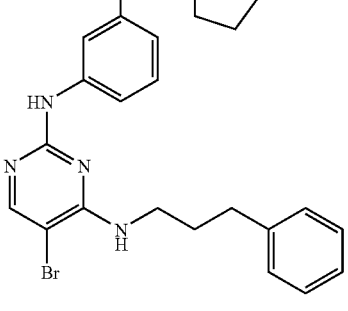 | 496 | 495.42 |
| 604 | 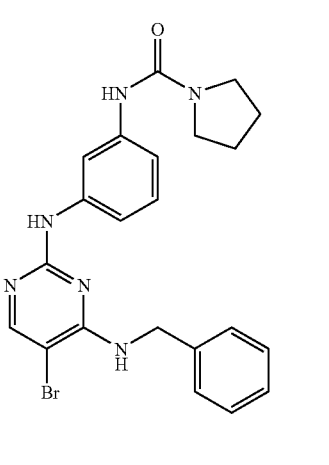 | 468 | 467.37 |
| 605 | 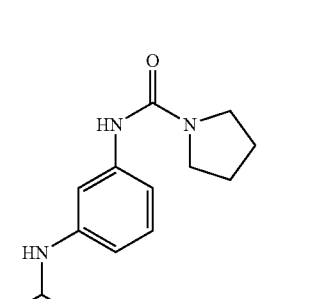 | 417 | 416.28 |

-continued

| Example | Structure | ESI-MS | Mol-Weight |
|---|---|---|---|
| 606 | 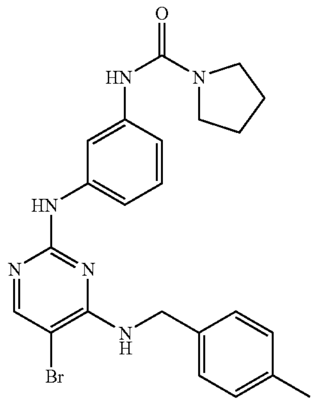 | 482 | 481.40 |
| 607 | 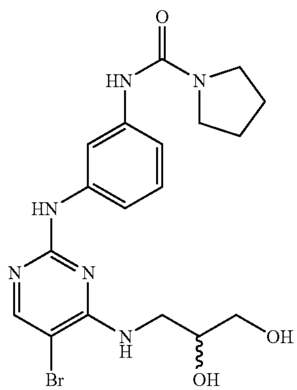 | 452 | 451.32 |
| 608 | 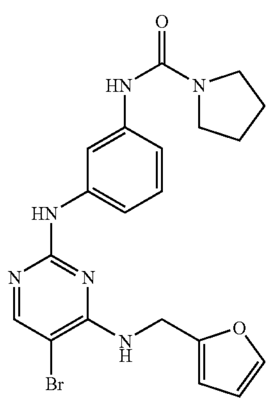 | 458 | 457.33 |
| 609 | 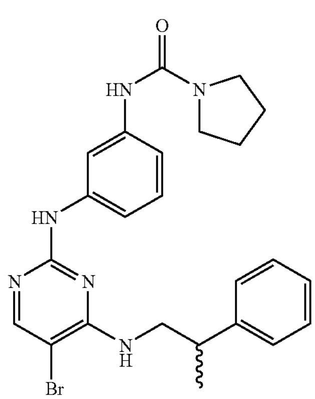 | 496 | 495.42 |

-continued
| Example | Structure | ESI-MS | Mol-Weight |
|---|---|---|---|
| 610 | 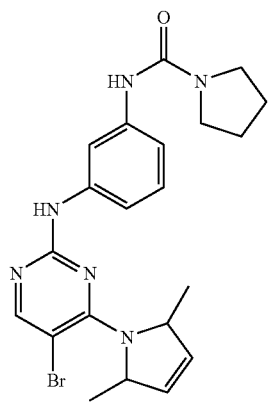 | 458 | 457.37 |
| 611 | 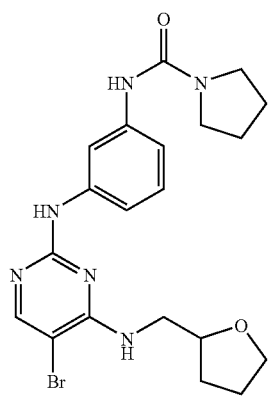 | 462 | 461.36 |
| 612 | 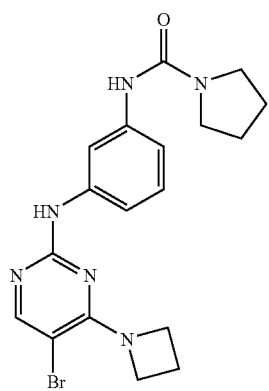 | 418 | 417.31 |

-continued
| Example | Structure | ESI-MS | Mol-Weight |
|---|---|---|---|
| 613 | 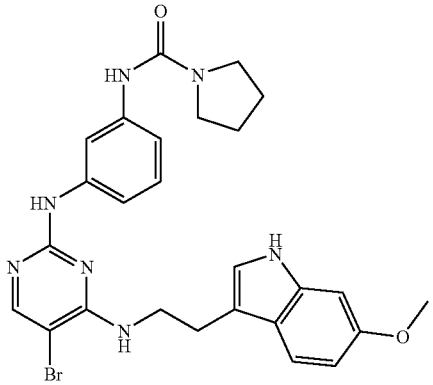 | 551 | 550.46 |
| 614 | 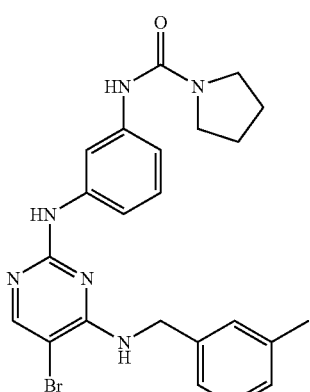 | 482 | 481.40 |
| 615 | 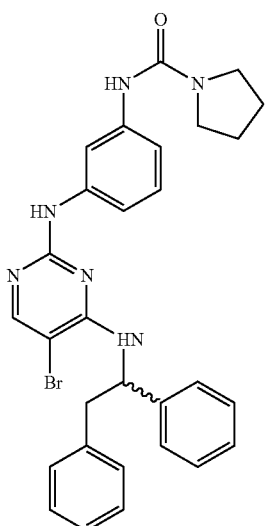 | 558 | 557.49 |

-continued
| Example | Structure | ESI-MS | Mol-Weight |
|---------|-----------|--------|------------|
| 616 | 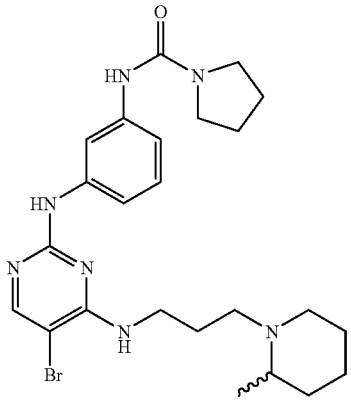 | 517 | 516.49 |
| 617 | 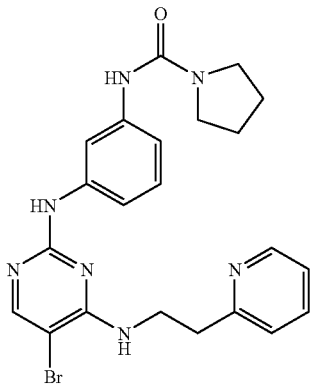 | 483 | 482.38 |
| 618 | 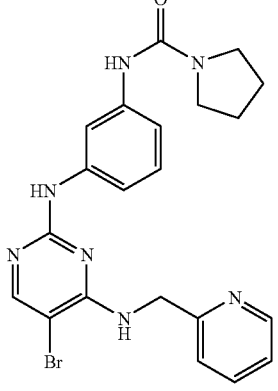 | 469 | 468.36 |
| 619 | 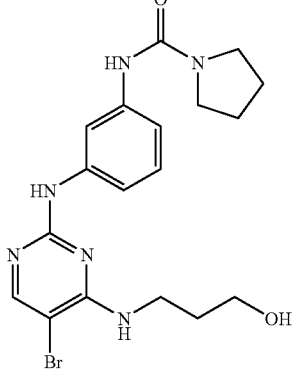 | 436 | 435.32 |

-continued

| Example | Structure | ESI-MS | Mol-Weight |
|---------|-----------|--------|------------|
| 620 | 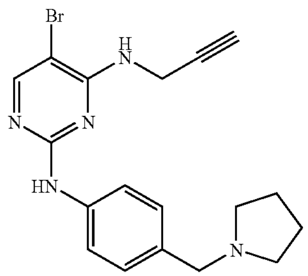 | 287 | 386.30 |
| 621 | 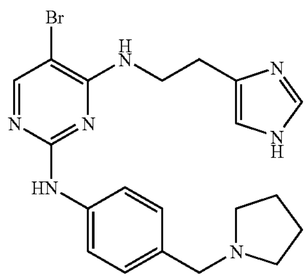 | 443 | 442.36 |
| 622 | 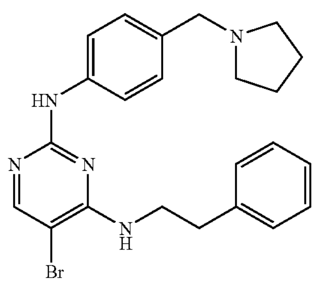 | 453 | 452.40 |
| 623 | 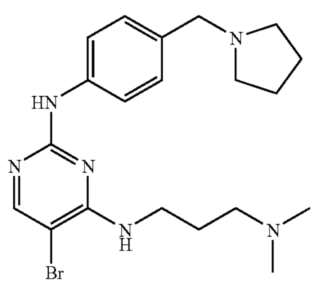 | 434 | 433.40 |
| 624 | 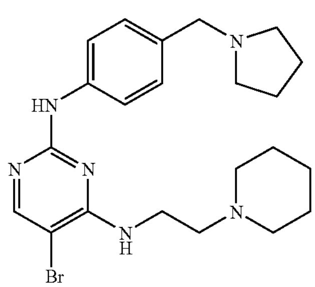 | 460 | 459.43 |

-continued

| Example | Structure | ESI-MS | Mol-Weight |
|---|---|---|---|
| 625 | 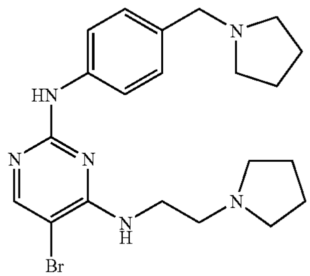 | 446 | 445.41 |
| 626 | 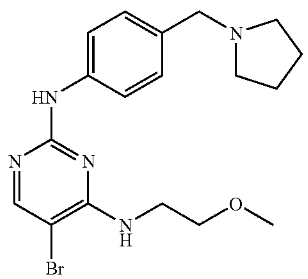 | 407 | 406.33 |
| 627 | 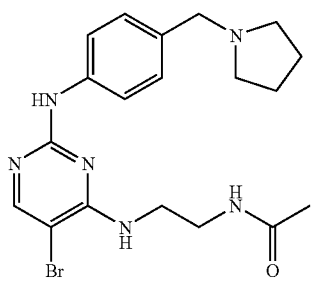 | 434 | 433.35 |
| 628 | 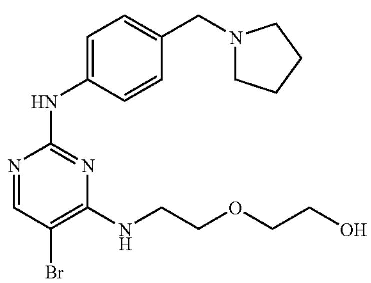 | 437 | 436.35 |
| 629 | 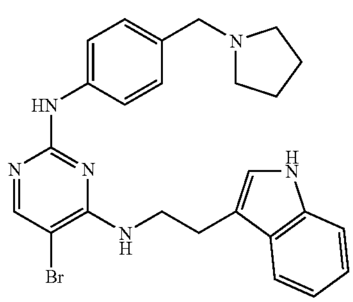 | 492 | 491.43 |

-continued

| Example | Structure | | ESI-MS | Mol-Weight |
|---|---|---|---|---|
| 630 | 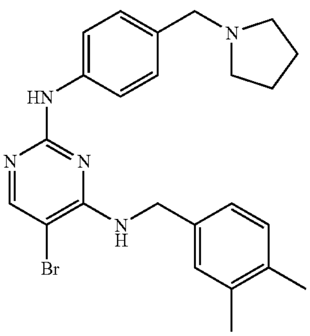 | | 467 | 466.42 |
| 631 | 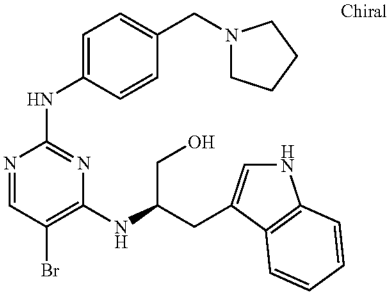 | Chiral | 522 | 521.46 |
| 632 | 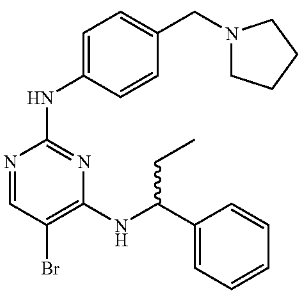 | | 467 | 466.42 |
| 633 | 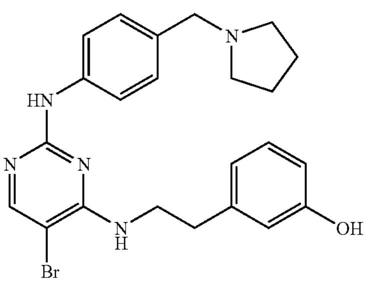 | | 469 | 468.40 |
| 634 | 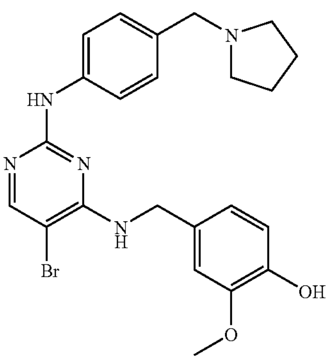 | | 485 | 484.40 |

-continued
| Example | Structure | ESI-MS | Mol-Weight |
|---|---|---|---|
| 635 | 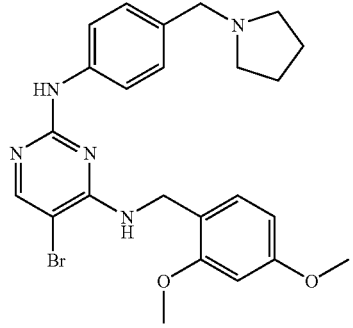 | 499 | 498.42 |
| 636 | 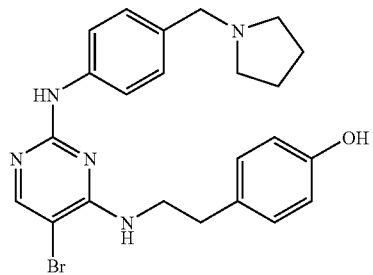 | 469 | 468.40 |
| 637 | 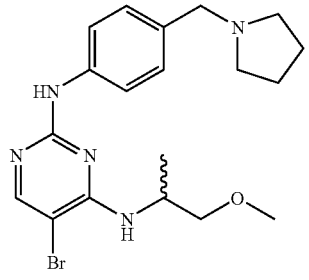 | 420 | 420.35 |
| 638 | 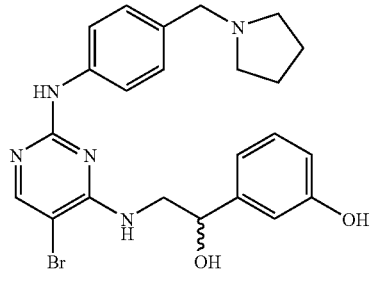 | 485 | 484.40 |
| 639 | 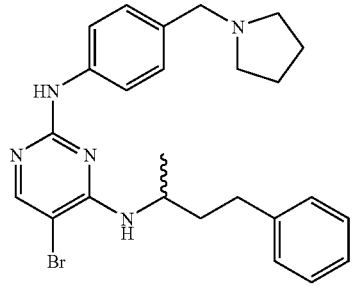 | 481 | 480.45 |

-continued

| Example | Structure | ESI-MS | Mol-Weight |
|---------|-----------|--------|------------|
| 640 | 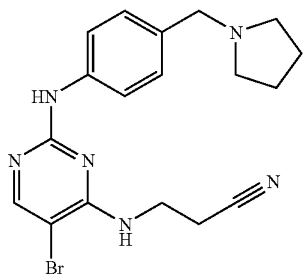 | 402 | 401.31 |
| 641 | 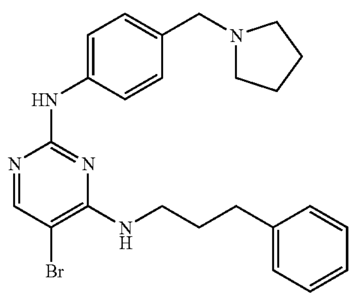 | 467 | 466.42 |
| 642 | 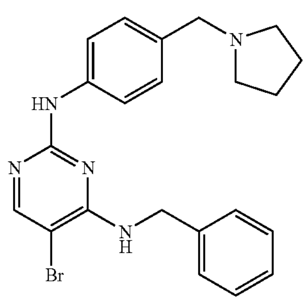 | 439 | 438.37 |
| 643 | 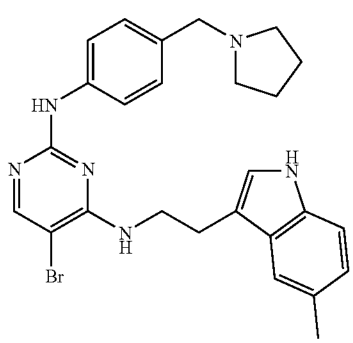 | 506 | 505.46 |
| 644 | 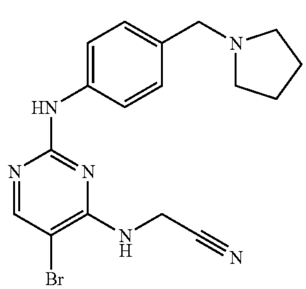 | 388 | 387.28 |

-continued

| Example | Structure | ESI-MS | Mol-Weight |
|---|---|---|---|
| 645 | 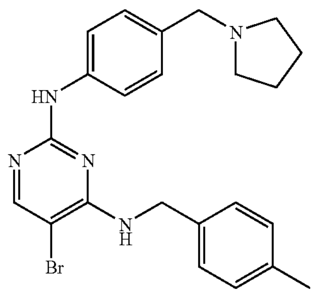 | 453 | 452.40 |
| 646 | 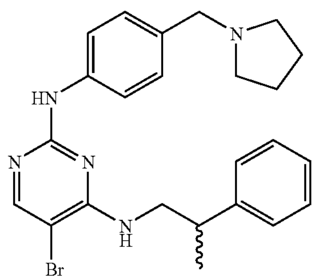 | 467 | 466.42 |
| 647 | 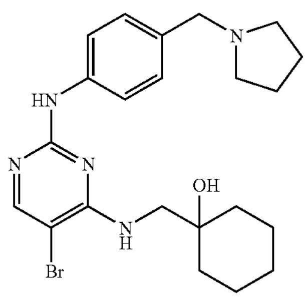 | 461 | 460.42 |
| 648 | 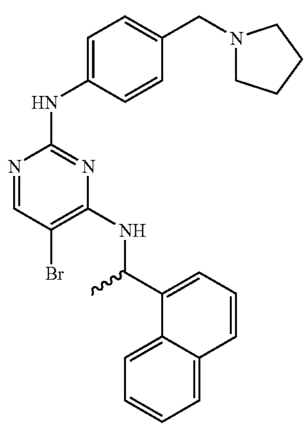 | 503 | 502.46 |
| 649 | 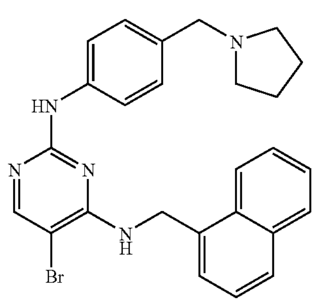 | 489 | 488.43 |

-continued

| Example | Structure | ESI-MS | Mol-Weight |
|---|---|---|---|
| 650 | 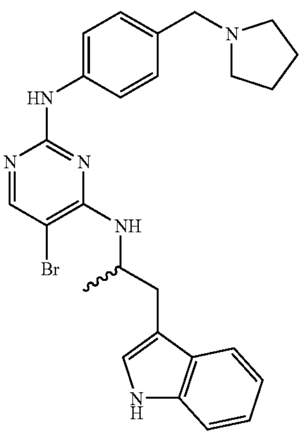 | 506 | 505.46 |
| 651 | 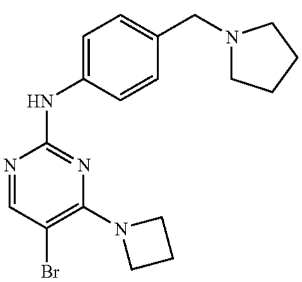 | 389 | 388.31 |
| 652 | 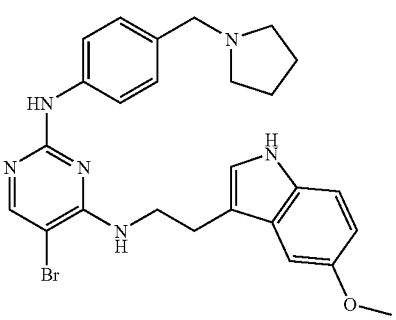 | 522 | 521.46 |
| 653 | 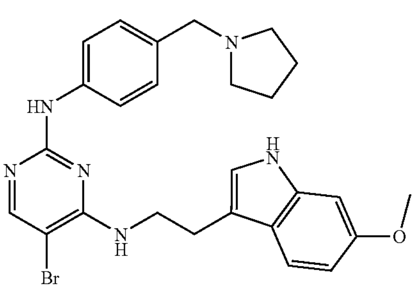 | 522 | 521.46 |

| Example | Structure | ESI-MS | Mol-Weight |
|---|---|---|---|
| 654 | 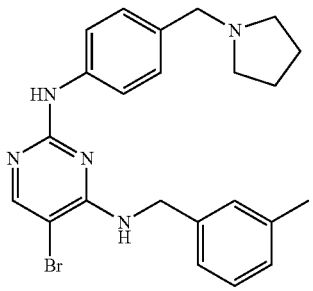 | 453 | 452.40 |
| 655 | 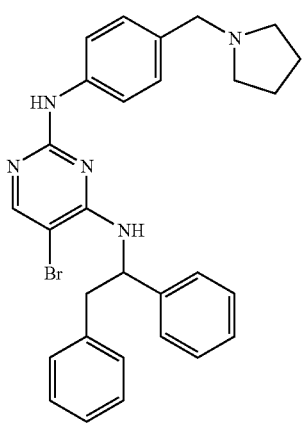 | 529 | 528.50 |
| 656 | 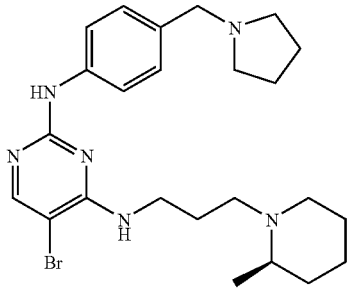 | 488 | 487.49 |
| 657 | 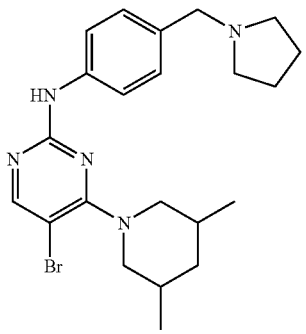 | 445 | 444.42 |

-continued
| Example | Structure | ESI-MS | Mol-Weight |
|---------|-----------|--------|------------|
| 658 | 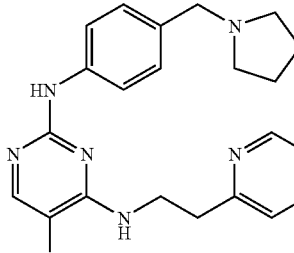 | 454 | 453.39 |
| 659 | 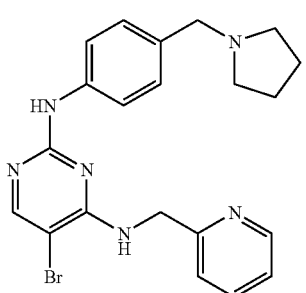 | 440 | 439.36 |
| 660 | 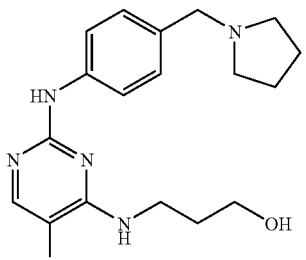 | 407 | 406.33 |
| 661 | 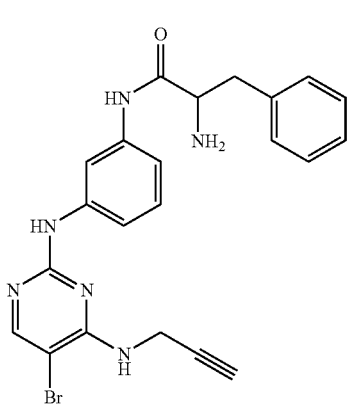 | 466 | 465.35 |

-continued

| Example | Structure | ESI-MS | Mol-Weight |
|---|---|---|---|
| 662 | 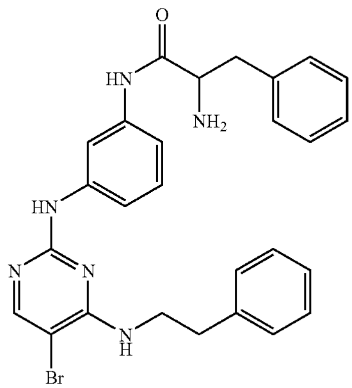 | 532 | 531.46 |
| 663 | 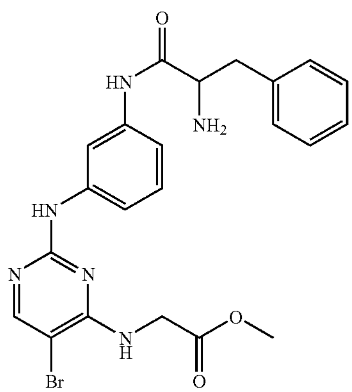 | 500 | 499.37 |
| 664 | 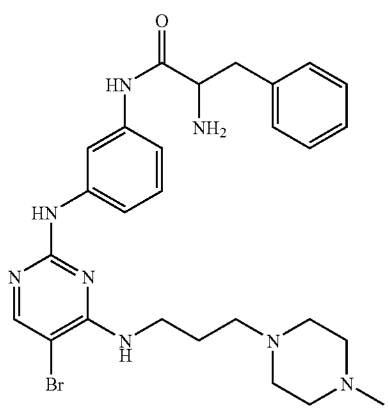 | 568 | 567.53 |
| 665 | 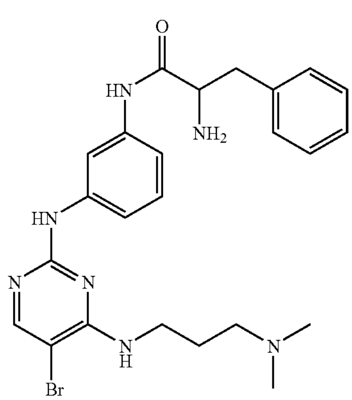 | 513 | 512.45 |

-continued

| Example | Structure | ESI-MS | Mol-Weight |
|---|---|---|---|
| 666 | 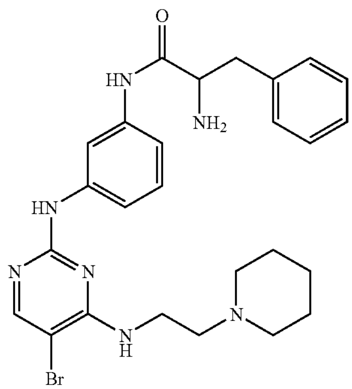 | 539 | 538.49 |
| 667 | 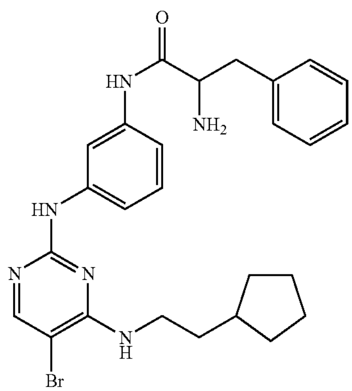 | 525 | 524.46 |
| 668 | 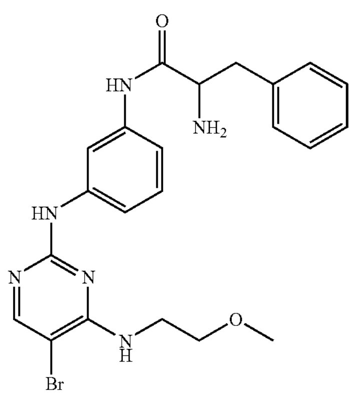 | 486 | 485.38 |
| 669 | 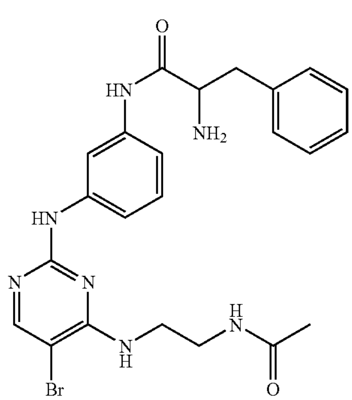 | 513 | 512.41 |

-continued

| Example | Structure | ESI-MS | Mol-Weight |
|---|---|---|---|
| 670 | 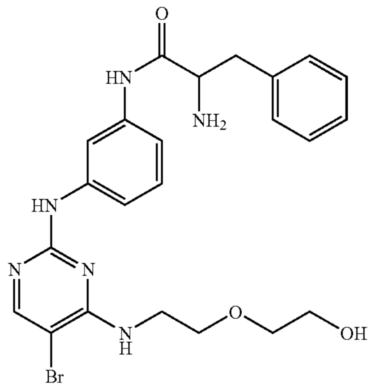 | 516 | 515.41 |
| 671 | 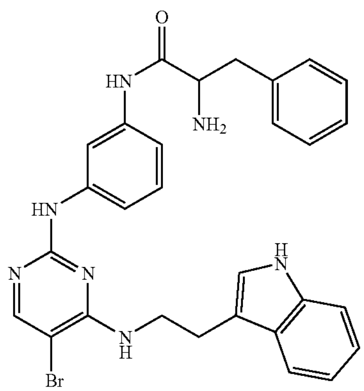 | 571 | 570.49 |
| 672 | 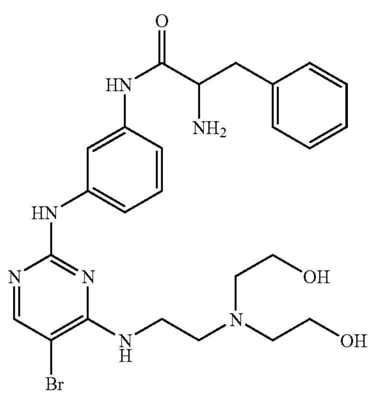 | 559 | 558.48 |
| 673 | 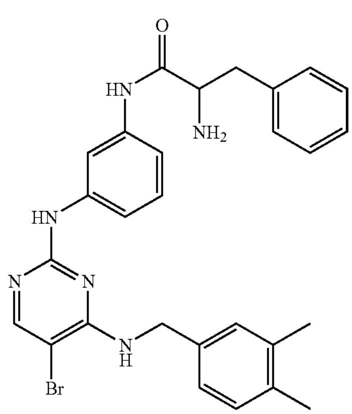 | 546 | 545.48 |

-continued

| Example | Structure | ESI-MS | Mol-Weight |
|---------|-----------|--------|------------|
| 674 | 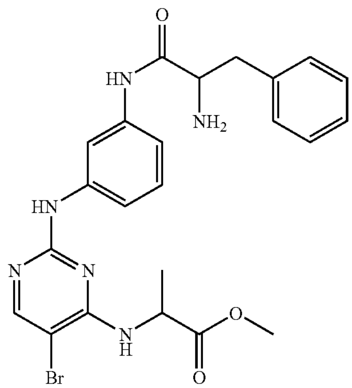 | 514 | 513.39 |
| 675 | 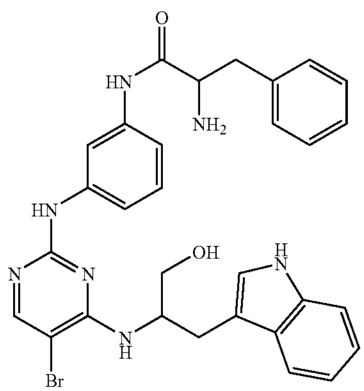 | 601 | 600.52 |
| 676 | 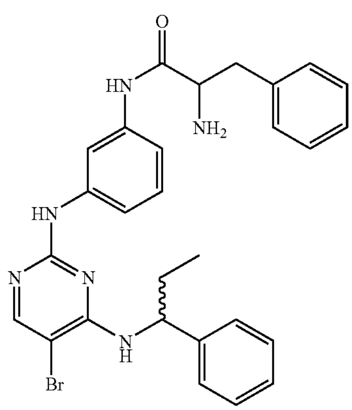 | 546 | 545.48 |
| 677 | 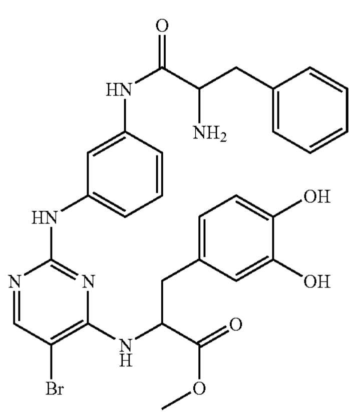 | 622 | 621.49 |

-continued
| Example | Structure | ESI-MS | Mol-Weight |
|---|---|---|---|
| 678 | 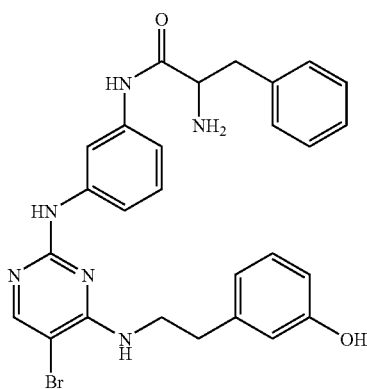 | 548 | 547.45 |
| 679 | 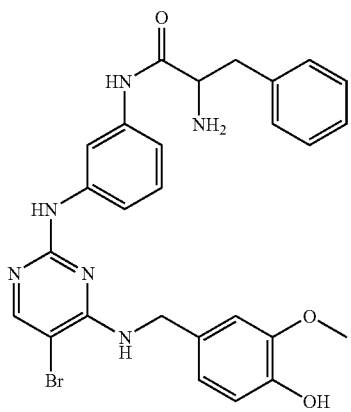 | 564 | 563.45 |
| 680 | 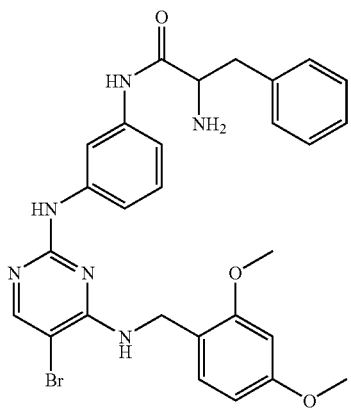 | 578 | 577.48 |

-continued

| Example | Structure | ESI-MS | Mol-Weight |
|---|---|---|---|
| 681 | 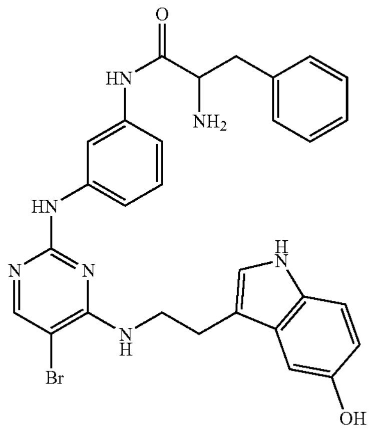 | 587 | 586.49 |
| 682 | 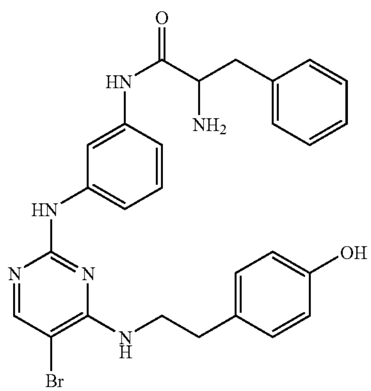 | 548 | 547.45 |
| 683 | 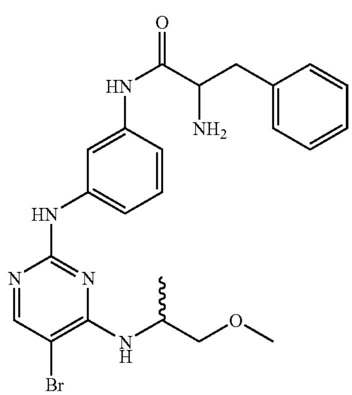 | 500 | 499.41 |
| 684 | 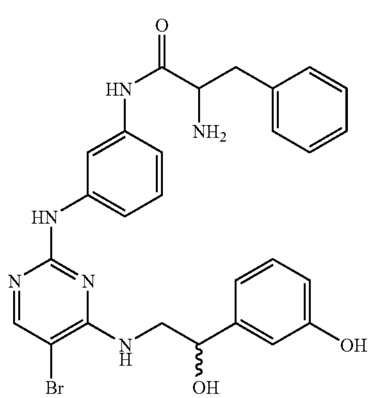 | 564 | 563.45 |

-continued
| Example | Structure | ESI-MS | Mol-Weight |
|---|---|---|---|
| 685 | 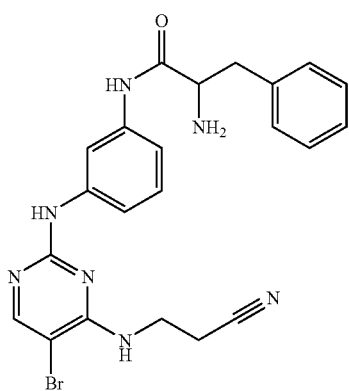 | 481 | 480.37 |
| 686 | 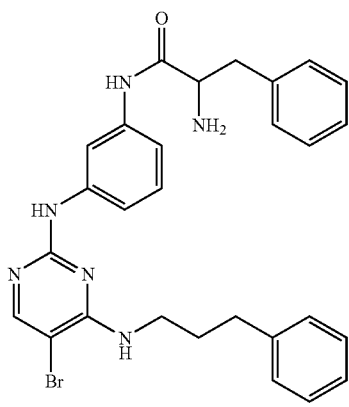 | 546 | 545.48 |
| 687 | 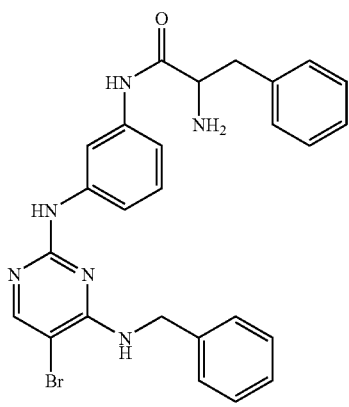 | 518 | 517.43 |

-continued

| Example | Structure | ESI-MS | Mol-Weight |
|---|---|---|---|
| 688 | 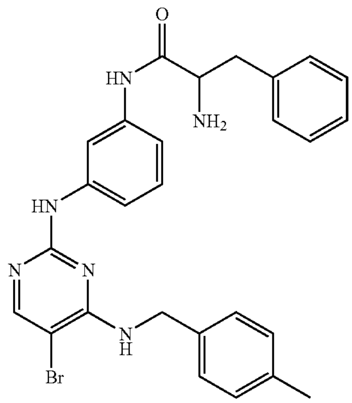 | 532 | 531.46 |
| 689 | 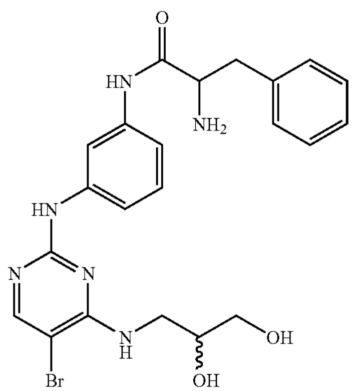 | 502 | 501.38 |
| 690 | 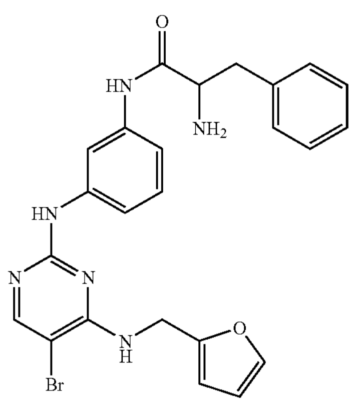 | 508 | 507.39 |
| 691 | 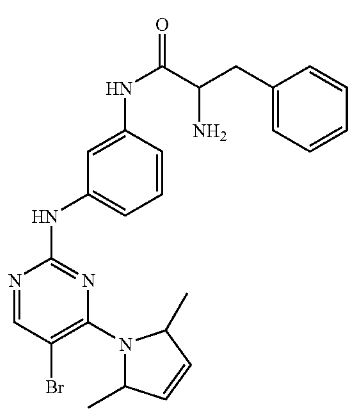 | 508 | 507.43 |

| Example | Structure | ESI-MS | Mol-Weight |
|---|---|---|---|
| 692 | 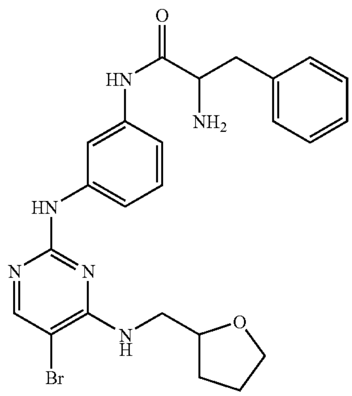 | 512 | 511.42 |
| 693 | 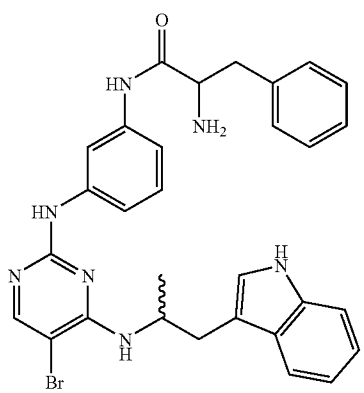 | 585 | 584.52 |
| 694 | 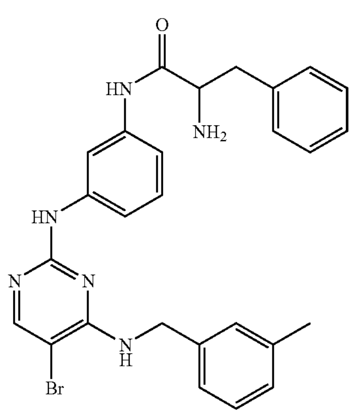 | 532 | 531.46 |

| Example | Structure | ESI-MS | Mol-Weight |
|---|---|---|---|
| 695 | 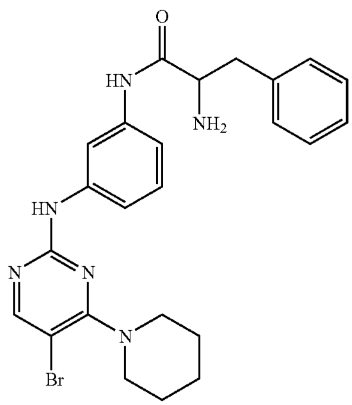 | 496 | 495.42 |
| 696 | 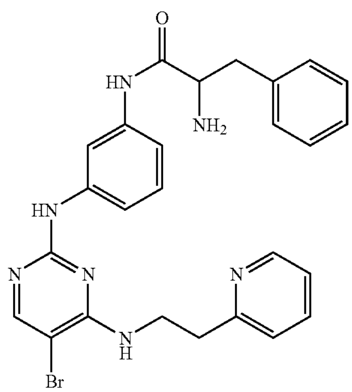 | 510 | 509.45 |
| 697 | 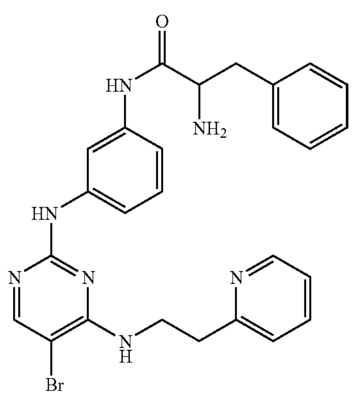 | 533 | 532.44 |
| 698 | 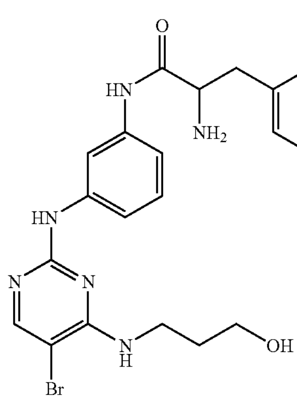 | 486 | 485.38 |

-continued

| Example | Structure | ESI-MS | Mol-Weight |
|---|---|---|---|
| 699 | 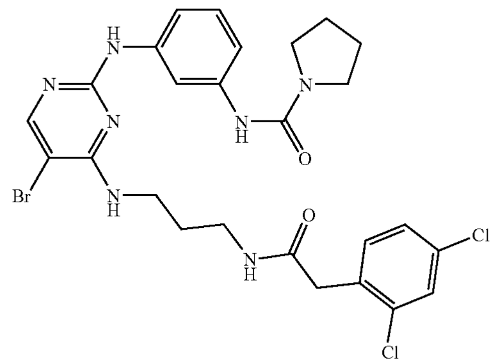 | 622 | 621.37 |
| 700 | 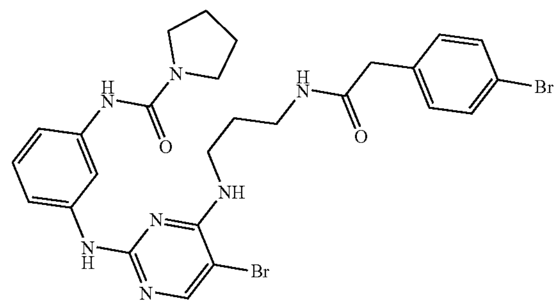 | 632 | 631.37 |
| 701 | 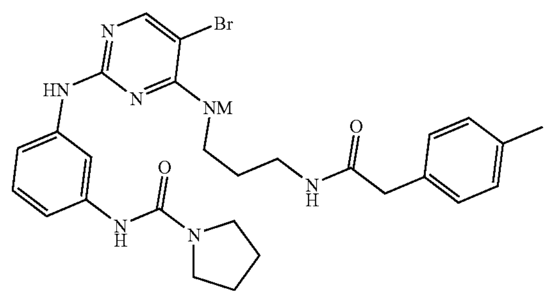 | 567 | 566.51 |
| 702 | 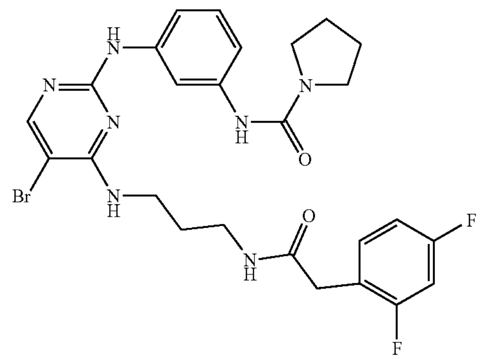 | 589 | 588.48 |

-continued

| Example | Structure | ESI-MS | Mol-Weight |
|---------|-----------|--------|------------|
| 703 | 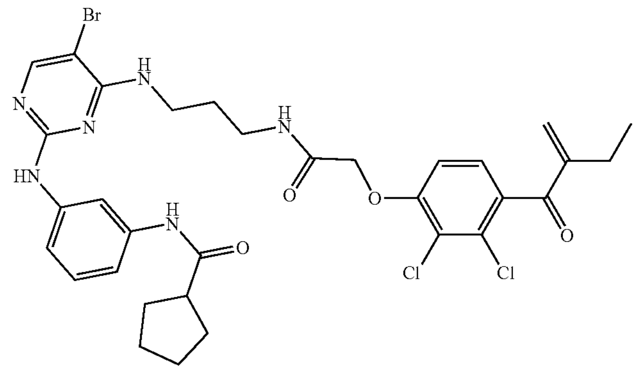 | 720 | 719.47 |
| 704 | 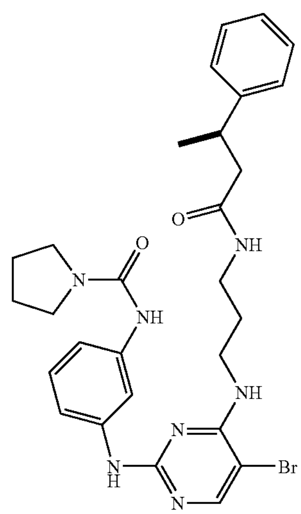 | 581 | 580.53 |
| 705 | 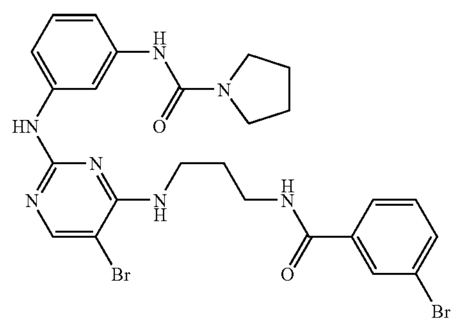 | 618 | 617.35 |
| 706 | 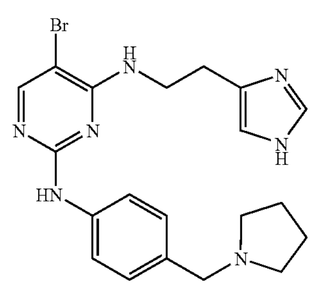 | 443 | |

-continued

| Example | Structure | ESI-MS | Mol-Weight |
|---|---|---|---|
| 707 | 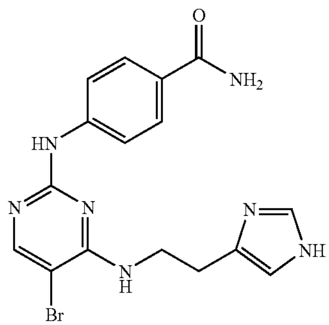 | 402 | |
| 708 | 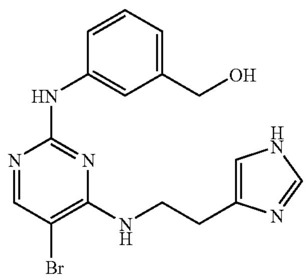 | 389 | |
| 709 | 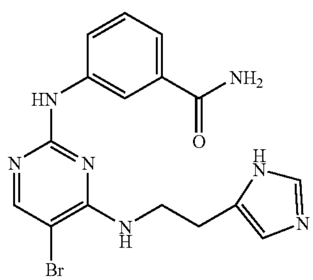 | 402 | |
| 710 | 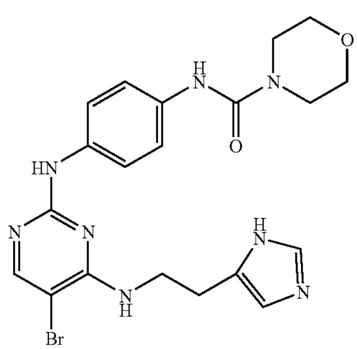 | 487 | |
| 711 | 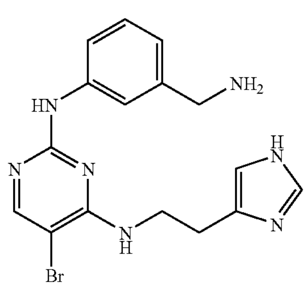 | 388 | |

-continued

| Example | Structure | ESI-MS | Mol-Weight |
|---|---|---|---|
| 712 | 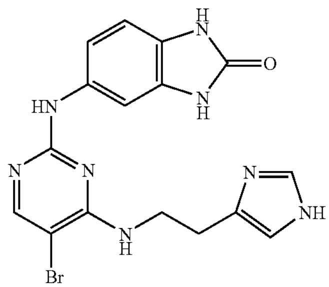 | 415 | |
| 713 | 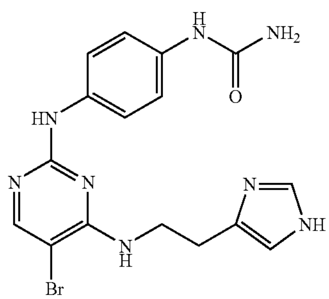 | 417 | |
| 714 | 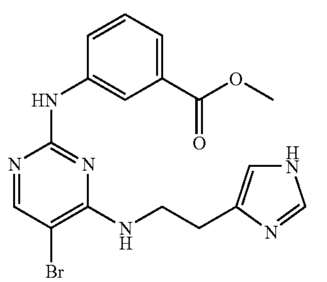 | 417 | |
| 715 | 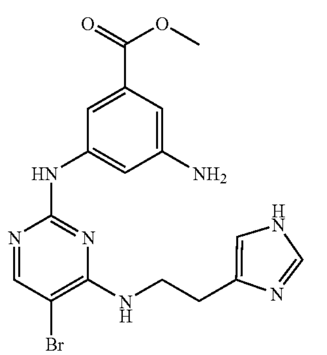 | 432 | |

-continued
| Example | Structure | ESI-MS | Mol-Weight |
|---|---|---|---|
| 716 | 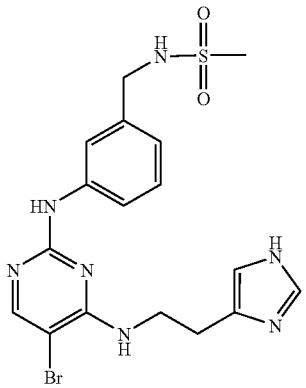 | 466 | |
| 717 | 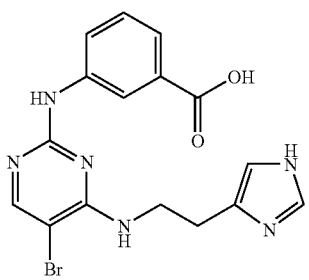 | 403 | |
| 718 | 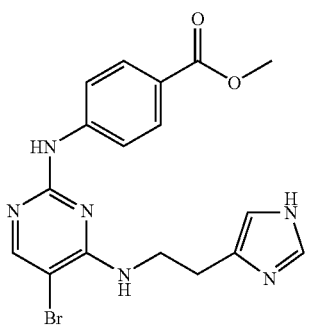 | 417 | |
| 719 | 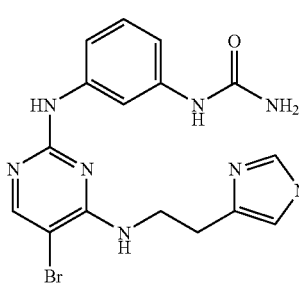 | 417 | |
| 720 | 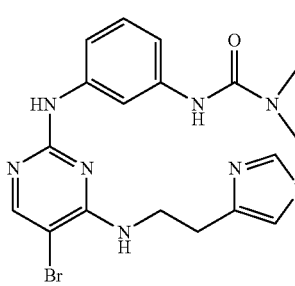 | 471 | |

-continued

| Example | Structure | ESI-MS | Mol-Weight |
|---|---|---|---|
| 721 | 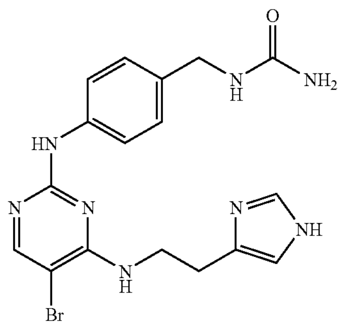 | 431 | |
| 722 | 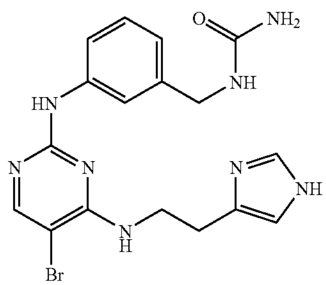 | 432 | |
| 723 | 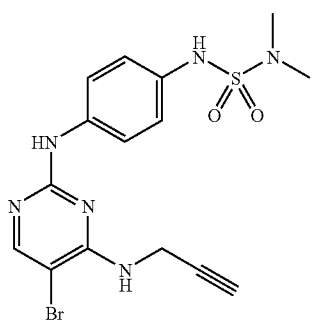 | 426 | |
| 724 | 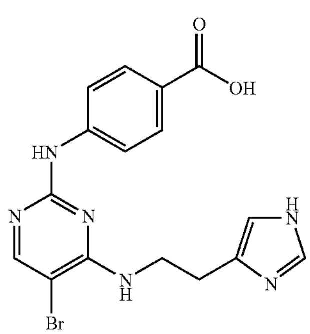 | 403 | |
| 725 | 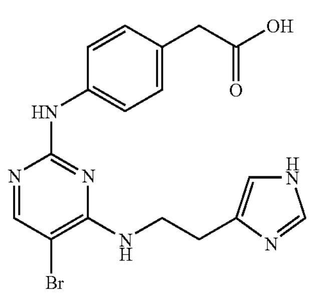 | 417 | |

-continued

| Example | Structure | ESI-MS | Mol-Weight |
|---------|-----------|--------|------------|
| 726 | 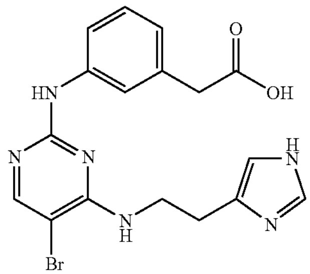 | | 417 |
| 727 | 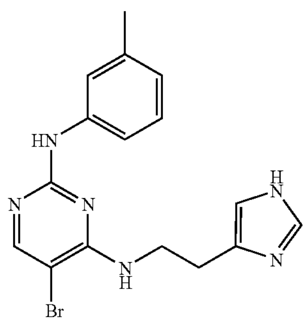 | | 373 |
| 728 | 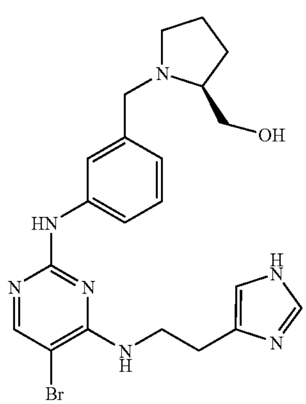 | | 471 |
| 729 | 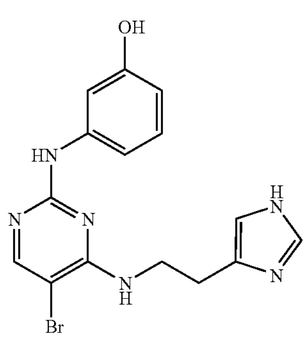 | | 374 |

-continued

| Example | Structure | ESI-MS | Mol-Weight |
|---|---|---|---|
| 730 | 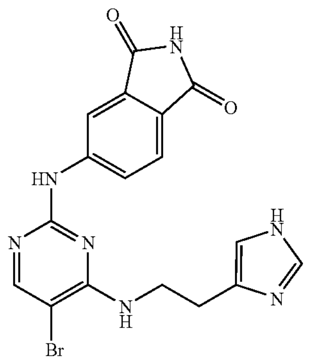 | | 458 |
| 731 | 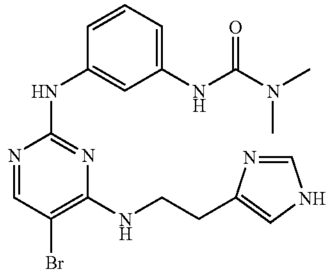 | | 428 |
| 732 | 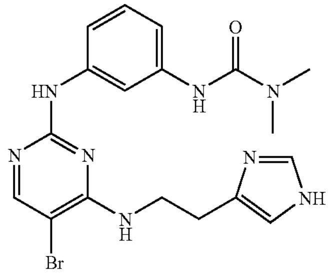 | | 445 |
| 733 | 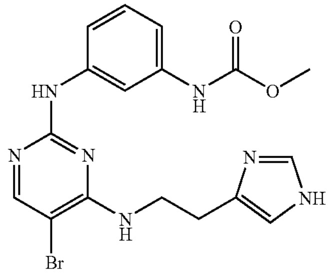 | | 432 |
| 734 | 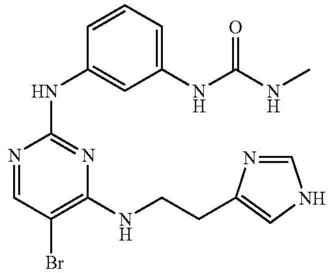 | | 431 |

-continued

| Example | Structure | ESI-MS | Mol-Weight |
|---------|-----------|--------|------------|
| 735 | 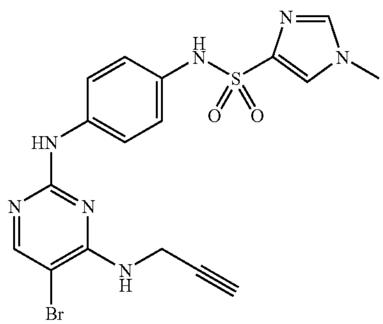 | 463 | |
| 736 | 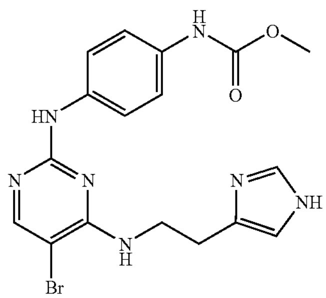 | 432 | |
| 737 | 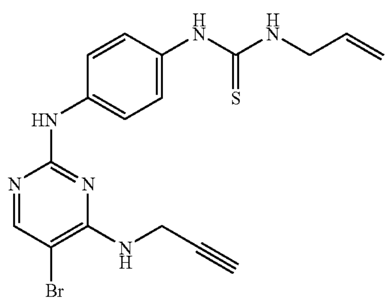 | 418 | |
| 738 | 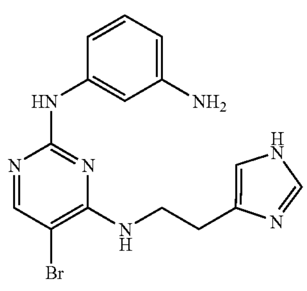 | 373 | |
| 739 | 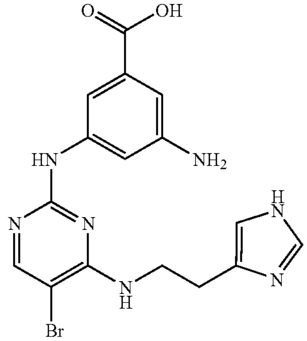 | 418 | |

| Example | Structure | ESI-MS | Mol-Weight |
|---------|-----------|--------|------------|
| 740 | 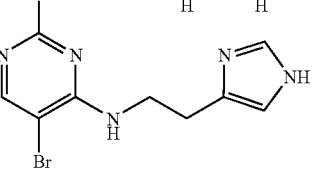 | 458 | |
| 741 | 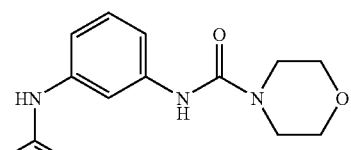 | 488 | |
| 742 | 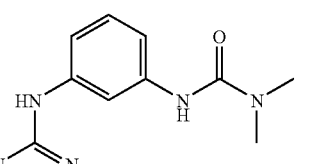 | 409 | |
| 743 | 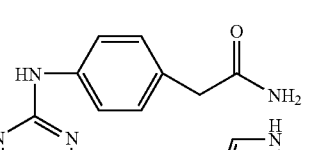 | 417 | |
| 744 | 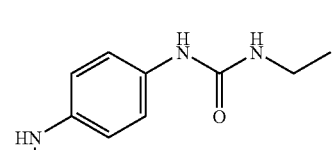 | 390 | |

-continued

| Example | Structure | ESI-MS | Mol-Weight |
|---|---|---|---|
| 745 | 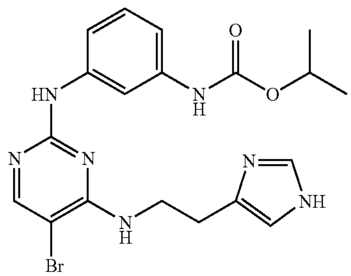 | | 459 |
| 746 | 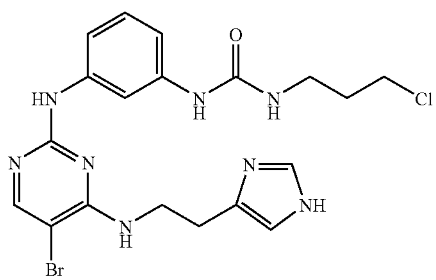 | | 459 |
| 747 | 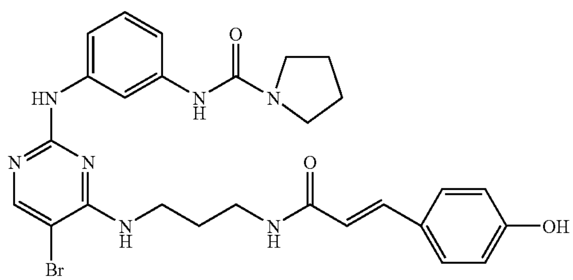 | | 581 |
| 748 | 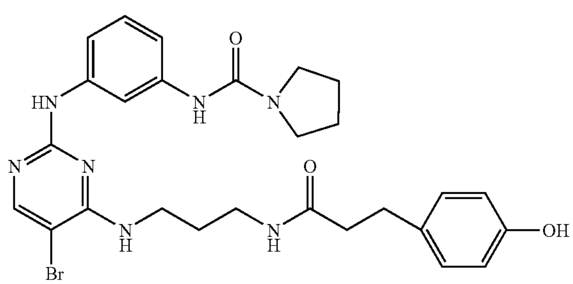 | | 583 |
| 749 | 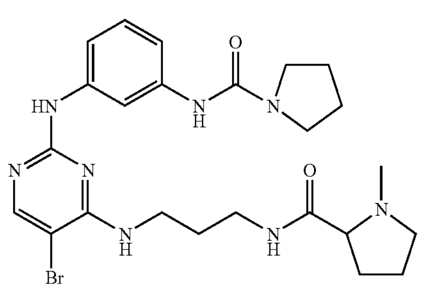 | | 543 |

-continued

| Example | Structure | ESI-MS | Mol-Weight |
|---|---|---|---|
| 750 | 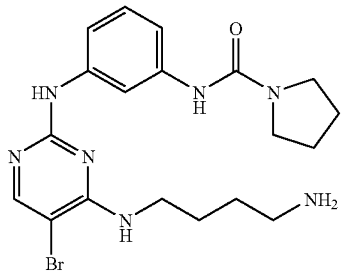 | 448 | |
| 751 | 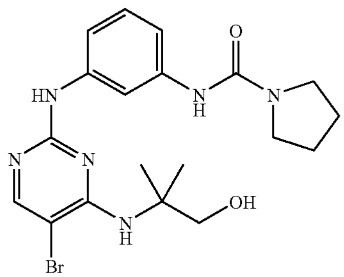 | 450 | |
| 752 | 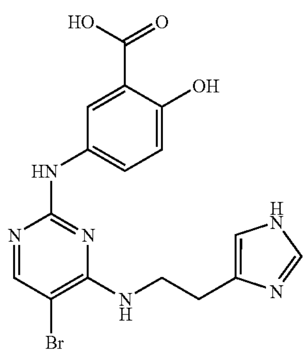 | 419 | |
| 753 | 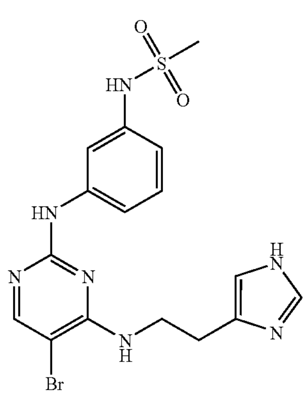 | 452 | |

-continued
| Example | Structure | ESI-MS | Mol-Weight |
|---|---|---|---|
| 754 | 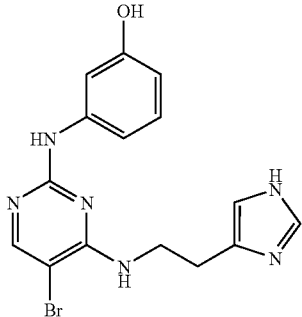 | 375 | |
| 755 | 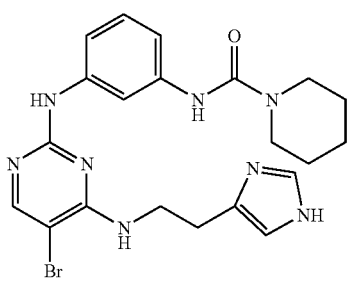 | 485 | |
| 756 | 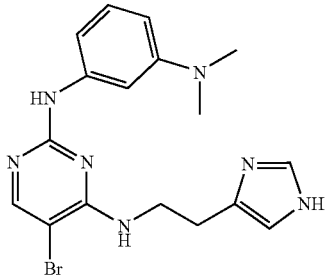 | 403 | |
| 757 | 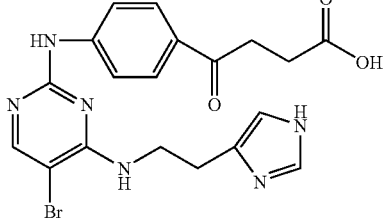 | 460 | |
| 758 | 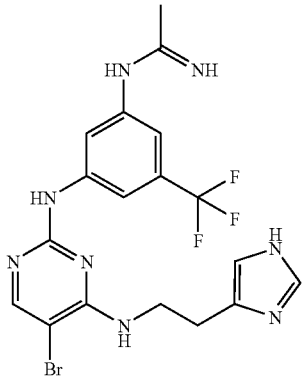 | 482 | |

-continued
| Example | Structure | ESI-MS | Mol-Weight |
|---|---|---|---|
| 759 | 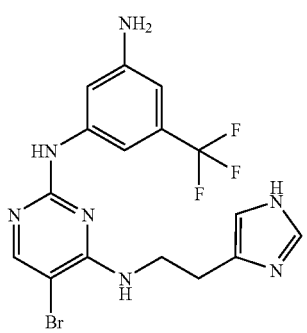 | 441 | |
| 760 | 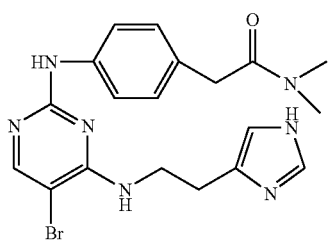 | 443 | |
| 761 | 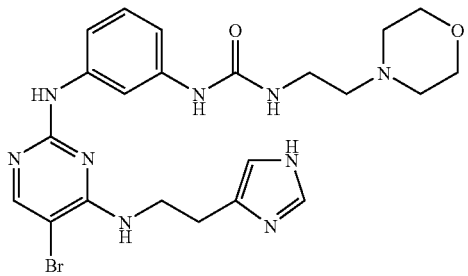 | 529 | |
| 762 | 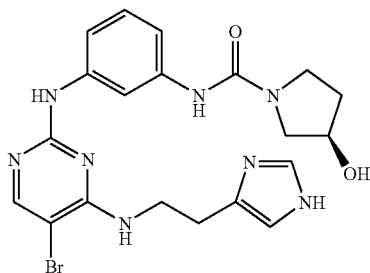 | 487 | |
| 763 | 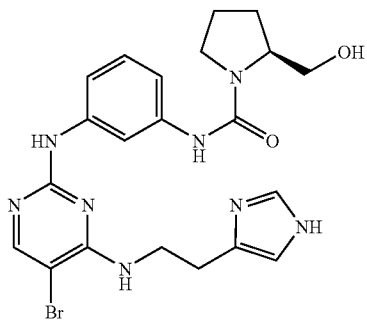 | 501 | |

-continued
| Example | Structure | ESI-MS | Mol-Weight |
|---|---|---|---|
| 764 | 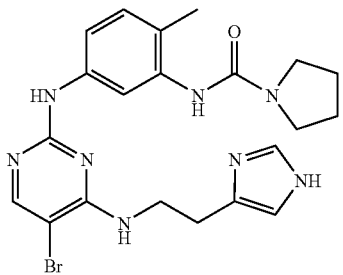 | | 485 |
| 765 | 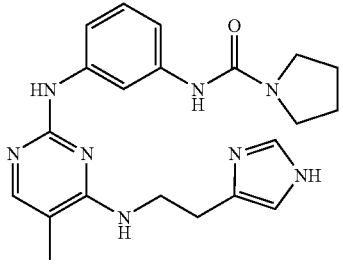 | | 406 |
| 766 | 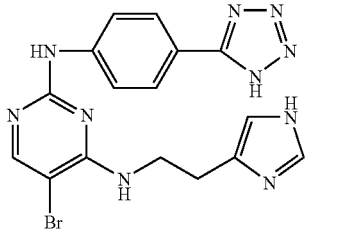 | | 427 |
| 767 | 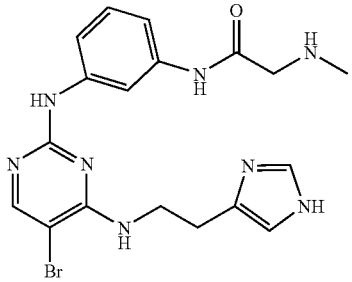 | | 446 |
| 768 | 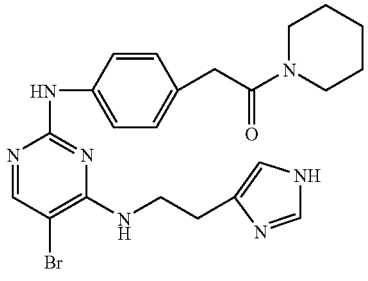 | | 483 |

-continued

| Example | Structure | ESI-MS | Mol-Weight |
|---------|-----------|--------|------------|
| 769 | 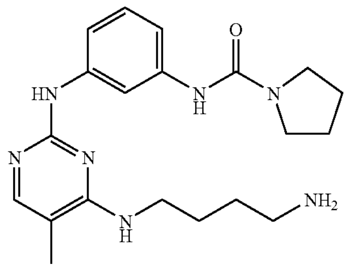 | 383 | |
| 770 | 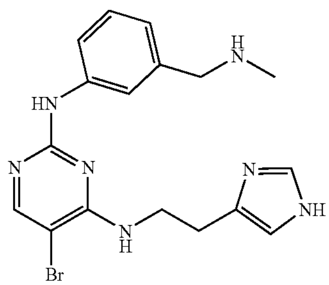 | 403 | |
| 771 | 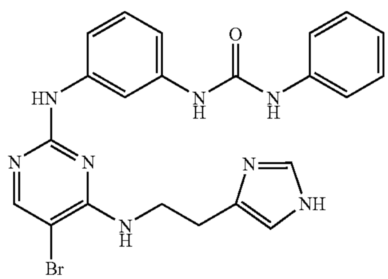 | 493 | |
| 772 | 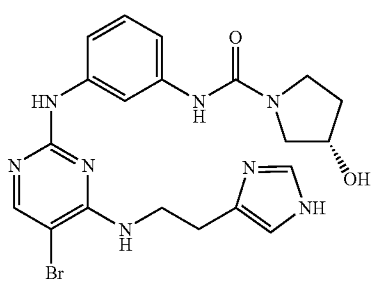 | 487 | |
| 773 | 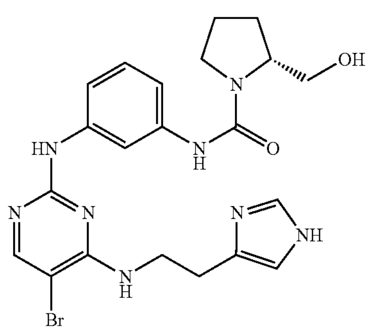 | 501 | |

| Example | Structure | ESI-MS | Mol-Weight |
|---|---|---|---|
| 774 | 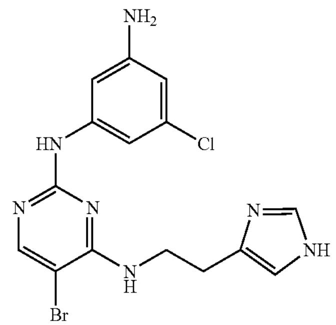 | 407 | |
| 775 | 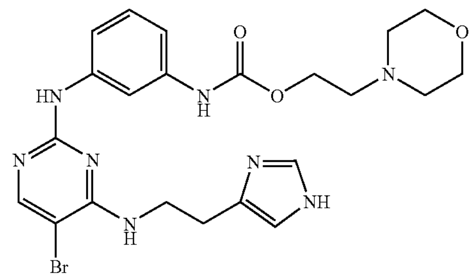 | 530 | |
| 776 | 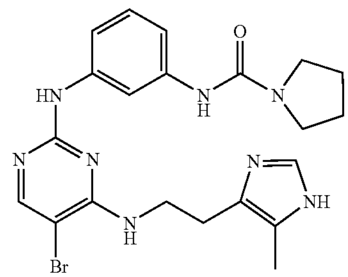 | 486 | |
| 777 | 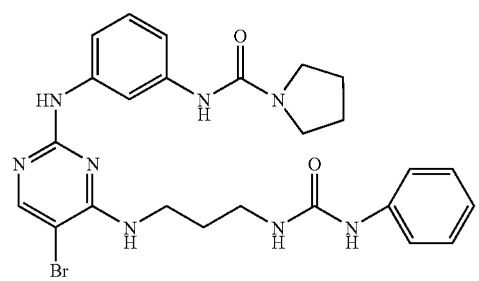 | 552 | |
| 778 | 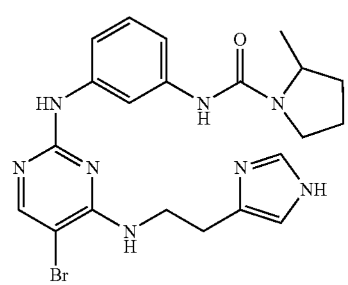 | 485 | |

-continued
| Example | Structure | ESI-MS | Mol-Weight |
|---|---|---|---|
| 779 | 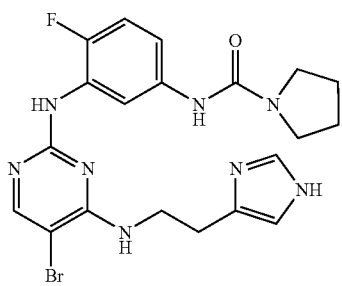 | 489 | |
| 780 | 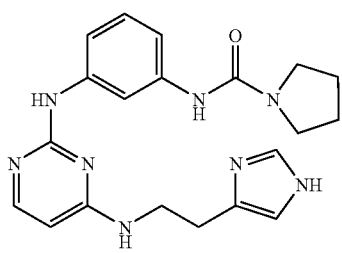 | 392 | |
| 781 | 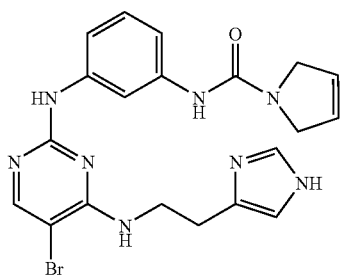 | 469 | |
| 782 | 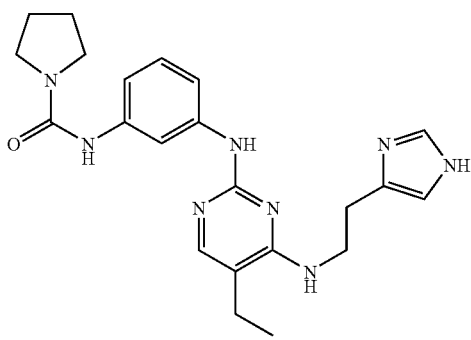 | 421 | |
| 783 | 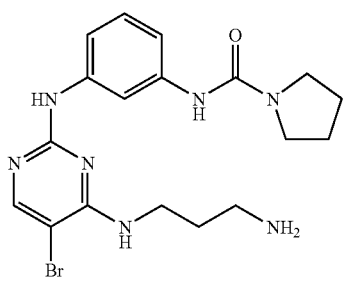 | 433 | |

-continued

| Example | Structure | ESI-MS | Mol-Weight |
|---|---|---|---|
| 784 | 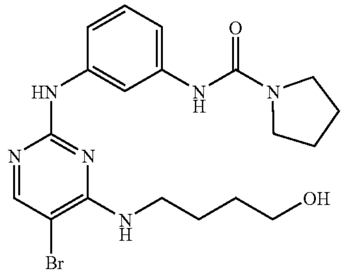 | 449 | |
| 785 | 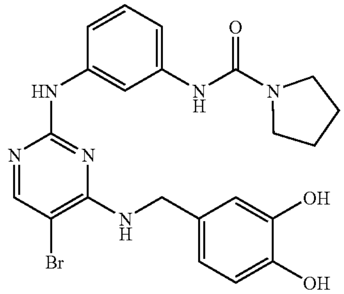 | 499 | |
| 786 | 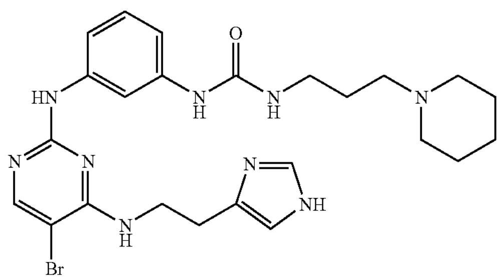 | 541 | |
| 787 | 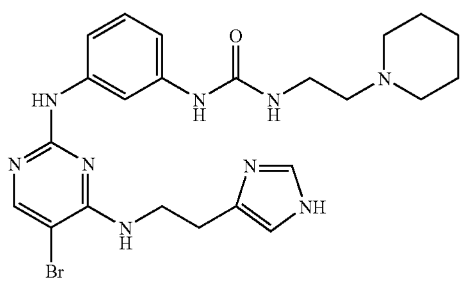 | 527 | |
| 788 | 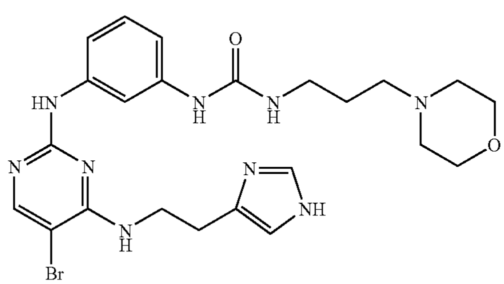 | 544 | |

-continued

| Example | Structure | ESI-MS | Mol-Weight |
|---|---|---|---|
| 789 | 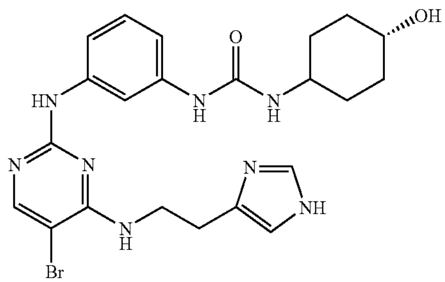 | 514 | |
| 790 | 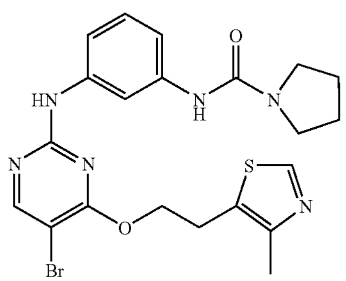 | 504 | |
| 791 | 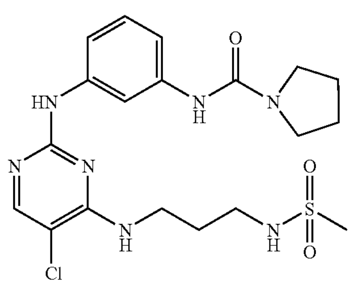 | 467 | |
| 792 | 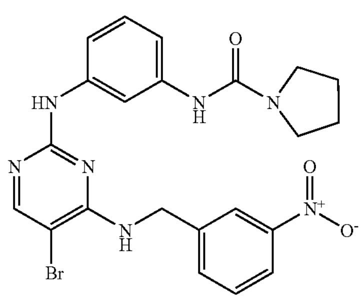 | 512 | |
| 793 | 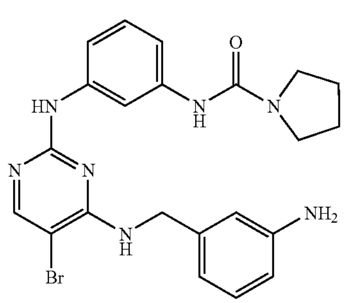 | 482 | |

| Example | Structure | ESI-MS | Mol-Weight |
|---|---|---|---|
| 794 | 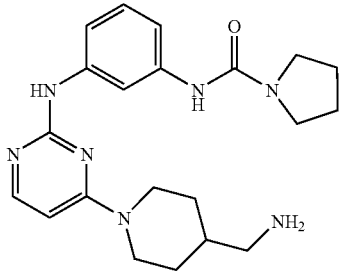 | 395 | |
| 795 | 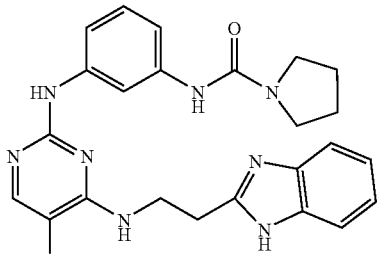 | 521 | |
| 796 | 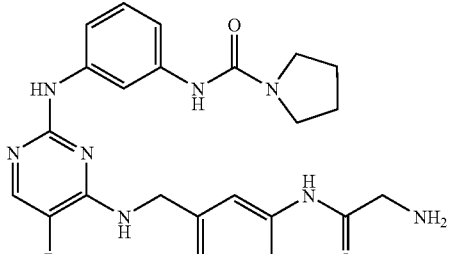 | 540 | |
| 797 | 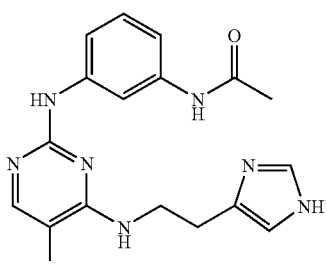 | 415 | |
| 798 | 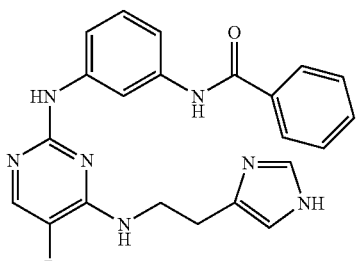 | 477 | |

-continued

| Example | Structure | ESI-MS | Mol-Weight |
|---|---|---|---|
| 799 | 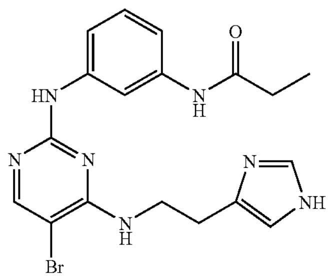 | 429 | |
| 800 | 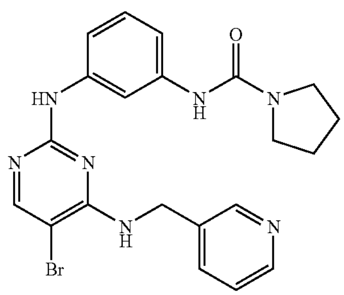 | 467 | |
| 801 | 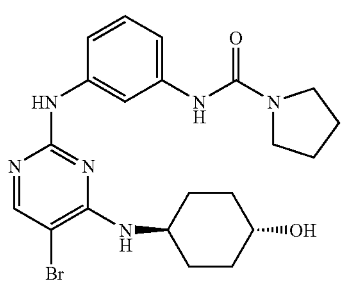 | 474 | |
| 802 | 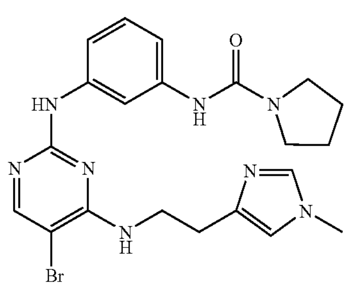 | 485 | |
| 803 | 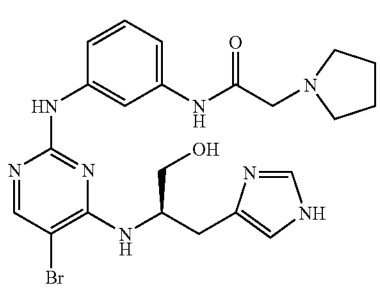 | 501 | |

-continued

| Example | Structure | ESI-MS | Mol-Weight |
|---|---|---|---|
| 804 | 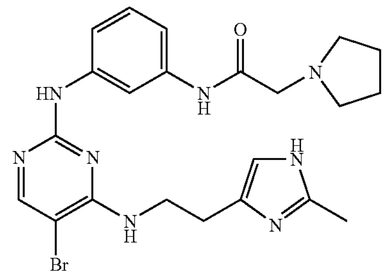 | 486 | |
| 805 | 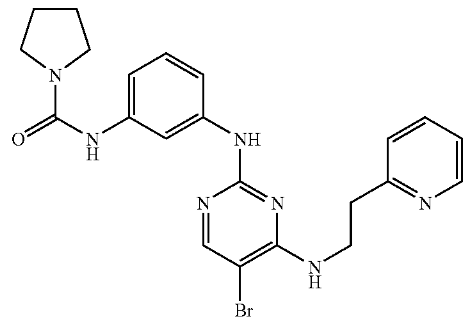 | 483 | |
| 806 | 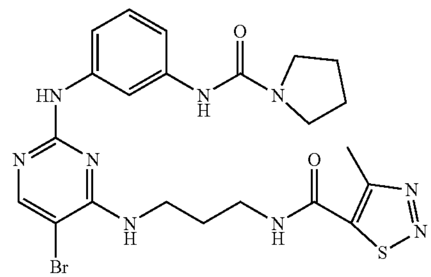 | 561 | |
| 807 | 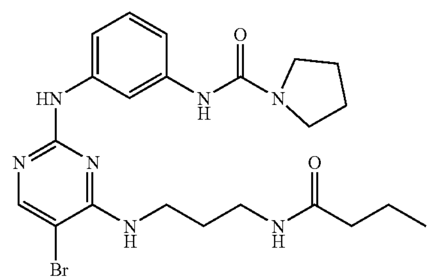 | 505 | |
| 808 | 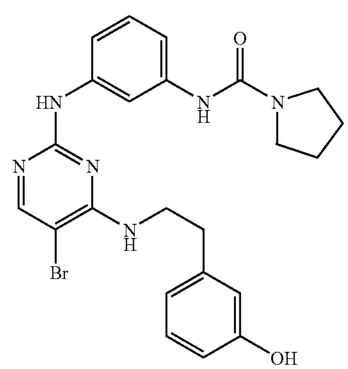 | 498 | |

| Example | Structure | ESI-MS | Mol-Weight |
|---|---|---|---|
| 809 | 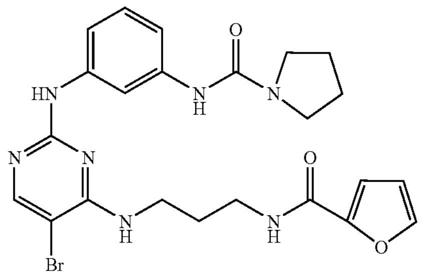 | 529 | |
| 810 | 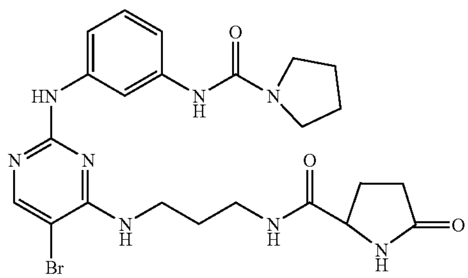 | 546 | |
| 811 | 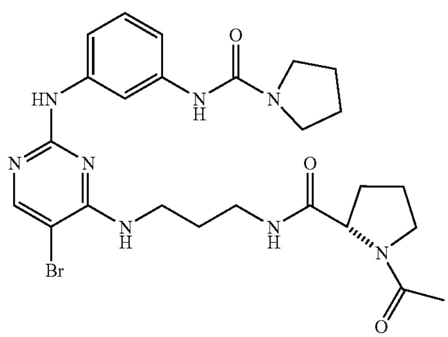 | 574 | |
| 812 | 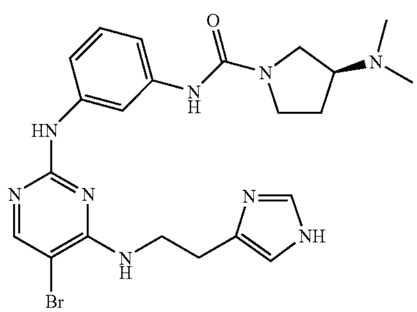 | 515 | |
| 813 | 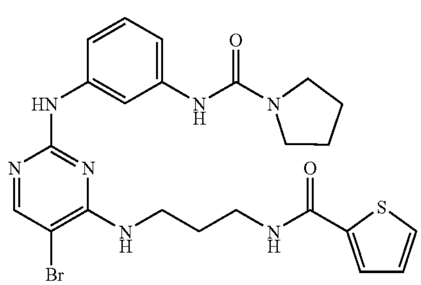 | 544 | |

-continued

| Example | Structure | ESI-MS | Mol-Weight |
|---|---|---|---|
| 814 | 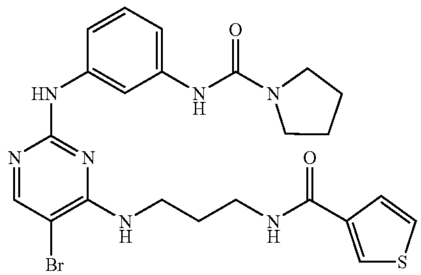 | 544 | |
| 815 | 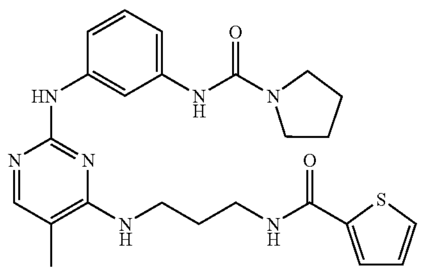 | 479 | |
| 816 | 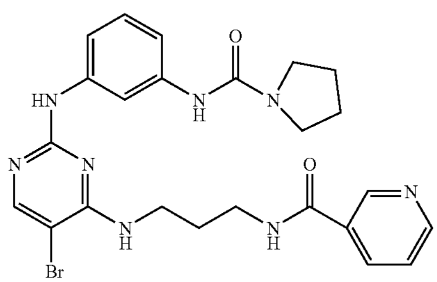 | 538 | |
| 817 | 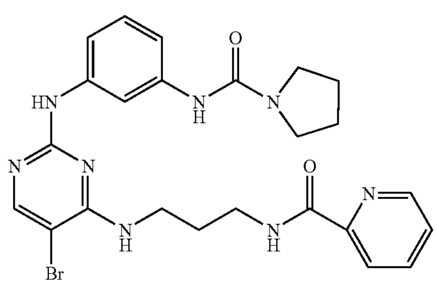 | 538 | |
| 818 | 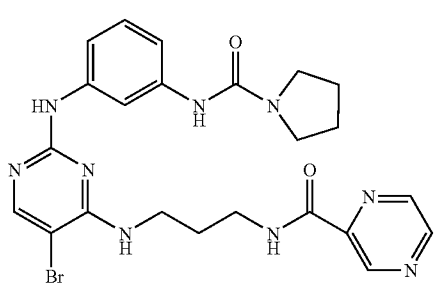 | 539 | |

-continued

| Example | Structure | ESI-MS | Mol-Weight |
|---|---|---|---|
| 819 | 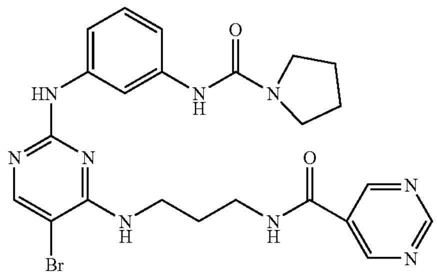 | 539 | |
| 820 | 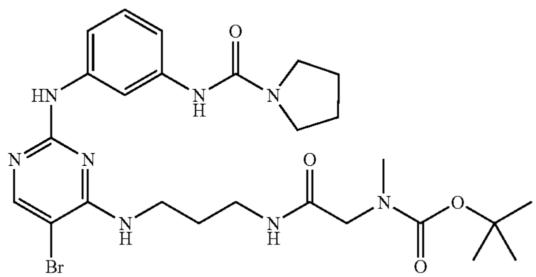 | 604 | |
| 821 | 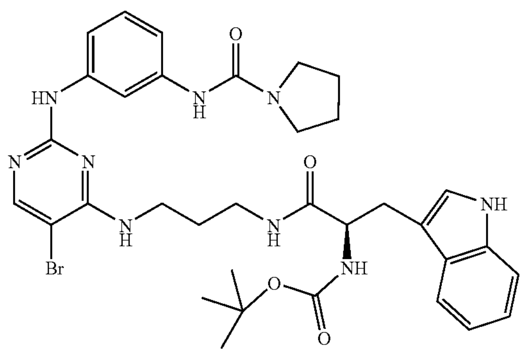 | 719 | |
| 822 | 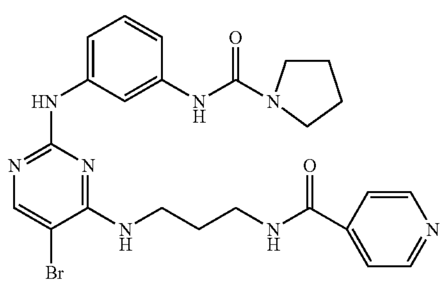 | 538 | |
| 823 | 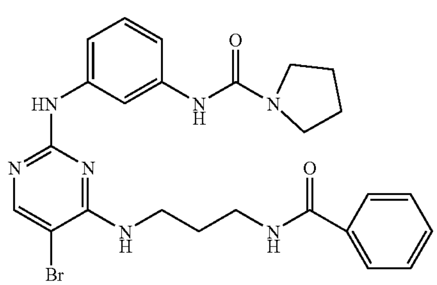 | 537 | |

-continued

| Example | Structure | ESI-MS | Mol-Weight |
|---|---|---|---|
| 824 | 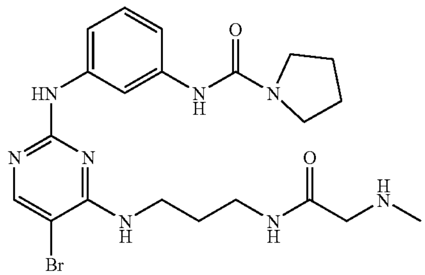 | 504 | |
| 825 | 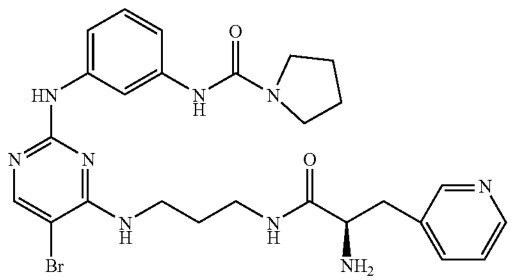 | 581 | |
| 826 | 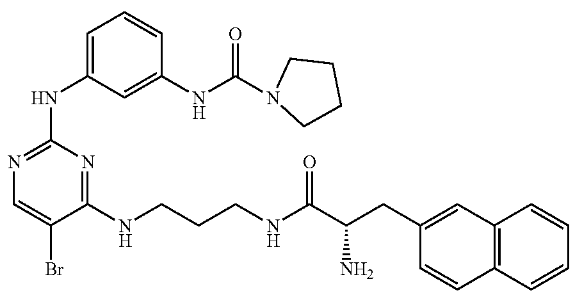 | 630 | |
| 827 | 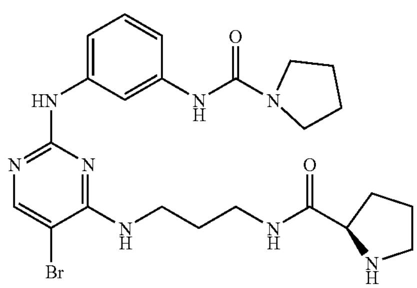 | 530 | |
| 828 | 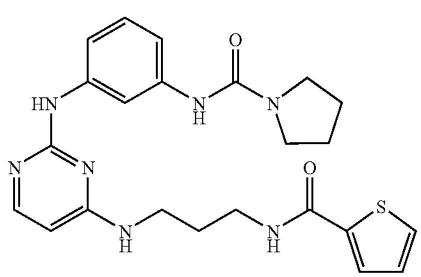 | 465 | |

-continued

| Example | Structure | ESI-MS | Mol-Weight |
|---|---|---|---|
| 829 | 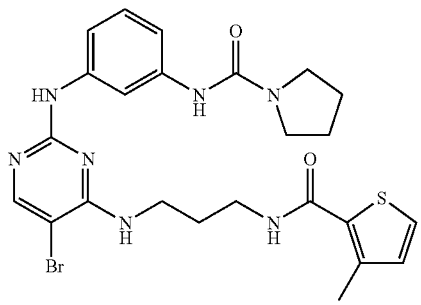 | 557 | |
| 830 | 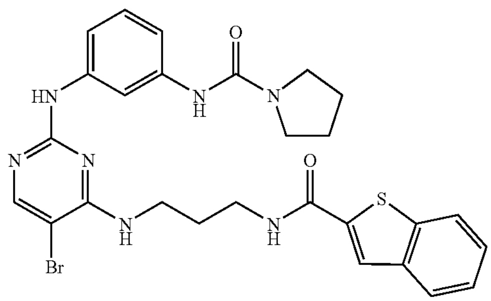 | 593 | |
| 831 | 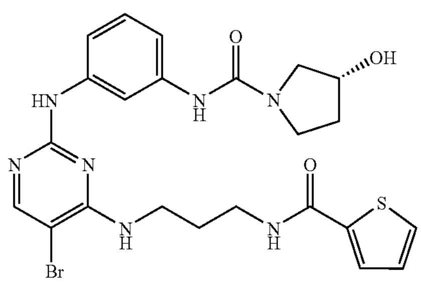 | 560 | |
| 832 | 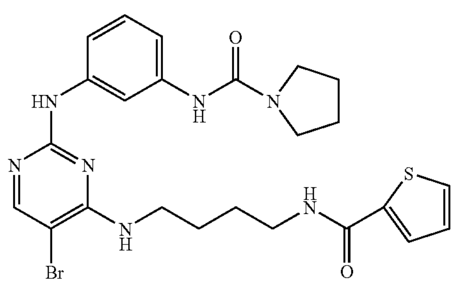 | 557 | |
| 833 | 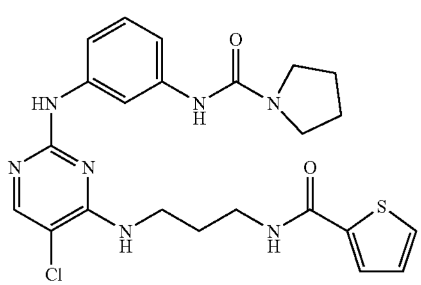 | 500 | |

-continued

| Example | Structure | ESI-MS | Mol-Weight |
|---|---|---|---|
| 834 | 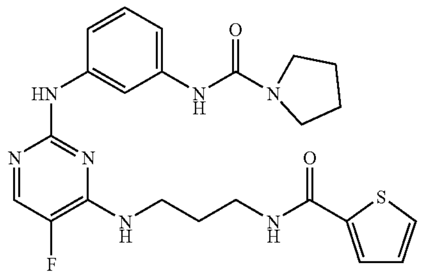 | 483 | |
| 835 | 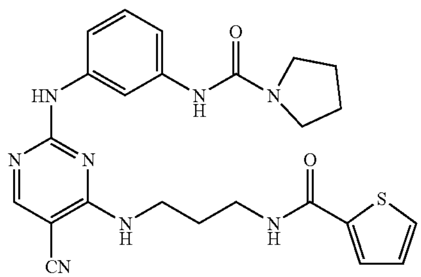 | 490 | |
| 836 | 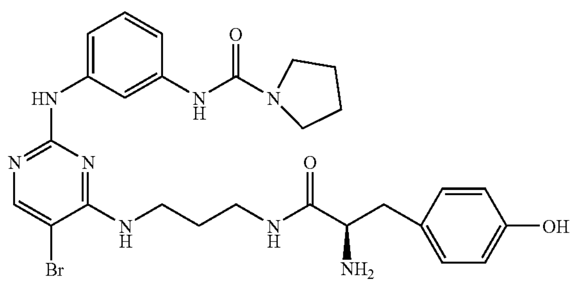 | 596 | |
| 837 | 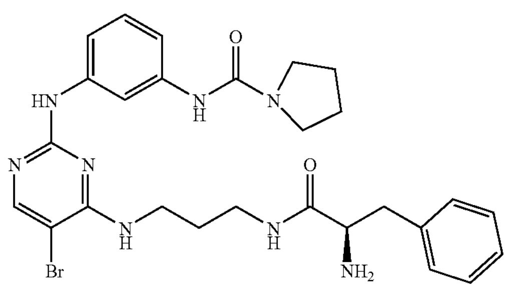 | 580 | |
| 838 | 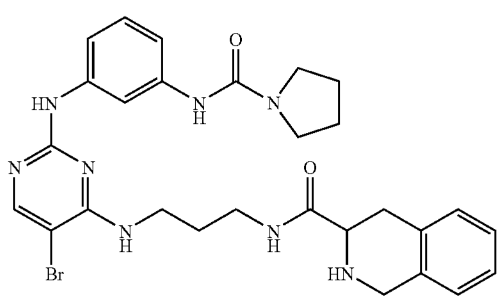 | 592 | |

| Example | Structure | ESI-MS | Mol-Weight |
|---|---|---|---|
| 839 | 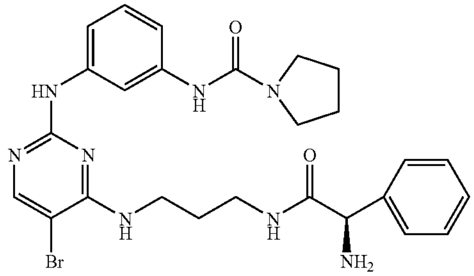 | 566 | |
| 840 | 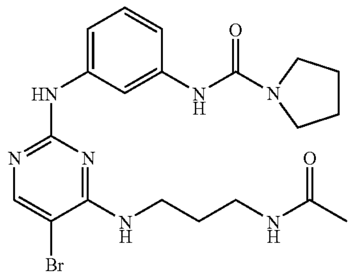 | 475 | |
| 841 | 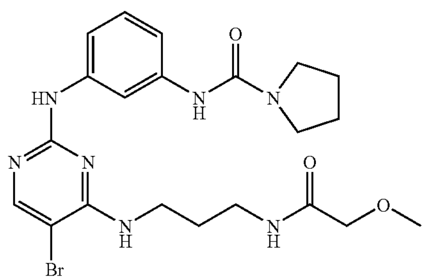 | 505 | |
| 842 | 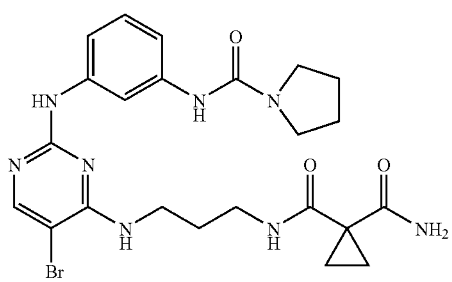 | 544 | |
| 843 | 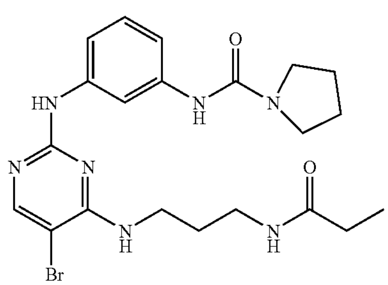 | 489 | |

-continued

| Example | Structure | ESI-MS | Mol-Weight |
|---|---|---|---|
| 844 | 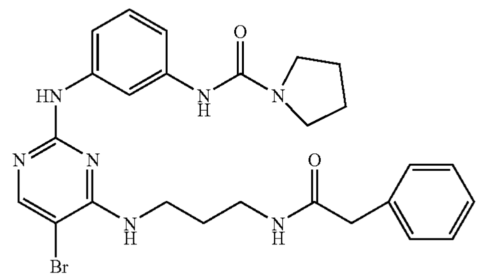 | 551 | |
| 845 | 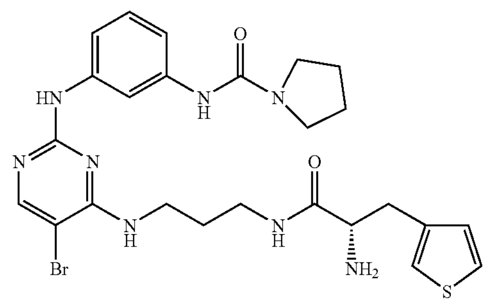 | 586 | |
| 846 | 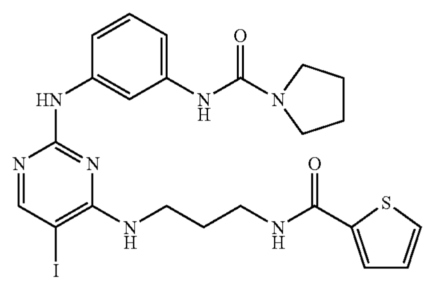 | 591 | |
| 847 | 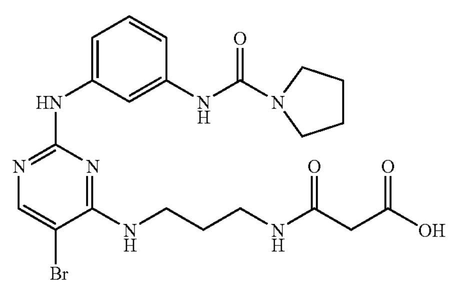 | 519 | |
| 848 | 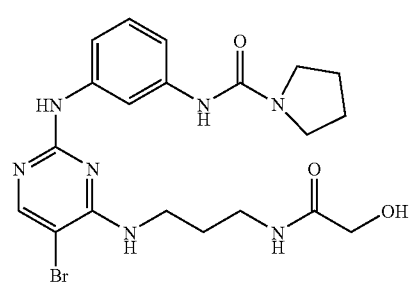 | 491 | |

-continued

| Example | Structure | ESI-MS | Mol-Weight |
|---|---|---|---|
| 849 | 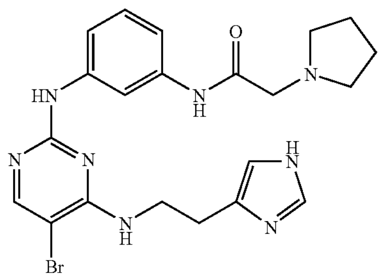 | 484 | |
| 850 | 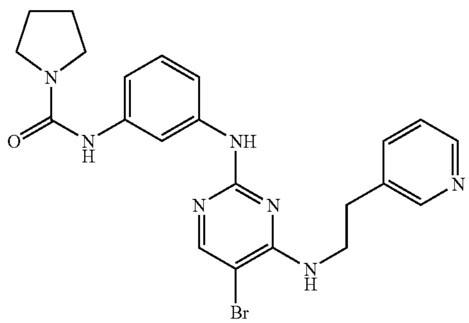 | 482 | |
| 851 | 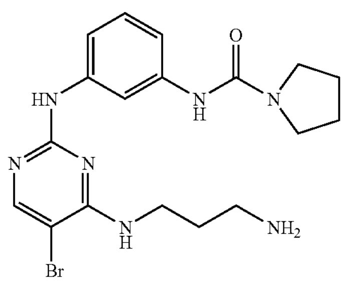 | 433 | |
| 852 | 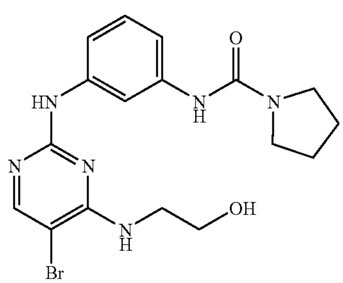 | 420 | |
| 853 | 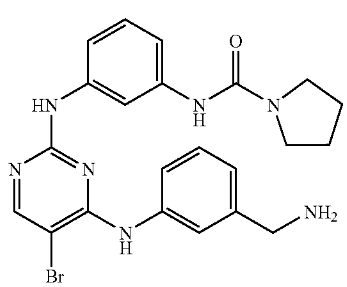 | 482 | |

-continued

| Example | Structure | ESI-MS | Mol-Weight |
|---------|-----------|--------|------------|
| 854 | 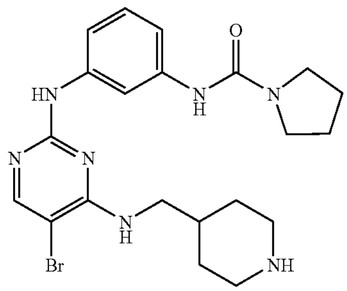 | 474 | |
| 855 | 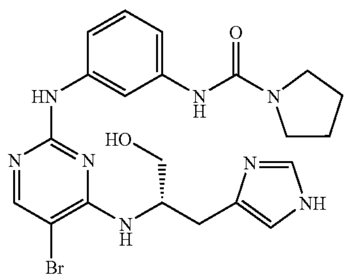 | 501 | |
| 856 | 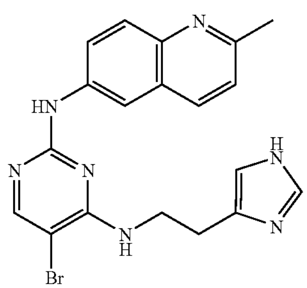 | 425 | |
| 857 | 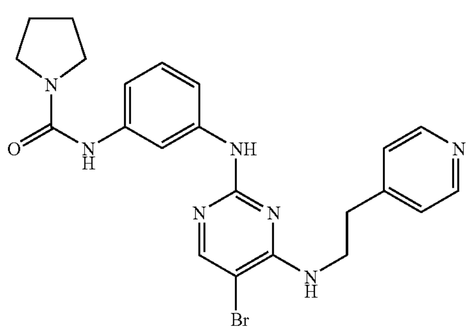 | 482 | |
| 858 | 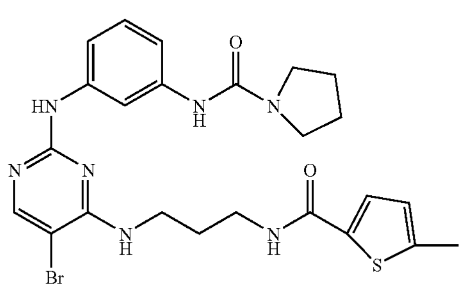 | 557 | |

-continued
| Example | Structure | ESI-MS | Mol-Weight |
|---|---|---|---|
| 859 | 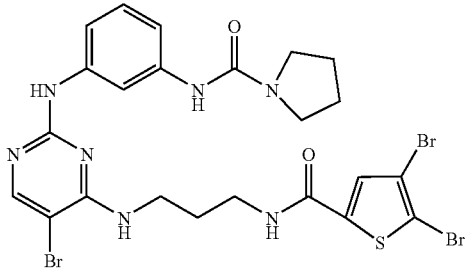 | | 699 |
| 860 | 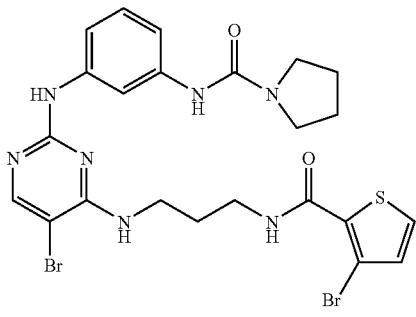 | | 621 |
| 861 | 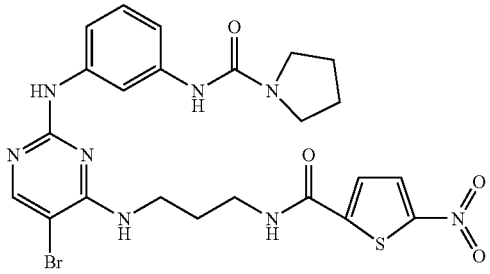 | | 588 |
| 862 | 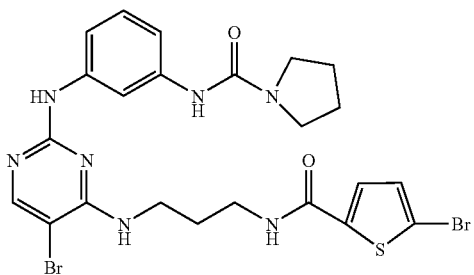 | | 621 |
| 863 | 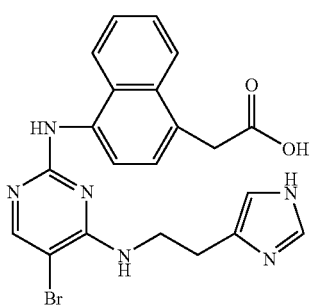 | | 468 |

-continued

| Example | Structure | ESI-MS | Mol-Weight |
|---|---|---|---|
| 864 | 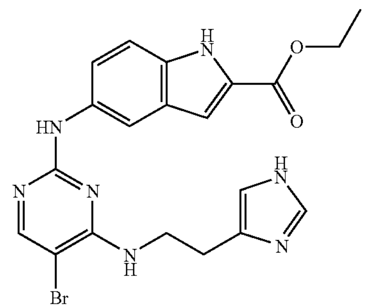 | 471 | |
| 865 | 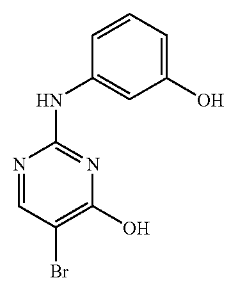 | 283 | |
| 866 | 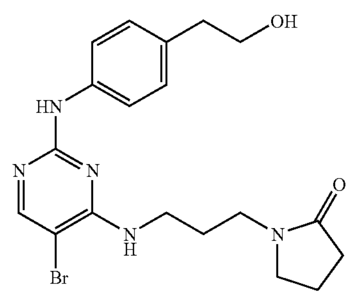 | 435 | |
| 867 | 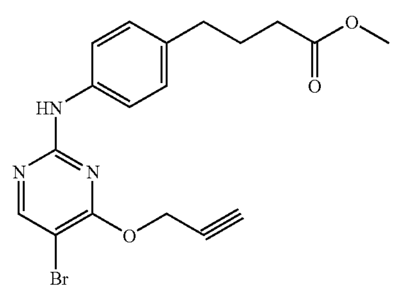 | 405 | |
| 868 | 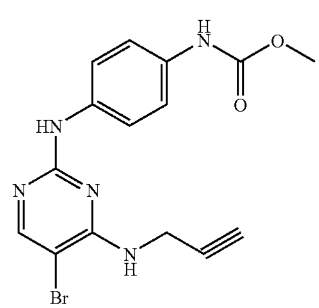 | 377 | |

-continued

| Example | Structure | ESI-MS | Mol-Weight |
|---|---|---|---|
| 869 | 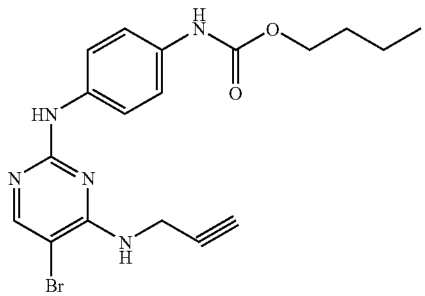 | 419 | |
| 870 | 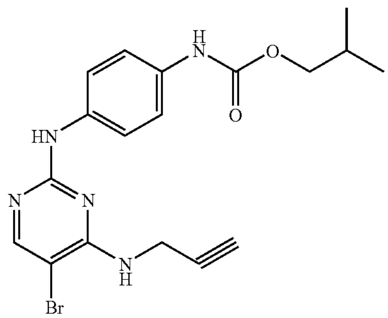 | 419 | |
| 871 | 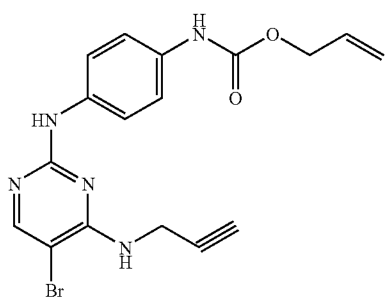 | 403 | |
| 872 | 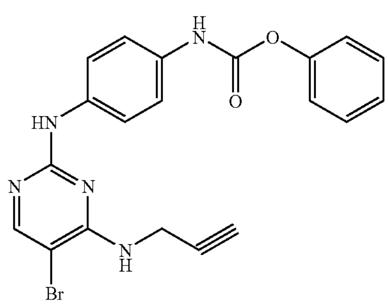 | 439 | |
| 873 | 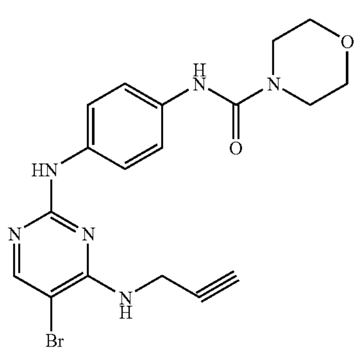 | 433 | |

| Example | Structure | ESI-MS | Mol-Weight |
|---|---|---|---|
| 874 | 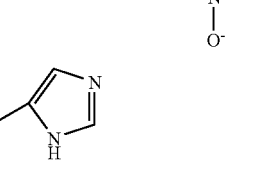 | 539 | |
| 875 | 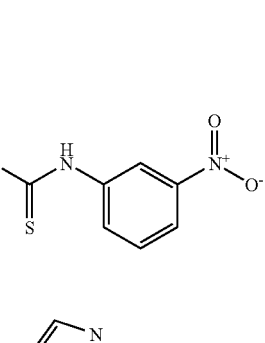 | 555 | |
| 876 | 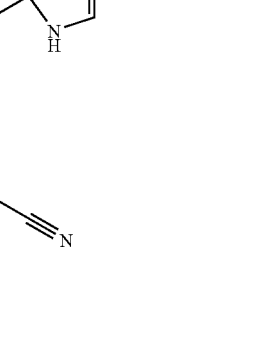 | 398 | |
| 877 | 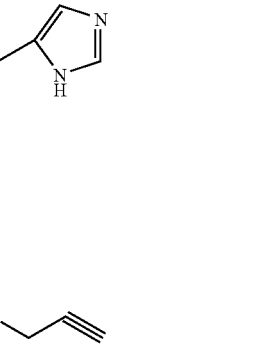 | 342 | |

-continued

| Example | Structure | ESI-MS | Mol-Weight |
|---|---|---|---|
| 878 | 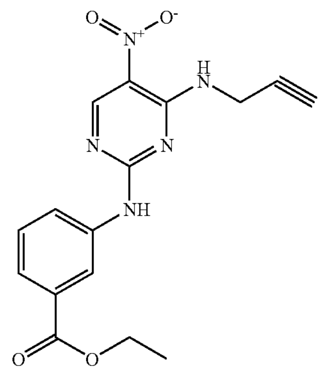 | 342 | |
| 879 | 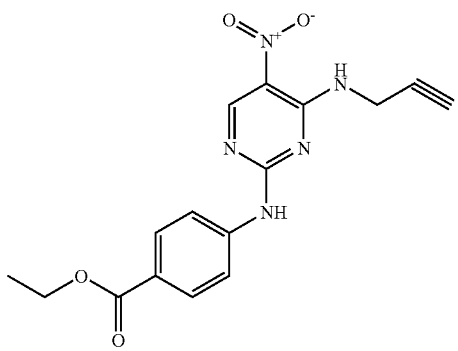 | 342 | |
| 880 | 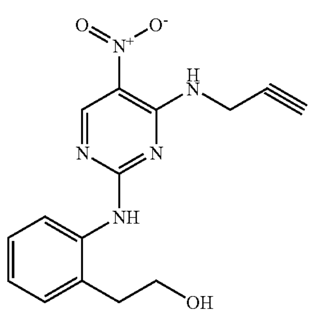 | 314 | |
| 881 | 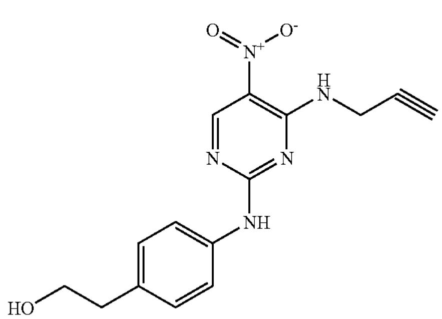 | 314 | |

Without further elaboration, it is believed that one skilled in the art can, using the preceding description; utilize the present invention to its fullest extent. The preceding preferred specific embodiments are, therefore, to be construed as merely illustrative, and not limitative of the remainder of the disclosure in any way whatsoever. Also, any preceding examples can be repeated with similar success by substituting the generically or specifically described reactants and/or operating conditions of this invention for those used in such examples.

Throughout the specification and claims, all temperatures are set forth uncorrected in degrees Celsius and, all parts and percentages are by weight, unless otherwise indicated.

The entire disclosures of all applications, patents and publications, cited herein and of corresponding EUROPEAN application No. 02026607.8, filed 28 Nov. 2002, and U.S. Provisional Application Ser. No. 60/430,084, filed 2 Dec. 2002, are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of formula (I)

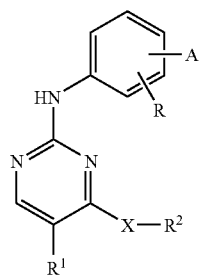

in which
A or B in each case independently of one another represent hydrogen or the group —$NO_2$, —$NH_2$, —$NR^3R^4$, —$N(C_{1-6}$-hydroxyalkyl$)_2$, —NH(CO)—$R^5$, —NH-COOR$^6$, —$NR^7$—(CO)—$NR^8R^9$, —$NR^7$—(CS)—$NR^8R^9$, —CO—$NR^8R^9$, —$SO_2$—$CH_3$, 4-bromo-1-methyl-1H-pyrazolo-3yl or $C_{1-6}$-alkyl optionally substituted in one or more places, the same way or differently with cyano, halogen, hydroxy or the group —$NH_2$, —NH—(CO)—$R^5$, —$SO_2$—$NHR^3$, —COOR$^5$, —CONR$^8R^9$, —O—(CO)—$R^5$, —O—(CO)—$C_{1-6}$-alkyl-$R^5$,
X represents an oxygen atom or the group —NH—,
$R^1$ represents halogen,
$R^2$ represents $C_{1-6}$-alkyl optionally substituted in one or more places, the same way or differently, with hydroxy, imidazolyl or the group —$NH_2$, —NH—(CO)O—$CH_2$-phenyl, —NH—(CO)H, —NH—(CO)-phenyl, —NH—(CO)—$CH_2$—O-phenyl, —NH—(CO)—$CH_2$-phenyl, —NH—(CO)—CH($NH_2$)$CH_2$-phenyl, —NH—(CO)—$CH_2$—CH($CH_3$)-phenyl, —NH—(CO)—CH(NH2)-($CH_2$)$_2$—COOH,

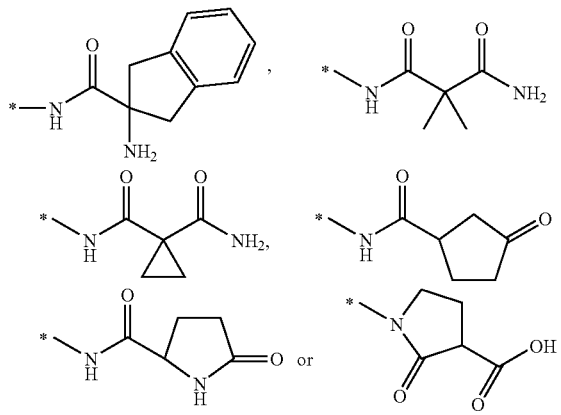

wherein phenyl can optionally be substituted in one or more places, the same or differently with halogen, $C_{1-6}$-alkyl or —(CO)—C($CH_2$)—$C_2H_5$,
$R^3$ or $R^4$ in each case independently of one another represent hydrogen or $C_{1-6}$-alkyl optionally substituted in one or more places, the same way or differently, with hydroxy, phenyl or hydroxyphenyl,
or
$R^3$ and $R^4$ together form a $C_{3-6}$-heterocycloalkylring containing at least one nitrogen atom and optionally can be interrupted by one or more oxygen and/or sulfur atoms and/or can be interrupted by one or more —(CO)— groups in the ring and/or optionally can contain one or more possible double bonds in the ring, wherein the $C_{3-6}$-heterocycloalkylring can optionally be substituted with $C_{1-6}$-alkyl, $C_{1-6}$-alkyl-COOH or $C_{1-6}$-alkyl-NH2,
$R^5$ represents $C_{1-6}$-alkyl, $C_{2-6}$-alkenyl, $C_{3-6}$-cycloalkyl or phenyl each can optionally be substituted in one or more places, the same way or differently, with halogen, hydroxy, phenyl or with the group —$NH_2$, —NH(CO)—O—$C_{1-6}$-alkyl, wherein phenyl can optionally be substituted in one or more places, the same way or differently, with halogen, hydroxy or $C_{1-6}$-alkyl,
$R^6$ represents $C_{1-6}$-alkyl, $C_{2-6}$-alkenyl or phenyl,
$R^7$ represents hydrogen or $C_{1-6}$-alkyl and
$R^8$ or $R^9$ in each case independently of one another represent hydrogen, $C_{1-6}$-alkyl, $C_{2-6}$-alkenyl, $C_{3-6}$-cycloalkyl, aryl or phenyl, wherein aryl or phenyl can optionally be substituted in one or more places, the same way or differently, with hydroxy or the group —$NO_2$ or —$N(C_{1-6}$-alkyl$)_2$
or
$R^8$ and $R^9$ together form a $C_{3-6}$-heterocycloalkylring containing at least one nitrogen atom and optionally can be interrupted by one or more oxygen and/or sulfur atoms and/or can be interrupted by one or more —(CO)— groups in the ring and/or optionally can contain one or more possible double bonds in the ring, wherein the $C_{3-6}$-heterocycloalkylring can optionally be substituted with the group —$NH_2$,
wherein when X represents —NH—, B represents hydrogen and $R^2$ represents $C_{1-6}$-alkyl substituted with —$NH_2$, then A represents —NH—(CO)—$C_6$-cycloalkyl-$NH_2$, or a diastereomer, enantiomer or pharmaceutically acceptable salt thereof.

2. A compound according to claim 1, in which

A or B in each case independently of one another represent hydrogen, tetrazolyl or the group —N(CH$_3$)$_2$, —NH—(CO)-pyrrolidinyl, —NH—(CO)-pentyl, —NH—(CO)-hexyl, —NH—(CO)-hexyl-NH$_2$, —NH—(CO)—C$_3$H$_7$, —NH—(CO)—CH$_2$-phenyl, —NH—(CO)—CH$_2$—NH$_2$, —NH—(CO)—C$_2$H$_4$—NH$_2$, —NH—(CO)—CH(NH$_2$)—CH$_3$, —NH—(CO)—CH(NH$_2$)-hydroxyphenyl, —NH—(CO)—CH(NH$_2$)—CH$_2$-phenyl, —NH—(CO)—CH(NH$_2$)—CH$_2$-hydroxyphenyl, —NH—(CO)—CH(NH—(CO)—CH$_3$)—CH$_2$-phenyl, —NH—(CO)—CH$_2$—NH—(CO)—CH$_3$, —NH—(CO)—N(C$_2$H$_5$)(C$_2$H$_4$-piperidinyl), —NH—(CO)—N(CH$_3$)(C$_2$H$_4$-piperidinyl), —NH—(CO)—CH$_2$—NH(CH$_3$), —CH$_2$—N(CH$_3$)$_2$, —NH—(CO)NH—CH$_2$—COOH, hydantoinyl, —CH$_2$—COOH wherein pyrrolidinyl can optionally be substituted with hydroxy or the group —NH$_2$, —N(CH$_3$)$_2$ or —NH—(CO)—CH$_3$, and wherein hydantoinyl can be substituted with —CH$_3$, —CH$_2$—COOH, or —(CO)-thiazolidinonyl, X represents the group —NH—, R$^1$ represents halogen and R$^2$ represents the group —NH—(CO)-phenyl or C$_2$- or C$_3$-alkyl both can optionally be substituted in one or more places, the same way or differently, with cyano, hydroxy, phenyl, naphthyl, imidazolyl, thiazolyl, pyridyl, 2-oxazolinyl, piperidinyl, —NH$_2$, —NH—CH$_2$-thienyl, —NH-pyridinyl-NO$_2$, —NH-thiazolyl, —SO$_2$-thienyl, —SO$_2$—NH$_2$—SO$_2$—CH$_3$, —SO$_2$—C$_3$H$_7$, pyrrolidinonyl substituted with —COOH, —NH—(CO)—NH-thienyl, —NH—(CO)—NH-phenyl, —NH—(CO)—NH—C$_2$H$_5$, —NH—(CO)—C(CH$_3$)$_3$, —NH—(CO)—S—C$_2$H$_5$, —NH—(CS)—NH—C$_2$H$_5$, —NH—(CO)—C$_2$H$_5$, —NH—(CO)-thienyl, —(CO)—NH—NH$_2$, —(CO)—NH—CH$_2$—(CO)—NH$_2$, —(CO)—NH—C$_2$H$_5$, —COOH, wherein phenyl or imadazolyl, thiazolyl can optionally be substituted in one or more places, the same way or differently, with hydroxy, —CH$_3$, —NH—(CO)—CH$_2$—NH$_2$, —COOC$_2$H$_5$, —COOC(CH$_3$)$_3$,

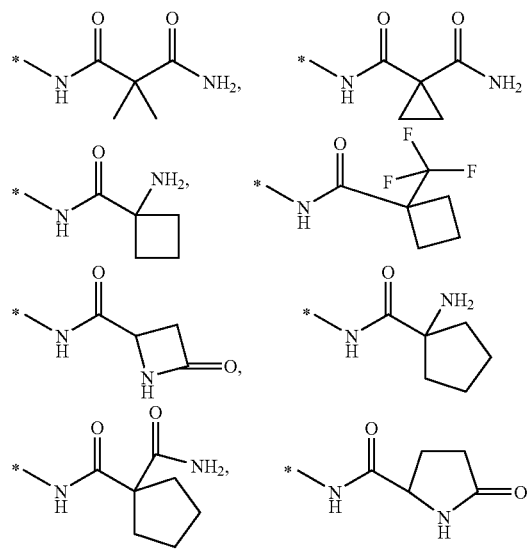

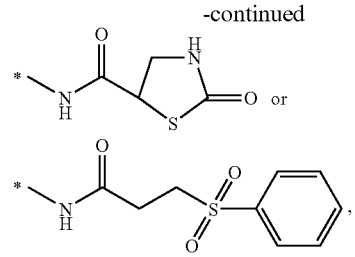

or a diastereomer, enantiomer or pharmaceutically acceptable salt thereof.

3. A compound according to claim 1, in which

A or B in each case independently of one another represent hydrogen or the group —NH—(CO)-pyrrolidinyl, —NH—(CO)-piperidinyl, —NH—(CO)-morpholinyl, —NH—(CO)-hexyl-NH2, —NH—(CO) —CH(NH2)-hydroxyphenyl, —NH—(CO) —CH(NH2) —CH2-hydroxyphenyl, hydantoin optionally substituted with —CH3, X represents the group —NH—, R$^1$ represents halogen and R$^2$ represents —C$_2$H$_4$-imidazolyl or —C$_3$H$_7$ which can optionally be substituted in one or more places, the same way or differently with the group —NH—CH$_2$-thienyl, —NH—(CO) —C$_2$H$_5$, —NH—(CO) —C(CH$_3$)$_3$,

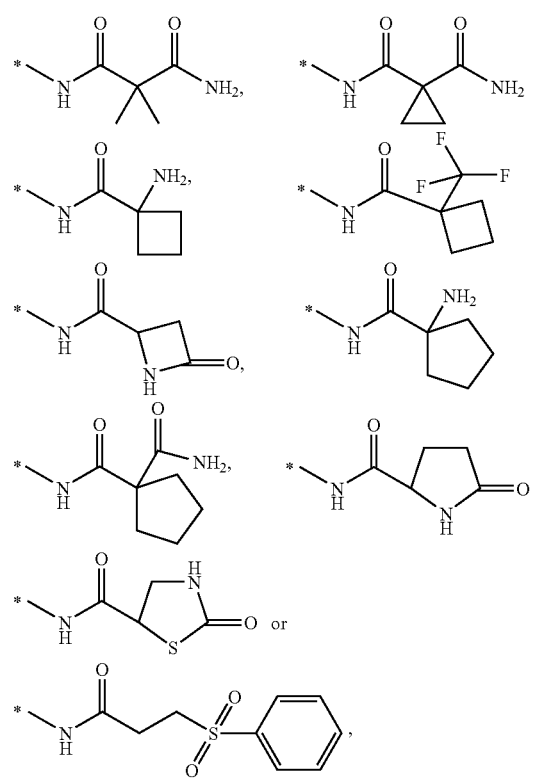

or a diastereomer, enantiomer or pharmaceutically acceptable salt thereof.

4. A compound, which is

N-[3-[[5-bromo-4-[[3-[[[1-(trifluoromethyl)cyclobutyl]carbonyl]amino]propyl]amino]-2-pyrimidinyl]amino]phenyl]-1-pyrrolidinecarboxamide, N-[3-[[5-bromo-4-[[3-[[1-oxo-3-(phenylsulfonyl)propyl]amino]propyl]amino]-2-pyrimidinyl]amino]phenyl]-1-pyrrolidinecarboxamide, N-[3-[[5-bromo-2-[[3-[(1-pyrrolidinylcarbonyl)aminophenyl]amino]-4-pyrimidinyl]amino]propyl]-2,2-dimethyl-propanediamide, N-[3-[[4-[[3-[[(1-aminocyclopentyl)carbonyl]amino]propyl]amino]-5-bromo-2-pyrimidinyl]amino]phenyl]-1-pyrrolidinecarboxamide, N-[3-[[4-[[3-[[(1-aminocyclobutyl)carbonyl]amino]propyl]amino]-5-iodo-2-pyrimidinyl]amino]phenyl]-1-pyrrolidinecarboxamide, $N^1$-[3-[[5-bromo-2-[[3-[(1-pyrrolidinylcarbonyl)aminophenyl]amino]-4-pyrimidinyl]amino]propyl]-1,1-cyclopentanedicarboxamide, (4R)-N-[3-[[5-bromo-2-[[3-(2,5-dioxo-1-imidazolidinyl)phenyl]amino]-4-pyrimidinyl]amino]propyl]-2-oxo-4-thiazolidinecarboxamide, (4R)-N-[3-[[5-bromo-2-[[3-(3-methyl-2,5-dioxo-1-imidazolidinyl)phenyl]amino])-4-pyrimidinyl]amino]propyl]-2-oxo-4-thiazolidinecarboxamide, 3-[3-[[5-bromo-4-[[2-(1H-imidazol-4-yl)ethyl]amino]-2-pyrimidinyl]amino]phenyl]-2,4-imidazolidinedione, 3-[3-[[5-bromo-4-[[2-(1H-imidazol-4-yl)ethyl]amino]-2-pyrimidinyl]amino-]phenyl]-1-methyl-2,4-imidazolidinedione, N'-[3-[[5-bromo-4-[[2-(1H-imidazol-4-yl)ethyl]amino]-2-pyrimidinyl]amino]phenyl]-N-ethyl-N-8-(1-piperidinyl)ethyl]-urea, N-[3-[[5-bromo-4-[[3-[(2,2-dimethyl-1-oxopropyl)amino]propyl]amino]-2-pyrimidinyl]amino]phenyl]-1-pyrrolidinecarboxamide, N-[3-[[2-[[3-[[(2S)-2-amino-3-(4-hydroxyphenyl)-1-oxopropyl]amino]phenyl]amino]-5-bromo-4-pyrimidinyl]amino]propyl]-2,2-dimethyl-propanediamide, N-[3-[[2-[[3-[[(1-aminocyclohexyl)carbonyl]amino]phenyl]amino]-5-bromo-4-pyrimidinyl]amino]propyl]-2,2-dimethyl-propanediamide, N-[3-[[2-[[3-[[(2S)-2-amino-2-phenylacetyl]amino]phenyl]amino]-5-bromo-4-pyrimidinyl]amino]propyl]-2,2-dimethyl-propanediamide, N-[3-[[2-[[3-[[(2R)-2-amino-1-oxo-3-phenylpropyl]amino]phenyl]amino]-5-bromo-4-pyrimidinyl]amino]propyl]-5-oxo-2-pyrrolidinecarboxamide, N-[3-[[2-[[3-[[(2R)-2-amino-1-oxo-3-phenylpropyl]amino]phenyl]amino]-5-bromo-4-pyrimidinyl]amino]propyl]-2,2-dimethyl-propaneiamide, $N^1$-[3-[[5-bromo-2-[[3-[[(2S)-2-pyrrolidinylcarbonyl]amino]phenyl]amino]-4-pyrimidinyl]amino]propyl]-1,1-cyclopropanedicarboxamide, N-[3-[[5-bromo-2-[[3-(2,5-dioxo-1-imidazolidinyl)phenyl]amino]-4-pyrimidinyl]amino]propyl]-2,2-dimethyl-propanediamide, N-(3-((5-bromo-4-((2-(1H-imidazol-4-yl)ethyl)amino)-2-pyrimidinyl)amino)phenyl)-4-morpholinecarboxamide, N-(3-((5-bromo-4-((2-(1H-imidazol-4-yl)ethyl)amino)-2-pyrimidinyl)amino)phenyl)-1-pyrrolidinecarboxamide, N-(3-((5-bromo-4-((3-((2-thienylcarbonyl)amino)propyl)amino)-2-pyrimidinyl)amino)phenyl)-1-pyrrolidinecarboxamide, N1-(3-((5-bromo-2-((3-(((1-pyrrolidinylcarbonyl)amino)phenyl)amino)-4-pyrimidinyl)-amino)propyl)-1,1-cyclopropanedicarboxamide, N-(3-((5-bromo-4-((3-((1-oxopropyl)amino)propyl)amino)-2-pyrimidinyl)amino)phenyl)-1-pyrrolidinecarboxamide, N-(3-((5-iodo-4-((3-((2-thienylcarbonyl)amino)propyl)amino)-2-pyrimidinyl)amino)phenyl)-1-pyrrolidinecarboxamide, N-[3-[[5-bromo-4-[[3-[[[(2S)-5-oxo-2-pyrrolidinyl]carbonyl]amino]propyl]amino]-2-pyrimidinyl]amino]phenyl]-1-pyrrolidinecarboxamide, N-[3-[[5-bromo-4-[[3-[[[(2S)-4-oxo-2-azetidinyl]carbonyl]amino]propyl]amino]-2-pyrimidinyl]amino]phenyl]-1-pyrrolidinecarboxamide, (4R)-N-[3-[[5-bromo-2-[[3-[(1-pyrrolidinylcarbonyl)amino]phenyl]amino]-4-pyrimidinyl]amino]propyl]-2-oxo-4-thiazolidinecarboxamide or N-[3-[[4-[[3-[[(1-aminocyclobutyl)carbonyl]amino]propyl]amino]-5-bromo-2-pyrimidinyl]amino]phenyl]-1-pyrrolidinecarboxamide, or a pharmaceutically acceptable salt thereof.

5. A compound according to claim 1, in which

A or B in each case independently of one another represent hydrogen or the group —NH—$C_2H_4$—OH, —NH—$CH_2$-hydroxyphenyl, —NH—(CO)-pyrrolidinyl, —NH—(CO)—CH($NH_2$)—$CH_2$-phenyl, —NH—(CO)-pentyl-$NH_2$, —NH—(CO)-hexyl-$NH_2$, —NH—(CO)—$CH_2$—$NH_2$, —NH—(CO)—CH($NH_2$)-hydroxyphenyl, —NH—(CO)—$CH_2$-hydroxyphenyl, —NH—(CO)—$CH_2$-methylphenyl, —NH—(CO)—$C_2H_4$-dihydroxyphenyl, —NH—(CO)—CH(OH)-phenyl, —NH—(CO)—CH($NH_2$)—$CH_2$(OH), —NH—(CO)—C($CH_3$)$_2NH_2$, —NH—(CO)—H($C_2H_5$), —$CH_2$OH, —(CO—NH-cyclopropyl,—(CO—NH—CH($CH_3$)$_2$, wherein pyrrolidinyl can optionally be substituted with hydroxy or the group —$NH_2$, X represents an oxygen atom or the group —NH—, $R^1$ represents halogen and $R^2$ represents —$C_2H_5$ optionally substituted in one or more places, the same way or differently, with hydroxy, imidazolyl or represents $C_3H_7$ or $C_4H_8$ optionally substituted in one or more places, the same way or differently with the group —$NH_2$, —NH—(CO)—CH($NH_2$)—$C_2H_4$—COOH, —NH—(CO)-phenyl, NH—(CO)—$CH_2$-phenyl, —NH—(CO)—$CH_2$—CH($CH_3$)-phenyl, —NH—(CO)—$CH_2$—O-phenyl, —NH—(CO)O—$CH_2$-phenyl, —NH—(CO)—CH($NH_2$)$CH_2$-phenyl,

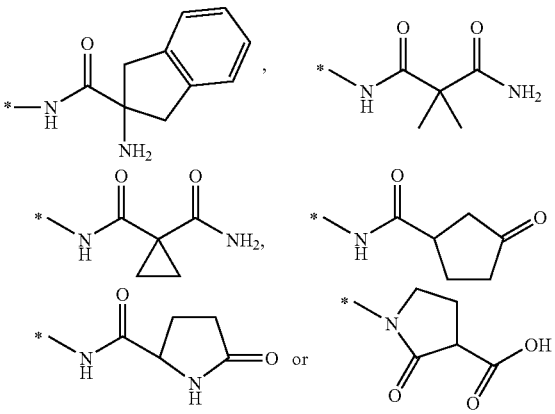

wherein phenyl can optionally be substituted in one or more places, the same or differently, with halogen, —$CH_3$ or —(CO)—C($CH_2$)($C_2H_5$), or a diastereomer, enantiomer or pharmaceutically acceptable salt thereof.

6. A compound, which is
N-[3-[[2-[[3-[[(2R)-2-amino-1-oxo-3-phenylpropyl]amino]phenyl]amino]-5-bromo-4-pyrimidinyl]amino]propyl]-2,2-dimethyl-propanediamide,
1-[3-[[2-[[3-[[(2R)-2-amino-1-oxo-3-phenylpropyl]amino]phenyl]amino]-5-bromo-4-pyrimidinyl]amino]propyl]-2-oxo-3-pyrrolidinecarboxylic acid,
N-[3-[[5-bromo-4-[[3-[[(5-oxo-2-pyrrolidinyl)carbonyl]amino]propyl]amino]-2-pyrimidinyl]amino]phenyl]-1-pyrrolidinecarboxamide,
Pyrrolidine-1-carboxylic acid [3-(5-bromo-4-{3-[2-(2,4-dichloro-phenyl)-acetylamino]-propylamino}-pyrimidin-2-ylamino)-phenyl]-amide,
Pyrrolidine-1-carboxylic acid [3-(5-bromo-4-{3-[2-(4-bromo-phenyl)-acetylamino]-propylamino}-pyrimidin-2-ylamino)-phenyl]-amide,
Pyrrolidine-1-carboxylic acid (3-{5-bromo-4-[3-(2-p-tolyl-acetylamino)-propylamino]-pyrimidin-2-ylamino}-phenyl)-amide,
Pyrrolidine-1-carboxylic acid [3-(5-bromo-4-{3-[2-(2,4-difluoro-phenyl)-acetylamino]-propylamino}-pyrimidin-2-ylamino)-phenyl]-amide,
Pyrrolidine-1-carboxylic acid {3-[5-bromo-4-(3-{2-[2,3-dichloro-4-(2-methylene-butyryl)-phenoxy]-acetylamino}-propylamino)-pyrimidin-2-ylamino]-phenyl}-amide,
Pyrrolidine-1-carboxylic acid [3-(5-bromo-4-{3-[3-(2,3-dichloro-phenyl)-butyrylamino]-propylamino}-pyrimidin-2-ylamino)-phenyl]-amide,
Pyrrolidine-1-carboxylic acid (3-{5-bromo-4-[3-(3-bromo-benzoylamino)-propylamino]-pyrimidin-2-ylamino}-phenyl)-amide,
N-(3-((4-((4-aminobutyl)amino)-5-bromo-2-pyrimidinyl)amino)phenyl)-1-pyrrolidinecarboxamide,
N-[3-[[2-[[3-[[(2R)-2-amino-1-oxo-3-phenylpropyl]amino]phenyl]amino]-5-bromo-4-pyrimidinyl]amino]propyl]-2,2-dimethyl-propanediamide,
N-[3-[[(2S)-2-Amino-1-oxo-3-phenylpropyl]amino]-5-[[5-bromo-4-(prop-2-ynyloxy)pyrimidin-2-yl]amino]phenyl]pyrrolidine-1-carboxamide,
N-[3-[[(2R)-2-Amino-1-oxo-3-phenylpropyl]amino]-5-[[5-bromo-4-(prop-2-ynyloxy)pyrimidin-2-yl]amino]phenyl]pyrrolidine-1-carboxamide,
(αR)-α-Amino-N-[3-[[5-bromo-4-(prop-2-ynyloxy)pyrimidin-2-yl]amino]-5-(hydroxymethyl)phenyl]benzenepropanamide,
2-[3-(5-Bromo-4-prop-2-ynyloxy-pyrimidine-2-ylamino)-5-hydroxymethyl-phenylamino]-ethanol,
(2R)-Amino-N-[3-hydroxymethyl-5-(4-prop-2-ynyloxy-pyrimidine-2-ylamino)-phenyl]-3-phenyl-propionamide,
3-((2R)-Amino-3-phenyl-propionylamino)-5-(5-bromo-4-prop-2-ynyloxy-pyrimidine-2-ylamino)-N-cyclopropyl-benzamide,
3-((2R)-Amino-3-phenyl-propionylamino)-5-(5-bromo-4-prop-2-ynyloxy-pyrimidin-2-ylamino)-N-isopropyl-benzamide,
Phenylmethyl [3-[[2-[[3-[[(ethylamino)carbonyl]amino]phenyl]amino]-5-(hydroxymethyl)pyrimidine-4-yl]amino]propyl]carbamate,
Pyrrolidine-1-carboxylic acid (3-{4-[3-((2R)-amino-3-phenyl-propionylamino)-propylamino]-5-bromo-pyrimidine-2-ylamino}-phenyl)-amide,
Pyrrolidine-1-carboxylic acid (3-{4-[3-((2S)-amino-3-phenyl-propionylamino)-propylamino]-5-bromo-pyrimidine-2-ylamino}-phenyl)-amide,
2-[3-(5-Bromo-4-prop-2-ynyloxy-pyrimidine-2-ylamino)-phenylamino]-ethanol,
1-Amino-cyclopentancarbonylic acid[3-(5-bromo-4-prop-2-ynyloxy-pyrimidine-2-ylamino)-phenyl]-amide,
1-Amino-cyclohexancarbonylic acid-[3-(5-bromo-4-prop-2-ynyloxy-pyrimidine-2-ylamino)-phenyl]-amide,
(2S)-Amino-N-[3-(5-bromo-4-prop-2-ynyloxy-pyrimidine-2-ylamino)-phenyl]-3-phenyl-propionamide,
(2R)-Amino-N-[3-(5-bromo-4-prop-2-ynyloxy-pyrimidine-2-ylamino)-phenyl]-3-phenyl-propionamide,
2-{[3-(5-Bromo-4-prop-2-ynyloxy-pyrimidine-2-ylamino)-phenylamino]-methyl}-phenol,
(2R)-Amino-N-[3-(5-bromo-4-prop-2-ynyloxy-pyrimidine-2-ylamino)-phenyl]-3-(4-hydroxy-phenyl)-propionamide,
N-[3-(5-Bromo-4-prop-2-ynyloxy-pyrimidine-2-ylamino)-phenyl]-3-(3,4-dihydroxy-phenyl)-propionamide,
N-[3-(5-Bromo-4-prop-2-ynyloxy-pyrimidine-2-ylamino)-phenyl]-2-hydroxy-(2S)-phenyl-acetamide,
N-[3-(5-Bromo-4-prop-2-ynyloxy-pyrimidine-2-ylamino)-phenyl]-2-hydroxy-(2R)-phenyl-acetamide,
(2S)-Amino-N-[3-(5-bromo-4-prop-2-ynyloxy-pyrimidine-2-ylamino)-phenyl]-3-hydroxy-propionamide,
(2R)-Amino-N-[3-(5-bromo-4-prop-2-ynyloxy-pyrimidin-2-ylamino)-phenyl]-3-hydroxy-propionamide,
2-Amino-N-[3-(5-bromo-4-prop-2-ynyloxy-pyrimidine-2-ylamino)-phenyl]-2-methyl-propionamide,
(2S)-Amino-N-[3-(5-bromo-4-prop-2-ynyloxy-pyrimidine-2-ylamino)-phenyl]-3-(4-hydroxy-phenyl)-propionamide,
(2S)-Amino-N-[3-(5-bromo-4-prop-2-ynyloxy-pyrimidine-2-ylamino)-phenyl]-3-p-tolyl-propionamide or
(2R)-Amino-N-[3-(5-bromo-4-prop-2-ynyloxy-pyrimidine-2-ylamino)-phenyl]-3-p-tolyl-propionamide,
or a pharmaceutically acceptable salt thereof.

7. A compound according to claim 1, in which
A or B in each case independently of one another represent hydrogen or the group —SO$_2$—CH$_3$, —NO$_2$, —NH$_2$, —CF$_3$, —CH$_2$—NH—(CO)—NH$_2$, —CH$_2$-pyrrolidinyl, —NH—(CO)—CH$_3$, —NH—(CO)-hexyl-NH$_2$, —NH—(CO)-phenyl, —NH—(CO)-pyrrolidinyl, —NH—(CO)—CH(NH$_2$)—CH$_2$-phenyl, NH—(CO)—OCH$_3$, —NH—(CO)—OCH(CH$_3$)$_2$, —NH—(CO)—OC$_2$H$_4$-morpholino, —NH—(CO)—NH-cyclopropyl, —NH—(CO)-morpholino, —NH—(CO)—NH—C$_2$H$_4$-morpholino, —NH—(CO)—NH-hydroxycycloalkyl, hydantoinyl,
wherein pyrrolidinyl can optionally be substituted with hydroxy or the group —NH$_2$ and
wherein hydantoinyl can optionally be substituted with the group —CH$_3$ or thiazolidinonyl,
X represents the group —NH—,
R$^1$ represents halogen and
R$^2$ represents CH$_2$-dihydroxyphenyl, C$_2$H$_4$-imidazolyl, or C$_3$H$_7$ optionally substituted in one or more places, the same way or differently, with

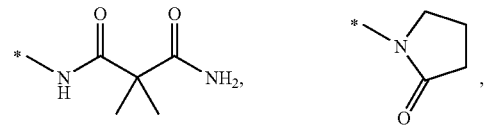

-continued

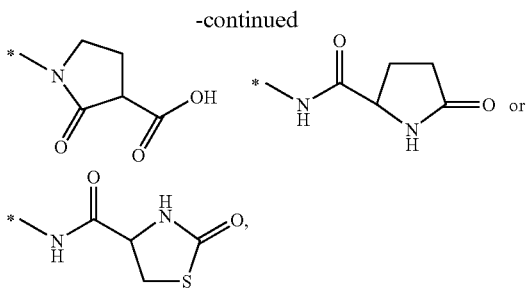

or a diastereomer, enantiomer or pharmaceutically acceptable salt thereof.

8. A compound, which is
4-((4-((2-(1H-imidazol-4-yl)ethyl)amino)-5-iodo-2-pyrimidinyl)amino)-benzenesulfonamide,
N-((3-((5-bromo-4-((2-(1H-imidazol-4-yl)ethyl)amino)-2-pyrimidinyl)amino)phenyl)methyl)-urea,
1-((3-((5-bromo-4-((2-(1H-imidazol-4-yl)ethyl)amino)-2-pyrimidinyl)amino)phenyl)methyl)-3-pyrrolidinol,
(3-((5-bromo-4-((2-(1H-imidazol-4-yl)ethyl)amino)-2-pyrimidinyl)amino)phenyl)-carbamic acid methyl ester,
N2-(3-aminophenyl)-5-bromo-N4-(2-(1H-imidazol-4-yl)ethyl)-2,4-pyrimidinediamine,
N-(3-((5-bromo-4-((2-(1H-imidazol-4-yl)ethyl)amino)-2-pyrimidinyl)amino)phenyl)-N'-cyclopropyl-urea,
N-(3-((5-bromo-4-((2-(1H-imidazol-4-yl)ethyl)amino)-2-pyrimidinyl)amino)phenyl)-4-morpholinecarboxamide,
(3-((5-bromo-4-((2-(1H-imidazol-4-yl)ethyl)amino)-2-pyrimidinyl)amino)phenyl)-carbamic acid 1-methylethyl ester,
N-(3-((5-bromo-4-((2-(1H-imidazol-4-yl)ethyl)amino)-2-pyrimidinyl)amino)phenyl)-methanesulfonamide,
N2-(3-amino-5-(trifluoromethyl)phenyl)-5-bromo-N4-(2-(1H-imidazol-4-yl)ethyl)-2,4-pyrimidinediamine,
N-(3-((5-bromo-4-((2-(1H-imidazol-4-yl)ethyl)amino)-2-pyrimidinyl)amino)phenyl)-N'-(2-(4-morpholinyl)ethyl)-urea,
N2-(3-amino-5-chlorophenyl)-5-bromo-N4-(2-(1H-imidazol-4-yl)ethyl)-2,4-pyrimidinediamine,
(3-((5-bromo-4-((2-(1H-imidazol-4-yl)ethyl)amino)-2-pyrimidinyl)amino)phenyl)-carbamic acid 2-(4-morpholinyl)ethyl ester,
N-(3-((5-bromo-4-((2-(1H-imidazol-4-yl)ethyl)amino)-2-pyrimidinyl)amino)phenyl)-N'-(4-hydroxycyclohexyl)-urea,
N-(3-((5-bromo-4-((2-(1H-imidazol-4-yl)ethyl)amino)-2-pyrimidinyl)amino)phenyl)-acetamide,
N-(3-((5-bromo-4-((2-(1H-imidazol-4-yl)ethyl)amino)-2-pyrimidinyl)amino)phenyl)-benzamide,
(4R)-N-[3-[[5-bromo-2-[[3-[(1-pyrrolidinylcarbonyl)amino]phenyl]amino]-4-pyrimidinyl]amino]propyl]-2-oxo-4-thiazolidinecarboxamide,
3-[3-[[5-bromo-4-[[2-(1H-imidazol-4-yl)ethyl]amino]-2-pyrimidinyl]amino]phenyl]-2,4-imidazolidinedione,
3-[3-[[5-bromo-4-[[2-(1H-imidazol-4-yl)ethyl]amino]-2-pyrimidinyl]amino]phenyl]-1-methyl-2,4-imidazolidinedione,
1-[3-[[2-[[3-[[(2R)-2-amino-1-oxo-3-phenylpropyl]amino]phenyl]amino]-5-bromo-4-pyrimidinyl]amino]propyl]-2-oxo-3-pyrrolidinecarboxylic acid,
1-[3-[[2-[[3-[[(1-aminocyclohexyl)carbonyl]amino]phenyl]amino]-5-bromo-4-pyrimidinyl]amino]propyl]-2-oxo-3-pyrrolidinecarboxylic acid,
N-[3-[[2-[[3-[[(2R)-2-amino-1-oxo-3-phenylpropyl]amino]phenyl]amino]-5-bromo-4-pyrimidinyl]amino]propyl]-5-oxo-2-pyrrolidinecarboxamide,
N-[3-[[2-[[3-[[(2R)-2-amino-1-oxo-3-phenylpropyl]amino]phenyl]amino]-5-chloro-4-pyrimidinyl]amino]propyl]-2,2-dimethyl-propanediamide,
3-[3-[[5-bromo-4-[[(3 ,4-dihydroxyphenyl)methyl]amino]-2-pyrimidinyl]amino]phenyl]-2,4-imidazolidinedione,
3-[3-[[5-bromo-4-[[(3 ,4-dihydroxyphenyl)methyl]amino]-2-pyrimidinyl]amino]phenyl]-1-methyl-2,4-imidazolidinedione,
(4R)-N-[3-[[5-bromo-2-[[3-(2,5-dioxo-1-imidazolidinyl)phenyl]amino]-4-pyrimidinyl]amino]propyl]-2-oxo-4-thiazolidinecarboxamide,
N-[3-[[5-bromo-2-[[3-(2,5-dioxo-1-imidazolidinyl)phenyl]amino]-4-pyrimidinyl]amino]propyl]-5-oxo-2-pyrrolidinecarboxamide,
N-[3-[[5-bromo-2-[[3-(2,5-dioxo-1-imidazolidinyl)phenyl]amino]-4-pyrimidinyl]amino]propyl]-2,2-dimethyl-propanediamide,
3-[3-[[5-bromo-4-[[3-(2-oxo-1-pyrrolidinyl)propyl]amino]-2-pyrimidinyl]amino]phenyl]-2,4-imidazolidinedione,
(4R)-N-[3-[[5-bromo-2-[[3-(3-methyl-2,5-dioxo-1-imidazolidinyl)phenyl]amino]-4-pyrimidinyl]amino]propyl]-2-oxo-4-thiazolidinecarboxamide or
(4R)-N-[3-[[5-bromo-2-[[3-[2,5-dioxo-3-[[(4R)-2-oxo-4-thiazolidinyl]carbonyl]-1-imidazolidinyl]phenyl]amino]-4-pyrimidinyl]amino]propyl]-2-oxo-4-thiazolidinecarboxamide,
or a pharmaceutically acceptable salt thereof.

9. A pharmaceutical composition comprising at least one compound according to claim 1 and a pharmaceutically acceptable carrier, diluent or excipient.

10. method of treating Kaposis sarcoma, Hodgkin's disease or leukemia comprising administering to a patient in need thereof an effective amount of a pharmaceutical composition according to claim 9.

11. A method according to claim 10, wherein the patient treated is a mammal.

12. A method of claim 11, wherein the mammal is a human.

13. pharmaceutical composition comprising at least one compound according to claim 2 and a pharmaceutically acceptable carrier, diluent or excipient.

14. A method of treating Kaposis sarcoma, Hodgkin's disease or leukemia comprising administering to a patient in need thereof an effective amount of a pharmaceutical composition according to claim 13.

15. A method of treating rheumatoid arthritis comprising administering to a patient in need thereof an effective amount of a pharmaceutical composition according to claim 9.

16. A compound according to claim 1, wherein X represents an oxygen atom.

17. A compound according to claim 1, wherein X represents the group —NH—.

18. A compound according to claim 1, wherein
A or B in each case independently of one another represent hydrogen or the group —$NO_2$, —$NH_2$, —$NR^3R^4$, —$N(C_{1-6}$-hydroxyalkyl$)_2$, —NH(CO)—$R^5$, —NH-COOR$^6$, —$NR^7$—(CO)—$NR^8R^9$, —$NR^7$—(CS)—$NR^8R^9$, —CO—$NR^8R9$, —$SO_2$—$CH_3$, 4-bromo-1-methyl-1H -pyrazolo-3yl or $C_{1-6}$-alkyl optionally substituted in one or more places, the same way or differently with cyano, hydroxy or the group —NH$_2$, —NH—(CO)—R$^5$, —SO$_2$—NHR$^3$, —COOR$^5$, —CONR$^8$R$^9$, —O—(CO)—R$^5$, —O—(CO)—C$_{1-6}$-alkyl-R$^5$.

19. A compound according to claim 1, wherein R$^2$ represents C$_{1-6}$-alkyl optionally substituted in one or more places, the same way or differently, with hydroxy, imidazolyl or the group —NH—(CO)O—CH$_2$-phenyl, —NH—(CO)H, —NH—(CO)-phenyl, —NH—(CO)—CH$_2$—O-phenyl, —NH—(CO)—CH$_2$-phenyl, —NH—(CO)—CH(NH$_2$)CH$_2$-phenyl, —NH—(CO)—CH$_2$—CH(CH$_3$)-phenyl, —NH—(CO)—CH(NH$_2$)—(CH$_2$)$_2$—COOH,

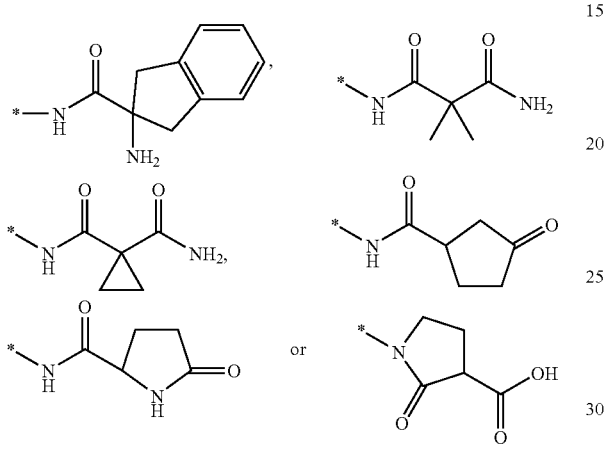

wherein phenyl can optionally be substituted in one or more places, the same or differently with halogen, C$_{1-6}$-alkyl or —(CO)—C(CH$_2$)—C$_2$H$_5$.

20. A compound according to claim 1, wherein R$^2$ represents a straight chain or branched chain C$_{1-6}$-alkyl substituted in one or more places, the same way or differently, with hydroxy, imidazolyl or the group —NH$_2$, —NH—(CO)O—CH$_2$-phenyl, —NH—(CO)H, —NH—(CO)-phenyl, —NH—(CO)—CH$_2$—O-phenyl, —NH—(CO)—CH$_2$-phenyl, —NH—(CO)—CH(NH$_2$)CH$_2$-phenyl, —NH—(CO)—CH$_2$—CH(CH$_3$)-phenyl, —NH—(CO)—CH(NH2)—(CH$_2$)$_2$—COOH,

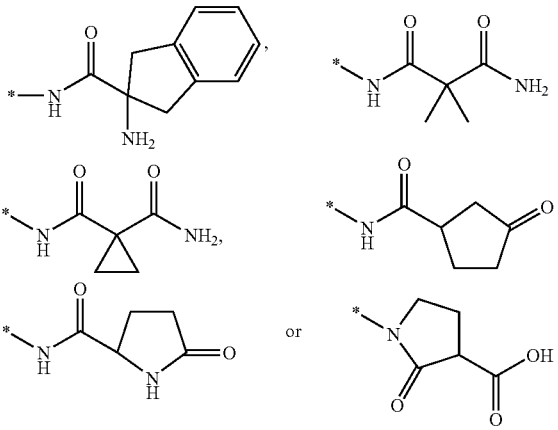

wherein phenyl can optionally be substituted in one or more places, the same or differently with halogen, C$_{1-6}$-alkyl or —(CO)—C(CH$_2$)—C$_2$H$_5$.

21. A pharmaceutical composition comprising at least one compound according to claim 20 and a pharmaceutically acceptable carrier, diluent or excipient.

22. A method of treating Kaposis sarcoma, Hodgkin's disease or leukemia comprising administering to a patient in need thereof an effective amount of a pharmaceutical composition according to claim 21.

\* \* \* \* \*

UNITED STATES PATENT AND TRADEMARK OFFICE
CERTIFICATE OF CORRECTION

PATENT NO. : 7,504,410 B2  Page 1 of 1
APPLICATION NO. : 10/722591
DATED : March 17, 2009
INVENTOR(S) : Joachim Kuhnke It is certified that error appears in the above-identified patent and that said Letters Patent is hereby corrected as shown below:

Title page Item (75), Inventors: line 3, reads "Hercules, CA" should read -- San Ramon, CA --
Title page Item (75), Inventors: line 6, reads "Hercules, CA" should read -- El Sobrante, CA --
Column 477, line 32, reads "—$SO_2$—$NH_2$—$SO_2$—$CH_3$," should read
-- —$SO_2$—$NH_2$, —$SO_2$—$CH_3$, --
Column 479, line 28, reads "...N-ethyl-N-8-(1-..." should read
-- ...N-ethyl-N-[2-(1-... --
Column 479, line 47, reads "...propaneiamide," should read -- ...propanediamide, --
Column 480, line 29-30, reads "— (CO—NH-cyclopropyl, —(CO—NH—$CH(CH_3)_2$," should read -- — (CO)—NH-cyclopropyl, —(CO)—NH—$CH(CH_3)_2$, --
Column 482, line 54, reads "or thiazolidinonyl," should read
-- or —(CO)-thiazolidinonyl, --
Column 482, line 57, reads "$CH_2$-dihydroxyphenyl, $C_2H_4$-imidazolyl," should read
-- —$CH_2$-dihydroxyphenyl, —$C_2H_4$-imidazolyl, --
Column 482, line 58, reads "$C_3H_7$" should read -- —$C_3H_7$ --
Column 484, line 65, reads "...—$NR^8R9$," should read -- ...—$NR^8R^9$, --

Signed and Sealed this

Twenty-first Day of July, 2009

JOHN DOLL
*Acting Director of the United States Patent and Trademark Office*